US007255997B1

(12) United States Patent
Maertens et al.

(10) Patent No.: US 7,255,997 B1
(45) Date of Patent: Aug. 14, 2007

(54) SEQUENCES OF HEPATITIS C VIRUS GENOTYPES AND THEIR USE AS THERAPEUTIC AND DIAGNOSTIC AGENTS

(75) Inventors: Geert Maertens, Brugge (BE); Lieven Stuyver, Lede (BE)

(73) Assignee: N.V. Innogenetics S.A., Ghent (BE)

( * ) Notice: Subject to any disclaimer, the term of this patent is extended or adjusted under 35 U.S.C. 154(b) by 1112 days.

(21) Appl. No.: 09/638,693

(22) Filed: Aug. 15, 2000

Related U.S. Application Data

(63) Continuation of application No. 08/362,455, filed as application No. PCT/EP94/01323 on Apr. 27, 1994.

(30) Foreign Application Priority Data

Apr. 27, 1993 (EP) .................................. 93401099
Aug. 5, 1993 (EP) .................................. 93402019

(51) Int. Cl.
*G01N 33/53* (2006.01)
*C07K 14/00* (2006.01)
*C07K 14/02* (2006.01)

(52) U.S. Cl. .................... 435/7.1; 530/350; 530/387.1; 530/328

(58) Field of Classification Search ................ 530/330, 530/329, 327, 326, 325, 324, 350, 322; 435/7.1
See application file for complete search history.

(56) References Cited

U.S. PATENT DOCUMENTS

| | | | | |
|---|---|---|---|---|
| 5,350,671 | A | 9/1994 | Houghton et al. ............. | 435/5 |
| 5,372,928 | A | 12/1994 | Miyamura et al. ............. | 435/5 |
| 5,514,539 | A | 5/1996 | Bukh et al. .................... | 435/5 |
| 5,846,704 | A | 12/1998 | Maertens et al. ............. | 435/5 |
| 5,882,852 | A | 3/1999 | Bukh et al. .................... | 435/5 |
| 6,416,946 | B1 * | 7/2002 | Chien et al. ................... | 435/5 |
| 6,548,244 | B2 | 4/2003 | Maertens et al. ............. | 435/5 |
| 6,762,024 | B2 | 7/2004 | Maertens ....................... | 435/6 |

FOREIGN PATENT DOCUMENTS

| | | |
|---|---|---|
| EP | 0419182 | 3/1991 |
| EP | 0 463 848 A2 | 1/1992 |
| EP | 0 532 167 | 3/1997 |
| GB | 2 239 245 A | 6/1991 |
| JP | 6-319563 | 11/1994 |
| WO | WO92/19743 | 11/1992 |
| WO | WO93/00365 | 1/1993 |
| WO | WO93/06126 | 4/1993 |
| WO | WO93/10239 | 5/1993 |
| WO | WO93/10239 A2 * | 5/1993 |
| WO | WO94/25601 | 11/1994 |
| WO | WO95/01442 A | 1/1995 |

OTHER PUBLICATIONS

Flores et al, Nucleic Acids Re. 18, 901 (1990).*
Shuldiner et al, J. Biol. Chem. 264: 9428 (1989).*
Yuan et al, Proc. Natl. Acad. Sci. USA 80: 1169 (1983).*
Williams et al, Biochemistry 31: 9768 (1992).*
Horie et al, Biochemistry 106: 1 (1989).*
Rosel et al, J. Virol. 56: 830 (1985).*
Driesel et al, "Hepatitis C virus (HCV) genotype distribution in German isolates: studies on the sequence variability in the E2 and NS5 region", Arch Virol (1994) 139: 379-388.
Kato et al, "Molecular Cloning of the Human Hepatitis C Virus Genome Form Japanese Patients with Non-A Non-B Hepatitis", Proc. Natl. Acad. Sci. USA, vol. 87, 1990, pp. 9254-9258.
Van Doorn et al, :Sequence Analysis of Hepatitis C Virus Genotypes 1 to 5", Database Genban 'Online Accession No. X78863, May 20, 1994, XP002017147.
Hotta et al, "Subtype Analysis of Hepatitis C Virus in Indonesia", Database Genban 'Online!Accession No. D26387, Feb. 4, 1994, XP002017146.
European Search Report, EP 99 11 8785.
S.W. Chan et al., "Analysis of a new hepatitis C type and its phylogenetic relationship to existing variants", J. of General Virology (1992), vol. 73, pp. 1131-1141.
S. Mori et al., "A new type of hepatitis C in patients in Thailand", Biochemical and Biophysical Research Communications, vol. 183, No. 1, 1992, pp. 334-342.
T.A. Cha et al., "At least five related but distinct genotypes of hepatitis C virus exist", Proc. National Acad. Sci., USA, vol. 89, pp. 7144-7148, Aug. 1992.
A. Weiner et al., "Variable and hypervariable regions are found in the regions of HCV corresponding to the flavivirus envelope and NS1 proteins", Virology. 180, (1991) pp. 842-848.
K. Chayama et al., "Genotypic subtyping of hepatitis C virus", Journal of Gastronenterology and Hepatology, vol. 8, (1993) pp. 150-156.
L. Stuyver et al., "Analysis of the putative E1 envelope and NS4a epitope regions of HCV type 3", Biochemical and Biophysical Research Communications, vol. 192, No. 2, 1993, pp. 635-641.
L. Stuyver et al., "Typing of hepatitis C virus isolates and characterization of new subtypes using a line probe assay", Journal of General Virology, vol. 74, 1993, pp. 1093-1102.

(Continued)

*Primary Examiner*—James Martinell
(74) *Attorney, Agent, or Firm*—Nixon & Vanderhye P.C.

(57) ABSTRACT

The present invention relates to a polynucleic acid composition comprising or consisting of at least one polynucleic acid containing 8 or more contiguous nucleotides corresponding to a nucleotide sequence from the region spanning positions 417 to 957 of the Core/E1 region of HCV type 3; and/or the region spanning positions 4664 to 4730 of the NS3 region of HCV type 3; and/or the region spanning positions 4892 to 5292 of the NS3/4 region of HCV type 3; and/or the region spanning positions 8 023 to 8 235 of the NS5 region of the BR36 subgroup of HCV type 3a; and/or the coding region of HCV type 4a starting at nucleotide 379 in the core region; and/or the coding region of HCV type 4; and/or the coding region of HCV type 5, with said nucleotide numbering being with respect to the numbering of HCV nucleic acids as show in Table 1, and with said polynucleic acids containing at least one nucleotide difference with known HCV type 1, and/or HCV type 2 genomes in the above-indicated regions, or the complement thereof.

13 Claims, 111 Drawing Sheets

OTHER PUBLICATIONS

P. Simmonds et al., Mapping of aerotype-specific immunodominant epitopes in the NS4 region of hepatitis C virus, Journal of Clinical Microbiology, vol. 31, 1993, pp. 1493-1503.

George et al., in Macromolecular Sequencing and synthesis, Selected Methods and Applications, Schlesinger (ed.), 1988, Alan R. Liss, Inc., New York, pp. 127-149.

Chen et al. Virology, 188: 102 (1992).

Wallace et al., Methods Enzymol. 152: 432 (1987).

Bukh, PNAS 89: 4942 (1992).

Innis et al., PCR Protocols: A Guide to Methods and Applications, 1990, (Innis et al. (ed.), Academic Press, New York, pp. 3-11.

Liu, et al, "Genomic typing of hepatitis C viruses present in China", GENE, vol. 114, No. 2, pp. 245-250 (1992).

Stuyver et al, "Classification of hepatitis C viruses based on phylogenetic analysis . . . ", Proceedings of the National Academy of Sciences of USA, vol. 91, No. 21, pp. 10134-10138 (1994).

Van Doorn et al, "Analysis of hepatitis C virus genotypes by a line probe assay . . . ", Journal of Hepatology, vol. 21, No. 1, pp. 122-129 (1994).

Bukh et al, "At least 12 genotypes of hepatitis C virus predicted by sequence . . . ", Proceedings of the National Academy of Sciences of USA, vol. 90, pp. 8234-8238 (1993).

Bukh et al, "Sequence analysis of the core gene of the 14 hepatitis C virus genotypes", Proceedings of the National Academy of Sciences of USA, vol. 91, pp. 8239-8424 (1994).

Enomoto et al, "There are two major types of hepatitis C virus in Japan", Biochem. Biophys. Res. Commun., vol. 170, No. 3, 1990, pp. 1021-1025, XP002017145.

Tokita et al, "Hepatitis C virus variants from Vietnam are classifiable . . . ", Proceedings of the National Academy of Sciences of USA, vol. 91, No. 23, pp. 11022-11026 (1994).

Stuyver et al, "Hepatitis C virus genotyping by means of 5'-UR/core . . . ", Virus Research, vol. 38, No. 2-3, pp. 137-157 (1995).

Qu et al, Journal of General Virology, vol. 75, No. 5, pp. 1063-1070 (1994).

Majzoub et al, Journal of Biological Chemistry, 1983, vol. 258:14061-14064.

Co et al, Proc. Natl. Acad. Sci. USA 88(7) 2869 (1991).

* cited by examiner

Figure 1

```
                 7932                                                      7981
                 CTCCACAGTCACTGAGAGGACGGACATCCGTACGGAGGAGGCAATCTACCAAT
HCV-1    1a      ---A--G-------AT----------------------T----AT---T---
HCV-J    1b      ---A----------------C---A----------GTT-----T---T----
BE90     1b      ---A----------------C---A----------GTT-----T---T----
2TY4     1c                                                       --A-----
4TY4     1c                                                       --A--T--
HC-J6    2a      ---A--C-------------A-------A-G--T-------T-C--A--T-GGG
HC-J8    2b      ---A--C-------G-----G-------AA-A--A--AT-C--A--T--GG
NE91     2b      ---A--C-------G-----G-------AA-A--A--A--C--A--T---G
EB12     2b                        -G----T--AA-A--A--AT-C--A--T--GG
ARG6     2c                                                       --A--T--GG
ARG8     2c                                                       ------G---
I10      2c                                                       ------G---
T983     2c                                                       --T-TG---
NE92     2c                                          -A--A--T-------T-C--A---TTG
CHR20    2d      ---A--G-------G-----G-------A--GGT---A----A--A---G-
CHR21    3a      ---T--T-------ACAG----------A--GGT---A-----AG--A---
CHR22    3a      ---G--T-------ACAG----------A--GGT---A-----AG--A---
T1       3a      ---A--T-------ACAG----------A--GGT---A-----AG--A---
T7       3a      ---A--T-------ACAG----------A--GGT---A-----AG--A---
NE93     3a      ---A--T-------ACAG----------A--GGT---A-----AG--A---
NZL13    3a      ---G--T-------ACAG----------A--GGT---A-----AG--A--T-
EB1      3a      ---A--T-------ACAG----------A--GGT---A-----AG--A---
EB2      3a                                                       --A-----
EB3      3a                                                       --A-----
EB7      3a                                                       --A-----
T9       3b      ---T--T-------ACAT----------A--G-----------AG--A---
T10      3b      ---T--T-------ACAG----------A--G---A-------AG--A---
BE98     3c                                                                GG
```

Figure 1 - Continued 1

| | | 7932 | | | | | | | | | 7981 |
|---|---|---|---|---|---|---|---|---|---|---|---|
| GB48 | 4c | ---- | ---- | T-- | A-- | C-- | A-AG | ---- | ---- | A-GGTC | ---- | ---- | AGG | ---- | ---- | T-- | G- |
| GB116 | 4c | ---- | ---- | T-- | A-- | C-- | A-AG | ---- | ---- | A-GGTC | ---- | ---- | AGG | --A | ---- | T-- | G- |
| GB215 | 4c | ---- | ---- | T-- | A-- | C-- | A-AA | ---- | ---- | A-GGTC | ---- | ---- | AGG-A | ---- | ---- | T-- | G- |
| GB358 | 4c | ---- | ---- | T-- | A-- | C-- | A-AG | ---- | ---- | A-GGTC | ---- | ---- | AGG-G | ---- | ---- | T-- | G- |
| GB809 | 4e | ---- | ---- | T-- | G-- | ---- | A | ---- | ---- | AAGGTC | --A | ---- | A-A-G | ---- | ---- | T-- | G- |
| CAM600 | 4e | ---- | ---- | T-- | G-- | ---- | A | ---- | ---- | A-GGTC | --A | ---- | A-A-G | ---- | ---- | T-- | G- |
| CAMG22 | 4f | ---- | ---- | ---- | ---- | ---- | A--A | ---- | ---- | A-GGTC | ---- | ---- | A-AGG | ---- | ---- | ---- | G- |
| GB549 | 4g | ---- | ---- | ---- | G-- | ---- | C--A--G--T | ---- | ---- | A-G--C | ---- | ---- | A-AG | ---- | ---- | ---- | G- |
| GB438 | 4h | ---- | ---- | ---- | G-- | ---- | A--G | ---- | ---- | TA-GGTC | ---- | ---- | A-AG | ---- | ---- | T-- | G- |
| CAR4/1205 | 4i | -C-- | ---- | C-- | G-- | N--- | ---- | G---- | ---- | N--A-GGTC | ---- | ---- | A-AGG | ---- | ---- | T-- | G- |
| CAR1/501 | 4j | ---- | ---- | G-- | T--GN | C--- | ---- | G---- | ---- | A-G--A | ---- | ---- | GA-AGG | ---- | ---- | T-- | G- |
| EG-13 | 4k | ---- | ---- | ---- | ---- | ---- | ---- | ---- | ---- | ---- | ---- | ---- | G-- | ---- | ---- | T-- | G- |
| EG-19 | 4k | ---- | ---- | ---- | ---- | ---- | ---- | ---- | ---- | ---- | ---- | ---- | G-- | ---- | ---- | T-- | G- |
| BE95 | 5a | ---- | G-- | C-- | T--C | ACAT | ---- | AATG | --C | --A | ---- | T-C | --T | ---- | ---- | ---- | -- |
| BE96 | 5a | ---- | A-- | C-C | U--C | ACAT | ---- | ATTG | ---T | --A | ---- | T-C | --A | ---- | ---- | ---- | -- |
| CHR18 | 5a | ---- | G-- | C-- | T--C | ACAT | ---- | AATG | --T | --A | ---- | T-T | --T | ---- | ---- | ---- | -- |
| CHR19 | 5a | ---- | G-- | C-- | T--C | ACAT | ---- | AATG | --T | --A | ---- | T-C | --T | ---- | ---- | ---- | -- |

Figure 1 - Continued 2

| | | SEQ ID | 7982 8031 |
|---|---|---|---|
| HCV-1 | 1a | | GTTGTGACCTCGACCCCCAAGCCCGCGTGGCCATCAAGTCCCTCACCGAG |
| HCV-J | 1b | | --------T-G-C----G-----A-GCA------A-G---G-----A--- |
| BE90 | 1b | 213 | --------T-G-C----G-G---A-ACA------A-----G-----A--- |
| 2TY4 | 1c | | ----------GC-----G-C--A-----T--------AAAT-----T--- |
| 4TY4 | 1c | | ----------GC-----G-C--A----CT--------AAAT-----T--- |
| HC-J6 | 2a | | C----TC-T-GCC-GAGG-G----A-ACT-----AC-C--A--G--T--- |
| HC-J8 | 2b | | C----TCT--GCCT-AAG-----A-AACT-T---AC-C--G-----T--- |
| NE91 | 2b | 215 | C----TC---GCC--AAG-G---A-AACT-T---AC-C--G--------- |
| EB12 | 2b | | C----TC---GCCT-AAG-G---A-AACT-T---AC-C--G-----T--- |
| ARG6 | 2c | | CC---TCA--GCCTGAGG-G--T--AACT-----AC-C--A--G--T--- |
| ARG8 | 2c | | CC---TCA--GCC-GAGG-G--T--AACT--T--AC-C--A--G--T--- |
| I10 | 2c | | CC--CTCA--GCCTGAGG-G-----AACT--T--AC-C--A--G--T--- |
| T983 | 2c | | C----TCA--GCCT-AGG-G--T--GACT--T--AC-C--AT-G--T--- |
| NE92 | 2d | 145 | C---CTCTT-ACC-GAG--G--A--GACT-----AC-C--A--G--T--- |
| CHR20 | 3a | | -C---A----T--A--GG-G---A-GAAA-TG---TCC--------G--- |
| CHR21 | 3a | | -C---A----T--A--GG-G---A-GAAA-TG---TCC--------G--- |
| CHR22 | 3a | | -C---A----T--A--GG-G---A-GAAA-TG---TCC--------G--A |
| T1 | 3a | | -C---A----T--A--GG-G---A-GAGA-TG---TCC--------G--- |
| T7 | 3a | | -----A-T--T--G--GG-G---A-GAAA-TG---TCC--------G--- |
| NE93 | 3a | 217 | -C--CA----T--A--GG-G---A-GAAA-TG---TCC--------G--- |
| NZL13 | 3a | | -C---A----T--A--GG-G---A-GAAA-TG---TCC--------G--- |
| EB1 | 3a | | -C---A----T--A--GG-G---A-GAAA-TG---TCC--------G--- |
| EB2 | 3a | | -C---A----T--A--GG-G---A-GAAA-TG---TCC--------G--A |
| EB3 | 3a | | -C---A----T--A--GG-G---A-AAAA-TG---TCC--------G--- |
| EB7 | 3a | | -C---A----T--A--GG-G---A-GAA--TG---TCC--------G--- |
| BR33 | 3a | 9,11 | -----G--- |
| BR34 | 3a | 1,3 | -----G--A |
| BR36 | 3a | 5,7 | -----G--- |
| T9 | 3b | | -C--------T--G--AG-G--T--GAA---G----GCG-T-----A--- |

Figure 1 - Continued 3

| | | SEQ ID | 7982 | | | | | | | | | | | 8031 |
|---|---|---|---|---|---|---|---|---|---|---|---|---|---|---|
| T10 | 3b | 149 | -C------ | ---- | -T- | -G- | -AG-G- | -T- | -GAA- | --G- | ---- | -GCG-T- | ---- | -A--- |
| BE98 | 3c |  | CC------ | -A- | -GGA-G- | -G- | -TA-GAG- | -TG- | -A-CT- | -A-- | ---- | ---G--- | ---- | ---- |
| GB48 | 4c | 106 | -------- | ---- | ----G-- | -G- | ------- | -AA- | --A- | --T-CCG | ---- | -A--A- | ---- | ---- |
| GB116 | 4c | 108 | -------- | ---- | ----G-- | -G- | ------- | -AGA | --A- | --T-CCG | ---- | -A--A- | ---- | ---- |
| GB215 | 4c | 110 | -------- | ---- | ----G-- | -G- | ------- | -AA- | -TA- | --T-CCG | ---- | -A--A- | ---- | ---- |
| GB358 | 4c | 112 | -------- | ---- | ----G-- | -G- | ------- | -AA- | --A- | --T-CCG | ---- | -A--A- | ---- | ---- |
| GB809 | 4e | 116 | -------- | ---- | ----G-- | -G- | ------- | -AA- | --A- | --T-CTG | ---- | -A--A- | ---- | ---- |
| CAM600 | 4e | 201 | -------- | ---- | ----G-- | -G- | ------- | -AA- | -TA- | -AGCCG | ---- | ---G-- | ---- | ---- |
| CAMG22 | 4f | 203 | -------- | -T-- | ----G-- | -G- | ------- | -AA- | -TA- | -A-CCG | ---- | ---G-- | ---- | ---- |
| GB549 | 4g | 205 | -------- | ---- | ----G-- | -TG- | --A---- | -AA- | -TA- | -ATCTG | ---- | ---T-A | ---- | ---- |
| GB438 | 4h | 207 | -C--C--- | ---- | ----G-- | -G- | ------- | -AA- | -TG- | -ATCCG | ---- | -A--G- | -A- | ---- |
| CAR4/1205 | 4i | 209 | -C----A- | -T-- | -G--GN- | -G- | -T-N--- | -AA- | -TG- | -ATCCG | -T- | ---A--A | ---- | ---- |
| CAR1/501 | 4j | 211 | -C------ | ---- | ----G-- | -A- | --GG--- | -AA- | --T- | ---CG | ---- | -A--- | ---- | ---- |
| EG-13 | 4k |  | ---C---- | -A-- | ----G-- | -G- | ------- | -AA- | --T- | -T-CTG | ---- | ---T- | ---- | ---- |
| EG-19 | 4k |  | -------- | -AGT | --G--G- | -T-G-G | ------- | -AA- | --T- | -T-CTG | ---- | ---A--A | ---- | ---- |
| BE95 | 5a | 159 | CA------ | -T-- | -GC-G-- | -G- | --A---- | -CA- | --A- | --ACG | ---- | -A--- | ---- | ---- |
| BE96 | 5a | 161 | CA------ | -TCGC-G | ----G-- | -G- | --C--A- | -CA- | --A- | --ACG | ---- | -A--- | ---- | ---- |
| CHR18 | 5a |  | CA-TGT-- | -T-GC-G | --TG-G- | -G- | -T--- | --A- | --A- | --ACG | ---- | -A--- | ---- | ---- |
| CHR19 | 5a |  | CA-TGT-- | -T-GC-G | --TG-G- | -G- | -A--- | --C- | ---- | -A--ACG | ---- | -A--- | ---- | ---- |

Figure 1 - Continued 4

| | | 8032 | | | | | 8081 |
|---|---|---|---|---|---|---|---|
| | | AGGCTTTATGTTGGGGGCCCTCTTACCAATTCAAGGGGGAGAACTGCGG | | | | | |
| HCV-1 | 1a | ---------------------------------------------- | | | | | |
| HCV-J | 1b | C--------------T--C--G--T-----G-A-----C-------- | | | | | |
| BE90 | 1b | C-------A-C----T--C--G--T-----------A-----C----T-- | | | | | |
| 2TY4 | 1c | --AT-G--C--C--A--G--C--C-------------A-----T--A--- | | | | | |
| 4TY4 | 1c | --AT-G--C--C--T--G--CT-G--T---------AA--C-------- | | | | | |
| HC-J6 | 2a | --A-----C--G--A--G--CA-GTT---CAGC-A-----CC-----C-- | | | | | |
| HC-J8 | 2b | --A-----C--A--A--G--CA-G--A---CAGC-AA----C-ATC---- | | | | | |
| NE91 | 2b | --A-----C--C--G--A--CA-G-TA---CAGC-AA----C-ATC---- | | | | | |
| EB12 | 2b | --A-----C--C--A--G--CA-G--A---CAGC-AA----C-ATC---- | | | | | |
| ARG6 | 2c | --A-----C--C--A-----G--CA-G--A---CAGC-AA----C-ATC---- | | | | | |
| ARG8 | 2c | --A-----G--C--A-----G--CA-G--A---CAGC-A-----CC-ATC---- | | | | | |
| I10 | 2c | --A-----A--C--A-----G--CA-G--A---CAGC-A-----C-ATC---- | | | | | |
| T983 | 2c | --A--G--C--C--G--A--CA-G--A---CAGC-AA----C-TC----- | | | | | |
| NE92 | 2d | --A--A--C--G--A--G--CA-GCTA---CAGC-AA----C-A-C---- | | | | | |
| CHR20 | 3a | ----C----CTGC--------A-GTT---CAGC-A-----CCC-G---T-- | | | | | |
| CHR21 | 3a | ----C----CTGC--------A-GTT---AGC-A-----CCC-G---T-- | | | | | |
| CHR22 | 3a | ----C----CTGC--------A-GTT---CAGC-A-----CCC-G---T-- | | | | | |
| T1 | 3a | ----C----CTGC--------A-GTT---CAGC-A-----CCC-A---T-- | | | | | |
| T7 | 3a | ----C----CTGC--A-----A-GTA---CAGC-A-----TCC-G---T-- | | | | | |
| NE93 | 3a | ----C----CTGC--A-----A-GTTT--CAGC-A-----CCC-G---T-- | | | | | |
| NZL13 | 3a | ----C----CTGC--------A-GTT---CAGC-A-----CCC-G---T-- | | | | | |
| EB1 | 3a | ----C----CTGC--------CA-GTT---CAGC-A-----CCC-G---T-- | | | | | |
| EB2 | 3a | ----C----CTGC--------CA-GTT---CAGC-AA----CCC-G---T-- | | | | | |
| EB3 | 3a | ----C----CTGC--------A-GTT---CAGC-A-----CCC-G---T-- | | | | | |
| EB7 | 3a | ----C----CTGC--------A-GTT---CAGC-A-----CCC-G---T-- | | | | | |
| BR33 | 3a | ----C----CTGC--------A-GTTT--CAGC-A-----CCC-G---T-- | | | | | |
| BR34 | 3a | ----C----CTGC--------A-GTT---CAGC-A-----CCC-G---T-- | | | | | |
| BR36 | 3a | ----C----CTGC--------A-GTTT--CAGC-AA----CCC-G---T-- | | | | | |
| T9 | 3b | C---G----CA-C--A----T--CA-GTA---CAGT-A-----CTCC-G---- | | | | | |

Figure 1 - Continued 5

| | | | | | | | | | |
|---|---|---|---|---|---|---|---|---|---|
| T10 | 3b | C----- | -G- | -CA-C- | -A- | -T- | -CA-GTA- | -CAGT-A- | -CTCC-G----- |
| BE98 | 3c | C----- | ----- | -CTG- | --T- | -T- | -A-GTT- | -CAGC-A- | -AC-AC----- |
| GB48 | 4c | --A- | -C- | -C- | -G- | -T- | -CA-GCAT- | -CAGC-A- | -A--CCTG--- |
| GB116 | 4c | --A- | -C- | -C- | -G- | -T- | -CA-GCAT- | -CAGC--- | -A--CCTG--- |
| GB215 | 4c | --A- | -C- | ----- | -G- | -T- | -CA-GCAT- | -AGC-AA- | -A--CCTG--- |
| GB358 | 4c | --A- | -C- | -C- | -G- | -T- | -CA-GCAT- | -CAGC-A- | -A--CCTG--- |
| GB809 | 4e | --A- | -C- | -C- | -G- | -T- | -CA-GCAT- | -CAGC-A- | -A--CCTG--T-- |
| CAM600 | 4e | --A- | -C- | -C- | -G- | -C- | -CA-GCAT- | -CAGC-A- | -A--CCTT--T-- |
| CAMG22 | 4f | --A- | -C- | ----- | -G- | ----- | -A-GTA- | -AGC-GTA- | -A--CCTT----- |
| GB549 | 4g | --A- | -C- | -C- | -G- | -T- | -CA-GCA- | -CAGC--- | -A--CCTA----- |
| GB438 | 4h | --A- | -C- | -CAAG- | -C- | ----- | -CA-GTA- | -C--C-A- | -----CCTA----- |
| CAR4/1205 | 4i | --A- | -C- | -C- | -G- | ----- | -CA-GCA- | -CAGC-A- | -----CCTA----- |
| CAR1/501 | 4j | --A- | -C- | ----- | -G- | ----- | -A-GCA- | -CAGC-A- | -A--CCTG--T-- |
| EG-13 | 4k | --A- | -C- | -C- | -G- | ----- | -CA-GTT- | -CAGC-A- | -A--CCTG----- |
| EG-19 | 4k | --A- | -C- | -C- | -G- | ----- | -CA-GCA- | -CAGC-A- | -A--CCTT--T-- |
| BE95 | 5a | --A- | -C- | -C- | -G- | ----- | -CA-GCA- | -AGC-A- | -A--CCTT--T-- |
| BE96 | 5a | C-C- | -C- | -CTG- | --A- | ----- | -CA-GTA- | -CAGC-A- | -C-AC-G--T-- |
| CHR18 | 5a | C-CT- | -G- | -TCTG- | --A- | ----- | -CA-GTAT- | -CAGC-A- | -C-AC-A--T-- |
| CHR19 | 5a | C-C- | -G- | -CTG- | --A- | ----- | -CA-GTAT- | -CAGC-A- | -C-AC-A--T-- |

Figure 1 - Continued 6

```
                8082                                                              8131
HCV-1    CTATCGCAGGTGCCGCGCCGAGCGGCGTACTGACAACTAGCTGTGTGGTAACA
HCV-J    T---C-------------A-T---G-------G-----------C---C----
BE90     ---C-A------------A-----C-------C---------------C----
2TY4     ------------T-----------C-------C---------------C----
4TY4     ------------T-----C-----C-------C---------------C----
HC-J6    G--CA-GC-T--------C-----G-G-T---C-------ATG--G----T--
HC-J8    ---CA-GC-T--------A-----T-TT-C--C-------ATG--G----T--
NE91     T--CA-GC-T--------A-----T--TT-C--C------ATG--G----T--
EB12     T--CA-GC-T--------A-----T--TT-C--C------ATG--G----T--
ARG6     G--CA-GC-T--------------A--G--C--C------ATG-----------
ARG8     G--CA-GC-T--------------CA--G--C--C------ATG--C-------
I10      G--CA-GC-T--------------A--G--C--C------ATG--C-------
T983     T--CA-GC-T--------------TG-G--C--C------ATG--C-------
NE92     A--CA-AC-C--------C-----A--GT-C--C------ATG--A---T---
CHR20    T-----C-T--------T-T--T-A--C----C-T--C----------TC--C-
CHR21    T-----C-T--------T-T--T-A--T----C-T--C----------TC--C-
CHR22    T-----C-T--------T-T--T-A--C----C-T--C----------TC--C-
T1       T-----C-T--------T----T-C-T-A---C-T--C----------TC--C-
T7       T-----C-T--------T----T-A--C----C-T--C----------TC--C-
NE93     T-----C-T--------T----C-T-A---C-T--C----------TC--C-
NZL13    T----C-C-T--------T----T-C-T-A---C-T--C----------TC--C-
EB1      T----C-T--------T----T-C-T-A---C-T--C----------TC--C-
EB2      T----C-T--------T----T-C-T-A---C-T--C----------TC--C-
EB3      T----C-T--------T----T-C-T-A---C-T--C----------TC--C-
EB7      T----C-T--------T----T-C-T-A---C-T--C----------TC--C-
BR33     T----C-C---T------T----T-C-T-A---C-T--C------T-TC--C-
BR34     T----C-C---------T----T-C-T-A---C-T--C----------TC--C-
BR36     T----C-T--------T----T-C-T-A---C-T--C----------TC--C-
T9       ---------C-------------CT---------C-T----------TC--C----T-
```

Figure 1 - Continued 7

|  |  | 8082 |  | 8131 |
|---|---|---|---|---|
| T10 | 3b | ----------C--C------------C----------CT--C-T--C----TC--C--T- |  |  |
| BE98 | 3c | T--C----C--C--------T--T--T--G---G--AC--C--C-----TC--G--- |  |  |
| GB48 | 4c | G-------A--T----A------------CTAC--C--C----TC--G--- |  |  |
| GB116 | 4c | G-------A----T--------------CTAC--C--C----TC--G--- |  |  |
| GB215 | 4c | G-------A------A------------CTAC--C--C----TC--G--- |  |  |
| GB358 | 4c | G-------A------A------------CTAC--C--C----TC--G--- |  |  |
| GB809 | 4e | G----T--A------------------TAC--C--C----TC--G--- |  |  |
| CAM600 | 4e | G----------------A----------TAT--C--C----TC--G--- |  |  |
| CAMG22 | 4f | G--C--T--A---------------TAC--C--A----TC--G--- |  |  |
| GB549 | 4g | GC-A--G---------A------G--CTAC--C--C----TC--G--- |  |  |
| GB438 | 4h | GCT---G----------A------G--TAC--C--C----TC--G--- |  |  |
| CAR4/1205 | 4i | -ATC--T--A---------------TTAC--C--G----TC--A--- |  |  |
| CAR1/501 | 4j | AC-A----C-----------A------GT-C--C--C----TC--G--- |  |  |
| EG-13 | 4k | G----G--A--T-G--A-----A--CT-T--G--C----TC--A--- |  |  |
| EG-19 | 4k | G----G--A----G--A-----A--CTAT--G--C----TC--A--- |  |  |
| BE95 | 5a | T-------A------C------TT-C--C--C--TATG--C--- |  |  |
| BE96 | 5a | T-------A------C------CT-C--C--C--TATG--C--- |  |  |
| CHR18 | 5a | T----T--A------C------CT-C--C--C--TATG--C--- |  |  |
| CHR19 | 5a | T--C--T--A------C------CT-C--C--C--TATG--C--- |  |  |

Figure 1 – Continued 8

```
                    8132                                                              8181
        CCCTCACTTGCTACATCAAGGCCCGGGCAGCCTTCTCGAGCCGCAGGGCTC
HCV-1  1a  ---------------------------------------------------
HCV-J  1b  -----A--T---T-G------ACT--G-------------T---AA----
BE90   1b  ---T--A--T---C-A-----TCT----------------T---GAA---
2TY4   1c  -T-------C-----------TA---------------------------
4TY4   1c  -T-------C-----------TA---------------------------
HC-J6  2a  --A------A----TG-G--A---TTA--G------AAG--T-----A-A
HC-J8  2b  --A-G--A--T---------A---TT---------G--AAG--T-----A
NE91   2b  --A-G--G--T---------A---TT---------G---AA--------A
EB12   2b  --A-G--A------------A---TT---------G---CAA--T--G--A
ARG6   2c  -A-------G----G-G--A---TAAA--G--A---AAC---G--CA-T
ARG8   2c  -A-------G----G-G--A------A----G--G---AAC---G--CA-T
I10    2c  -G-------G----G-G--A------A-A--G--G---AAC---G--CA-T
T983   2c  -A--T----G--T-G-G--A------AA------G--CAAC---TG--CA-T
NE92   2d  -A-------G----G-G--------A-AA-------AAG--T--G--CA-A
CHR20  3a  -AA------T------------TA-A--G--T-CGAAG----------C-
CHR21  3a  -AA------T------------TA-A--G--TGCGAAG------------
CHR22  3a  -AA------T----------A-TA-A--G--TGCCGA-----------C-
T1     3a  -AA------T------------ACA--G--TGCGAAG-----------C-
T7     3a  -GA------T------------ACA--G--TGCAA-G-----------C-
NE93   3a  -AA------T------------ACAA--G--GCGAAG-----------C-
NZL13  3a  -AA------T------------ACA--G--TGC-AAG-------AAC---
EB1    3a  -AA------T----------A--TACA--G------CGAG--------C-
EB2    3a  -AA------T------------ACA--G------CGAG--------C-
EB3    3a  -AA------T------------ACA--G------CAAG--------C-
EB7    3a  -AA------T------------ACA--G------CAA---------C-
BR33   3a  -AA------T------------ACA--G--TGCAAA-----------C-
BR34   3a  -AA------T------------ACA--G--TGCAA-G----------C-
BR36   3a  -AA------T----------A-ACA--G--GCAAA------------C-
T9     3b  -AA-A----C--T---------ACT----------A-CA-G--T--G--T--
```

Figure 1 - Continued 9

```
                       8132                                                 8181
T10         3b    -AA-A--C--T-------------ACT--G---A-CA-G--T--G--T---
BE98        3c    -AA-----C--T-------A--AAA------TACCAA---T--C--AA-T

GB48        4c    -A--G--G----------C----A----TCA--C---TATCAA--G--G-----G
GB116       4c    -A--G--G----------TC---A----TCA--C---TATCA---G--G-----G
GB215       4c    -A--G--G----------TC---A----TCA--C---TATCA---G--G-----G
GB358       4c    -A--G--G----------C----A----TCA--C---ATCA-G--GT--------G
GB809       4e    -A--G--G----------C----A----TCA--C---TATCA---G--G------G
CAM600      4e    -AA-G--G----------C-T-------TCA------ATCA-G--T--G------A
G22         4f    -A--G--G----------C-T--A----TCA------ATCA-G--T--G------G
GB549       4g    -T--G--G----------T-C-------ACA--G---ACCAA---T--C--A
GB438       4h    -TG-A--G--T--TC-------------GTT--G--TAC-A-G--------T--G
CAR4/1205   4i    -GG-G--A----------C-T--A----ACA------ACCA-G--T---------G
CAR1/501    4j    -G--G-------------C----A----ACA--G---ACCA-G--------G--CT-G
EG-13       4k    -A--G--G----------C-T--A----ACA--T---TAC-A--C---CT-A
EG-19       4k    -G--G--G----------C-A--A----AC---C---TAT-A---G--G-----G
BE95        5a    -G--G--G----------C----A----ACA--C---TAT-A-G--G--A--A
BE96        5a    -A--G--G-------------------------------A
CHR18       5a    -A--G--G-------T----------TTTA--CT-----A---T
CHR19       5a    -A--G--G------------------TTCA--C--------A
```

Figure 1 - Continued 10

```
                 8182                                                        8231
             CAGGACTGCACCATGCTCGTGTGTGGCGACGACTTAGTCGTTATCTGTGA
HCV-1   1a
HCV-J   1b   ---------G--------AAC--A-----C-T----------------
BE90    1b   ---------G-----------C--G----C-T----------------
2TY4    1c   -G-----------------------------------------------
4TY4    1c   ---------------------------------------------
HC-J6   2a   ATT-CGCC---A----G--A--C----T-----G--T--C----CA--
HC-J8   2b   GT-----CCTGTT---T-G--------A-------C-G-------CA--
NE91    2b   GT-----CC-GT-----G---------A-------C-G-------CG--
EB12    2b   GT-----CC-GTT
ARG6    2c   GTT-C-CC---
ARG8    2c   GTT-CTCC---
I10     2c   GTT-CTCC---
T983    2c   GTT-CT-C---
NE92    2d   ATT-C-CC---G-----G------C-------TC----T--C----CA-
CHR20   3a   -G-A--CCGGA-T--C--T--C--A--T--TC-G----TC-G---GG-GGC--
CHR21   3a   -G-AC-CCGGA-T-T--C--T--C--A--T--TC-G--T--TC-G---GG-GGC--
CHR22   3a   -G-A--CCGGA-T-T--C--T--C--A--T--TC-G--T--TC-G---GG-GGC--
T1      3a   -G-A--CCGGA-T-T--C--T--C--A--T--TC-G--T--TC-G---GG-GGC--
T7      3a   -G-A--CCGGA-T-T--C--T--C--A--T--TC-G-----AG-GGC--
NE93    3a   -G-A--CCGGA-T-T--C--T--C--A--T--TC-G-----GG-GGC--
NZL13   3a   -G-A--CCGGA-T-T--C--T--C--A--T--TC-G-----GG-GGC--
EB1     3a   -G-A-TCCGGA-                                  -GG-GGC--
EB2     3a   -G-A--CCGGA-
EB3     3a   -G-A--CCGGA-
EB7     3a   -G-A--CCGGA-
BR33    3a   -G-A--CCGGA-T--T--T--C--A--T--T--G-----GG-GGC--
BR34    3a   -G-A--CCGGA-T-T--T--C--C--A--T--TC-G-----GG-GGC--
BR36    3a   -G-AG-CCGGA-T-T--C--T--C--A--T--TC-G-----GG-GGC--
T9      3b   A-A---CCAT-TT--C--T--C--C--A-----T---G--G-A-C--
```

Figure 1 - Continued 11

```
               8182                                                         8231
T10      A-A---CCAT--T-C--T--C--C--A----T--G--G---G-G-C---
BE98     A-AA-TCCAT-AT-C--T--C--C--A--T----G----G---TGC---

GB48     AGA----------------T-G--C------T--T----C-G--T--C---GC---
GB116    AGA----------------T-G--C------T--T----C-G----C--TGC---
GB215    AGA--------T-------G--C-A------T--T----C-G----C--TGC---
GB358    AGA----------------T-G--C------T--T----C-G----C---GC---
GB809    A----T-------------G--T--C--T-------C-------C---GCC---
CAM600   A------------------G--T--C--T-------------G----GC---
G22      A------------------G----T-------T-----------------GC---
GB549    A-A-GT--------G----G----T----A-----------C----C---
GB438    A-A--T--------T----G--A--C--T------------------TGCC---
CAR4/1205 A----T--------------G--C--C--N----C-G--T--C--TGC---
CAR1/501 A-A-T---------------G--C--C--T---------------T-CC---
EG-13    AGA------T
EG-19    A-A---A----T
BE95     -G----------GC-C--G--------T----TC-T--G-CC-----C--
BE96     -G----A-----GC-C--G--------T----TCAT--G-CC-----C--
CHR18    --------------GC-C--G--------T--T--TC-T--G-CC--T--C--
CHR19    --------------GC-C--G--------T-TTAC--G--G-CC--T--C--
```

Figure 1 - Continued 12

```
             8232                                                        8271
        AAGCGCGGGGGTCCAGGAGGACGCGGCGAGCCTGAGAGCC
HCV-1  1a
HCV-J  1b   G--T----AAC--------------T----GC---AC-----
BE90   1b   --------AAC----A-----------------AC---T-
HC-J6  2a   G----CA---AC-G--------A-CG--A-----------
HC-J8  2b   G---CAA--TAA-G--------A-CGA-A---------T
NE91   2b   G---CA---TAA-G--------A-CGA-A---------T
NE92   2d   G--TCA---AC-G-----------A-CG--A---AC----
CHR20  3a   G--T-AT--C---G--C----TAGA--AGC----------
CHR21  3a   G--T-AT--C---G--C----TAGAA-AGC---C------
CHR22  3a   G--T-AT--C---A--T----TAGA--AGC----G-----
T1     3a   G----AT--C---G--T----TAGA--AGC----------
T7     3a   G--T-AT--C---G--C----TAG-A--GC----------
NE93   3a   G--T-AT--C---G--C----TAGA--AGC----------
NZL13  3a   G--T-AT--C---G--T----TAGA--AGC----------
BR33   3a   G--T
BR34   3a   G--T
BR36   3a   G--T
T9     3b   ----TGC--C---G--------AGA--AGCT---C-----
T10    3b   ----TGC--C---G--------AGA--AGCT---C-----
BE98   3c   G--T--A---G-T--------AGA---
```

Figure 1 - Continued 13

| | 8232 | | 8271 |
|---|---|---|---|
| GB48 | 4c | G----AT--C---AG------------AAACGACC---CG----- |
| GB116 | 4c | -----AT--C---AG------------AAACGAGC---CG----- |
| GB215 | 4c | G----AT--C---AG------------AAACGAGC---CG---T- |
| GB358 | 4c | G----AT--C---TG------------AAACGAGC---CG----- |
| GB809 | 4e | G----GT--C---TG------------AA-CGAGC---CG---T- |
| CAM600 | 4e | -----GT--C---G-------------AA-CGAGC---CG---T- |
| G22 | 4f | -----AT--T---G-A-----------CGCCGAGC---CG---T- |
| GB549 | 4g | G----GC--C---AG------------T--AAGAGC---CC---- |
| GB438 | 4h | -----GT--C---GG------------CCGAGC---CC---- |
| CAR4/1205 | 4i | G----ATT--CA-AG-C----------AA-CAAGC---CC-NA-T |
| CAR1/501 | 4j | G----C---T--GG-------------TC-CANA-C--NNC--C-N |
| BE95 | 5a | G----CA---ACA--C-----------T-AA---A---------- |
| BE96 | 5a | G----CA---ACA--C-----------T-AA---A---------- |
| CHR18 | 5a | G----CA---ACG--C-----------T-AA----A--------- |
| CHR19 | 5a | G----CAA--ACG--C-----------T-AA---T-------T- |

Figure 2

|  | SEQ ID | 2645 STVTESDIRTEEAIYQCCDLDPQARVAIKSLTERLYVGGPLTNSRGENCG 2694 |
|---|---|---|
| HCV-1 1a |  |  |
| HCV-J 1b |  | ----N-------S------A-E--Q-R--------------K-Q---- |
| BE90 1b | 214 | ----N---V--S------A-E--Q-------I--------K-Q---- |
| 2TY4 1c |  | ------------H-D------N-----------------K------ |
| 4TY4 1c |  | ------------H-D--A---N----------------K------ |
| HC-J6 2a |  | ----R-------S--RA-S-PEE-HT--H---------MF--K-QT-- |
| HC-J8 2b |  | ----R-------S--A-S-PQE--TV-H---------M---K-QS-- |
| BE90 2b | 216 | ----R-------S--A-S-PQE--TV-H---------MI--K-QS-- |
| EB12 2b |  | ------------A-S-PQE--TV-H---------M---K-QS-- |
| ARG8 2c |  | ------------S-S-PEE--T--H---------M---K-QS-- |
| I10 2c |  | ------------LS-S-PEE--T--H---------M---K-QS-- |
| T983 2c |  | ------------A-S-PQE--T--H---------M---K-QS-- |
| NE92 2d | 146 | ----R-------S--LA-S-PE---T--H---------ML--K-QT-- |
| CHR20 3a |  | ----Q---V--E------N-E-E--KV-S--------C---MF--K-AQ-- |
| CHR21 3a |  | ----Q---V--E------N-E-E--KV-S--------C---MF--K-AQ-- |
| CHR22 3a |  | ----Q---V--E------N-E-E--KV-S--------C---MF--K-AQ-- |
| T1 3a |  | ----Q---V--E------N-E-E--KV-S--------C---MF--K-AQ-- |
| T7 3a |  | ----Q---V--E------N-E-E--RV-S--------C---MF--K-AQ-- |
| NE93 3a | 218 | ----Q---V--E------N-E-E--KV-S--------C---MY--K-VQ-- |
| NZL13 3a |  | N---Q---V--E------N-E-E--KV-S--------C---MF--K-AQ-- |
| EB1 3a |  | ----------------------N-E-E--KV-S--------C---MF--K-AQ-- |
| EB2 3a |  | ------------------N-E-E--KV-S--------C---MF--K-AQ-- |
| EB3 3a |  | ------------------N-E-E--KV-S--------C---MF--K-AQ-- |
| EB7 3a |  | ------------------N-E-E--KV-S--------C---MF--K-AQ-- |
| BR33 3a | 10,12 | ----------------E-E--K--SA---------C---MF--K-AQ-- |
| BR34 3a | 2,4 | ----H-------E-------E-E--K--SA---------C---MF--K-AQ-- |
| BR36 3a | 6,8 | ----------------E-E--K--SA---------C---MF--K-AQ-- |
| T9 3b |  | ------------------------------------I----MY--K-LQ-- |
| T10 3b |  | ----Q-------E-------------------------I----MY--K-LQ-- |
| BE98 3c | 150 | ------------A---KDE--RV-T-----------C----MF--K-QH-- |

Figure 2 - Continued 1

| | | | 2645 | | | | 2694 |
|---|---|---|---|---|---|---|---|
| EG13 | 4a | | | | V----- | N-E-E--K--TA----- | -----MH--K-DL-- |
| EG19 | 4a | | | | V----- | S-ELE--KV-TA----- | -----MI--K-DL-- |
| GB48 | 4c | 107 | -----K--- | -V--EV----- | -----E-E--K--TA----- | -----MH--K-DL-- |
| GB116 | 4c | 109 | -----K--- | -V--EV----- | -----E-E--R--TA----- | -----MH----DL-- |
| GB215 | 4c | 111 | -----K--- | -V--EV----- | -----E-E--KV-TA----- | -----MI--K-DL-- |
| GB358 | 4c | 113 | -----K--- | -V--EV----- | -----E-E--K--TA----- | -----MH--K-DL-- |
| GB809 | 4c | 117 | -----K--- | -V--EV----- | -----E-E--KV-AA----- | -----MI--K-DL-- |
| CAM600 | 4e | 202 | -----R--- | -KV-EV----- | -----E-E--KV-TA----- | -----MI--K-DL-- |
| CAMG22 | 4f | 204 | -----R--- | -V--EV----- | -----E-E--KV-SA----- | -----MY--K-DL-- |
| GB549 | 4g | 115 | -----R--- | -V--EV----- | -----E-ET-KV-SA----- | -----MI----DL-- |
| GB438 | 4h | 208 | -----R--- | -V--E------ | -----E-E--KV-SA---K- | -----MY--K-DL-- |
| CAR4/1205 | 4i | 210 | P-----R--- | -X-V-EV----- | -N-EXDX-KV-NA----- | -----MI--K-DL-- |
| CAR1/501 | 4j | 212 | ---X-R--- | GEV----- | -----E-E--KV-TA----- | -----MF--K-DL-- |
| BE95 | 5a | 160 | -----H--M- | -----S----- | -----S----Q-E---A--R----Q---C---MY--K-QQ-- |
| BE96 | 5a | 162 | --A--H--L- | -----S----- | -----S----SQ-D--A--R----Q--FC---MY--K-QQ-- |
| CHR18 | 5a | | ---H--M- | -----S----- | -----SLY-Q-E------R----Q----C---MY--K-QQ-- |
| CHR19 | 5a | | ---H--M- | -----S----- | -----SLY-Q-E---A--R----Q----C---MY--K-QQ-- |

Figure 2 - Continued 2

```
                2695                                              2744
         YRRCRASGVLTTSCGNTLTCYIKARAACRAAGLQDCTMLVCGDDLVVICE
HCV-1  1a  ------------------L--T-----K-------N--------------
HCV-J  1b  ------------------L--S-----K----------------------
BE90   1b  ----------------------------R---------------------
2TY4   1c  -----------------------L--------------------------
4TY4   1c  -----------------------L--------------------------
HC-J6  2a  ---------M---I---V--L---K----IIAP---------------S-
HC-J8  2b  ---F---M---M-------L---K----IV-PV---------------S-
NE91   2b  ---F---M---M-------L---K----IV-PV---------------S-
EB12   2b  ---F---M---M-------L---K----IV-PV-----------------
ARG8   2c  ---------M---------V-------N----IVAP--------------
I10    2c  ---A-----M---------V-------N----IVAP--------------
T983   2c  ---V-----M-------V-K---N-V--IVAS------------------
NE92   2d  ---F---M---I---V---V---Q---K----IIAP------------S-
CHR20  3a  ---------P---F---I---------SK---RNPDF-----------VA-
CHR21  3a  ---------P---F---I---------AK---RTPDF-----------VA-
CHR22  3a  ---------P---F---I---------AE---RNPDF-----------VA-
T1     3a  ---------P---F---I------T--AK---RNPDF-----------VA-
T7     3a  ---------P---F---I------T--A----RNPDF-----------VA-
NE93   3a  ---------P---F---I------TT-AK---RNPDF-----------VA-
NZL13  3a  ---------P---F---I------T--AK--N-RNPDF----------VA-
EB1    3a  ---------P---F---I------T--E----RNPD------------VA-
EB2    3a  ---------P---F---I------T--E----RNPD------------VA-
EB3    3a  ---------P---F---I------T--K----RNPD------------VA-
EB7    3a  ---------P---F---I------T--K----RNPD------------VA-
BR33   3a  ---------P---F---I------T--AK---RNPDF-----------VA-
BR34   3a  ---------P---F---I------T--A----RNPDF-----------VA-
BR36   3a  ---------P---F---I------T--AK---RSPDF-----------VA-
T9     3b  ---------P---F---I------T--S----K-PSF-----------VS-
T10    3b  ---------P---F---I------T--S----K-PSF-----------VS-
BE98   3c  ---------P---F---L------K--TK---IKNPSF------------A-
```

SUBSTITUTE SHEET (RULE 26)

Figure 2 - Continued 3

```
                  2695                                              2744
GB48      4c    -------Y---F------L--S--IK----R-----------------A-
GB116     4c    -------Y---F------L--S---I----R-----------------A-
GB215     4c    -------Y---F------L--S---I--S-R---------Y-------A-
GB358     4c    -------Y---F------L--S---I----R-----------------A-
GB809     4c    -------Y---F--M---L--S---I----K-----------------A-
CAM600    4e    -------Y---F------L--S---I----K-----------------A-
CAMG22    4e    -------Y---F------L--T--TK----K-----------------A-
GB549     4f    Q------Y---F------FL--T---V---T-----KG-S--------A-
GB438     4g    L------Y---F--V---L--V---T----K-----------------A-
CAR4/1205 4h    I------Y---F--V---L--T---T----K-----------------A-
CAR1/501  4i    Q------Y---F------L--T---T----K-----------------A-
EG13      4j    -------F---F------L--T---T----R-----------------S-
EG19      4k    -------F---F------L--T---I----R-----------------
          4k    -------Y---F------L--T---I----K-S---------------

BE95      5a    -------F---M--M---L--S----R-R---L---------A------
BE96      5a    -------F---M--M---L--S---T--R-Y-L------H-A------
CHR18     5a    -------F---M--M---L--S---K----L-----------A------
CHR19     5a    -------F---M--M---S------K----L-------VT--A------
```

Figure 2 - Continued 4

```
                      2745            2757
                      SAGVQEDAASLRA
HCV-1    1a           -------------
HCV-J    1b           ---T-----A---
BE90     1b           ---T--------V

HC-J6    2a           -Q-TE--ERN---
HC-J8    2b           -Q-NE--ERN---
NE91     2b           -Q-NE--ERN---
NE92     2d           -Q-TE--ERN---

CHR20    3a           -D--D--R-A---
CHR21    3a           -D--D--RTA---
CHR22    3a           -D--N--R-A-G-
T1       3a           -D--D--R-A---
T7       3a           -D--D--RTA---
NE93     3a           -D--D--R-A---
NZL13    3a           -D--D--R-A---
BR33     3a
BR34     3a
BR36     3a
T9       3b           -C--E--R-A---
T10      3b           -C--E--R-A---
BE98     3c           ---ID--R-
```

Figure 2 – Continued 5

| | | 2745 | 2757 |
|---|---|---|---|
| GB48 | 4c | -D--E---KRP-G- | |
| GB116 | 4c | -D--E---KRA-G- | |
| GB215 | 4c | -D--E---KRA-GV | |
| GB358 | 4c | -D--E---KRA-G- | |
| GB809 | 4e | -G--E---KRA-G- | |
| CAM600 | 4e | -G--E---KRA-G- | |
| G22 | 4f | -D--E---RRA-G- | |
| GB549 | 4g | -G--E---RA--- | |
| GB438 | 4h | -G--E---RA--- | |
| CAR4/1205 | 4i | -I-ID--KQA--T | |
| CAR1/501 | 4j | ----E--PXTX-P | |
| BE95 | 5a | -Q-TH--E----- | |
| BE96 | 5a | -Q-TH--E-N--- | |
| CHR18 | 5a | -Q-TH--K----- | |
| CHR19 | 5a | -Q-TH--E-C--V | |

```
         101
HCV-1   1a  TTTACTTGTTGCCGCCGCCAGGGGCCCTAGATTGGGTGTGCGCGACGAGA
HCV-J   1b  -----C-------------------C--G-------------T---T--G
HC-J6   2a  -A-------------------C---C--G-------------A--A--G
HC-J8   2b  -A-------C-----------C---C--G-------------A--A--G
NE92    2d  -A-------------------C---CC-G-------------------G
EB1     3a  -A---G---------------A---AC-------------T-----C-T
NZL1    3a  -A---G---------------A---AC-------------------C-T
HCV-TR  3b  -A--TG--C-----T------A---AC-------------AGTAC-T
BE98    3c  -G--C-A--A-----------CCAG---------------T-AGT-C-C
GB358   4c  ---------------------C--G-----------------T--G
GB809   4e  -----------------------G-------------------TC-G
CAM600  4e  -----------------------C-G-----------------TC-G
GB724   4?  -----------------------CC-G----------------TC-G
EG-29   4?  ------------------------GA-----------------TC-G
BE95    5a  ------------------------GA-----------------TC-G

151
HCV-1   1a  AAGACTTCCGAGCGGTCGCAACCTCGAGGTAGACGTCAGCCTATCCCCAA
HCV-J   1b  ------------------------T--A--G--A--A---------------
HC-J6   2a  ----G---------C--G--A---T--A--G--C---------C-----T--
HC-J8   2b  ----T------A--C--G--T--AC-----C--------------G---
NE92    2d  --A-----------C--G--A--T--G--G--C-----------------
EB1     3a  --A---T--A--------A--G-----C--AC------A--------------
NZL1    3a  --A---T--A--------A--G-----C--AC------A--------------
HCV-TR  3b  --A---T--A--------A--G-----C--AC------A--------------
BE98    3c  ----G--------------G-----CAAACAG---C-T----------
GB358   4c  ----G---------------CA----G--C--A--C----------
GB809   4e  ----G---------------T--G-----------------C---A-------
CAM600  4e  ----G---------------T--G--G--C--A-------------
GB809   4e  ----G---------------T--G--C--A--------------
GB724   4?  ----G---------------T--C--AC--------A--------------
EG-29   4?  ----G---------------T--G-----C--A--------------
BE95    5a  ----G--A------------C--T--AC-G-------------------A---
```

Figure 3 - Continued 2

```
             201
HCV-1    GGCTCGTCGGCCCGAGGGCAGGACCTGGGCTCAGCCCGGGTACCCTGGC
HCV-J    -------C----------------T------------------------
HC-J6    --A---G--CT--ACT----AAT-----GAA-A---A--A--------
HC-J8    --A---G--CT--ACC----A-T-----GAA-----A--A--T-----
NE92     A-A---G--C---ACT----A-T-----GAA-A---A--A--------
EB1      A-A---G--C---ACT----A-T-----GAA-A---A--A--------
3a       ---G-------AG---A-----T--------------------G----
NZL1     ---G-------AG---A---C-T--------------------------
HCV-TR   --------CTC-G-------C-T--------------------------
BE98     ---G--C--AA---------T----------------------------
GB358    --A---AT-T----A---T---------------------------A--
GB809    --G--C--AT---------AT------G----------T----------
CAM600   --G--C--AA---------AT------G----------T----------
GB724    --G--C---T-----------T------G----------------C---
EG-29    --G------AT--------A--T------G--AG---------------
BE95     --G--C-A----AC----C--T------A--A--A--A--T--A-----
                                 G----A----------------

251
HCV-1    CCCCTTCTATGGCAATGAGGGCTGCGGGTGGGCGGGATGGCTCCTGTCTCCC
HCV-J    -------------------C------TATG----A-----------A----
HC-J6    ----A--C--G------C---G-----ACT--C----A---------C---
HC-J8    ----G--C--A--C-------G-----T---C---------T-----C---
NE92     ----G--C--G----------G-----T--------CT--A--G---C---
EB1      ----------------T-C---------C-------A--G-------C---
3a       ------------T--C---------------------A--G------C--A
NZL1     ------------T--C---------------------A--G------C--A
HCV-TR   -----------C--G--A------T--T---T--A-----------C--A
BE98     ----A---------G--------------------A--G------T-C---
GB358    ----------------------------T------A--G-----------G
GB809    -T--T--C--T----T----T--T--T--------A--G------C--T
GB809    ----T--C-----------------T--------------G----C--T
CAM600   ----T--C-----------------T--------------------C--T
GB724    ------------------------------------------------T
EG-29    -T--T--C--T-----------------------A--G----G-C--C--T
BE95     ----T--C-C-----------CT-------------A--G----G-C--C--T
```

Figure 3 - Continued 3

```
        301
HCV-1   CGTGGCTCTCGGGCCTAGCTGGGGCCCCACAGACCCCCGGCGTAGGTCGCG
HCV-J   ---------------------T----------------------------
HC-J6   --A--T--C--T---CTCT-------------AT------A-------C--
HC-J8   --C--G-----T----CT--------------C-------A--A--A---
NE92    --A--G-----C--GTCA--------------A-T-----AC----A---
HC-J8   --A--G-----C--GTCA--------A-T---A-T-----AC---A----
EB1     --C-----T--ATCT-----------------A-AT-----A---C--
3a      --C-----T--ATC------------------A-AT---------C--
NZL1    ---T-----T--T-------------------A-AT----G-----C--
HCV-TR  --C-----C--GTCG-----------------A-AT-----C---A
BE98    --C--G-----GTCT-----------------T-AT--T-----G---C--
GB809   --C--N-----N-GTCT---------------AT--T-----N-G--A--C
CAM600  --C-----ATCT--------------------A-AT--T-----G--A--
GB724   -----------AT-------------------AT----------G--A--
BE95    --A-----------------------------AT-----------A-AA--

351
HCV-1   CAATTTGGGTAAGGTCATCGATACCCTTACGTGCGGCTTCGCCGACCTCA
HCV-J   T----------------------------A-------------------
HC-J6   ---CG---------------------------------T----------
HC-J8   -------C-GA----------A----------T--T--T----------
NE92    ---C-------------------------------T----T---------
HC-J8   -------------------------------------T----T-------
EB1     --------A----------------------C----G-------------
3a      --------A-----------------------A------A---------
NZL1    ---C--T---------------------------A---T-A---------
HCV-TR  ---CC-----------------------------A---A-----------
GB809   ---C-------------------------------A---A---------
CAM600  ---C------------------------------G---------------
GB724   -----------------------------------G-------------
BE95    T------------------------------------A--------T--
```

Figure 3 - Continued 4

```
        401
HCV-1   TGGGGTACATACCGCTCGTCGGCGCCCCTCTTGGAGGCGCTGCCAGGGCC
HCV-J   ----------------T------T-------C--A--G------------
HC-J6   ------------C--TG-----A--------G--C--C-----TC----A--T
HC-J8   ------------C--TG-----T--------------GG-------TC----A--T
NE92    ------------C--TG------------------AG----T--T-TC----A--T
NZL1    ------------C-----------------T---G-A------TC--A--A---
HCV-TR  -----------T------------------------G-A------TC--A--A---
GB809   ---------A--C-----T--A---------G-G-G--T-----TC--A------
CAM600  ---------A--C-----T--A--------CG-G-G--T-----TC----------
GB724   ---------A--C----------G------CG-G-C--G-----TC----------
BE95    ---------A--C------------------CA----G------TC--A-----T
5a      ------T--C---------A----G----CA----G------TC--A-----T

451
HCV-1   CTGGCGCATGGCGTCCGGGTTCTGGAAGACGGGCGTGAACTATGCAACAG
HCV-J   ----A-----------T-------G----------G--T--T-T-----
HC-J6   ---C-----------GA-A--C----G----------G--T--T-----
HC-J8   ----A--C--T----TA---C----G------GA-A--T--C------
NE92    ---C-----------GA-A------------------GA-A---------
NZL1    ---C-----------GA----CC--T-----------GA-A--T-TC---
NZL1    ---C--T-------T--GA---CA--T-GG---A---------------
HCV-TR  ---C--T-----------GA---CA--T-G-------GA-C---C-----
GB809   ---A--C--T----T--TA---C-G------------GA-C--T------
CAM600  ---A-----T----T--TA---C-G------------GA-T----N-G---
GB724   ---------------A---C-G--------G------GA-T----N-G---
BE95    --C--A--C---T---GA--------C--T--G-----G--A--------
```

Figure 4

```
                            379                                                              428
           SEQ ID NO        ACGTGCGGGCTTCGCCCGACCTCATGGGGTACATACCGCTCGTCGGCGCCC
HCV-1      1a               --------------------------------------------------
HCVEC1     1a               --------------------------------------------------
HCVHCT18   1a               ----------------T---------------------------------
HCVHCT23   1a               --------------------------------------------T-----
HCVHCT27   1a               ----------------T---------------------------------
HCVTH      1a               -A------------------------T-----------------------
HCV-J      1b               --------------------------------------------T-----

HC-J6      2a               ---T--T--T----------------------C--TG------A------
HC-J8      2b               ---T--T--T----------------------C--TG------T------
NE92       2d               ---T--T--T----------------------C--TG-------------

HD10       3a               ----------------------------------T---------T-----
BR33       3a               ----------------------------------T---------T-----
BR36       3a               ----------------------------------T---------T-----
NZL15      3a               ----------------------------------C---------------
HCV-TR     3b               ---T--A---------------------------T---------------

GB809_4    4a               --C-----------------------A-------C----------G----
GB116      4c               --T-------T---------------A-------C---------A-----
GB215      4c               --T-------T---------------A-------C---------A-----
GB358      4c               --T-------T---------------A-------C---------A-----
GB809_2    4c               --A-----------------------A-------C------T--A-----
CAM600     4e               --A-----------------------A-------C------T--A-----
CAMG22     4e               --A-----------------------A-------C---------A-----
CAMG27     4f               ----------T-C-------------A-------C------T--G-----
CAMG27     4f               ------------------------- A-------C---------A-----
GB549      4g               --------------G-----------A-------C---------G-----
GB438      4h               --C-----------------------A-------C---------A-----
CAR4/1205  4i               --C-----------------------A-------C---------------
```

Figure 4 - Continued 1

| | | | | | | | | | |
|---|---|---|---|---|---|---|---|---|---|
| CAR4/901 | 4? | 181 | G--------- | ------- | ---T---- | ----A--- | ---C---- | --A----- | ------- |
| BE95 | 5a | 143 | -----A---- | ------- | ---T---- | -------- | ---C---- | --A----- | --G---- |
| BE100 | 5a | 195 | -----A---- | ------- | -------- | -G------ | ---C---- | --A----- | --G---- |

```
CAR4/901   4?   CG-G--T----TC-----A---------C--T--TA---C-G----G-
BE95       5a   CG----G----TC--A----T--C--A--C--T--GA----C--T--G-
BE100      5a   CG----G----TC--A----T--C--A--T--GA----T--G-
```

Figure 4 : Continued 4

```
                479                                                      528
         ACGGGCGTGAACTATGCAACAGGGAACCTTCCTGGTVGTGCTCTTTCTCTATC
HCV-1 1a  ----------------------------------------------------
HCVEC1 1a ----------------------------------------------------
HCVHCT18 1a ----------------------------------------------------
HCVHCT23 1a ---------------------------------------C--T--------
HCVHCT27 1a ----------------------------------------------C-----
HCVTH  1a ----------------------------------------------------
HCV-J  1b ----------------------T--G--C-----------------------

HC-J6  2a ---G--T--T-------------T-A--C-----------C--T--------
HC-J8  2b ---GA-A--T--C----------TT-A--C----------C--T--------
NE92   2d ---GA-A-----------------T-G--C----------C--T--------

HD10   3a ---GA-A--T-TC----------TT-G--C----------C--T--------
BR33   3a ---GA-A---TC-----------TT-G--C----------C--T--------
BR36   3a ---GA-A--T-TC----------TT-G--C----------C--T--------
NZL15  3a ---GA-A--T-TC-----------T-G--C----------C--T-------T
HCV-TR 3b ---A---------------------T--------------C--T-------T

GB809_4 4a ---GA-T---------G--------T----C---------C--T--------
GB116   4c ---TA-T--T---------------T--C-C---------------T-----
GB215   4c ---A-C--T----------------T--C-C---------------T-----
GB358   4c ---GA-C--T--C------G-----T--C-C---------C--T--------
GB809_2 4c ---GA-C--------------------C-C----------C--T--------
CAM600  4e ---GA-C--T---------------T--C-C---------C--T--------

CAMG22 4f ---GA-T------------------T--C-----------C--T--------
CAMG27 4f ---GA-A-----------------T---C-----------C--T--------
GB549  4g ---GA-T------------------T--C-----------C--T--------
GB438  4h ---GA-C--T--C-----------T---C-----------C--T--------
```

Figure 4 - Continued 5

```
CAR4/1205  4i  ----GA-C--T-----------------------T-------------
CAR4/901   4?  ----GA-T-----C--------------------T-------------
BE95       5a  ----G--A-----C--------------------TT-A--C-------
BE100      5a  ----G--------T--------------------T--G----------
```

Figure 4 : Continued 6

```
              529                                                          578
HCV-1     1a  TTCCTTCTGGCCCCTGCTCTCTTGCTTGACTGTGCCCGCTTCGGCCTACCA
HCVEC1    1a  -----T--------------------------------------------
HCVHCT18  1a  ---------------------C---------------A------------
HCVHCT23  1a  ------------------A------C---------A--------------
HCVHCT27  1a  --------------T----------C------A-----------------
HCVTH     1a  -------------------------C------------------------
HCV-J     1b  ------------------------TC---------A--------------
HCV-J     1b  -----CT-A--TT---G--------T----CA-C--A----C--T----G-

HC-J6     2a  ---T-G-----------G--C----A-C--CACC--G-TC--C--TGC-G-
HC-J8     2b  --TT-G--T--T--T--G--T----G-C--A---TG--A-TG--T--AGTGG-
S83       2c  ------------------------G-C--A----A----A-TG--T--AGTGG-
                                                               GTGG-
NE92      2d  ---T-AT----------A-----TA-C------G-TC--C-G--TG--

HD10      3a  ----------T--T-----T---------A-TCCAT--A---AG-TAGTCTAG-
BR33      3a  ----------T--T-----T---------A-TCCAT--A---AG-T-GTCTAG-
BR36      3a  ----------T--T-----T---------A-T-CAT--A---AG-TAGTCTAG-
NZL15     3a  ----------T--T-----T---------A-T-CAT--A---AG-CAGTCTAG-
HCV-TR    3b  ---C--C--T--CT-----C-------------TGC-----G--T-G--TAG-
```

Figure 4 - Continued 7

```
              529                                                              578
GB809_4   4a  -----C-----A--T--G---C-C-----C--A--G--A--TG-G--
Z4        4a                                                          G-G----
Z1        4b                                                          GTG----
GB116     4c  -C---CT----A--T--T--G----C-----T---A-C--A---GT-A-
GB215     4c  -A---CT----A--T--T--G----C-----T---A-C-----AT---
GB358     4c  -----CT----A--T--T--G----C-----T---A-C----GT-A-
Z6        4c                                                          GTTA---
Z7        4c                                                          GT-A---
DK13      4d                                                          ---A---
GB809_2   4e  -----CT----A-------T--G----C-C-----T---G-----G-GTTA-
CAM600    4e  -----CT----G--C--T--G----C-----T---A-A-----GTTA-
G22       4e  -----------A-------T--G----C-----C-----TGTG---
G27       4f  -----------A-------T--G----C-----C---A--TGTG---
GB549     4f  -----------A-------T--G----C-----C-----GC-G---
GB438     4g  ----------A--A-----T--G-----------G---T--TC-G---
CAR4/1205 4h  -----CT---TA--T-----GC---C-A-----C---A---AT----
CAR4/901  4i  -C---T-AA--T-------G-----C-----T---C-----TC-G---
          4?  -N---------A-------T--G-----------G---C-----TC-G---

BE95      5a  --TA----T--T---T-----G--TC-----C-----G---T--AGTT-C
BE100     5a  ---A----T--A---T-----G----C-----C-----G---T--AGTT-C
SA4       5a                                                          GTT-C
```

Figure 4 - Continued 8

```
                  579                                                           62
HCV-1      1a     AGTGCGCAACTCCACGGGGCTTTACCACGTCACCAATGATTGCCCTAACT
HCVEC1     1a     ------------------------------T-------------------
HCVHCT18   1a     ------------------------------T------------C------
HCVHCT23   1a     ------------------------------T-------------------
HCVHCT27   1a     ---A---------T----CA----------T---------------T---
HCVTH      1a     ---------------------------------------C-----C----
HCV-J      1b     G--------GTGT-C---A-A----T------G---C---T-C------

HC-J6      2a     ---AAG----AT--GTACCGGC---ATG--G----C---C----A-C--TG
HC-J8      2b     ---CA-G---ATT-GTTCTAGC---T----C--T-------T-A---A
S83        2c     G--CAAGG--A--GGC-ACTCC---ATGCCG--C------T-C------
NE92       2d     G--CAAG---A---GCA-CTC----ATG--A------C---AG---A

ID10       3a     GTG---G---A-GT-T---C--C--TGT-C-T----C---C--TT-C--TA
BR33       3a     GTG---G---TA-GT-T---C--C--TGT-C-T----C---C--TT-C--TA
BR36       3a     GTG---G---TA-GT-T---C--C--TGT-C-T----C---C--TT-C--TA
NZL15      3a     GTG---G---TA-GT-T---C--C--GT-C-T----C---C--TT-C--TA
HCV-TR     3b     GTACACG---A-GT-T---C--A--TGTGC-T----C---C---T----TG
```

Figure 4 - Continued 9

|  |  | 579 |  | 628 |
|---|---|---|---|---|
| GB809_4 | 4a | CTAC--G--TG--TT----CA-C---T----A-------- | ----C--T--G--T- |
| Z4 | 4a | CTAC--G--TG--TT----CA-C---T----A-------- | ----T--G--T- |
| Z1 | 4b | CTAC--G--TG--TT----CG-C---T--T---------- | -------A |
| GB116 | 4c | CTAT-----G--T-----CG-C---T--TA---------- | ----C---G--T- |
| GB215 | 4c | CTAT-----TG--T-----CG-C---T------------- | ----C---G----- |
| GB358 | 4c | CTAT-----TG--T-----CA-C---T----A-------- | ----C---G----- |
| Z6 | 4c | CTAT-----TG--T-----CG-C---T------------C | ----C---G----- |
| Z7 | 4c | CTAT-----TG--T-----CG-C---T----A-------C | ----C---G----- |
| DK13 | 4d | CTAT-A----AG--T-----TG-C---T----------- | ----C---G----- |
| GB809_2 | 4e | CTAT-----TG--TT----CG----T----A-------- | ----C---G--TG |
| CAM600 | 4e | CTAT-----TG--TT----CA----T----A-------- | ----C---G--TG |
| G22 | 4f | TTAT-----A--T-----CA-C-----C----------- | ----C---G----- |
| G27 | 4f | TTAT-A----A--T-----CA-C---T----A----T--- | ----C---G----- |
| GB549 | 4g | CTAC--G---AT-T-----CA----T-------------- | ----C---G----- |
| GB438 | 4h | CTAC--G--TG-AT-----CA-C---T------------- | -------G----- |
| CAR4/1205 | 4i | CTAT-----TG--TT---ACGG---TT-TA---------- | -------G----- |
| CAR4/901 | 4? | CTAT-----G--TGT-T----CA-C---T-------- | ----G--T- |
| BE95 | 5a | CTAC--A--TG--T--T----A-----T--T--------- | -------A----- |
| BE100 | 5a | CTAC--A--TG--T--T----A-C---T--T--------- | -------A----- |
| SA4 | 5a | CTAC--A----G--T--T----G-----T--T-------- | -------A----- |

Figure 4 - Continued 10

|  |  | 629 | | | | | | | | | 678 |
|---|---|---|---|---|---|---|---|---|---|---|---|
| HCV-1 | 1a | CGAGTATTGTGTACGAGAGCGGCCGATGCCATCCTGCACACTCCGGGGTGC |
| HCVEC1 | 1a | ----C--------------------------------------------- |
| HCVHCT18 | 1a | ---------A-------A-----C-------------------------T |
| HCVHCT23 | 1a | -----------------------C---------G---------------T |
| HCVHCT27 | 1a | -----------------A---------CA----A--T-------------T |
| HCVTH | 1a | ----------------------T-----------G---------------T |
| HCV-J | 1b | -A-------------T---A-G--CATG---A-------C---------- |
| HC-J6 | 2a | AT--C---ACC-GGC-ACTCCAG-C--TG-----C--GTC--C------T |
| HC-J8 | 2b | AC--C---CACC-GGC--CTCA-T--C--AG-T--C--TCT---T--A--- |
| S83 | 2c | -T-----C--T-GGC--CTT-AA-GA--AG-G---T---T---A------ |
| NE92 | 2d | GT---C--C-GGC--CTCAGG-----TG-T--T--GTC--C------T |
| HD10 | 3a | GC----------------T----C-AT--C-TT--T------A--C--C-- |
| BR33 | 3a | GT----------------T----C-AT--C-TT--T------G-G--C--C--T |
| BR36 | 3a | GC---------------------C-AT--C-TT--T------A--C--C-- |
| NZL15 | 3a | GC----------------T----C-AT---T---T------A--C--C--T |
| HCV-TR | 3b | G---C-----------------C-AA----TG---T----TTA--C--A-- |

Figure 4 - Continued 11

| | | 629 | | | | | | | | | | 678 |
|---|---|---|---|---|---|---|---|---|---|---|---|---|
| GB809_4 | 4a | -C- | -CG- | A- | -C- | -T- | -AA- | T- | A- | C- | CCAT- | -AT- | --- | --TTG- | --- | --- | --- | --- |
| Z4 | 4a | -C- | --- | A- | -C- | -T- | --- | -A- | T- | A- | C- | -CA- | --- | -A- | --TTG- | --- | --- | --- |
| Z1 | 4b | --- | --- | --- | --- | --- | --- | -A- | --- | AGC- | CCA- | --- | -A- | --TTG- | -A- | --- | -T |
| GB116 | 4c | -C- | -C- | A- | --- | --- | --- | T- | A- | T- | CCA- | --- | -A- | --CTC- | -T- | --- | --- |
| GB215 | 4c | -C- | --- | A- | --- | --- | --- | C- | A- | C- | CCA- | --- | -A- | --CT- | -A- | --- | --- |
| GB358 | 4c | --- | --- | --- | --- | --- | --- | A- | C- | AGC- | CCA- | --- | -A- | --CTC- | -A- | --- | -T |
| Z6 | 4c | -C- | --- | A- | --- | --- | -T- | C- | A- | AAC- | CCAG- | -T- | -A- | --CTC- | -A- | --- | --- |
| Z7 | 4c | --- | --- | --- | --- | --- | -T- | C- | AAC- | CCA- | --- | --- | -A- | --CTC- | -A- | --- | --- |
| DK13 | 4d | -C- | -AA- | --- | -T- | C- | AA- | C- | ATT- | CCA- | --- | -T- | -A- | --CTC- | -A- | --- | --- |
| GB809_2 | 4e | -C- | --- | A- | --- | --- | --- | -A- | C- | A- | CA- | --- | -T- | -A- | --CTC- | --- | -A- | --- |
| CAM600 | 4e | --- | --- | --- | --- | --- | --- | -A- | C- | AAA- | CA- | --- | -T- | -A- | --CTC- | --- | -A- | --- |
| G22 | 4e | -A- | -C- | A- | --- | C- | TT- | A- | T- | C- | CA- | --- | T- | --- | --CT- | --- | -A- | -A- | --- |
| G27 | 4f | T- | -C- | A- | --- | C- | TT- | A- | AGC- | CA- | --- | -T- | --- | TCT- | --- | -A- | -A- | --- |
| GB549 | 4f | T- | -C- | A- | --- | --- | -T- | A- | T- | A- | C- | CAT- | --- | -A- | TCTA- | -A- | --- | -T |
| GB438 | 4g | -T- | --- | A- | --- | --- | -T- | A- | C- | A- | C- | CA- | --- | -A- | CTA- | --- | -C- | --- | -T |
| CAR4/1205 | 4h | -C- | --- | --- | --- | --- | -T- | A- | C- | AGA- | CCA- | --- | -T- | CT- | --- | --- | --- |
| CAR4/901 | 4i | -T- | -C- | -A- | --- | --- | -T- | A- | C- | ATC- | CCA- | --- | -A- | --- | -TTA- | -A- | --- | --- |
| | 4? | -C- | -C- | -A- | --- | --- | --- | --- | --- | --- | --- | --- | --- | --- |
| BE95 | 5a | -TTCC- | -A- | -C- | --- | -T- | --- | A- | ATA- | CCTG- | --- | -A- | --- | -G- | A- | --T- | -T- | --- |
| BE100 | 5a | -TTCC- | -A- | -C- | --- | -T- | --- | A- | AT- | -CTG- | --- | -A- | --- | -G- | A- | --T- | -C- | --- |
| SA4 | 5a | -TTCC- | -A- | --- | -T- | --- | --- | T- | ATA- | CCTG- | --- | -T- | --- | TG- | A- | --T- | -T- | --- |

Figure 4 - Continued 12

```
              679                                                              728
HCV-1      1a GTCCCTTGCGTTCGTGAGGGCAACGCCCTCGAGGTGTTGGGTGGCGATGAC
HCVEC1     1a ------------------------AC-------T----------------
HCVHCT18   1a ------------------------AC-------T--------G-------
HCVHCT23   1a ------------------C----AT-------T--------G-------
HCVHCT27   1a ------------------C------------A------------------
HCVTH      1a ------------------------------AA-------C--G-AG----
HCV-J      1b --G--C-----C--G---A-T--TTT---CC-T--C----A----C-C--

HC-J6      2a ----G-----AGAAA-T---G--TA-A---TC----C----A-AC--G-CT-
HC-J8      2b ----A--T-AGAA---TAATGG-A---T-CAT--C----A-ACAAG-A---
S83        2c ----T-AG--ACC-C-----T---TC-A-------C---C--G-TG-
NE92       2d ----T-AGGAGA---------ATA--CC-C------A-AC--G-TT-

HD10       3a --A-----T----AG--C---T--TA-A--TGC---C----ACCC-AG---
BR33       3a --A-----T--C-AG--C------TA-G--T-CA---C----ACCC-AG-A-
BR36       3a A-A-----T--C-AG--C------TA-A--C-C----C----ACCC-AG---
NZL15      3a --A-----T--C-AG--C------TA-A--T-C----C----ACCC-AG---
HCV-TR     3b --G--C----CACAACC--------CAA-ATCA---C----ACAA--G-CT-
```

Figure 4 - Continued 13

| | | 679 | | | | | | | 728 |
|---|---|---|---|---|---|---|---|---|---|
| GB809_4 | 4a | --A--C----- | ----- | --GA-G-CC--G- | ----TG--TC-T--C- | ---AC-C--G-A- | ----- |
| Z4 | 4a | --A--C--T-- | --GATGACT- | -G----A-A- | --C-T---C-T--C- | ---AC-C--G- | ----- |
| Z1 | 4b | ----C--T--G | ---GAC--AG | ---TA-T--TC-C--C- | -----C-CT- | ----- | ----- |
| GB116 | 4c | T-A--C--T- | ---GA-G-TT- | -G--TCAG--AC-C--C- | -----CC-T- | ----- | ----- |
| GB215 | 4c | T-A--C--T- | ---GA-G-TT- | -G--TCAG--AC-T--C- | -----CC-CT- | ----- | ----- |
| GB358 | 4c | T-A--C--T- | ---GA-G-TT- | -G--TCAG--AC-C--C- | -----CC-C- | ----- | ----- |
| Z6 | 4c | T-G--C--T- | ---GA-G-TT- | -G--TCAG--AC-C--C- | -----CC-T- | ----- | ----- |
| Z7 | 4c | --A--C--T- | ---GA-G--- | ----CAG--AC-C--C- | -----CC-T- | ----- | ----- |
| DK13 | 4d | --T------- | ---GA-G--A- | -G---AAG--T-CA--C- | ---T-TC-C- | ----- | ----- |
| GB809_2 | 4e | --A--C--T- | --GAAGACC- | -G---CAG----C------ | -----CC-C- | ----- | ----- |
| CAM600 | 4e | --A--C--T- | ---GA-GACT- | -G---CAG----C------ | -----CC-C- | ----- | ----- |
| G22 | 4f | ----T----- | ---AA-AACT- | -G---CAG--TC---C- | ---A--CT- | ----- | ----- |
| G27 | 4f | ----T----- | ---GA-AACT- | -G---CAG--AC-A--C- | ---A-A--CT- | ----- | ----- |
| GB549 | 4g | ----C----- | ---GA-AACC- | -G----A-------C-- | ---C-----TC-TT-A- | ----- | ----- |
| GB438 | 4h | --G--C----- | ---GA-AACT- | -G---T-T----C-T--C- | ---A-TC-TT-A- | ----- | ----- |
| CAR4/1205 | 4i | --G--C--T- | --GAAGACC- | -G---TCAG----C------ | -----TC-C- | ----- | ----- |
| CAR4/901 | 4? | A-A--C----- | ---GA-GACC- | -G----TT----C-C--C- | ---AT-TC-- | ----- | ----- |
| BE95 | 5a | ----G------ | --T--CATGACA--T- | -T-TGAGT--A--C------ | --CCAA--T-- | ----- | ----- |
| BE100 | 5a | ----G------ | --T--CA-GA-A-AT- | -T-TGAGT----- | ---C---- | --CCAA--T-- | ----- |
| SA4 | 5a | ----G------ | --T--CA-GC-A-AT- | -T-T-AGT-A---C------ | --CCAA---C-- | ----- |

Figure 4 - Continued 14

```
              729                                                           778
HCV-1      CCCTACGGTGGCCACCAGGGATGGCAAACTCCCCGGACGCAGCTTCGAC
HCVEC1  1a ---C--------------------------------A-A---------
HCVHCT18 1a ---C--------------C-----------------A-A---------
HCVHCT23 1a ---C--------------------A-----------A-A---------
HCVHCT27 1a ---C--A---------------C------A------------------
HCVTH   1a ---C--------------------C-----------A-A---------
HCV-J   1b T---C----C-C--GG--------A-CA----GCA----A-C---ACAA-A----

HC-J6   2a A---G-AT-------GTGCA-C-GCC-GGCGC--T-A--CA-GGCT-A--GA
HC-J8   2b A---C-AC-------TGTG-AAC-CC--GGTGCG-T-A-TCGTAGC--G---A
S83     2c ---C-ATC-C---TA--TC-ACCTGGCGCT-T-A-T-A-GGC--G---C
NE92    2d G---C-ATA-A--TGTG--CC-ACCTGGTGCG-TTA-C-A-GGC--G--GA

HD10    3a A-----A-------AGT----T-C-T-GG-GCAA--A-CG-TTC-A-A--CA
BR33    3a A-----A-------AGT----T-C-T-GGGGCAA--A-CG-TTC-A-A--CA
BR36    3a A-----A-------AGT--A-T-C-T-GG-GCAA--A-CG-TTC-A-A--CA
NZL15   3a A-----A-------AGT----T-C-T-GG-GCAA-TA-TG-TTC-A-A--CA
HCV-TR  3b AA-G----------GTT----ACCCTGGGCG--GA--A-CG--TC-A-C---A
```

Figure 4 - Continued 15

```
                          729                                                  778
GB809_4    4a    A-----------TG--GTATCCATGG-CGCT--GCTCGA-TCCT-C--G-
Z4         4a    G-----A-----TGT-GCAC-CCCGGGCGCT--GCTTGA-TC-T-C--G-
Z1         4b    ---C--T-----G-GCCCT--CC---CGCA--GTTAGA-TCCA-G--CA
GB116      4c    T--C--C-----GG-GCCTT-C-TTGGTGCT--GCTAGAATCC--C--GA
GB215      4c    T--C--C-----GG-GCCTT-CAT-GGTGCT--A-TTGAATCCT-C--GA
GB358      4c    T--C--C-----GG-GCCTT-CAT-GGCGCT--GCTTGAATCC--C--GA
Z6         4c    T--C--C-----GGTGTCTT--AT-GGTGCT--GCTTGACTCC--C--GA
Z7         4c    T--C--C-----GG-GCCTT--AT-GGTGCA--GCTTGAATCCA-C--GA
DK13       4d    ---C--C-----TG-GCAAC--CTG--TGCT--GCTTGA-TCTT-GA---
GB809_2    4e    T--C--A-----GT-GCCTT-C-T-GGTGCT--GCTCGA--CCT-G--G-
CAM600     4e    T--C--A--A--GT-GCCAT-C-C-GGTGCT--GCTTGA--CCT-G--G-
G22        4f    ---C--C-----G--GCCAT-CCTTGGCGCT--ACTCGA-TCCA-G--G-
G27        4f    ---T--------G--GCCAC-CATTGGCGCT--ACTTGA-TCCA-G--G-
GB549      4g    A--C--T-----TG--CCCT---TTGGCGCG--GCTCGAATCCA-G--G-
GB438      4h    A--C--T--A--GT-CCCT-CCT-GGGGCT--ACTT---TCTG-A--G-
CAR4/1205  4i    ---C--C-----GG--CCAC-CCTACGTGCT--GCTTT--TCCT-A--GG
CAR4/901   4?    A------T----TG-TCCCT-CCT-GGGGCT--GCTT---TC--A--G-

BE95       5a    -----AC--T-AG--CC-AGCCT-GG-GCAGT-A--G-T-CT-----GA
BE100      5a    ---C---T-AG--CC-AGCTT-GG-GCAGT-A--G-CC-----GA
SA4        5a    ---C---T--T-AG--CC-A--CT-GG-GCGGT-A--G-T-CT-----GA
```

Figure 4 - Continued 16

```
                 779                                                 828
HCV-1       GTCACATCGATCTGCTTGTCGGGAGCGCCACCCTCTGTTCGGCCCTCTAC
HCVEC1   1a ------------------------------------------C-------
HCVHCT18 1a ------------------------------------------C------T
HCVHCT23 1a ------------------------------------------C-------
HCVHCT27 1a ----------------T--------------T--C-------C------T
HCVTH    1a -------------------------------------------C------
HCV-J    1b -C-----G----T---C--T---GCG--TG-T-------C--TA-G---
HC-J6    2a CG------T--CA--G----GAT-TC------G----C--T--T-----
HC-J8    2b CA------G---CA--A-C--AAT-GCA--T--GGC--C-----T-G--T
S83      2c CA--------A-CA-C--GAT-TCT--T--GG------T----T--T--T
NE92     2d CG--T--T--ACCA-CA-T-CATC----T--GT-T--C--T---G----
HD10     3a -G--TG-A--CA--T-G--G--CGCG-----GA-G--C--T--T-----
BR33     3a ----TG-G--C---T-A--A--CGCG-----GA-G--C--T--G-----
BR36     3a ----TG-G--C--AT-A--G--CGCG-----GA-G--C--T--G-----
NZL15    3a ----TG-G--C--AT-A--A--CGCG-----GA-G--C--T--G-----
HCV-TR   3b CC--TG-G---A----G--A--CGCACGACAA--G--------G------
```

Figure 4 - Continued 17

```
                 779                                                              828
GB809_4    4a    -G---TG-G---C---AA-G---A---TGCG------G-G-------T--T------T
Z4         4a    -A---TG-G---CT-AA-G---A---CGCG------TT-G-------T-----------T
Z1         4b    -G---TG-A---C---A-G---A---TGCG---T--TA-G-------C----T-----
GB116      4c    ----TG-G--------A-G---A---TGCG---T---TG-G------C----T--T---
GB215      4c    -A---G-G---CA--A-G---G---CGCT---T---TG-G------C----T--T---
GB358      4c    ----TG-G---C---A-G---A---TGC----T---TGCG------C----T--T---
Z6         4c    -A---TG-G---C---A-G---G---CGC----T---TG-A-----C---T-------
Z7         4c    -A---TG-G---C---A-G---A---CGCT--T---AG-G------C----T------
DK13       4d    -----G-G--------A-G---G---CG----T'-----------C------------
GB809_2    4e    -C---TG-G---C---A-G---A---TGCT------G-G-------C----------
CAM600     4e    -----TG-G---C---A-G---A---TGCT------A-G-------C----A-----
G22        4f    -----G-G---T---A-G---G---C-CT--T---AT-G-------C---A---A---
G27        4f    -----TG-G---T---A-G---A---C-CT------AT-G-------C----A-----
GB549      4g    -G---G-G---CT-AA-G---G---TGC-------G---------C----T-----G-
GB438      4h    AG---TG-G---C---A-G---G------GCG------T-A------C----T-----
CAR4/1205  4i    CG--TG-G---C---AA-G---G------GC-------GGCA----C----TT-T---
CAR4/901   4?    -G---TG-G---T---A-G---G---TGCA------T--------T---C--------

BE95       5a    -AGC-G-T--CTAC---A-CG--AG-G---TG------C---C--GT-A--
BE100      5a    -AGC-G-T---TACT-G--G---AG-G---TG------C---C--GT-A--
SA4        5a    -GGC-G-T--CTACT-A-CG--AG-G---TG------C---C---A---A--
```

Figure 4 - Continued 18

```
              829                                              878
HCV-1    1a   GTGGGGGACCTATGCGCGGGTCTCTGTCTTTCTTGTCGGCCAACTGTTCACCTT
HCVEC1   1a   -----------G-----------------C------------T-----------
HCVHCT18 1a   -----T-G---------------------------------T------------
HCVHCT23 1a   -------T-----CA----------------------T----------------
HCVHCT27 1a   -----T-G---------------------------------T------------
HCVTH    1a   -------T-----CA----------------------T-------------T--
HCV-J    1b   --T----T---C-----A---C--T-----C----TC---G-------------

HC-J6    2a   -------C-------TGGG---GA-G-----CA-C---GA----TTG-------
HC-J8    2b   --A---TG-G-----G-C---GA-GA---C-ATCG--GGCT---TGG-------
S83      2c   -------G-G---T-CG-GC-GA-G---C---CT--CG-CG--GT-G-------
NE92     2d   A-A---A--------G--T--CG-G--GA-GT-G-CTTCT---G-C---T-A--

HD10     3a   ---T--TA-G---T---G-C-----C---C---A---GCC-----G--------
BR33     3a   ---T--TA-G---T---G-C-----C---C---A---GCC-----G--------
BR36     3a   ---T--A-G---T---G-------C---G---A---GCC-----G---------
NZL15    3a   ---T--TA-G---T---G-------C---G---A---GCC-----G---------
HCV-TR   3b   --C-----GCT-T----------G------------G--A---GC---------
```

Figure 4 - Continued 19

| | | 829 | | | | | | | | 878 |
|---|---|---|---|---|---|---|---|---|---|---|
| GB809_4 | 4a | --T--A----- | ---C | --T- | -AGG- | -CT- | -C--A- | -G- | -G--GA | ----- |
| Z4 | 4a | --T------- | ---C | --- | -AGG- | -C-- | -C--GA | -G- | -G--GA | --A--T-- |
| Z1 | 4b | A-T--A----- | --T- | -G-- | -AGGC | ---- | -C--A- | -G- | --G--- | -GA----- |
| GB116 | 4c | A-C------- | ---G | ---- | -TGGC | --A- | -T-G-- | -T- | -T--GA | ---TT-T-- |
| GB215 | 4c | A-T------- | --T- | -G-- | -TGGC | --A- | -CT-G- | -T- | -T--GA | ---TT-T-- |
| GB358 | 4c | A-C--A----- | ---G | ---- | -TGGC | --A- | -T-G-- | -T- | -T--GA | ---TT-T-- |
| Z6 | 4c | --T--A----- | --T- | -G-- | -TGG- | -CA- | -CT-G- | -T- | ---GA | ---T--- |
| Z7 | 4c | A-T------- | --T- | -G-- | -TGGC | --A- | -T-G-- | -T- | -T--GA | ---TT-T-- |
| DK13 | 4d | A-C--A----- | ---G | -G-- | --GG- | -T-- | -G--CT | -G- | -T----- | ------- |
| GB809_2 | 4e | --C------- | ---C | ---- | -TGGCT | --A- | -CT-G- | --A- | ------ | ------- |
| CAM600 | 4e | A-C--C----- | --T- | -G-- | -TGGCT | --A- | -CT-G- | --G- | ---A-- | ------- |
| G22 | 4f | --T------- | ---G | ---- | --GGCA | --A- | -C--A- | -CG- | ---GA | ------- |
| G27 | 4f | A-T--A----- | --T- | -G-- | -AGGCA | --A- | ---A-- | -G- | -GA | ---A--- |
| GB549 | 4g | A-C--A----- | --T- | ---- | -AGG- | ---- | -C-- | -G- | -G--GA | ------- |
| GB438 | 4h | A-C--A----- | ---AT | ---- | -AGG- | ---- | -CT-G- | -CA- | -G--GA | --G--GT-- |
| CAR4/1205 | 4i | A-T--A----- | --T- | -G-- | --GG- | ---- | -G-- | --- | -T-G-CG | ---TA- |
| CAR4/901 | 4? | --C--A----- | ---C | --T- | -AGG- | ---- | -C--A- | -G- | -A--GA | ------- |
| BE95 | 5a | --A--A----- | -GCG | -T-- | -G-AC-A | ---- | -CT-G- | -A- | -----A | -----A |
| BE100 | 5a | --T--A----- | -GCG | -T-- | -G-AC-A | ---- | -T-G-- | -A- | -----A | -----A |
| SA4 | 5a | --C------- | -GCG | ---- | -G-A-- | --G- | -T-G-- | -A- | -----A | -----A |

Figure 4 - Continued 20

```
          879                                                              928
HCV-1    1a  CTCTCCCAGGCGCCACTGGACGACGCCAAGGTTGCAATTGCTCTATCTATC
HCVEC1   1a  --------------------------------------------------
HCVHCT18 1a  -----------------------G-AC----C--T---------------
HCVHCT23 1a  ---------------------------A----C-----------------C
HCVHCT27 1a  ----C----------------A---------------------------C
HCVTH    1a  --------------------------------------A-----------
HCV-J    1b  ---A--TC-C---GT-TGA-----GTA---A-------------------
HC-J6    2a  ---G--ACA--A--------TTTGT-----AC----------C------C
HC-J8    2b  A--A--ACAA-------AACTTC--C----AG---C--T---C------C
S83      2c  G--G--ACAA-A----TAC-TTTGTC--G-AA---C--T---C--A----C
NE92     2d  ---G--CA--AT--TAA-TTTGTC--G-AC-----C--T---C--A----C
HD10     3a  -AGA--TC-T-----TCAA---GTC--GACC--T--C-----AC-G---C
BR33     3a  -AGA--C-C------TCAA---GTC--GACC--T--C-----GC-G---C
BR36     3a  -AGA--TC-T-----TCAA---GTC--GACC--T--C-----GC-G---C
NZL15    3a  -AGA--TC-A-----TCAA---GTC--GACC--T--C-----GC-G---C
HCV-TR   3b  -AGA--TC-C-----AC----CGT---GACG-------C-----G--A--C
```

Figure 4 - Continued 21

```
                     879                                                     928
GB809_4     4a   -CAG--GC-T-------------C-------G-A---T------C-----A
Z4          4a   TCGG--GC-T-------------C-------G-AG----------C-----CA
Z1          4b   -CGA--GC-C--G----------C---C---G-A-----C-----C------
GB116       4c   -CAG--GC-A-------------C-------G-AC----T-----C------
GB215       4c   -CGG--AC-A-------------T-------G-AC----T-----C-----CG
GB358       4c   -CAG--GC---------------T-------G-AC----T-----C-----CG
Z6          4c   -CAG--GC-A-------------T-------G-AC----T-----C-----CG
Z7          4c   -CAG--GC-A-------------T-------G-AC----T-----C-----CG
DK13        4d   -CAA--TC-C-------------C---C---AC------T-----C-----CA
GB809_2     4e   -CAA--GC-A-------------C-------G-AC--T-T-----C-----CG
CAM600      4e   -CAA--GC-A--T----------C---T---G-AC----T-----C-----CA
G22         4f   -CGG---C-C-T--------T--C---C---G-AG----T-----C--C---
G27         4f   -AGG---C-C-TG----------C---C---G-AG----T-----C------
GB549       4g   -CGG--GC-C-----T-------T---C---G-AC------C---C------G
GB438       4h   -CAA---C---T--T--------T---T---G-A-----T-----C------G
CAR4/1205   4i   -CGG--AC-CATT-TGAA-----C---T---G-AC----------C-----CT
CAR4/901    4?   -CAG--GC-C-------------T---T---G-AC----------C--T--CG

BE95        5a   TAGG--TC-C-AG----GCT---GT--GAAC-----C--T--C--T----CA
BE100       5a   TAGG--TC-C-AG----TGCT--GT----G-AC---C--T--C--T----CA
SA4         5a   TAGG--TC-C-AG----ACT---GT----AC-----------------T--CA
```

Figure 4 – Continued 22

```
                929                          957
HCV-1      1a   CCGGCCATATAACGGGTCACCGCATGGCA
HCVHCT18   1a   -----------C----G------------
HCVHCT23   1a   -----------------------------
HCVHCT27   1a   ----------------A------------
HCVTH      1a   -----------------------------
HCV-J      1b   ------------CG--T-A---------T

HC-J6      2a   -T--TACC--C---T--A---------G
HC-J8      2b   AA--T-C---C---C---C---T------
S83        2c   -G---GC---T---A------------T
NE92       2d   -A-------C---T--A--T--G----G

HD10       3a   -A------C-TT-A--A----A----T
BR33       3a   -A------C-TT-A--A----A----T
BR36       3a   -A------C-TT-A--A----A----T
NZL1.5     3a   -A------C-TT-A--A----A----T
HCV-TR     3b   -A------G-TT-A--A----T----G
```

Figure 4 - Continued 23

| | | 929 | 957 |
|---|---|---|---|
| GB809_4 | 4a | -T------- | C--C--C--A-G----G |
| Z4 | 4a | -T------- | C--C--C--A-G----G |
| Z1 | 4b | -T--T--CG-CT | --C--C--A-G----C |
| GB116 | 4c | -G--G--CG-T | ---C--C--A-G---- |
| GB215 | 4c | -G--G--CG-C | ---T--C--G-A---- |
| GB358 | 4c | -G--G--CG-T | ---C--C--A-G---- |
| Z6 | 4c | -A--G---- | ---C--C--A-G---- |
| Z7 | 4c | -G--G--CG-T | ---A--C--A-A---- |
| DK13 | 4d | -A--A---- | ---C--A--A-A----T |
| GB809_2 | 4e | -A--G----T | ---T--C---T-G----T |
| CAM600 | 4e | -G------- | C---------T-G----G |
| G22 | 4f | -G------- | C---------TA-A----G |
| G27 | 4f | -A------- | C---------A-A----T |
| GB549 | 4g | AT------- | C--C--C--TA-A----C |
| GB438 | 4h | TG------- | C--C--C--A-G---- |
| CAR4/1205 | 4i | -A--G---- | C--C--C--------- |
| CAR4/901 | 4? | T-------- | C--A----A-A----T |
| BE95 | 5a | GT----G-T | --C--C-----G----G |
| BE100 | 5a | GT----CG-C | --C--C---C-T-AG---- |
| SA4 | 5a | GT------- | --C--C-----G----- |

Figure 5

```
                SEQ ID   MSTNPKPQKKNKRNTNRRPQDVKFPGGGQIVGGVYLLLPRRGPRLGVRATR
HCV1     1a     1        
HCV J    1b              ------R-T-----------------------------------------

HCJ6     2a              ------R-T-----------------------------------------
HCJ8     2b              ------R-T-----------------------------------------
NE92     2d     144      ------R-T-----------------------------------------

EB1      3a              ------R-T----I----------------V-------------------
NZL1     3a              ---L--R-T----I----------------V-------------------
HCV-TR   3b              ---L--RQT----L---N------------V-------------C-----
BE98     3c     148      ---L--R-T----X----------------V-------------Q---V-

GB358    4c     192      ------R-T-----M-----------------------------------
GB809    4e     164      ---L--R-T-----M-----------------------------------
CAM600   4e     166      ------R-T-----M-----------------------------------
GB724    4?     194      ------R-T-----M-----------------------------------
EG-29    4?              ---R--------------------------------------------V-
BE95     5a     152      ------R-T-------------------------------------M---
```

Figure 5 - Continued 1

| | | KTSERSQPRGRRQPIPKAR | RPEGRTWAQ | PGYPWPLYGNEGCGWAGWLLSP |
|---|---|---|---|---|
| HCV1 | 1a | ------------------- | --------- | ---------------------- |
| HCVJ | 1b | ------------------- | ----M---- | ---------------------- |
| HCJ6 | 2a | ----------------D-- | -ST-KS-GK | -------L-------------- |
| HCJ8 | 2b | ----------------D-- | -ST-KS-GK | ---------------------- |
| NE92 | 2d | ----------------D-- | --T-KS-GK | -------L-------------- |
| EB1 | 3a | ------------------- | -S----S-- | ---------------------- |
| NZL1 | 3a | ------------------- | -S----S-- | ---------------------- |
| HCV-TR | 3b | -----------KQ-HL--- | SR----S-- | ----------K---L------- |
| BE98 | 3c | ------------S------ | --T---S-- | ---------------------- |
| GB358 | 4c | ------------------- | -S----S-- | ---------------------- |
| GB809 | 4e | ------------------- | -S----S-- | ---------------------- |
| CAM600 | 4e | ------------------- | --T---S-- | ---------------------- |
| GB724 | 4? | ------------------- | -S----S-- | -----A---------------- |
| EG-29 | 4? | ------------------- | -S----S-- | ---------------------- |
| BE95 | 5a | ------------------- | Q-T---S-G | ------------A---L----- |

V-core

Figure 5 - Continued 2

```
              101                                    126
              RGSRPSWGPTDPRRRSRNLGKVIDTL
HCV1    1a    -------------------------
HCVJ    1b    -------------------------
HCJ6    2a    ------N---H-------V------
HCJ8    2b    ------T---H-------R----I-
NE92    2d    ----------H--------------

NZL1    3a    ------N------------------
HCV-TR  3b    ------N------------F-----
BE98    3c    ------N------------------

GB809   4e    ------N------------------
CAM600  4e    -X--X-N---X--------------
GB724   4?    ------N------------------

```
          127                                                            176
          TCGFADLMGYIPLVGAPLGGAARALAHGVRVLEDGVNYATGNLPGCSFSI
HCV-1    1a  --------------------------------------------------
HCVEC1   1a  --------------------------------------------------
HCVHCT18 1a  --------------------------------------------------
HCVHCT23 1a  -----------------------R--------------------------
HCVHCT27 1a  ---------------------------------------------L----
HCVTH    1a  --------------------------------------------------
HCV-J    1b  --------------------------------------------------

HC-J6    2a  ------------V-------V-----------------------------
HC-J8    2b  ------------V-------V--V--------I-----------------
NE92     2d  ------------V-------V--V--------I-----------------

HD10     3a  ------------V-------V--V----A---I--F--------------
BR33     3a  ------------V-------V--V----A---I--F--------------
BR36     3a  ------------V-------V--V----A---I--F--------------
NZL1     3a  ------------V-------V--V----A---I--F--------------
HCV-TR   3b  ------------V-------V--V----A-G-------------------
```

Figure 5 - Continued 4

| | | 127 | 176 |
|---|---|---|---|
| GB809_4 | 4a | ------------------------------------------ | ----V--V------AV---I------ |
| GB116 | 4c | ------------------------------------------ | -----V--V------AV---I------ |
| GB215 | 4c | ------------------------------------------ | -----V--V-E----AV---I------ |
| GB358 | 4c | ------------------------------------------ | -----V--V-E----AV---I------ |
| GB809_2 | 4e | ------------------------------------------ | -----V--V------AV---I------ |
| CAM600 | 4e | ------------------------------------------ | -----V--V------AV---I------ |
| CAMG22 | 4f | ------------------------------------------ | -----V--V------AV---I------ |
| CAMG27 | 4f | ---S-------------------------------------- | -----V--V------AV---I------ |
| GB549 | 4g | ------------------------------------------ | -----V--V------AV---I------ |
| GB438 | 4h | ------------------------------------------ | -----V--V------A----I------ |
| CAR4/1205 | 4i | ------------------------------------------ | -----V--V------AV---I------ |
| CAR4/901 | 4? | A----------------------------------------- | -----V--V------AV---I------ |
| BE95 | 5a | ------------------------------------------ | ---G-V--V---------P-------- |
| BE100 | 5a | -----V------------------------------------ | ---G-V--V------------------ |

Figure 5 - Continued 5

```
             177                                                    226
             FLLALLSCLTVPASA YQVRNSTGLYHIV TNDCPNSSI VYEAADAILHIT PGC
HCV-1    1a  --------------- ------------- --------- ------------ ---
HCVEC1   1a  --------------- ----S-------- --------- ------------ ---
HCVHCT18 1a  --------------- -H----------- --------- -----------A ---
HCVHCT23 1a  --------------- ------------- --------- ------------ ---
HCVHCT27 1a  --------------- ----S-I------ --------- ---T--T---S- ---
HCVTH    1a  --------------- ------------- --------- ------------A ---
HCV-J    1b  ----I---------- -E---VS-I---- ----S---- -------M-M-- ---

HC-J6    2a  ----I-T-V------ AE-K-ISTG-M-- ----T-D-- TWQLQA-V---V ---
HC-J8    2b  ----V--V------- VE---ISSS-YA- ----S-N-- TWQLT--V---L ---
S83      2c  --------------- VE-KDTGDS-MP- ----S---- -WQLEG-V---- ---
NE92     2d  ----I---V-G---- L--K-TSSS-M-- ----Q---- -WQLR--V---- ---

HD10     3a  ----F---IH--AS- LEW--TS---VL- ----S---- ----D-V----- ---
BR33     3a  ----F---IH--AG- LEW--TS---VL- ----S---- ----D-V----A ---
BR36     3a  ----F---IH--AS- LEW--TS---VL- ----S---- ----D-V----- ---
NZL1     3a  ----F---IH--AS- LEW--TS---VL- ----S---- ----D-V----- ---
HCV-TR   3b  ----F---C---G-- LEYT-TS---VL- ----S-G-- ----E-V----L ---
```

|  |  | 177 | V1 |  | V2 | 226 |
|---|---|---|---|---|---|---|
| GB809_4 | 4a |  | EHY--AS-I--I |  | ---TDHII---L |  |
| Z4 | 4a |  | EHY--AS-I--I |  | --DIII---L |  |
| Z1 | 4b |  | VHY--AS-V--I | --T | --TEHI--M-L |  |
| GB116 | 4c | S------- | VNY--AS-V--I |  | --DYII---L |  |
| GB215 | 4c | Y------- | IHY--AS-V--I |  | --DIII---L |  |
| GB358 | 4c | ----T--- | VNY--AS-I--I |  | --TEHI---L |  |
| Z6 | 4c |  | VNY--AS-V--I |  | --EHQ---L |  |
| Z7 | 4c |  | VNYH-AS-V--I |  | M--EHII---L |  |
| DK13 | 4d |  | -NY--S-V--I |  | ---TDYII---L |  |
| GB809_2 | 4e | ------G | VNY--AS-V--I | --A | ---TDNII---L |  |
| CAM600 | 4e | ----T--- | VNY--AS-I--I | --A | --TEHII---L |  |
| CAMG22 | 4f |  | VHYH-TS-I--L |  | F--VHII---L |  |
| CAMG27 | 4f |  | VHYH-TS-I--I |  | F--EHII---L |  |
| GB549 | 4g |  | QHY--IS-I--I |  | --DHII--M-L |  |
| GB438 | 4h | ---V--R | QHY--AS-I--I |  | --DHII--M-L |  |
| CAR4/1205 | 4i | S--E------ | IHY--ASDG-YI |  | --ENII---L |  |
| CAR4/901 | 4? | X------- | QHY--VS-I--I |  | --DHII--M-L |  |
| BE95 | 5a | -I------- | VPY--AS-I--- |  | --DNL---A |  |
| BE100 | 5a | -I------- | VPY--AS-I--- |  | --D-L----A |  |
| SA4 | 5a |  | VPY--AS-V--- |  | --DNL---A |  |
| IIK2 | 6a |  | LTYG--S----L |  | -L--DAM---L |  |

Figure 5 - Continued 7

|  |  | 227 | V3 |  | V4 |  | 276 PUTATIVE |
|---|---|---|---|---|---|---|---|
|  |  | VPC | VREGNASRCWVAM | TPTVA | TRDGKLPATQ | LRRHID | LLVGSATLCSALY |
| HCV-1 | 1a | --- | ------------ | ----- | ---------- | ------ | ------------- |
| HCVEC1 | 1a | --- | --H---V----- | ----- | -----T---- | ------ | ------------- |
| HCVHCT18 | 1a | --- | --H---V----- | ----- | -----T---- | ------ | ------------- |
| HCVHCT23 | 1a | --- | ---D-V------ | ----- | -K-------- | ------ | ------------- |
| HCVHCT27 | 1a | --- | ------K--PV- | A---- | -----N---- | ------ | ------------- |
| HCVTH | 1a | --- | ------------ | ----- | ---R---T-- | ------ | ------A-A---- |
| HCV-J | 1b | --- | --S-F------- | ---L- | A-NSSI-T-T | I----V | -----A-A---M- |
|  |  |  |  |  |  |  |  |
| HC-J6 | 2a | --- | EKV--T----IPV | S-N-- | VQQPGALTQG | --T--- | MV-M--------- |
| HC-J8 | 2b | --- | ENDNGTLH--IQV | --N-- | VKHRGALTRS | --T-V- | MI-MA--A----- |
| s83 | 2c | --- | E-TA-V----PV | A-NL- | ISQPGALTKG | ---A-- | II--M---V---- |
| NE92 | 2d | --- | EEK---I---IPV | S-NI- | VSQPGALTKG | --T--- | TIIA----F---- |
|  |  |  |  |  |  |  |  |
| HD10 | 3a | --- | -QD--T-A--TPV | ----- | V--YVGATTAS | I----V | M----A--M--- |
| BR33 | 3a | --- | -QD--T-T--TPV | ----- | V--YVGATTAS | I-S-V- | -----A--M--- |
| BR36 | 3a | I-- | -QD--T-T--TPV | ----- | VKYVGATTAS | I-S-V- | -----A--M--- |
| NZL1 | 3a | --- | -QD--T-T--TPV | ----- | V--YVGATTAS | I-S-V- | -----A--M--- |
| HCV-TR | 3b | --- | -TT--Q-S--TTV | ST--- | V-TLGVTTAS | I-T-V- | M---ARQ----- |

Figure 5 - Continued 8

|  |  | 227 | V3 |  | V4 |  | PUTATIVE 276 |
|---|---|---|---|---|---|---|---|
| GB809_4 | 4a | ---- | --A--V-----TPV | ---- | AVSMDA-LES | F----V- | -M--A--V--V--- |
| Z4 | 4a | ---- | -MT--T-----TPV | ---- | VAHPGA-LES | F----V- | -M--A-------- |
| Z1 | 4b | ---- | ---TE-T-----PL | ---- | APYPNA-LES | M----V- | -M--A--M---F- |
| GB116 | 4c | L--- | ---V--Q------L | ---- | APYVGA-LES | ---S-V- | -M--A--V----- |
| GB215 | 4c | L--- | ---V--Q------L | S--- | APYIGA-VES | F----V- | -M--A--V----- |
| GB358 | 4c | L--- | ---V--Q------L | ---- | APYIGA-LES | ---S-V- | MM--A--A----- |
| Z6 | 4c | L--- | ---V--Q------L | ---- | VSYIGA-LDS | -----V- | -M--A--A----- |
| Z7 | 4c | ---- | ---Q---------L | ---- | APYIGA-LES | I----V- | -M--A--V----- |
| DK13 | 4d | ---- | ---KT------SL | ---- | AQHLNA-LES | -----V- | -M--A--V----- |
| GB809_2 | 4e | ---- | ---KT--Q-----L | ---- | SPYVGA-LEP | -----V- | -M--G-------- |
| CAM600 | 4e | ---- | ---T---Q-----L | ---- | SPYAGA-LEP | -----V- | -M--A--V----- |
| CAMG22 | 4f | ---- | ---T---Q-----L | -L-- | APYLGA-LES | M----V- | -M--A--M----- |
| CAMG27 | 4f | ---- | ---T---------I-L | -L-- | APHIGA-LES | M----V- | -M--T-------- |
| GB549 | 4g | ---- | ---T--T-----PL | ---- | APYVGA-LES | M----V- | -M--T-------- |
| GB438 | 4h | ---- | ---T--V-----IPL | ---- | VPYLGA-L-S | V-Q-V- | -M--A--V----- |
| CAR4/1205 | 4i | I--- | ---KT--Q------L | -L-- | APHLRA-LSS | --A-V- | -M--A--A---F- |
| CAR4/901 | 4? | I--- | ---T--V-----SL | ---- | APYLGA-L-S | -----V- | -M--A------- |
| BE95 | 5a | ---- | -MT--V------QI | ---LS | APSLGAVTAP | ---AV- | Y--A--G--A--- |
| BE100 | 5a | ---- | --KD-V------QI | ---LS | APSFGAVTAP | ----AV- | Y----G--A--- |
| SA4 | 5a | ---- | --QD-V-K-----QI | ---LS | APNLGAVTAP | ---AV- | Y--A--G--A--- |
| HK2 | 6a | L--- | ---VDDR-T--H-V | ----L | IPNAST---G | F----V- | --A--A-VV--S-- |

Figure 5 - Continued 9

| | | 277 TRANSMEMBRANE DOMAIN | V5 | 319 |
|---|---|---|---|---|
| | | VGDLCGSVFLVGQLFTF | SPRRHWTTQG | CNCSIYPGHITGHRMA |
| HCV-1 | 1a | ---------------- | ---------- | ---------------- |
| HCVEC1 | 1a | ---------------- | ---------- | ---------------- |
| HCVHCT18 | 1a | -------I-------- | -------D-- | ---------------- |
| HCVHCT23 | 1a | ---------------- | -------D-- | ---------------- |
| HCVHCT27 | 1a | -------I-------- | ---------- | ---------------- |
| HCVTH | 1a | ---------S------ | ---YE-V-D- | ----VS---------- |
| HCV-J | 1b | ---------------- | ---------- | --------T------- |
| HC-J6 | 2a | ----G-M-AA-M-IV- | --QH--FV-D | ---------Q------ |
| HC-J8 | 2b | -V--A-MILS-A-MV- | --Q--NF--E | ---------------- |
| S83 | 2c | -V--ALM-AA-VVVV- | --QH-TFV-E | -----------R---- |
| NE92 | 2d | I---A-M-AS-V-II- | --QH-KFV-D | ---------------- |
| HD10 | 3a | --M-A-----A----- | R----Q-V-T | ----L---LS------ |
| BR33 | 3a | --M-A-----A----- | R----Q-V-T | ----L---LS------ |
| BR36 | 3a | --M-A-----A----- | R----Q-V-T | ----L---LS------ |
| NZL1 | 3a | --M-A-----A----- | R----Q-V-T | ----L---LS------ |
| HCV-TR | 3b | ---AF-A-----A--- | R----T-V-T | --------VS------ |

Figure 5 - Continued 10

|  |  | 277 TRANSMEMBRANE DOMAIN |  | V5 |  | 319 |
|---|---|---|---|---|---|---|
| GB809_4 | 4a | ------GA----M- | -- | Q------D | ----T------ | -- |
| Z4 | 4a | ------GA--M--MI | -- | R------E | ----T------ | -- |
| Z1 | 4b | I------G------ | D- | R------D | ----VS----- | -- |
| GB116 | 4c | I------G------ | S- | Q------D | ----A------ | -G |
| GB215 | 4c | I------G------ | S- | R------D | ----A--V--- | -- |
| GB358 | 4c | I------G------ | S- | Q------D | ----A------ | -- |
| Z6 | 4c | ------GA------ | S- | Q------D | ----A--V--- | -- |
| Z7 | 4c | I------G------ | -- | Q------D | ----A------ | -- |
| DK13 | 4d | I--V--G------ | -- | Q------D | ----A--V--- | -- |
| GB809_2 | 4e | I------GL------ | -- | Q------D | ----T------ | -- |
| CAM600 | 4e | I------GL------ | -- | R------E | ----T------ | -- |
| CAMG22 | 4f | I------GI--A--M | -- | R--L---D | ----T------ | -- |
| CAMG27 | 4f | I------GI------M | N- | R--L---E | ----D------ | -- |
| GB549 | 4g | I------G------ | -- | R------D | ----V------ | -- |
| GB438 | 4h | I--II--G---A--MV | S- | Q------D | ----S------ | -- |
| CAR4/1205 | 4i | I------G--A--- | -I | R--I--E--D | ----V------ | -- |
| CAR4/901 | 4? | I------G------ | -- | Q------D | ----V------ | -- |
| BE95 | 5a | ---A--AL------M | -Y | R--Q-A-V-N | ----S--V--- | -- |
| BE100 | 5a | ---A--AL------M | -Y | R--Q-A-V-D | ----S--V--- | -Q |
| SA4 | 5a | ---A--A------M | -Y | R--Q-T-V-D | ----S------ | -- |
| IIK2 | 6a | I------L--A---- | -- | Q------D | ----T--V--- | -- |

Figure 6

```
              4648                                                    4698
       GTGTGCCAGGACCACCATCTTGAATTTTGGGAGGGGCGTCTTTACAGGCCTCACT
HCV-1  --C-------------------C--A--G--C-----A-----------C------C
HCV-J  -----------A----------------G--------CA--T--C--C--------A
HC-J6  --A--T--A----C--G--G--C-----A-CG-----------------T-----A
HC-J8  --A--T--A----C--G--G--C-----A-CG-----------------T-----A
HCCl53                     -A--C-----------A--------C--T--A--A---
EB1
EB2
EB6
EB7
                                  ↑
                                4664

4699                                                    4750
       CATATAGATGCCCCACTTTCTATCCCAGACAAAGCAGAGTGGGGAGAACCTT
HCV-1  --C-----------CT-G--------C--A---GCA--A--C-----C
HCV-J  --C------------------T--A-----------ATCG-----A--TT-C
HC-J6  --C--T--C-----C--C-----------G------AG-A--A--A--T--
HC-J8  --C-----------C-----------------G--A-----CAG--ACTC---T-C
HCCl53 --C-----------------G--A-----T------CAG--ACTC---T-C
EB1                                       ---CAG--ACTC---T-C
EB2                                       ---CAG--ACTC---T-C
EB6                                       A---CAG--ACTC---T-C
EB7                                       A---CAG--ACTC---T-C
                                                ↑
                                              4731
```

Figure 6 - continued 1

```
               4751                                              4800
       CCTTACCTGGGTAGGCTACCAAGCCACCGTGTGCCGTAGGGCTCAAGCCCC
HCV-1  --C----------A-------A--------C----------G--T----
HCV-J  G-A---T-AAC---C-----G--T--A--------------CA------
HC-J6  G-G--T--AACG--C------G-----A--A-----C----AA-G----
HC-J8  T-G-T----ACT--C------------T--------C-C--G-G--T--
HCCl53 T-G------AACT--C-----------T--------CC-C--G--G--T-T
EB1    T-G------AACT--C-----------T--------CC-C--G--G--T--
EB2    T-G------AACT--C-----------T--------CC-C--G--G--T--
EB6    T-G------AACT--C-----------T--------CC-C--G--G--T--
EB7    T-G------AACT--C-----------T--------CC-C--G--G--T--

4801                                              4849
       TCCCCCATCGTGGGACCAGATGTGGAAGTGTTTGATTCGCCTCAAGCCCA
HCV-1  A--T---------------A-------------C-C--A--G--A----
HCV-J  C----G--C-----GTC--------------------C--A--------
HC-J6  ---T--T-------GT---------------C-A-C-A-G-----A--T
HC-J8  ----------AGT------G-----------C-CG-A--G--T-----A
HCCl53 ----------AGT------G-----C-----A---CCG-G--G--T----A
EB1    ----------AGT------G-----C-----A---CCG-G--A-------A
EB2    ----------AGT------G-----------A---CCG-G--G-------A
EB6    ----------AGT------G-----------A---CCG-G--G-------A
EB7    ----------AGT------G-----------A---CCG-G--G-------A
```

Figure 6 - continued 2

```
              SEQ ID NO   4850                                              4900
                          CCCTCCATGGGCCAACACCCCTGCTATACAGACTGGGGCGCTGTTCAGAAT
HCV-1          29         -A--G--------G-------G----G---G--A--A--C-----A---
HCV-J          31         -A---GTG--C--C-----T--C--G---C-CT----T----ACC--C
HC-J6          33         -A---GAC---T--C-----C--G---C-CT----T--C--GACC---
HC-J8          35         -A---GAC---T--C-----C--G---C-CT----T--C--GACC---
HCCL53         37         -A---A----T--G--T--T-----TC-GT----GC---C--A---
                                        ↑                    ↑
                                       4863                 4892
HD10-1-25      39                                            -C--A---
HD10-1-3                                                     -C--A---
HD10-1-3                                                     -C--A---
BR36-20-164                                                  -C--A---
BR36-20-166                                                  -C--A---
BR36-20-165
EB1                       -A--A--C--A--T--G-----T-----TC
EB2                       -A--A--A--T--G-----T-----TC
EB6                       -AT-A-----A--C--G-----T-----TC
EB7                       -AT-A-----A--C--G-----T-----TC
                                      ↑
                                     4878
```

Figure 6 - continued 3

```
           4901                                              4949
       GAAATCACCCTGACGCCACCCAGTCACCAAATACATCATGACATGCATGTC
HCV-1  
HCV-J    --GG----T--C--A----CA-A---------------G--------
HC-J6    --GG-------C----T--T--G-G---------GCC--C-----CA
HC-J8    --GG-------------T----C--G-G------GCC---G----CA
HCCl53   ------------------C--G-G-----A----------G-------
HD10-1-25 ------TG-T----A----CA----A-----------T---G-----
HD10-1-3  ------TG-T----A----C----A----------------G-----
BR36-20-164 ----TG-T----A----CA----A-----------T---G-----
BR36-20-166 ----TG-T----A----CA----A----------------G-----
BR36-20-165 ----TG-T----A----CA----A----------------G-----

4950                                              4990
       GGCCGACCTGGAGGTCGTCACGAGCACCTGGGTGCTCGTTG
HCV-1  
HCV-J    --T---------------T-------------A--A-
HC-J6    A-----------T---A-G--C-----G----CT-A-C--
HC-J8    A--T----C----A--A-G--A---T-A----C--G-CG-
HCCl53   A
HD10-1-25 A--T--T-----A--AAC---C--------T-GC---
HD10-1-3  A--T--T-----A--AAC---C--------T-GC---
BR36-20-164 A--T--T-----A--AAC---C--------TT-GC---
BR36-20-166 A--T--T-----A--AAC---C--------TT-GC---
BR36-20-165 A--T--T-----A--AAC---C--------TT-GC---
```

Figure 6 - continued 4

```
           4991                                                              5040
HCV-1      GCGGCGTCCTGGCTGCTTTGGCCGGTATTGCCTGTCAACAGGCTGCCTG
HCV-J      ----A------T--G----C---------C-----A-G-----A------
HC-J6      -G--G------T-----G--CG-C-----C-----G-G--C--G-T--T
HC-J8      -G--G--G---A--C--CG-----A--T--C------G-G--T-----A-T
HD10-1-25  -A--G------C--G--CC-A--G--C--C---T-----GTC--------T
HD10-1-3   -A--G------C--G--CC-A--G--C--C---T-----GTC--------T
BR36-20-164 -A--G------C--G--CC-A--G--C--C---T-----GTC--T--T--T
BR36-20-166 -A--G------C--G--CC-A--G--C--C---T-----GTC--T--T--T
BR36-20-165 -A--G------C--G--CC-A--G--C--C---T-----GTC--T--T--T 5041                                                              5090
HCV-1      GTCATAGTGGGCAGGGTCGTCTTGTCCGGGAAGCCGGCAATCATACCTGA
HCV-J      ---T-------A--A---------G---A--TG-T--T--C--
HC-J6      TG---CA-C---C-CT-GCA-G-TAA-CA-CGAG-C-TCG-TGC---G--
HC-J8      TC---CA-T---C-CC-ACA-C--AAT-ATCG-GT--TTG-GGCC--C--
HD10-1-25  --A--C------TCATA---AGC--GGG--C-----C--G-T--A--
HD10-1-3   --A--C------TCATA---AGC--GGG--C-----C--G-T--A--
BR36-20-164 --G--T------TCATA---AGC--GGG--C-----G-T--A--
BR36-20-166 --G--T------TCATA---AGC--GGG--C-----G-T--A--
BR36-20-165 --G--T------TCATA---AGC--GGG--C-----G-T--A--
```

Figure 6 - continued 5

```
            5091                                              5140
HCV-1       CAGGGAAGTCCTCTACCGAGAGTTCGATGAGATGGAAGAGTGCTCTCAGC
HCV-J       ------------------AG--------------------------TG--TCA-
HC-J6       --A---G-------TGAG-CT--T--------G--A--TG-CTCTA
HC-J8       --A---A--T-A--TGAG-CC--T--------A---G-CTCCA
HD10-1-25   --A---G--GT-G--T-A-C---A--------G------------G--AG
HD10-1-3    --A---G--GT-G--T-A-C---A--------G------------G--AG
BR36-20-164 --AA--G--GT-G--T-A-C-A-A---------------------A--AG
BR36-20-166 --AA--G--GT-G--T-A-C-A-A---------------------A--AG
BR36-20-165 --AA--G--GT-G--T-A-C-A-A---------------------A--AG 5141                                              5190
HCV-1       ACTTACCGTACATCGAGCAAGGGATGATGATGCTCGCCGAGCAGTTCAAGCAG
HCV-J       --C-C-T------------A---CA------A---A-----
HC-J6       GAGCGG-TCT---T--AG-G---CA-CG-A--A----AT-C-G---TCC
HC-J8       -AGCCG-CCT---T----G-----CA-CG-A-G--G---AT-C----ATCT
HD10-1-25   C-GCC--A------A----CTCA-G-AA-A---C-C------G--
HD10-1-3    C-GCC--A------A----CTCA-G-AA-A---C-C------G--
BR36-20-164 CTGCC--A--T--------A----CTCA-G-AA-A--TC-C-----GGA
BR36-20-166 CTGCC--A--T--------A----CTCA-G-AA-A--TC-C-----G-A
BR36-20-165 CTGCC--A--T--------A----CTCA-G-AA-A--TC-C-----G-A
```

Figure 6 - Continued 6

```
               5191                                              5240
HCV-1          AAGGCCCTCGGCCTCCTGCAGACCGGTCCCGTCAGGCAGAGGTTATCGC
HCV-J          ----G----AT-G-----A--A--CA----AAG--A--G----C-GCT--
HC-J6          ---AT--AA---T-AT-----CAA--T----ANA--A--TC-A-AC--ACA
HC-J8          ---ATA-AA------A--ACAG--CA-AA--G--A--TC-A-AC--ACA
HD10-1-25      ---AAT---T--A--G-----CGA--CA----AA--ACA--CT--C--T-A
HD10-1-3       ---AAT---T--A--G-----CGA--CA----AA--ACA--CT--C--T-A
BR36-20-164    --A-T---T--AT-G-----CGA--CA----AA--ACA--CT--C--T-A
BR36-20-166    --A-T---T--AT-G-----CGA--CA----AA--ACA--CT--C--T-A
BR36-20-165    --A-T---T--AT-G-----CGA--CA----AA--ACA--CT--C--T-A 5241                                              5290
HCV-1          CCCTGCTGTCCAGACCAACTGGCAAAAACTCGAGACCTTCTGGGCGAAGC
HCV-J          T--C-TG--GG--T----G----G-GCC--T----GT----------A--
HC-J6          A--C-----G---G-TTCT----CC--GG-A---CAA---------C-A-
HC-J8          G--A---A--A---T-ATCA----CC--G--T--ACAA--T-----C-A-
HD10-1-25      G--C-TAA--AGCTT----------------G--T--A----------CAC---
HD10-1-3       G--C-TAA--AGCTT----------------G--T--A----------CAC---
BR36-20-164    G--CATA--AACT------------------G--T---G---T----CAC---
BR36-20-166    G--CATA--AACT------------------G--T---G---T----CAC---
BR36-20-165    G--CATA--AACT------------------G--T---G---T----CAC---
```

Figure 6 - continued 7

| | 5292 |
|---|---|
| HCV-1 | AT |
| HCV-J | -C |
| HC-J6 | -C |
| HC-J8 | -C |
| HD10-1-25 | -- |
| HD10-1-3 | -- |
| BR36-20-164 | -- |
| BR36-20-166 | -- |
| BR36-20-165 | -- |

Figure 7

```
                    SEQ ID NO      1290        1300        1310        1320        1330
                                ITTGSPITYSTYGKFLADGGCSGGAYDIICDECHSTDATSILGIG
HCV-1      1a                   ---G----------C------------------------S-T---
HCV-J      1b                   V--------A-----------------A-------------AV-S-T---
HC-J6      2a                   V----DS-------I-----AA-----------------V---T---
HC-J8      2b                   ---AS-------------------------V---------Q---T---
BE95       5a       270

1340        1350        1360        1370        1380
                                TVLDQAETAGARLVVLATATPPGSVTVPIIPNIEEVALSTTGEIPFYGKAI
HCV-1      1a                   ------------------------I------T---------N---------
HCV-J      1b                   --------V--T-------------------T---------GQE-----R---
HC-J6      2a                   --------V-------------------T--T--S------GHE---------
HC-J8      2b                   ---------------------------------T-------PQE----V---R---
BE95       5a
```

Figure 7 - Continued 1

```
              1390       1400       1410       1420       1430
HCV-1   PLEVIKGGRHLIFCHSKKKCDELAAKLVALGINAVAYYRGLDVSVIPTSG
HCV-J   -I-A--------------------------------TG-L---------
HC-J6   --SY------------------------A-RGM-L-----------Q-
HC-J8   --AF------------------------A-RGM-V-----------Q-
BE95    --AF------------------------KQ-TS--V------A----A-

1440       1450       1460       1470       1480
HCV-1   DVVVVATDALMTGYTGDFDSVIDCNTCVTQTVDFSLDPTFTIETITLPQD
HCV-J   ---------------F---------------------------T-----
HC-J6   ---------------F-----------VA---V---------T-Q-V--
HC-J8   ---------------F-----------VA-S-I---------T-Q-V--
BE95    ---CS----------F-----------SA-------------T-V----
```

Figure 7 - Continued 2

```
             1490      1500      1510      1520      1530
          AVSRTQRRRGRTGRGKPGIYRFVAPGERPSGMFDSSVLCECYDAGCAWYEL
HCV-1  1a ----A-------RS-------T---------------------------
HCV-J  1b ----S-------RL---Y-ST--A-------V------A----------
HC-J6  2a ----S-------RL-V--Y-SS---------V------A----------
HC-J8  2b ----S-------RH----Y-SA----D----V----------------D-
BE95   5a 1540      1550      1560      1570      1580
          TPAETTVRLRAYMNTPGLPVCQDHLEFWEGVFTGLTHIDAHFLSQTKQSG
HCV-1  1a ---S--------L-------------S-------------------A--
HCV-J  1b ------------F-------------A------------G---------
HC-J6  2a ------------F-------------A----------N---M---G---
HC-J8  2b ------------I--------------------------------G---
BE95   5a                            D---S---------------Q---
BR36   3a  223
```

SEQ ID NO

Figure 7 - Continued 3

```
              1590      1600      1610      1620      1630
HCV-1   ENLPYLVAYQATVCARAQAPPPSWDQMWKCLIRLKPTLHGPTPLLYRLGA
HCV-J   -D------------------------------------------------
HC-J6   --FA--T----------K------V------T------V--------S-
HC-J8   --FA--T----------K------V------T----------------
BE95    --F--------------V--K---T-----ML------T--------P-
BR36    L-FST-T-----------------E-----------V-----------P-

1640      1650      1660      1670      1680
HCV-1   VQNEITLTHPVTKYIMTCMSADLEVVTSTWVLVGGVLAALAAYCLSTGCV
HCV-J   ----V--------I--A------------------------T--S----
HC-J6   -T-V-------I----A---Q---M------A------V--A------
HC-J8   -T-V-------I----A---Q--IM--S----A-----V--A------I
BE95    ----------I----A-------I-------------V----TV-S---
BR36    ----------C------------T-------L----------V------
```

Figure 7 - Continued 4

```
                      1690       1700                    1710       1720       1730
                      NS4-1                              NS4-5
       VIVGRVV LSGKPAIIPDREVLYREFDE MEEC      SQILPYIEQGMM LAEQFKQ
HCV-1  -------  --------------------  ----    ------------  -------
HCV-J  ---II-- ---R--V---------Q---  ----    AS--------Q-  ------- 
HC-J6  C-I--LH VNQRAVVA--K----EA---  ----    ASRAAL-E-QR-  I--ML-S
HC-J8  S-I--LH -NDRVVVA--K-I--EA---  ----    ASKAAL-E-QR-  M--ML-S
BR36   ---HIE- -G-----V--K----QQY--  ----    --AA-----AQV  I--II--E
BE95   A----II ----------------A-QQ  ----    -AS----MDETRA I--G---E
```

```
                      1740       1750                    1760
                      NS4-7
       K ALGLLQTASRQA EVIAPAVQTNWQKLETFWAKH
HCV-1  - ------------ ----------------------
HCV-J  - -----TK----- -AA--V-ESK-RA--V------
HC-J6  - IQ----Q--K-- QD-Q---AS-P-V-Q-------
HC-J8  - IQ----Q--T-- QD-Q--I-SS-P---Q------
BR36   - V----R-TQ-Q- A--E-I-T-----A--H--
BE95   - V--FIS-TGQK- -TLK--ATSV-N-A--Q---XTY
```

Figure 9

|  | SEQ ID NO | 1 | 50 |
|---|---|---|---|
| PC-3-4 | 49 | ATGAGCACGAATCCTAAACCTCAAAGAAAAACCAAAGAAACCACCAACCG | |
| PC-3-8 | 51 | ---------------------------------------------- | |
| PC-2-1 | 41 | ---------------------------------------------- | |
| PC-2-6 | 43 | ---------------------------------------------- | |
| PC C/E1 | 53 | ---------------------------------------------- | |

|  | | 51 | 100 |
|---|---|---|---|
| PC-3-4 | | TCGCCCACAGGACGTCAAGTTCCCGGGGCGGTGGTCAGATCGTTGGGGAG | |
| PC-3-8 | | ---------------------------------------------- | |
| PC-2-1 | | ---------------------------------------------- | |
| PC-2-6 | | ---------------------------------------------- | |
| PC C/E1 | | ---------------------------------------------- | |

Figure 9 - Continued 1

```
         101                                                   150
PC-3-4   TTTACTTGTTGCCGGCGCAGGGGCCCTAGGATGGGTGTGCGGGCGACTCGG
PC-3-8   --------------------------------------------------
PC-2-1   --------------------------------------------------
PC-2-6   --------------------------------------------------
PC C/E1  --------------------------------------------------

151                                                   200
PC-3-4   AAGACTTCGGAACGGTCGCAACCCCGTGGAACGGGCGTCAGCCTATTCCCAA
PC-3-8   --------------------------------------------------
PC-2-1   --------------------------------------------------
PC-2-6   --------------------------------------------------
PC C/E1  --------------------------------------------------
```

Figure 9 - Continued 2

```
        201                                               250
PC-3-4  GGCGCGCCAGCCCACGGGCCGGTCCTGGGGTCAACCCGGGTACCCTTGGC
PC-3-8  --------------------------------------------------
PC-2-1  --------------------------------------------------
PC-2-6  --------------------------------------------------
PC C/E1 --------------------------------------------------

251                                               300
PC-3-4  CCCTTTACGCCAATGAGGGCCTCGGGTGGGCAGGGTGGCTGCTCTCCCCT
PC-3-8  --------------------------------------------------
PC-2-1  --------------------------------------------------
PC-2-6  --------------------------------------------------
PC C/E1 --------------------------------------------------
```

Figure 9 - Continued 3

```
      301                                                350
PC-3-4  CGAGGCTCTCGGCCTAATTGGGGCCCCAATGACCCCCGGGGAAAATCGCG
PC-3-8  --------------------------------------------------
PC-2-1  --------------------------------------------------
PC-2-6  --------------------------------------------------
PC C/E1 --------------------------------------------------

351                                                400
PC-3-4  TAATTTGGGTAAGGTCATCGATACCCTAACGTGCGGATTCGCCGATCTCA
PC-3-8  --------------------------------------------------
PC-2-1  --------------------------------------------------
PC-2-6  --------------------------------------------------
PC C/E1 --------------------------------------------------
```

Figure 9 - Continued 4

```
        401                                           450
PC-3-4  TGGGGTATATCCCGCTCGTAGGCGGCCCCATTGGGGGCGTCGCAAGGGCT
PC-3-8  ---------------C---------------------------------
PC-2-1  -------------------------------------------------
PC-2-6  --------------------------------G----------------
PC-4-1  -------------------------------------------------
PC-4-6  -------------------------------------------------
PC C/E1 -----------Y-------------------R-----------------

SEQ ID NO  451                                           500
PC-3-4        45    CTCGGCACACGGTGTGAGGGTCCTTGAGGACGGGTAAACTATGCAACAGG
PC-3-8        46    --------------------------------------------------
PC-2-1              --------------------------------------------------
PC-2-6              --------------------------------------------------
PC-4-1              -----------------------------------------C--------
PC-4-6              --------------------------------------------------
PC C/E1             -------------------------------------------S------
```

Figure 9 - Continued 5

```
         501                                                 550
PC-3-4   GAATTACCCGGTTGCTCTCTTTCTCTATCTCTTATTCTTGCTCTTCTCTCGT
PC-3-8   ----------------------------------------------------
PC-2-1   ------------:::-------------------------------------
PC-2-6   ------------:::-------------------------------------
PC-4-1   ----------------------------------------------------
PC-4-6   ----------------------------------------------------
PC C/E1  ----------------------------------------------------

551                                                 600
PC-3-4   GTCTGACCGTTCCGGCCTCTGCAGTTCCCTACCGAAATGCCCTCTGGGATT
PC-3-8   ----------------------------------------------------
PC-4-1   ----------------------------------------------------
PC-4-6   ----------------------------------------------------
PC C/E1  ----------------------------------------------------
```

Figure 9 - Continued 6

```
        601                                              650
PC-3-4  TATCATGTTACCAATGATTGCCCAAACTCTTCCATAGTCTATGAGGCAGA
PC-3-8  --------------------------------------------------
PC-4-1  --------------------------------------------------
PC-4-6  --------------------------------------------------
PC C/E1 --------------------------------------------------

651                                              700
PC-3-4  TAACCTGATCCTACACGGCACCTGGTTGCCGTTGCCTTGTGTCATGACAGGTA
PC-3-8  --------------------------------------------------
PC-4-1  --------------------------------------------------
PC-4-6  --------------------------------------------------
PC C/E1 --------------------------------------------------
```

Figure 9 - Continued 7

```
     701
PC-3-4   ATGTGAGTAGATGCTGGGTCCAAATTACCCCTACACTGTCAGCCCCGAGC
PC-3-8   --------------------------------------------------
PC-4-1   --------------------------------------------------
PC-4-6   --------------------------------------------------
PC C/E1  --------------------------------------------------

751                                                 800
PC-3-4   CTCGGAGCAGTCACGGCTCCTCTTCGGAGAGCCGTTGACTACCTAGCGGG
PC-3-8   --------------------------------------------------
PC-4-1   --------------------------------------------------
PC-4-6   --------------------------------------------------
PC C/E1  --------------------------------------------------
```

Figure 9 - Continued 8

```
           801                                              850
PC-3-4     AGGGGCTGCCCTCTGCTCCGGCGTTATACGTAGGAGACGCGTGTGGGGCA
PC-3-8     --------------------------------------------------
PC-4-1     --------------------------------------------------
PC-4-6     --------------------------------------------------
PC C/E1    --------------------------------------------------

851                                              900
PC-3-4     CTATTCTTGGTAGGCCAAATGTTCACCTATAGGCCTCGCCAGCACGCTACG
PC-3-8     --------------------------------------------------
PC-4-1     --------------------------------------------------
PC-4-6     --------------------------------------------------
PC C/E1    --------------------------------------------------
```

Figure 9 - Continued 9

```
         901                                              950
PC-3-4   GTGCAGAACTGCAACTGTTCCATTTACAGTGGCCATGTTACCGGCCACCG
PC-3-8   --------------------------------------------------
PC-4-1   --------------------------------------------------
PC-4-6   --------------------------------------------------
PC C/E1  --------------------------------------------------

951
PC-3-4   GATGGCA
PC-3-8   -------
PC-4-1   -------
PC-4-6   -------
PC C/E1  -------
```

Figure 10

|  | SEQ ID NO |  | 3856 | 3890 |
|---|---|---|---|---|
| HCV-1 | 1a |  | ACCACTGGCAGCCCCATCACGTACTCCACCTACGG | |
| HCV-J | 1b |  | ----G---G-------------------------TT- | |
| HC-J6 | 2a |  | --G--C--GGCG------------------A--T-- | |
| HC-J8 | 2b |  | ----C--GGA-T-T----T--------------T--T-- | |
| PC1_37 | 5a | 197 | ----C--AGCTT-T-----A-----------T----- | |
| C1_48 | 5a | 199 | ----C--AGCTT-T-----A---------T------- | |
| BR36 | 3a | 222 | | |

|  |  | 3891 | 3940 |
|---|---|---|---|
| HCV-1 | 1a | CAAGTTCCTTGCCGACGGGGGTGCTCGGGGGCGCTTATGACATAATAA | |
| HCV-J | 1b | ----------------------T--A----C-----C----------- | |
| HC-J6 | 2a | ---A-------C-------T-G-C----G-A--C-----C--------C-- | |
| HC-J8 | 2b | -------TA-C--A--T--A--C--TG-A-CC--T--C-----C--C-- | |
| PC1_37 | 5a | ---------T--T--A------T--A--C-----GC----G-G--C-- | |
| PC1_48 | 5a | ---------T--T--A------T--A--C--------G-G--C-- | |
| BR36 | 3a | ---------T--T--A------T--A--C----------------- | |

|  |  | 3941 | 3990 |
|---|---|---|---|
| HCV-1 | 1a | TTTGTGACGAGTGCCACTCCACGGATGCCACATCCATCTTGGGCATCGGC | |
| HCV-J | 1b | -A----T--A-------A--T--CT-G--TA------------------- | |
| HC-J6 | 2a | -A--C--T--A-----TG--GT---CT--T--CA----TC-C-------A | |
| HC-J8 | 2b | -A--C-----A------T--AGT---C--T--TA----C--T-----T--A | |
| PC1_37 | 5a | -A--C-----------T---CA---C-----CA----TC-T--G--A--- | |
| PC1_48 | 5a | -A--C-----------T---CA---C-----CA----TC-T--G--A--- | |
| BR36 | 3a | -A--C--------------CA---------CA----TC-T--G--A--- | |

Figure 10 - Continued 1

```
               3991                                              4040
HCV-1    ACTGTCCTTGACCAAGCAGAGACTGCGGGGCGAGACTGGTTGTGCTCGC
HCV-J    --A-----G--T--G-------G--T--A---C-G--C--C-------
HC-J6    --A-----C--T---------A--C---TC--G---AAC---A--G--
HC-J8    --A--------T---------T----C--A--C-TC--G--A--G--TT-G--
PC1_37   -----------G----------------G--T--A--T--G--C----CT-G--
PC1_48   -----------G----------------G--T--A--T--G--C----CT-G--
BR36     -------------------------------G--T--A--T--G--C----CT-G--

4041                                              4090
HCV-1    CACCGGCCCACCCCCTCCGGGCTCCGTCACTGTGCCCCATCCCAACATCGAGG
HCV-J    -----------G------A--GA----C---A--C------------
HC-J6    T--G--T--G--C--C--G--A--G--AACC----C--------A-----
HC-J8    ---A-----G-----C--C--TA-G--G--AACT-----CAGT-------A-----
PC1_37   ---G-----------C-----C---AGT--G--AAC----C-------
PC1_48   ---G-----------C-----C---AGT--G--AAC----C-------
BR36     ---G-----------C-----C---AGT--G--AAC----C-------

4091                                              4140
HCV-1    AGGTTGCTCTGTCCACCACCGGAGAGATCCCTTTTTACGGCAAGGCTATC
HCV-J    -A--G--C-----A--T-----T--C--C--T---A--C--
HC-J6    ---G--C---CGGGCAGGAG--T-----C--C--T--G-G--G--T
HC-J8    ---G--C---TGGTCA-GAG--C--------T-----A-----T
PC1_37   -A--G--C---C-TCAGGAG--G-----G-T--C--C-----GA--C--T
PC1_48   -A--G--C---C-TCAGGAG--G-----G-T--C--C-----GA--C--T
BR36     -A--G--C---C-TCAGGAG--G-----G-T--C--C-----GA--C--T
```

Figure 10 - Continued 2

```
        4141                                              4190
HCV-1   CCCCTCGAAGTAATCAAGGGGGGAGACATCTCATCTTCTGTCATTCAAA
HCV-J   ---A-T--G-CC--------------A--G-------------C----C---
HC-J6   ---GTC-TAC----------A--A----CT-G-------C--C-----
HC-J8   ----A-CTT-C---------------C----CT-G-------T--C-----
PC1_37  -----T-CTT-T--A--------T--T-G---------C--------
PC1_48  -----T-CTT-T--A--------T--T-G---------C--------
BR36    -----T-CTT-T--A--------T--T-G---------C--------

4191                                              4240
HCV-1   GAAGAAGTGCGACGAACTCGCCCGCAAAGCTGGTCGCATTGGGCATCAATG
HCV-J   -------T------G-------------ACA-GCC-C--AC---
HC-J6   -------T------G------G--GGCC--TCGG-GTA----T-G--C-
HC-J8   -------G------G------A--GGCC--CCGG-GCA----TG-----
PC1_37  -----A--A--T--T----------AAGC-A---AC-AGCC----G-G--C-
PC1_48  -----A--A--T--T----------AAGC-A---AC-AGCC----G-G--C-
BR36    -----A--A--T--T----------AAGC-A---AC-AGCC----G-G--C-

4241                                              4290
HCV-1   CCGTGGCCTACTACCCGGGTCTTGACGTGTCCGTCATCCCGACCAGCGGC
HCV-J   -T--A--G--T----G--T------C--T------A----T----A
HC-J6   -A------A-----A-A--G--G----C----A--A--A--TCAG--A
HC-J8   ----T--A-----TA-G------C-------T--A--TCAA--A
PC1_37  ----T--A--T--TA-A-------A----CG-------A--C--A-CA--A
PC1_48  -----A--T--TA-A-------A----CG------------C--AGCA--A
BR36    -----A--T--TA-A------A----CG------------C--AGCA--A
```

Figure 10 - Continued 3

```
             4291                                              4340
HCV-1    GATGTTGTCGTCGTGGCAACCGATGCCCTCATGACCGGCTATACCGGCGA
HCV-J    --C--C--T-------A--C--T--A-----G--T-T------------
HC-J6    --C--A--G-----C--C-----C--------G--G-T----T--A---
HC-J8    --C--G--G--T--C--C--T-----A-----T--G--C---------
PC1_37   --C--G-----GTGCAGC----C--G-----G--A-TC-----------
PC1_48   --C--G-----GTGCAGC----C--G-----G--A-TC-----------
BR36     --C--G--------------C-----G--------G--A-TC--------

4341                                              4390
HCV-1    CTTCGACTCGGTGATAGACTGCAATACGTGTGTCACCCAGACAGTCGATT
HCV-J    ---T-----A-----C-----C--A------------------------
HC-J6    ---T-----C-----C-----CGTAGCG-----T--AGTT--A--C---
HC-J8    ---T-----C-----C-----T---GTTGCA---T-T----TT--T--C-
PC1_37   ---T-----T-----C---------CT-CGCC----T-----T--G--C-
PC1_48   ---T-----T-----C---------CT-CGCC----T-----T--G--C-
BR36     ---T-----T-----C---------CT-CGCC----T-----G--G--C-

4391                                              4440
HCV-1    TCAGCCTTGACCCTACCTTCACCATTGAGACAATCACGCTCCCCCAGGAT
HCV-J    ----T-G--T--C--------------G--CA-----G-----A--C
HC-J6    ----T-G-----C--A-------AACC---CAG--TG----T--A--C
HC-J8    ------G-----A------------CACC---TCAA--CG----T-----C
PC1_37   ---T-G--T--C--T-----------T-C----AG-G-----C
PC1_48   ---T-G--T--C--T-----------T-C----AG-G-----C
BR36     ---T-G--T--C--T-----------T-C----AG-G-----C
```

Figure 10 - Continued 4

```
                4441                                                         4490
HCV-1    GCTGTCTCCCGGCACTCAACGTCGGGGCAGGACTGGCAGGGGAAGCCAGG
HCV-J    --G--G--G--TG-G--G--G--A--T---------C-G-AGT--
HC-J6    -------A---T-GC--G--C-----C-C--G------A-GA-TG--
HC-J8    ------------T-G------A-A--G--A-----G-------CGATTG--
PC1_37   --A--G----A-A-GC---G---T------C-C---G--A--T-G--AC--
PC1_48   --A--G---A-A-GC---G---A---------C-C---G--A--T-G--AC--
BR36

4491                                                         4550
HCV-1    CATCTACAGATTTGTGGCACCGGGGGAGCGCCCCTCCGGCATGTTCGACT
HCV-J    -------G----A-T--A--A--G----A-----
HC-J6    T--T--T-G-A---TT-CA-T--T-----AG---A--A----T---A
HC-J8    -G-T-----G-A---TT-GT-A--C---A-G--G--T--G-------A
PC1_37   ---A----C-G-A---CT-GG-T--A---A-A--G--T-------
PC1_48   ---A---C-G-A---CT-GG-T--A----A-A--N--T-A-------
BR36

4551                                                         4590
HCV-1    CGTCCGTCCTCTGTGAGTGCTATGACGCAGGCTGTGCTTGGTATGAGCTC
HCV-J    -C--G---G------------------C--
HC-J6    GTGTA--G-------C-----C--T----GGCC--A---------T
HC-J8    GCGTA--G-------C-----T--C--GGCA--C-----C----T
PC1_37   -CGTG--G-----------T--C--A----A---C--T--G
PC1_48   -CGTG--G-----------C--T--A----G------T--G
BR36
```

Figure 10 - Continued 5

```
         4591                                               4640
HCV-1    ACGCCCCGCCGAGACTACACAGTTAGGCTACGAGCGTACATGAACACCCCGGG
HCV-J    ----------T----CT-G------T-G--G--T---C-A--T--A--A---
HC-J6    --A--A--G--T--------C--C---CA----A--TT-C-----A--T---
HC-J8    --A--T--T---------G--G--A--C--G--T--TT-C-----G--C---
PC1_37   --T--T--------------C--G---T-G--C--T----N-A-----C---
PC1_48   --T--T--------------C-----T-G--C--T----------A------
BR36     --T--T--------------C-----T-G--C--T-----------------

4641                                               4690
HCV-1    GCTTCCCCGTGTGCCAGGACCATCTTGAATTTTGGGAGGGGTCTTTACAG
HCV-J    -T-G-----C----------C--A--G--C-----A------C------
HC-J6    TT-G--T------A------G-----G----------CA--T--C--C-
HC-J8    TT-G----A--T--A-----C--G--G--C-----A--CG---------
PC1_37   ---C--T--C--T-------T-G-----C-----C-----G--G--C--G
PC1_48   ---C--T--C--T-------T-G-----C-----C-----G--G--C--G
BR36     -------------------------A--C--------A--------C--T 4691                                               4740
HCV-1    GCCTCACTCATATAGATGCCCACTTTCTATCCCAGACAAAGCAGAGTGGG
HCV-J    -----C--C---------------CT-G-----C--A---GCA--A
HC-J6    ----A--C-----------A-----C--T-----A------ATCG-
HC-J8    -T---A--C--T--C-----C-----C-----G-----AG-A--A
PC1_37   -G-----A-C--C--C--T---A-G--G--A--C--A-----G-----
PC1_48   -G-----A-C--C--C--T---A-G--G--A--C--A---G-----
BR36     -A--A-----C--------------G--A------T-----CAG--A
```

|          |
|----------|
| HCV-1    |
| HCV-J    |
| HC-J6    |
| HC-J8    |
| PC1_37   |
| PC1_48   |
| BR36     |

Figure 10 - Continued 6

```
          4741                                              4790
HCV-1     GAGAACCTTCCTTACCTGGTAGCGTACCAAGCCACCGTGTGCCGCTAGGGC
HCV-J     --C----C--C-----------A-------A--------C----------
HC-J6     --A---TT-CG-A---T-AAC--C-----G--T--A--------------
HC-J8     --A---T--G-G--T-AACG--C-----G-------A--A------C---
PC1_37    ----TT-C--A-----T---------------A--A--C--T-T-C-C--
PC1_48    ----TT-N--A-----T---------------A--A--C--T-T-C-C--
BR36      CTC---T-CT-G-T----ACT--C--------------T--------C-C 4791                                              4840
HCV-1     TCAAGCCCCTCCCCCCATCGTGGGACCAGATGTGGAAGTGTTTGATTCGCC
HCV-J     ---G--T--A--T--------A---------C-C--A--G-
HCV-J     CA------C-----G--C-----GTC-----------C----A-
HC-J6     CA------C-----G--C-----GTC-----------C----A-
HC-J8     AA-G--------T--T-------GT------------C-A-C-A-G-
PC1_37    GA----G--C------CAGC-----ACA-------A--CA--C-C--T-
PC1_48    GA----G--C------CAGC-----ACA-------A--CA--C-C--T-
BR36      G--G--T--------AGT--------G----------C--CG-A--G-

4841                                              4890
HCV-1     TCAAGCCCCACCCTCCATGGGCCAACACCCCTGCTATACAGACTGGGCGCT
HCV-J     -A-------A--G-----------G-------G-----G--A--A--C
HC-J6     -------A---GTG--C--C----T--C--G---C-CT-----T--
HC-J8     ----A--T-A--GAC---C----C--T--C--C--CT----T--C
PC1_37    ----A--G--NT-AAC---C--T--T-----CT-G---G----GC-C
PC1_48    ----A--G--TT-AAC---C--T--T-----CT-G---G----GC-C
BR36      -T-----A--A-----A--T--G--T--T----TC-GT----GC--
```

Figure 10 - Continued 7

```
                                                            4940
       4891
HCV-1  GTTCAGAATGAAATCACCCTGACGCACCCAGTCACCAAATACATCATGAC
HCV-J  ----------A----GG---T--C--A----CA-A--------------G-
HC-J6  ---ACC---C--GG------C-----T--G--G-------------GCC--
HC-J8  ---GACC--GG---------T----C--G--G--------------GCC--
PC1_37 -------C--------------A-------CA----------G---T--G-
PC1_48 -------C--N-----------A-------CA----------G---T--G-
BR36   ---C--A----------TG-T----A----CA----------G---T--G-

4990
       4941
HCV-1  ATGCATGTCGGCCCGACCTGGAGGTCGTCACGAGCACCTGGGTGCTCGTTG
HCV-J  -------T---------------------------T--------A--A---
HC-J6  C-----CAA-------T-----A-G--C-----G-----CT-A-C--
HC-J8  G-----CAA-T-----C---A--A-G---T-A-----C--G-CG---
PC1_37 T-----T--G---T----T------A-T--C----T--------T--G--
PC1_48 T-----T--G---T----T------A-T--C-N----T------T--G--
BR36   ------A--T---T----T----A--AAC--C--------------TT-GC--

5040
       4991
HCV-1  GCGGGCGTCCTGGCTGCTTTGGCCGCGTATTGCCTGTCAACAGGCTGCCGTG
HCV-J  -----A------T--G---C----------C------A-G-----A----
HC-J6  -G---G---T---G--CG-C--------A--T--C----G--G--C--G--T--T
HC-J8  -G---G--A--C--CG-----A--T--C----G--G--C--G--T----A-T
PC1_37 -G-------TG---G--CC----C----G--C---T--A-GGTG--T-CG--A
PC1_48 -G-------TG---G--CC----C----G--C---T--A-GGTG--T-CG--A
BR36   -A--G-------C---CC--A--G--C-----T------GTC--T--T
```

Figure 10 - Continued 8

```
        5041                                              5090
HCV-1   GTCATAGTGGGCAGGGTCGTCTTGTCCGGGAAGCCGGCAATCATACCTGA
HCV-J   ----T-----------A--A-----G--A--TG-T--T--C--
HC-J6   TG--CA-C---C-CT-GCA-G-TAA-CA-CGAG-C-TCG-TGC---G--
HC-J8   TC--CA-T---C-CC-ACA-C--AAT-ATCG-GT--TTG-GGCC--C--
PC1_37  -C-----C--T---A--A--C-C--T-----A--T---C----T--C--
PC1_48  -C-----C--T---A--A--C-C--T-----A--T---C----T--C--
BR36    --G--T----TCATA---AGC--GGG--C-----------G-T--A--

5091                                              5140
HCV-1   CAGGGAAGTCCCTCTACCGAGAGTTCGATGAGATGGAAGAGTGCTCTCAGC
HCV-J   ---------------AG----------------------TG--TCA-
HC-J6   --A---G----TGAG-CT--T-----G--A--TG-CTCTA
HC-J8   --A---A--T-A-TGAG-CC--T-----A---G-CTCCA
PC1_37  T----G--AT-A---AGC-A--T--------G----------GGCCT
PC1_48  T----G-CAT-A---AGC-A--T--------G----------GGCCT
BR36    --AA--G--GT-G--T-A-C-A-A------------------A--AG 5141                                              5190
HCV-1   ACTTACCGTACATCGAGCAAGGGATGATGCTCGCCCAGCAGTTCAAGCAG
HCV-J   --C-C--T--------------A---CA-----------A---
HC-J6   GAGCGG-TCT---T--AG-G---CA-CG-A-A----AT-C-G---TCC
HC-J8   -AGCCG-CCT---T---G-----CA-CG-A-G--G---AT-C----ATCT
PC1_37  CG--G--C--T--G--CG--ACACGTGCCA-T---GAT-A---AG-
PC1_48  CG--G--C--T--G--CG--GACACGTGCCA-T---GA--A---AG-
BR36    CTGCC--A--T-----A----CTCA-G-AA-A--TC-C------G-A
```

Figure 10 - Continued 9

```
              5191                                                    5240
HCV-1   AAGGCCCCTCGGCCTCCTGCAGACCGCGTCCCGTCAGGCAGAGGTTATCGC
HCV-J   ----G----AT-G-----A---CA--AAG--A--G----C-GCT--
HC-J6   ---AT--AA---T-AT-----CAA--T---AAA--A--TC-A-AC--ACA
HC-J8   ---ATA-AA-------A---ACAG--CA-AA-G--A--TC-A-AC--ACA
PC1_37  --A-TG------T--A-CAGC--GA-CGG--AGA----T--AAC-C-GAA
PC1_48  --A-TG------T--A-CAGC--GA-CGG--AGA----T--AAC-C-GAA
BR36    --A-T---T--AT-G------CGA--CA---AA--ACA--CT--C--T-A 5241                                                    5290
HCV-1   CCCTGCTGTCCAGACCAACTGGCAAAAACTCGAGACCTTTCTGGGCGAAGC
HCV-J   T--C-TG--GG--T----G----G-GCC--T---GT------A-
HC-J6   A--C----G---G-TTCT----CC--GG-A---CAA----C--A-
HC-J8   G--A---A-A---T-ATCA----CC--G--T--ACAA--T----C--A-
PC1_37  G--G--A-C-AC-T-TGTG---A-C--GGCT---CAG-----N-C-CAT
PC1_48  G--G--A-C-AC-T-TGTG---A-C--GGCT---CAG-----C-CAT
BR36    G--CATA--AACT-------------G--T---G----T---CAC---

5291
HCV-1   AT
HCV-J   -C
HC-J6   -C
HC-J8   -C
PC1_37  -C
PC1_48  -C
BR36    --
```

Figure 11

```
        1286
HCV-1   TTGSPITYSTYGKFLADGGCSGGAYDIIICDECHSTDATSILGIGTVLDQAETAGARLVV
HCV-J   ---G-------C------------------------S-T---------------------
HC-J6   ---A------------A--------------AV-S-T---------V--T----------
HC-J8   ----------------I----AA--------------V--T---------V----------
PC-1-48 ---DS----------------------------V-------Q--T---------------
PC-1-37 ---AS-----------------------------H-V----Q--T---------------

1346
HCV-1   LATATPPGSVTVPHPNIEEVALSTTGEIPFYGKAIPLEVIKGGRIILIFCIISKKKCDELAA
HCV-J   ------------I---------N------------I-A-----------------------
HC-J6   -------T----T---------GQE---R---SY-------------------------
HC-J8   --T--T--S-------------GHE-------AF-------------------------
PC-1-48 -X-X--------T---------PQE---V---XR----AF-------------------
PC-1-37 ---X--------T---------PQE-V---R----AF----N-----------------
```

| | SEQ ID NO |
|---|---|
| | 56 |
| | 58 |

Figure 11 - Continued 1

```
       1406
HCV-1  KLVALGINAVAYYRGLDVSVIPTSGDVVVVATDALMTGYTGDFDSVIDCNTCVTQTVDFS
HCV-J  --TG--L-----------------------------F-----------------------
HC-J6  A-RGM-L-------------------------Q---F------------------VA---V---
HC-J8  A-RGM-V-------------------------Q----------------------VA-S-I---

1466
HCV-1  LDPTFTIETITLPQDAVSRTQRRGRTGRGKPGIYRFVAPGERPSGMFDSSVLCECYDAGC
HCV-J  ------------T------A-----RS------T----------------------
HC-J6  -----T-Q-V---S-----RL---Y-ST--A---V------------A
HC-J8  -----T-Q-V---S-----RL-V-Y-SS------V------------A

1526
HCV-1  AWYELTPAETTVRLRAYMNTPGLPVCQDHILEFWEGVFTGLTIIIDAHFLSQTKQSGENLPY
HCV-J  ------S-------L-------------------S----------------A-D---
HC-J6  --------------F---------------A---------------------FA-
HC-J8  --------------F---------------A-----------G---FA-
```

Figure 11 - Continued 2

```
        1586
HCV-1   LVAYQATVCARAQAPPPSWDQMWKCLIRLKPTLHGPTPLLYRLGAVQNEITLTHPVTKYI
HCV-J   ------------------------------------------------------V---I-
HC-J6   -T------------T-------K-----T------V------S-T-V------V-----
HC-J8   -T--------------------K-----V------T------T--V------T--V---

1646
HCV-1   MTCMSADLEVVTSTWLVGGVLAALAAYCLSTGCVVIVGRVVLSGKPAIIPDREVLYREF
HCV-J   -A---------------------------T--S-----II---R-V------Q--
HC-J6   A---Q----M-----A-----V-----A---C-I--LHVNQRAVVA--K----EA-
HC-J8   A---Q----IM--S-----A-----V-----A---IS-I--LH-NDRVVVA--K-I--EA-
PC-1-48 -A--------I-X-------V-X--------TV-S-A----II---------A--XQ-
PC-1-37 -AF--P----I-X-------V-T-XX-----TV-S-A----II---------X---QQ- 1706                                                    1764
HCV-1   DEMEECSQHLPYIEQGMMLAEQFKQKALGLLQTASRQAEVIAPAVQTNWQKLETFWAKH
HCV-J   ----AS---------Q----------------TK---AA--V-ESK-RA--V----
HC-J6   ----ASRAAL--E-QRI--ML-S-IQ----Q--K--QD-Q----AS-P-V-Q----
HC-J8   ----ASKAAL--E-QRM--ML-S-IQ----Q--T--QD-Q--I-SS-P---Q----
PC-1-48 ----AS---MDETRAI-G---E-V--FIS-TGQK--TLK--ATSV-N-AXQ---TY
PC-1-37 ----AS---MDETRXI-G---E-V--FIS-TGQK--TLK--ATSV-N-ADQ--XTY
```

Figure 12

```
                330       340       350       360       370
                 |         |         |         |         |
HCV1    PTTALVMAQLLRIPQAILDMIAGAHWGVLAGIAYFSMVGNWAKVLVVLLL
HCVJ    ----------------VS-------VV---V------L-Y-------I-M---
HCJ6    --ATMIL-YAM-V-EV-I-I-G-------MF-L-----Q-A-----V-I---
HCJ8    --LTMIL-YAA-V-ELV-EI-F-G-----VF-L-----Q-A-----IAI---
NZL1    -AVGM-V-HV--L---TLF-IM-------I-----L--Y--Q-----AIIMVM
HCVTR   --IG--ISH-M-L---TLF-LVS-T------M--L----Q-------VI--IM
BE95    -------LV-----VVI-I----S-----FAA--YAS-A---T---VL--F--

380       390       400       410       420
                 |         |         |         |     *   |   *
                   E2
HCV1    FAGVDA ETHVTGGSAGHTVSGFVSLLAPGAKQNVQLINTNGSWHLNSTAL
HCVJ    ------|H------RVASSTQSL--W-SQ-PS-KI--V------I-R---
HCJ6    A-----|Q--TV---TA-NARTLTGMFSL--R-KI------I-R---
HCJ8    V-----|------T-YSS-QE--R--A--AG-FTT----LY------I-R---
NZL1    --S---|------H-YT---T-SRHTQA-AG-FDI-PQ-KL--V------I---
HCVTR   --S---|------N-YT-A--MAQSIYRLTDIFST-PS-KL--V-S----
BE95    ------|------T-QIS---SAQ-TY-IA-FITR--Q-KL------I-R---
```

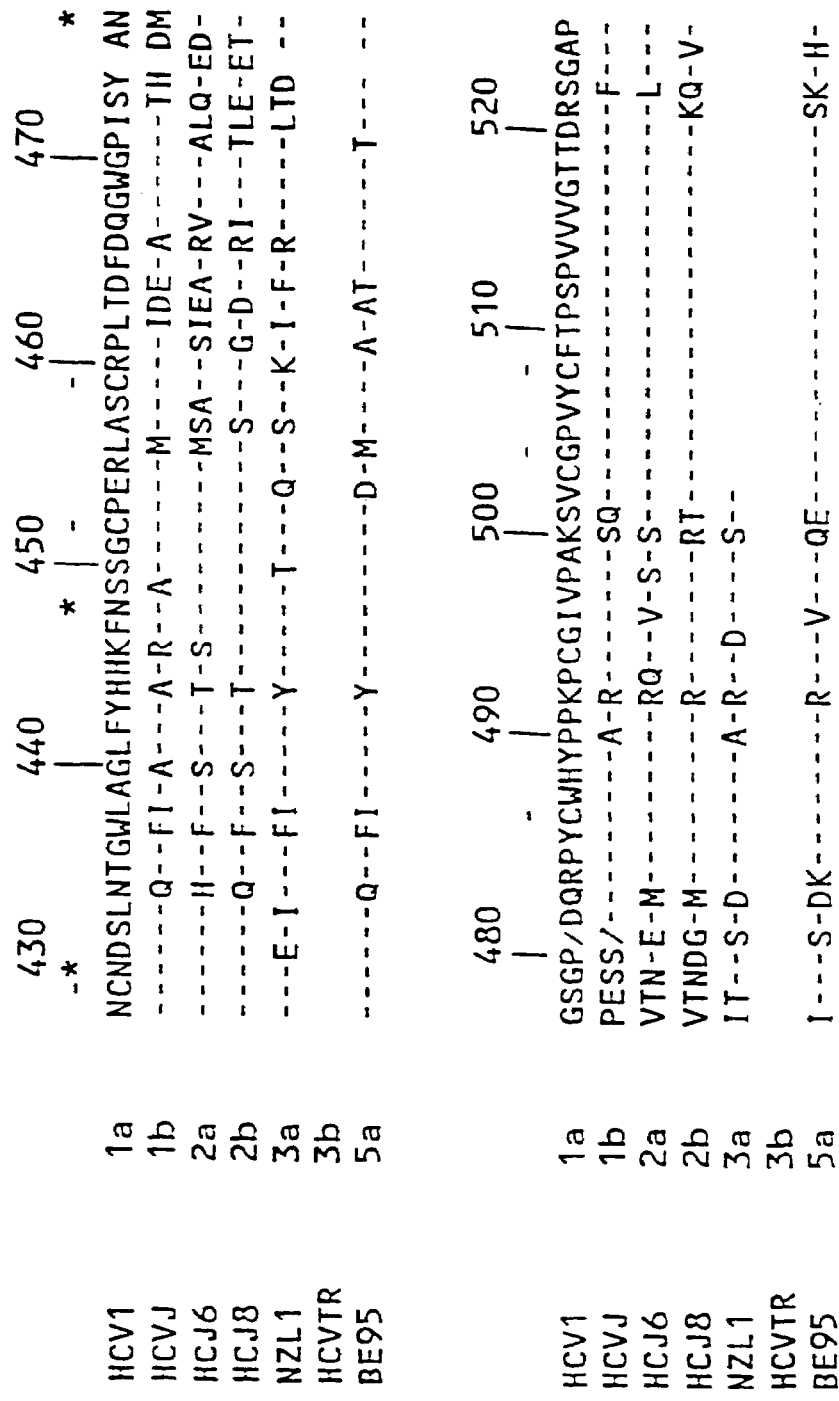
Figure 12 - Continued 1

Figure 12 - Continued 2

```
                      530        540
                       |          *
HCV1    1a    TYSWGENDTDVFVLNNTRPPL
HCVJ    1b    -----E---LL--TRP-QG
HCJ6    2a    --T--E----L---S----Q
HCJ8    2b    --T--E----L---S----R
NZL1    3a
HCVTR   3b
BE95    5a    --N--S-V--F-LM-----I
```

Figure 13

```
                    980
         SEQ ID     CCCCTACGACGGGCGTTGGTGTAATGGCTCAGCTGCTCCGGATCCCACAAGCC
HCV-1      1a       -----------G-A-----GG-A------------------A-----------
HCH-H      1a       ---------------------------------------------------
HC-J1      1a       -------G---------------------------------------------
HCV-J      1b       -A-----A---CC-A--GG-A--AT-G------A-------------------T
HCV-BK     1b       -G--C--A---CC-A--GG----T-G-------T-A-----------------T
HCV-J4.83  1b       -A-----A---CC-A--GG----T-G-------T-------------------T
HC-J4.91   1b       -A-----A---CC-A--GG----T-G-------T-A-----------------T
HCV-JTA    1b       -G-----A---CC-A--GG----T-G-------T-A-----------------T
HCV-JTB    1b       -G-----A---CC-A--GG----T-G-------T-A-----------------T
HCV-CHINA  1b       -G-----A---CC-A--GG----T-G-------T-A----------T------T
HCV-T      1b       -G-----A---TC-A--GG----T-G-------T-A----------T------T
HCV-JK1    1b       -G-----A---C--A--GG----T-G-------T-A-----------------T
HCUNK      1b       -A-----A---CC-A--GG-A--AT-G------A-------------------T
HCV-N      1b       -A-----A---CC-C----G---T-A-------T-A-----------------T
HC-J6      2a       -G--C--G-TA-CA--A-CC---GT-CGC-A-G---CG----CG-G-T-----
HC-J8      2b       -T--A--TCTTA-CA--A-CC-C-CT-CGCCGCT-TG-T--CG--CTG-----
HC-J5      2a       -A--C--G-CA-CA--A-CC---GT-CGC-A-G---CG----CG-G-TT----
HC-J7      2b       -A--A--TCTTA-CA--A-CC-C-CT-TGCCGCT-TG-T--TG-GCTA-----
NZL1       3a       ----A------GG-------G-----TG-C--G----TT-A--C--GA-----
HEM26      3a       ---CG-TGT--GTA------G-----CG-C--G----TT-G--C--GA-----
TH85       3a       ---CG-TGT--GTA------GG-A--TG-C--G----TT-G--C--GA-----
US114      3a       ---CG-CGT--GTA------GG----CG-T--G----TC-G--C--GA-----
BE95       5a      157  -A------A--TC--C-GG--C------T-A--G------T--C----TG
```

Figure 13 - Continued 1

```
                      1030
                      ATCTTGGACATGATCGCTGGTGCTCACTGGGGAGTCCTGGCGGGCATAGC  AA
HCV-1      1a         --------------------------------------------------  --
HCH-H      1a         ---A----------------------------------------------  --
HC-J1      1a         -----T--------------------------------------C-T---  --
HCV-J      1b         G-------G--G--G--G--C-----T-----------A-----------  --
HCV-BK     1b         G----------G--G--G--C-------------------------C-T-  --
HC-J4.83   1b         G----------G--G--G--C-------------------------C-T-  --
HC-J4.91   1b         G----------G--G--G--C-------------------------C-T-  --
HCV-JTA    1b         G-----T----G--G--G--C-------------A-----------C-T-  --
HCV-JTB    1b         G-----T----G--G--G--C-------------------------C-T-  --
HC-CHINA   1b         G-----T----G--G--G--C-------------A-----------C-T-  --
HCV-T      1b         G-----T----G--G-TG--C-------------------------C-T-  --
HCV-JK1    1b         G----------G--G-GG--C----------A--------------C-C-  --
HCUNK      1b         G----------G--G-TG--C-------------------------C-T-  --
HCV-N      1b         G---A------G--GA-A--GT-C--------------------C-T---  --
HC-J6      2a         ---A--C----G------G--G--------T-----C---A---TTC-T-  -G
HC-J8      2b         G---C--A---C--T-GC--G--------T-----T---GG---TTT-T-  -G
HC-J5      2a         G---C--C---C--TTTC-C-GC--G---T-----C---A---TTC-C--  --
HC-J7      2b         ---A--A----C--TAGC--G--------T-----C---GG---TTT-T-  -G
NZL1       3a         G---C--T-GG-TG-TTC-C-GC--G---T-----CA--T---------  -C
HEM26      3a         T-G---C----A--G--C--------C--T-----CA--T---------  -C
TH85       3a         T-G---C----A--A--C--G--C--C--T-----CA--T---------  -C
US114      3a         T-G---C--T-AG-A--C--G--A--C--T-----CA--T---------  -C
BE95       5a         G---A--T---C------A--GAGC--G----G------T---TTT-C-GCC  --
```

Figure 13 - Continued 2

| | | 1080 | | | | | |
|---|---|---|---|---|---|---|---|
| HCV-1 | 1a | GTATTTCTCCATGGTGGGGAACTGGGCGAAGGTCCTGGTAGTGCTGCTGC | | | | | |
| HCH-H | 1a | ---------- | ---------- | ---------- | ---------- | -T--- | ----- |
| HC-J1 | 1a | ---------- | ---------- | ---------- | ---------- | ----- | --A-- |
| HCV-J | 1b | C--C-AT--- | ---------- | ---------- | -T-------- | -T--A-T-- | -A---A- |
| HCV-BK | 1b | C--C-AT--- | -----C---- | ---------- | -T-------- | ---A-T-- | -A---A- |
| HC-J4.83 | 1b | C--C-AT--- | -------A-- | ---------- | -T-------- | ---A-T-- | -GC--A- |
| HC-J4.91 | 1b | C--C-AT--- | -------A-- | ---------- | -T-------- | ---A-T-- | -GC--A- |
| HCV-JTA | 1b | C--C-AT--- | ---------- | ---------- | -T-------- | -T--A-T-- | -A--T-A- |
| HCV-JTB | 1b | C--C-ATG-- | ---------T | ---------- | -T-------- | -T--A-T-- | -A--T-A- |
| HCV-CHINA | 1b | C--C-AT--- | ---------- | ---------- | -T-------- | -TT--A-T-- | -A---A- |
| HCV-T | 1b | C--C-AT--- | ---------- | ---------- | -T-------- | -T--AA-T-- | -A---A- |
| HCV-JK1 | 1b | C--C-AT--- | ---------- | ---------- | -T-------- | -T--A-T-- | -A---A- |
| HCUNK | 1b | C--C-AT--- | ---------- | ---------- | -T-------- | -T--AA-T-C-A- | -A---A- |
| HCV-N | 1b | C--C-AT--- | ---------- | ---------- | -T-------- | -TT--A-T-- | -A---A- |
| HC-J6 | 2a | C----C---- | ----T--CA- | -AGCG----- | -A--A----- | -G-T--CA-T-- | -TT---- |
| HC-J8 | 2b | C--------- | -------CAA | -AGCG----- | -C--A----- | -A-C--CCA-C-- | -C---T- |
| HC-J5 | 2a | C----C---- | ----T--CA- | -AGCG----- | -C-------- | -G-T--CA-C-- | -T---- |
| HC-J7 | 2b | C--------- | -------CA- | -AGCG----- | -C--A----- | -A-T--CCA-C-- | -C---C- |
| NZL1 | 3a | C-------A- | -------CA- | ----C----- | -C-------- | -GCAA-CA-CA- | -G-TA- |
| HEM26 | 3a | C-------A- | -------CA- | ----C--T-- | -C-------- | -GCTA-CA-CG- | -G-TA- |
| TH85 | 3a | C-------A- | ------CAA- | ---------- | -C-------- | -GCTA-CA-CA- | -G-TA- |
| US114 | 3a | C-------A- | -------CA- | ----C----- | -C-------- | -GCTA-CA-CA- | -G-TA- |
| BE95 | 5a | A--C-ATG-ATC | ------CT-- | ------A-C- | ---------- | -G--C-G--CT- | -T-T- |

Figure 13 - Continued 3

```
           1130
HCV-1    1a  TATTTGCCGGGCGTCGACGCGGAAACCCACGTCACCGGGGAAGTGCCGGC
HCH-H    1a  -------------------------------------A-----------
HC-J1    1a  -G-----------------------AT----T-------CAA----C--
HCV-J    1a  -C----------T---------G-C-C-------G--A-----G-TA-C-
HCV-BK   1b  -T----------T---------G---T-------G--A-----GGCGCAA-C-
HC-J4.83 1b  -C---C--------------G-----T--ACGT-G-----GGCG---A--
HC-J4.91 1b  -C------------------G---CG---T--ACGT-G-----GGTG-----
HCV-JTA  1b  -C------------------G---TC--TT--ACG--A-----GTCGCAA-CT
HCV-JTB  1b  -C------------------G---TC--TT--ACG--A-----GTCGCAA-CT
HCV-CHINA 1b -C------C-----------T-G--T---T------CGT-T-----GGCGCAG---
HCV-T    1b  -T------------------G-AGT---AT---GT-A--A--G-CA-TG-C-
HCV-JK1  1b  -C------------------G-ACT---T----GT-A-T---GCA---AA--
HCUNK    1b  -C-------------------GAACC------G--A-----GGCGCAA--T
HCV-N    1b  -T-----------------G-C-C---C------T-ACA--G-----GCAC-T-C-
HC-J6    2a  -GGCC---G--G--A--G--C---------TAC-GTT---TTC-A---CG
HC-J8    2b  -TG---G--A--G--T--AACC---T-TTC--G---CCAGGAA--G--T
HC-J5    2a  -GGCC--T--A--G--T----A-C---G-AC-GTT-C---TTC---T-CG
HC-J7    2b  -TG-C--A--A--G--T--AGC------A---T--C---CAA--G-C-
NZL1     3a  -G---CT-A--G------T---CC-C--AT-TAC----T---C-C--ATCT
HEM26    3a  -G---T-A--G------T---C---AT-TAC----T---C---TG-CT
TH85     3a  -G---T-A--G------T---C--G--A-G-A---T---C-C---A-CT
US114    3a  -G---T-A--G------T--CAGC--A--TA----T---C-CTC-ATG-CT
BE95     5a  -G---A--G------T--TACT---GA-TT-G--C--CTCCAG---C--
```

Figure 13 - Continued 4

```
              1180
           CACACTGTGTCTGGATTTGTTAGCCTCCTCGCACCAGGCGCCAAGCAGAA
HCV-1   1a -G---CAC-G----GC-----G-T----TA-------------------
HCH-H   1a -G-G-CA-------------C----T---A----------T--------
HC-J1   1a TC--GCACCCAGA-CC-C--GTC-TGG---T---A----C-ATCT----
HCV-J   1b A-A--CACCAACA-GC-C--GTC-A-GT------AGT--GC-GTCT---
HCV-BK  1b ----CACC--CACGC-C-CGTC-----T---T---T--G--GTCT----G
HC-J4.83 1b -G---CACC--C--G--CACGTC-----T---T---T--G--GTCT----
HC-J4.91 1b -G--CACACCCAGA-CG--CACGTC-T--T---A-C-A---GC-GGCC----G
HCV-JTA 1b -G-CACACCCAG--GG-C-CGTC-T--T---A-C-------GC-GGCC----
HCV-JTB 1b -G-T-CACCCTC--G--CACGTC-----T--TA----T--G---TCT----
HCV-CHINA 1b -G---CACCCACA-TC-C-CGTCT---T-TA---A--G--GTCC-----
HCV-T   1b -G--CACCCGGC-CG--CGTC-T--T---AGT--T---T-GGCT-----
HCV-JK1 1b -GGG-C-CTAGCTCGC-AACGTC---T-TAGC--T--GC-GGTT----C
HCUNK   1b ---CTCACCAGC--G--C-CGG-----T-TA----T--GC-GTCT----G
HCV-N   1b --T-AC-CCAGGACCC-CACCG--A-GT--T-C-TT--T---G------
HC-J6   2a -GT--C--CG-G--G--C-C-G---CACC---A-GT--T-CT-T----G
HC-J8   2b GCA--CACCAGG--C--CACC---CACC---A-T--TA-TA-T--T---
HC-J5   2a --T--C--TAGA--G-C-CC--A--T--AGC--T---T--CG----G-
HC-J7   2b -GTCA-ACCCAA-CG---C-G-T--TT-T-ACAT--C--C-A------
NZL1    3a --TG--ACCAGA--GA-A-C---T--TT-TA-TGTG-----CGC-----
HEM26   3a --TGA---C-ACA-G---C-----TT--AAT-GG----CGA--A
TH85    3a -GTGA---C-ACA-G--CAC-G--T-TT---C-GG--C---GT-----
US114   3a --A--GAC--A---CA-C-CCTCAT-TA--A-C-GC-----GC------
BE95    5a
```

Figure 13 - Continued 5

```
                  1230
                  CGTCCAGCTGATCAACACCAACGGGCAGTTGGCACCTCAATAGCACGGCCC
HCV-1      1a     -A-------------------------------A--------------T
HCH-H      1a     -A---------------------------------------------T-
HC-J1      1a     -A------------------------------A-------------T-
HCV-J      1b     AA---A--CG-G------------------C--A------C--G--T--
HCV-BK     1b     AA-----T--A---T--G------------C--A------C--G--T--
HC-J4.83   1b     AA----TG-G---T----------------C--A------C--G--T--
HC-J4.91   1b     AA----TG-G---T----------------C--A------C--G--T--
HCV-JTA    1b     AA-----C--A---T---------------C--A------C--G--T--
HCV-JTB    1b     AA-----C--A-------------------C--A------C--G--T--
HCV-CHINA  1b     GA-----T--A---T--T------------C--TA-----C--G--T--
HCV-T      1b     AA-----T--A---T---------------C--A------C--G--T--
HCV-JK1    1b     AA---A--TG-T------------------C--A------C--G--T-T
HCUNK      1b     -C-----C--A---T---------------C--TA-----C--G--T--
HCV-N      1b     AA-----T--A-------T-----------C--A------C--G--T--
HC-J6      2a     AA-----C-----C----------------C--A-A----CC-G--T--
HC-J8      2b     -C---T-TT-A---T--T------------C--A-A----CC-G--T--
HC-J5      2a     -C-T---C--T-------------------C--A------CC-G--C--
HC-J7      2b     TA--AGT--A--------------T----TCG-A------CC-G--C--
NZL1       3a     AC-G-----G--------------T----TCG-A------C--T--T--
HEM26      3a     AC-G-----G--------------T----TCG-A---A--C--T-----
TH85       3a     -C-G-----T--G-----------T----TCG-A------C--T-----
US114      3a     -C-G-----G--------------T----TCG-TA-----CC-----T--
BE95       5a     AC-G----C--A--T-------A---C---A---------C--G--C--
```

Figure 13 - Continued 6

```
         1280
HCV-1    1a   TGAACTGCAATGATAGCCTCAACACCGGCTGGTTGGCAGGGCTTTTCTAT
HCH-H    1a   ------------------A-----T--------------A-------C--
HC-J1    1a   ------------------A-----T--------------A---------A
HCV-J    1b   ----T-------------CTC---C-A---T--G-TCA-T--T-C---G-C
HCV-BK   1b   ------------------CTCT--C-G---T--G-TTC-T--C-C---G-C
HC-J4.83 1b   -A----------------CTC---C-----T--G-TCC-T--C-C---G-C
HC-J4.91 1b   -A--T-------------CTC---C-----T--G-TCC-T--C-C---G-C
HCV-JTA  1b   ------------------ATC---------T--G-TC--T--C-CA--G-C
HCV-JTB  1b   ------------------ATC------------G-TC--T--C-CA--G-C
HCV-CHINA 1b  ------------------CTC---------T--G-TTC-T--C-C---G-C
HCV-T    1b   -A----------------CTC---C-G---T--G-TTC-T--CTC---G-C
HCV-JK1  1b   ----T-------------GTC-A-------T--G-TC--T--C-C---G-C
HCUNK    1b   ----G-------------CTC---------T--G-TTG-T--C-C---G-C
HCV-N    1b   ------------------CTC---C-G---T--G-TCC-T--C-CC--G-C
HC-J6    2a   ------------------CTCTT-GC-------TCC-C--GTCA--G---C
HC-J8    2b   -C--T-------------C---T-AC-G--G--T-TCC-C--TTCCT-G--T-C
HC-J5    2a   ----T-------------CTC-T-G--------TTA-C--GTCC--G---C
HC-J7    2b   -C--T-------------T-GC-A--A--T-TC--C--T-CC--G--T--C
NZL1     3a   -A--T-------------GTC-A-A----------G-TTA-A--T---T-G--T--
HEM26    3a   ------------------GTC-A-A----------G-TCA-A--T---T-A--T--
TH85     3a   --------------------TC-A-A---------G-TCA-A--TA--T-G--T--
US114    3a   ------------------GTC-A-A----------G-TCA-A--T---T-GC-T--
BE95     5a   -T--T--T----C-----------C-G---T--G-TCA-A--C---C---C
```

Figure 13 - Continued 7

```
                    1330
              CACCACAAGTTCAACTCTTCAGGCTGTCCTGAGAGGCTAGCCAGCTGCCG
HCV-1     1a  --------------------------------------------------
HCH-H     1a  --G-----A-----------------------------T-G--------
HC-J1     1a  --A-----A---------------G-----C-----T-G----------
HCV-J     1b  GCA---G-------------G-G--C--G--C--A---C-CA-G--T---
HCV-BK    1b  ACA--T-GT-----------G----C--G--C--A---C-CA-G--CAG-
HC-J4.83  1b  ACA---G-------------G----C--G--C--A---C-CA-G-----
HC-J4.91  1b  ACA-----------------G----C--G--C--G---C-CA-G-----
HCV-JTA   1b  GCA-----------------G----C--A--C--A---C-CA-G----A-
HCV-JTB   1b  GCA-----------------G----C--A--C--A---C-CA-G----A-
HCV-CHINA 1b  ACA---G-------------G-G--C--A--CG-A---C-CA-G-----
HCV-T     1b  GCG---G-------------G-G--C--A--C--A---C-CA-G-----
HCV-JK1   1b  GTAA-G--------------G----T--A--CT-A---C-CA-G--T---T-
HCUNK     1b  A-AT--G-------------G-G--C--G--C--G---C-CT-G--CG-
HCV-N     1b  ACAT--G-------------G----C--A--C--G---G-CCA-G-----
HC-J6     2a  AC----GC------------G----A--------C--AC-CA-GT--GC-
HC-J8     2b  AC--------------AGC--T--------C--C--CT-GT-TTC----
HC-J5     2a  GT-A--CGC---------T-G--------A-----CC-TC-C--GT--GT-
HC-J7     2b  GT-AGACGT-------AGC--T--------C--C--CT-GT-TTC----
NZL1      3a  T-----T----------A-T--A-----C--A-------CAG-----AA
HEM26     3a  T-T---T----------A-T--A-----C--C-------CAG-----TAA
TH85      3a  T-----T----------A-T--A-----C--A-------CAG-----AA
US114     3a  T-TA--T----------A-T--A-----C--A----T--CAG-----AA
BE95      5a  T-----T-----------T--A---C--G--TC--A-G--T----TA-
```

Figure 13 - Continued 8

```
                 1380
HCV-1     1a     ACCCCTTACCGATTTGACCAGGGCTGGGGCCCTATCAGTTAT    GCCA
HCH-H     1a     --G--------------------------------------    ----
HC-J1     1a     --G--------------C-----------------------    ----
HCV-J     1b     C---A-CGAT--G--C-CT----G-------C-C-C-----    -AT-
HCV-BK    1b     CA--A--GA-A-G--C-------A---T--C--T-C-----    --TG
HC-J4.83  1b     C---A--GA-TGG--C-C-----A------C---CC-----    A-TG
HC-J4.91  1b     C---A--GA--GG--C-C-----A------C---CC-----    A-TG
HCV-JTA   1b     C---A--GA--GA--C-CT----A------C---CC-----    A--G
HCV-JTB   1b     CT--A-CGA-A-G--C-CT-------T---C---CC-----    A--G
HCV-CHINA 1b     CT--A--GA-A-G--C-CT-----------C---CC-----    A-TG
HCV-T     1b     C---A--GATACA--C--T-----------C---C------    A-TG
HCV-JK1   1b     TT--A--GA-A-G--C--T----A------C---CC-----    A-TG
HCUNK     1b     T---A--GA-AGG--C-CT--A-G------T---CC-----    --TG
HCV-N     1b     C---A--GATACA--C-CG----G------T---CCC----    A-TG
HC-J6     1b     CT--A--GA-A-G--C-------A------T---C------    --TG
HC-J8     2a     CAGTA-CGAG-CC--CGGGT---A------G-CT-ACAA--    GAG-A-
HC-J5     2b     CGGG--GGA------CG-ATC--------AA-CT-GGAA--    CGAAA-
HC-J7     2a     CAG-A-CGAG-C---CCGGATA-G-----A-CT-GCAA---    CGAG-AT
NZL1      2b     TAAG--GGAT-----CG-ATC--G-----AA-CT-GGAA--    CGAG-AT
HEM26     3a     G---A-C--TTTC--CAGG----A--------CT-A-CAG-    GAGA--
TH85      3a     G---A-C--TTCC--CAGG----G------T-CT-G-CAG-    -T--
US114     3a     G---A-C---TCC--CA-T----G------C-CT-G-CAG-    -T--
BE95      3a     G---A-C--TTCC--CAGG----G------C-CT-G-CAG-    -AA-
          5a     GG-----G--AC---------------AA-------C----    -T--
```

Figure 13 - Continued 9

```
              1430
HCV-1      1a  ACGGAAGCGGCCCC    GACCAGCGGCCCCTACTGCTGGCACTACCCCCA
HCH-H      1a  ------T-          ---G-A-----------------------T---
HC-J1      1a  --------          ------A--------T--T--------------
HCV-J      1b  TGCCTGAGA--T-G    ------A-G--A--T--T----------G-G--T
HCV-BK     1b  -GTCT---A--AT-A   ------A-G--A--T-------------A--T
HC-J4.83   1b  -GCCTGA-A----G    ---T--A-G--T--T-------T-----G-G--T
HC-J4.91   1b  -GCCT-A-A----G    ---T--A-G--T--T-------T-----G-G--T
HCV-JTA    1b  -GCCT---G-A--TG   ---T--A-G--T--T-------T-----G-A--T
HCV-JTB    1b  -GCCTG-G-A-TTG    ---T--A-G--T--T-------T-----G-A--T
HCV-CHINA  1b  -GCCTGATA+-T-G    ------A-G--T--T-------------G-G--T
HCV-T      1b  -G-CTGA-AT--AG    ------A-G--T--T-------------G-A--C
HCV-JK1    1b  -GTCTC--A--T-G    ---T--A-G--T--T-------T-----G-A--T
HCUNK      1b  -GCCTCAT-ATTTG    ------AA-G--T--T------------G-G--T
HCV-N      1b  -TCCT-AA-A---G    ------A-G--T--T-------T-----G-A---
HC-J6      2a  -T-TC-C-AAT--AGAG ---TAT-A-A--G--------A------A----
HC-J8      2b  --TC-C-AA-GATGGG- ---AT-A-G--G---------------------G
HC-J5      2a  -T-TC-C-AAT--AGAA ---TAT-A-A--A--------A------A----
HC-J7      2b  -T-TT-C-AA-GAGGAG ---AT-A-A--G-------T-------T--G
NZL1       3a  --ATC-C---T---TTCT ---TG-CA-A--A------------------G-A--T
HEM26      3a  --ATCTC---TT-GTCC ---AG-CAAA-G-------------------G-A--T
TH85       3a  --ATC-C---T---TCT ---TG-CAAA--A------------------G-A--T
US114      3a  --ATC-C--ATT-TTCT ---TG-CAAA--G------------------G-A--T
BE95       5a  --AT-TCG--T---AGT ---TG-CAAA--A---T--------------T---
```

Figure 13 - Continued 10

```
            1480
            AAACCTTGCGGTATTGTGCCCGCGAAGAGTGTG
HCV-1   1a  -G-----T--C----------------A----C---
HCH-H   1a  ----------------------------A----C--A
HC-J1   1a  ----------C------------T---TC-CAG---
HCV-J   1b  CG-----G--C-----A------T---TC-GAG---
HCV-BK  1b  CC---AA-TACC--C--A---------TC-CAG---
HC-J4.83 1b CG-----G--T-----A----------TC-CAG---
HC-J4.91 1b CG-----G--T-----A----------TC-CAG---
HCV-JTA 1b  CGG-AG----T-----A----------TC-CAG---
HCV-JTB 1b  CGG-AG----T-----A------T---TC-GAG---
HCV-CHINA 1b CG-AAG----T-----A----------TC-CAG---
HCV-T   1b  CGG-----G-T-----C----------TC-CAG---
HCV-JK1 1b  C------G--T-----C----------TT-CAG---
HCUNK   1b  C------G--T-----C-------A--TT-CAG---
HCV-N   1b  C---AG----T----CA-A--CT-CG-TCCGAG-C
HC-J6   2a  -G--AG----T---G-A--CT------GCTC-----
HC-J8   2b  -GG----------C--C---C---G--T-G--CG--T
HC-J5   2a  ---------G--T--C--A--C-----G-TC-----
HC-J7   2b  ---------G-----C--C--CT-G--T----CG---C
NZL1    3a  -G---------T-AC---C---C--G--ATCA----C
HEM26   3a  -G--------TACCG---C--A--ATCA----C
TH85    3a  -G-----TAAA-G---C--A--ATCA----C
US114   3a  -G-T---T-A--CC--C--G--ATCA----C
BE95    5a  CGG--G----AG-G---A--CC-AGAG--C
```

SEQUENCES OF HEPATITIS C VIRUS GENOTYPES AND THEIR USE AS THERAPEUTIC AND DIAGNOSTIC AGENTS

This is a continuation of application Ser. No. 08/362,455, filed Jan. 11, 1995, pending, which is a 371 application of PCT/EP94/01323, filed Apr. 27, 1994, the entire content of which is hereby incorporated by reference in this application.

The invention relates to new sequences of hepatitis C virus (HCV) genotypes and their use as therapeutic and diagnostic agents.

The present invention relates to new nucleotide and amino acid sequences corresponding to the coding region of a new type 2 subtype 2d, type-specific sequences corresponding to HCV type 3a, to new sequences corresponding to the coding region of a new subtype 3c, and to new sequences corresponding to the coding region of HCV type 4 and type 5 subtype 5a: a process for preparing them, and their use for diagnosis, prophylaxis and therapy.

The technical problem underlying the present invention is to provide new type-specific sequences of the Core, the E1, the E2, the NS3, the NS4 and the NS5 regions of HCV type 4 and type 5, as well as of new variants of HCV types 2 and 3. These new HCV sequences are useful to diagnose the presence of type 2 and/or type 3 and/or type 4 and/or type 5 HCV genotypes in a biological sample. Moreover, the availability of these new type-specific sequences can increase the overall sensitivity of HCV detection and should also prove to be useful for therapeutic purposes.

Hepatitis C viruses (HCV) have been found to be the major cause of non-A, non-B hepatitis. The sequences of cDNA clones covering the complete genome of several prototype isolates have been determined (Kato et al., 1990; Choo et al., 1991; Okamoto et al., 1991: Okamoto et al., 1992). Comparison of these isolates shows that the variability in nucleotide sequences can be used to distinguish at least 2 different genotypes, type 1 (HCV-1 and HCV-J) and type 2 (HC-J6 and HC-J8), with an average homology of about 68%. Within each type, at least two subtypes exist (e.g. represented by HCV-1 and HCV-J), having an average homology of about 79%. HCV genomes belonging to the same subtype show average homologies of more than 90% (Okamoto et al., 1992). However, the partial nucleotide sequence of the NS5 region of the HCV-T isolates showed at most 67% homology with the previously published sequences, indicating the existence of a vet another HCV type (Mori et al., 1992). Parts of the 5' untranslated region (UR), core, NS3, and NS5 regions of this type 3 have been published, further establishing the similar evolutionary distances between the 3 major genotypes and their subtypes (Chan et al., 1992).

The identification of type 3 genotypes in clinical samples can be achieved by means of PCR with type-specific primers for the NS5 region. However, the degree to which this will be successful is largely dependent on sequence variability and on the virus titer present in the serum. Therefore, routine PCR in the open reading frame, especially for type 3 and the new type 4 and 5 described in the present invention and/or group V (Cha et al., 1992) genotypes can be predicted to be unsuccessful. A new typing system (LiPA), based on variation in the highly conserved 5' UR, proved to be more useful because the 5 major HCV genotypes and their subtypes can be determined (Stuyver et al., 1993). The selection of high-titer isolates enables to obtain PCR fragments for cloning with only 2 primers, while nested PCR requires that 4 primers match the unknown sequences of the new type 3, 4 and 5 genotypes.

New sequences of the 5' untranslated region (5'UR) have been listed by Bukh et al. (1992). For some of these, the E1 region has recently been described (Bukh et al., 1993). Isolates with similar sequences in the 5'UR to a group of isolates including DK12 and HK10 described by Bukh et al. (1992) and E-b1 to E-b8 described and classified as type 3 by Chan et al. (1991), have been reported and described in the 5'UR, the carboxyterminal part of E1, and in the NS5 region as group IV by Cha et al. (1992; WO 92/19743), and have also been described in the 5'UR for isolate BR56 and classified as type 3 by the inventors or this application (Stuyver et al., 1993).

The aim of the present invention is to provide new HCV nucleotide and amino acid sequences enabling the detection of HCV infection.

Another aim of the present infection is to provide new nucleotide and amino acid HCV sequences enabling the classification of infected biological fluids into different serological groups unambiguously linked to types and subtypes at the genome level.

Another aim of the present invention is to provide new nucleotide and amino acid HCV sequences ameliorating the overall HCV detection rate.

Another aim of the present invention is to provide new HCV sequences, useful for the design of HCV vaccine compositions.

Another aim of the present invention is to provide a pharmaceutical composition cons sting of antibodies raised against the polypeptides encoded by these new HCV sequences, for therapy or diagnosis.

The present invention relates more particularly to a composition comprising or consisting of at least one polynucleic acid containing at least 5, and preferably 8 or more contiguous nucleotides selected from at least one of the following HCV sequences:

an HCV type 3 genomic sequence, more particularly in any of the following regions:
the region spanning positions 417 to 957 of the Core/E1 region of HCV subtype 3a,
the region spanning positions 4664 to 4730 of the NS3 region of HCV type 3,
the region spanning positions 4892 to 5292 of the NS3/4 region of HCV type 3,
the region spanning positions 8023 to 8235 of the NS5 region of the BR36 subgroup of HCV subtype 3a,
an HCV subtype 3c genomic sequence, more particularly the coding regions of the above-specified regions;
an HCV subtype 2d genomic sequence, more particularly the coding region of HCV subtype 2d;
an HCV type 4 genomic sequence, more particularly the coding region, more particularly the coding region of subtypes 4a, 4e, 4f, 4g, 4h, 4i, and 4j.
an HCV type 5 genomic sequence, more particularly the coding region of HCV type 5, more particularly the regions encoding Core, E1, E2, NS3, and NS4
with said nucleotide numbering being with respect to the numbering of HCV nucleic acids as shown in Table 1, and with said polynucleic acids containing at least one nucleotide difference with known HCV (type 1, type 2, and true 3) polynucleic acid sequences in the above-indicated regions, or the complement thereof.

It is to be noted that the nucleotide difference in the polynucleic acids of the invention may involve or not an amino acid difference in the corresponding amino acid sequences coded by said polynucleic acids.

According to a preferred embodiment, the present invention relates to a composition comprising or containing at least one polynucleic acid encoding an HCV polyprotein, with said polynucleic acid containing at least 5, preferably at least 8 nucleotides corresponding to at least part of an HCV nucleotide sequence encoding an HCV polyprotein, and with said HCV polyprotein containing in its sequence at least one of the following amino acid residues: L7, Q43, M44, S60, R67, Q70, T71, A79, A87, N106, K115, A127, A190, S130, V134, G142, I144, E152, A157, V158, P165, S177 or Y177, I178, V180 or E180 or F182, R184, I186, H187, T189, A190, S191 or G191, Q192 or L192 or I192 or V192 or E192, N 193 or H193 or P193, W194 or Y194, H195, A197 or I197 or V 197 or T197, V202, I203 or L203, Q208, A210, V212, F214, T216, R217 or D217 or E217 or V217, H218 or N218, H219 or V219 or L219, L227 or I227, M231 or E231 or Q231, T232 or D232 or A232 or K232, Q235 or I235, A237 or T 237, I242, I246, S247, S248, V249, S250 or Y250, I251 or V251 or M251 or F251, D252, T254 or V254, L255 or V255, E256 or A256, M258 or F258 or V258, A260 or Q260 or S260, A261, T264 or Y264, M265, I266 or A266, A267, G268 or T268, F271 or M271 or V271, I277, M280 or H280, I284 or A284 or L84, V274, V291, N292 or S292, R293 or I293 or Y293, Q294 or R294, L297 or I297 or Q297, A299 or K299 or Q299, N303 or T303, T308 or L308, T310 or F310 or A310 or D310 or V310, L313, G317 or Q317, L333, S351, A358, A359, A363, S364, A366, T369, L373, F376, Q386, I387, S392, I399, F402, I403, R405, D454, A461, A463, T464, K484, Q500, E501, S521, K522, H524, N528, S531, S532, V534, F536, F537, M539, I546, C1282, A1283, H1310, V1312, Q1321, P1368, V1372, V1373, K1405, Q1406, S1409, A1424, A1429, C1435, S1436, S1456, H1496, A1504, D1510, D1529, I1543, N1567, D1556, N1567, M1572, Q1579, L1581, S1581, F1585, V1595, E1606 or T1606, M1611, V1612 or L1612, P1630, C1636, P1651, T1656 or I1656, L1663, V1667, V1677, A1681, H1685, E1687, G1689, V1695, A1700, Q1704, Y1705, A1713, A1714 or S1714, M1718, D1719, A1721 or T1721, R1722, A1723 or V1723, H1726 or G1726, E1730, V1732, F1735, I1736, S1737, R1738, T1739, G1740, Q1741, K1742, Q1743, A1744, T1745, L1746, E1747 or K1747, I1749, A1750, T1751 or A1751, V1753, N1755, K1756, A1757, P1758, A1759, H1762, T1763, Y1764, P2645, A2647, K2650, K2653 or L2653, S2664, N2673, F2680, K2681, L2686, H2692, Q2695 or L2695 or 12695, V2712, F2715, V2719 or Q2719, T2722, T2724, S2725, R2726, G2729, Y2735, H2739, I2748, G2746 or I2746, I2748, P2752 or K2752, P2754, T2754, T2757 or P2757, with said notation being composed or a letter representing the amino acid residue by its one-letter code, and a number representing the amino acid numbering according to Kato et al., 1990.

Each of the above-mentioned residues can be found in any of FIG. 2, 5, 7, 11 or 12 showing the new amino acid sequences of the present invention aligned with known sequences of other types or subtypes of HCV for the Core, E1, E2, NS3, NS4, and NS5 regions.

More particularly, a polynucleic acid contained in the composition according to the present invention contains at least 5, preferably 8, or more contiguous nucleotides corresponding to a sequence of contiguous nucleotides selected from at least one of HCV sequences encoding the following new HCV amino acid sequences:

- new sequences spanning amino acid positions 1 to 319 of the Core/E1 region of HCV subtype 2d, type 3 (more particularly new sequences for subtypes 3a and 3c), new type 4 subtypes (more particularly new sequences for subtypes 4a, 4e, 4f, 4g, 4h, 4i and 4j) and type 5a, as shown in FIG. 5;
- new sequences spanning amino acid positions 328 to 546 of the E1/E2 region of HCV subtype 5a as shown in FIG. 12;
- new sequences spanning amino acid positions 1556 to 1764 of the NS3/NS4 region of HCV type 3 (more particularly for new subtypes 3a sequences), and subtype 5a, as shown in FIG. 7 or 11;
- new sequences spanning amino acid positions 2645 to 2757 of the NS5B region of HCV subtype 2d, type 3 (more particularly for new subtypes 3a and 3c), new type 4 subtypes (more particularly subtypes 4a, 4e, 4f, 4g, 4h, 4i and 4j) and subtype 5a, as shown in FIG. 2, Using the LiPA system mentioned above, Brazilian blood donors with high titer type 3 hepatitis C virus, Gabonese patients with high-titer type 4 hepatitis C virus, and a Belgian patient with high-titer HCV type 5 infection were selected. Nucleotide sequences in the core, E1, NS5 and NS4 regions which have not yet been reported before, were analyzed in the frame of the invention. Coding sequences (with the exception of the core region) of any type 4 isolate are reported for the first time in the present invention. The NS5b region was also analyzed for the new type 3 isolates. After having determined the NS5b sequences, comparison with the Ta and Tb subtypes described by Mori et al. (1992) was possible, and the type 3 sequences could be identified as type 3a genotypes. The new type 4 isolates segregated into 10 subtypes, based on homologies obtained in the NS5 and E1 regions. New type 2 and 3 sequences could also be distinguished from previously described type 2 or 3 subtypes from sera collected in Belgium and the Netherlands.

The term "polynucleic acid" refers to a single stranded or double stranded nucleic acid sequence which may contain at least 5 contiguous nucleotides to the complete nucleotide sequence (f.i. at least 6, 7, 8, 9, 10, 11, 12, 13, 14, 15 or more contiguous nucleotides). A polynucleic acid which is up till about 100 nucleotides in length is often also referred to as an oligonucleotide. A polynucleic acid may consist of deoxyribonucleotides or ribonucleotides, nucleotide analogues or modified nucleotides, or may have been adapted for therapeutic purposes. A polynucleic acid may also comprise a double stranded cDNA clone which can be used for cloning purposes, or for in vivo therapy, or prophylaxis.

The term "polynucleic acid composition" refers to any kind of composition comprising essentially said polynucleic acids. Said composition may be of a diagnostic or a therapeutic nature.

The expression "nucleotides corresponding to" refers to nucleotides which are homologous or complementary to an indicated nucleotide sequence or region within a specific HCV sequence.

The term "coding region" corresponds to the region of the HCV genome that encodes the HCV polyprotein. In fact, it comprises the complete genome with the exception of the 5' untranslated region and 3' untranslated region.

The term "HCV polyprotein" refers to the HCV polyprotein of the HCV-J isolate (Kato et al., 1990). The adenine residue at position 330 (Kato et al., 1990) is the first residue of the ATG codon that initiates the long HCV polyprotein of 3010 amino acids in HCV-J and other type 1b isolates, and of 3011 amino acids in HCV-1 and other type 1a isolates, and of 3033 amino acids in type 2 isolates HC-J6 and HC-J8 (Okamoto et al., 199¹).

This adenine is designated as position 1 at the nucleic acid level, and this methionine is designated as position 1 at the amino acid level, in the present invention. As type 1a isolates contain 1 extra amino acid in the NS5a region, coding sequences of type 1a and 1b have identical numbering in the Core, E1, NS3, and NS4 region, but will differ in the NS5-b region as indicated in Table 1. Type 2 isolates have 4 extra amino acids in the E2 region, and 17 or 18 extra amino acids in the NS5 region compared to type 1 isolates, and will differ in numbering from type 1 isolates in the NS3/4 region and NS5b regions as indicated in Table 1.

More preferably the definition of HCV types is concluded from the classification of HCV isolates according to their nucleotide distances calculated as detailed below:

(1) based on phylogenetic analysis of nucleic acid sequences in the NS5b region between nucleotides 7935 and 8274 (Choo et al., 1991) or 8261 and 8600 (Kato et al., 1990) or 8342 and 8681 (Okamoto et al., 1991), isolates belonging to the same HCV type show nucleotide distances of less than 0.34, usually less than 0.33, and more usually of less than 0.32, and isolates belonging to the same subtype show nucleotide distances of less than 0.135, usually of less than 0.13, and more usually of less than 0.125, and consequently isolates belonging to the same type but different subtypes show nucleotide distances ranging from 0.135 to 0.34,

TABLE 1

| | Region | Positions described in the present invention* | Positions described for HCV-J (Kato et al., 1990) | Positions described for HCV-1 (Choo et al., 1991) | Positions described for HC-J6, HC-J8 (Okamoto et al. 1992) |
|---|---|---|---|---|---|
| Nucleotides | NS5b | 8023/8235 | 8352/8564 | 8026/8238 | 8433/8645 |
| | | 7932/8271 | 8261/8600 | 7935/8274 | 8342/8681 |
| | NS3/4 | 4664/5292 | 4993/5621 | 4664/5292 | 5017/5645 |
| | | 4664/4730 | 4993/5059 | 4664/4730 | 5017/5083 |
| | | 4892/5292 | 5221/5621 | 4892/5292 | 5245/5645 |
| | | 3856/4209 | 4185/4528 | 3856/4209 | 4209/4762 |
| | | 4936/5292 | 5265/5621 | 4936/5292 | 5289/5645 |
| | | coding region of present invention | 330/9359 | 1/9033 | 342/9439 |
| Amino Acids | NS5b | 2675/2745 | 2675/2745 | 2676/2746 | 2698/2768 |
| | | 2645/2757 | 2645/2757 | 2646/2758 | 2668/2780 |
| | NS3/4 | 1556/1764 | 1556/1764 | 1556/1764 | 1560/1768 |
| | | 1286/1403 | 1286/1403 | 1286/1403 | 1290/1407 |
| | | 1646/1764 | 1646/1764 | 1646/1764 | 1650/1768 |

Table 1: Comparison of the HCV nucleotide and amino acid numbering system used in the present invention (*) with the numbering used for other prototype isolates. For example, 8352/8564 indicates the region designated by the numbering from nucleotide 8352 to nucleotide 8564 as described by Kato et al. (1990). Since the numbering system of the present invention starts at the polyprotein initiation site, the 329 nucleotides of the 5' untranslated regiondescribed by Kato et al. (1990) have to be substracted, and the corresponding region is numbered from nucleotide 8023 ("8352-329") to 8235 ("8564-329").

The term "HCV type" corresponds to a group of HCV isolates of which the complete genome shows more than 74% homology at the nucleic acid level, or of which the NS5 region between nucleotide positions 7932 and 8271 shows more than 74% homology at the nucleic acid level, or of which the complete HCV polyprotein shows more than 78% homology at the amino acid level, or of which the NS5 region between amino acids at positions 2645 and 2757 shows more than 80% homology at the amino acid level, to polyproteins of the other isolates of the group, with said numbering beginning at the first ATG codon or first methionine of the long HCV polyprotein of the HCV-J isolate (Kato et al., 1990). Isolates belonging to different types of HCV exhibit homologies, over the complete genome, of less than 74% at the nucleic acid level and less than 78% at the amino acid level. Isolates belonging to the same type usually show homologies of about 92 to 95% at the nucleic acid level and 95 to 96% at the amino acid level when belonging to the same subtype, and those belonging to the same type but different subtypes preferably show homologies of about 79% at the nucleic acid level and 85–86% at the amino acid level.

usually ranging from 0.1384 to 0.2477, and more usually ranging from 0.15 to 0.32, and isolates belonging to different HCV types show nucleotide distances greater than 0.34, usually greater that 0.35, and more usually of greater than 0.358, more usually ranging from 0.1384 to 0.2977.

(2) based on phylogenetic analysis of nucleic acid sequences in the core/E1 region between nucleotides 378 and 957, isolates belonging to the same HCV type show nucleotide distances of less than 0.38, usually of less than 0.37, and more usually of less than 0.364, and isolates belonging to the same subtype show nucleotide distances of less than 0.17, usually of less than 0.16, and more usually of less than 0.15, more usually less than 0.135, more usually less than 0.134, and consequently isolates belonging to the same type but different subtypes show nucleotide distances ranging from 0.15 to 0.38, usually ranging from 0.16 to 0.37, and more usually ranging from 0.17 to 0.36, more usually ranging from 0.133 to 0.379, and isolates belonging to different HCV types show nucleotide distances greater than 0.34, 0.35, 0.36, usually more than 0.365, and more usually of greater than 0.37, (3) based on phylogenetic analysis of nucleic acid sequences in the NS3/NS4 region between nucleotides 4664 and 5292 (Choo et al., 1991) or between nucleotides 4993 and 5621(Kato et al., 1990) or between nucleotides 5017 and 5645 (Okamoto et al., 1991), isolates belonging to the same HCV type show nucleotide distances of less than 0.35, usually of less than 0.34, and more usually of less than 0.33, and isolates belonging to the same subtype show nucleotide distances of less than 0.19, usually of less than 0.18, and more usually of less than 0.17, and consequently isolates belonging to the same type but different subtypes show nucleotide distances ranging from 0.17 to 0.35, usually ranging from 0.18 to 0.34, and more usually ranging from 0.19 to 0.33, and isolates belonging to different HCV types show nucleotide distances greater than 0.33, usually greater than 0.34, and more usually of greater than 0.35.

in the present invention might still fluctuate according to international conventions or guidelines. For example, "type 4" might be changed into "type 5" or "type 6".

The term "subtype" corresponds to a group of HCV isolates of which the complete polyprotein shows a homology of more than 90% both at the nucleic acid and amino acid levels, or of which the NS5 region between nucleotide positions 7932 and 8271 shows a homology of more than 90% at the nucleic acid level to the corresponding parts of the genomes of the other isolates of the same group, with said numbering beginning with the adenine residue of the initiation codon of the HCV polyprotein. Isolates belonging to the same type but different subtypes of HCV show

TABLE 2

Molecular evolutionary distances

| Region | Core/E1 579 bp | E1 384 bp | NS5B 340 bp | NS5B 222 bp |
|---|---|---|---|---|
| Isolates* | 0.0017 – 0.1347 | 0.0026 – 0.2031 | 0.0003 – 0.1151 | 0.000 – 0.1323 |
|  | (0.0750 ± 0.0245) | (0.0969 ± 0.0239) | (0.0637 ± 0.0229) | (0.0607 ± 0.0205) |
| Subtypes* | 0.1330 – 0.3794 | 0.1645 – 0.4869 | 0.1384 – 0.2977 | 0.117 – 0.3538 |
|  | (0.2786 ± 0.0363) | (0.3761 ± 0.0433) | (0.2219 ± 0.0341) | (0.2391 ± 0.0399) |
| Types* | 0.3479 – 0.6306 | 0.4309 – 0.9561 | 0.3581 – 0.6670 | 0.3457 – 0.7471 |
|  | (0.4703 ± 0.0525) | (0.6308 ± 0.0928) | (0.4994 ± 0.0495) | (0.5295 ± 0.0627) |

Figures created by the PHYLIP program DNADIST are expressed as minimum to maximum (average±standard deviation). Phylogenetic distances for isolates belonging to the same subtype ('isolates'), to different subtypes of the same type ('subtypes'), and to different types ('types') are given.

In a comparative phylogenetic analysis of available sequences, ranges of molecular evolutionary distances for different regions of the genome were calculated, based on 19,781 pairwise comparisons by means of the DNA. DIST program of the phylogeny inference package PHYLIP version 3.5C (Felsenstein, 1993). The results are shown in Table 2 and indicate that although the majority of distances obtained in each region fit with classification of a certain isolate, only the ranges obtained in the 340 bp NS5B-region are non-overlapping and therefor conclusive. However, as was performed in the present invention, it is preferable to obtain sequence information from at least 2 regions before final classification of a given isolate.

Designation of a number to the different types of HCV and HCV types nomenclature is based on chronological discovery of the different types. The numbering system used homologies of more than 74% at the nucleic acid level and of more than 78% at the amino acid level.

The term "BR36 subgroup" refers to a group of type 3a HCV isolates (BR36, BR33, BR34) that are 95%, preferably 95.5%, most preferably 96% homologous to the sequences as represented in SEQ ID NO 1, 3, 5, 7, 9, 11 in the NS5b region from position 8023 to 8235.

It is to be understood that extremely variable regions like the E1, E2 and NS4 regions will exhibit lower homologies than the average homology of the complete genome of the polyprotein.

Using these criteria, HCV isolates can be classified into at least 6 types. Several subtypes can clearly be distinguished in types 1, 2, 3 and 4: 1a, 1b, 2a, 2b, 2c, 2d, 3a, 3b, 4a, 4b, 4c, 4d, 4e, 4f, 4g, 4h, 4i and 4j based on homologies of the 5' UR and coding regions including the part of NS5 between positions 7932 and 8271. An overview of most of the reported isolates and their proposed classification according to the typing system of the present invention as well as other proposed classifications is presented in Table 3.

TABLE 3

HCV CLASSIFICATION

|  | OKAMOTO | MORI | NAKAO | CHA | PROTOTYPE |
|---|---|---|---|---|---|
| 1a | I | I | Pt | GI | HCV-1, HCV-H, HC-J1 |
| 1b | II | II | KI | GII | HCV-J, HCV-BK, HCV-T, HC-JK1, HC-J4, HCV-CHINA |
| 1c |  |  |  |  | HC-G9 |
| 2a | III | III | K2a | GIII | HC-J6 |
| 2b | IV | IV | K2b | GII | HC-J8 |
| 2c |  |  |  |  | S83, ARG6, ARG8, I10, T983 |
| 2d |  |  |  |  | NE92 |
| 3a | V | V | K3 | GIV | E-b1, Ta, BR36, BR33, HD10, NZL1 |
| 3b |  | VI | K3 | GIV | HCV-TR, Tb |
| 3c |  |  |  |  | BE98 |

TABLE 3-continued

HCV CLASSIFICATION

| OKA-MOTO | MORI | NAKAO | CHA | PROTOTYPE |
|---|---|---|---|---|
| 4a | | | | Z4, GB809-4 |
| 4b | | | | Z1 |
| 4c | | | | GB116, GB358, GB358, GB215, Z6, Z7 |
| 4d | | | | DK13 |
| 4e | | | | GB809-2, CAM600, CAM736 |
| 4f | | | | CAM622, CAM627 |
| 4g | | | | GB549 |
| 4h | | | | GB438 |
| 4i | | | | CAR4/1205 |
| 4j | | | | CAR1/501 |
| 4k | | | | EG29 |
| 5a | | | GV | SA3, SA4, SA1, SA7, SA11, BE95 |
| 6a | | | | HK1, HK2, HK3, HK4 |

The term "complement" refers to a nucleotide sequence which is complementary to an indicated sequence and which is able to hybridize to the indicated sequences.

The composition of the invention can comprise many combinations. By way of example, the composition of the invention can comprise:
- two (or more) nucleic acids from the same region or,
- two nucleic acids (or more), respectively from different regions, for the same isolate or for different isolates,
- or nucleic acids from the same regions and from at least two different regions (for the same isolate or for different isolates).

The present invention relates more particularly to a polynucleic acid composition as defined above, wherein said polynucleic acid corresponds to a nucleotide sequence selected from any of the following HCV type 3 genomic sequences:
- an HCV genomic sequence having a homology of at least 67%, preferably more than 69%, more preferably 71%, even more preferably more than 73%, or most preferably more than 76% to any of the sequences as represented in SEQ ID NO 13, 15, 17, 19, 21, 23, 25 or 27 (HD10, BR36 or BR33 sequences) in the region spanning positions 417 to 957 of the Core/E1 region as shown in FIG. 4;
- an HCV genomic sequence having a homology of at least 65%, preferably more than 67%, preferably more than 69%, even preferably more than 70%, most preferably more than 74% to any of the sequences as represented in SEQ ID NO 13, 15, 17, 19, 21, 23, 25 or 27 (HD1, BR36 or BR33 sequences) in the region spanning positions 574 to 957 of the E1 region as shown in FIG. 4;
- an HCV genomic sequence as having a homology of at least 79%, more preferably at least 81%, most preferably more than 83% or more to any of the sequences as represented in SEQ ID NO 147 (representing positions 1 to 346 of the Core region of HVC type 3c, sequence BE98) in the region spanning positions 1 to 378 of the Core region as shown in FIG. 3;
- an HCV genomic sequence of HVC type 3a having a homology of at least 74%, more preferably at least 76%, most preferably more than 78% or more to any of the sequences as represented in SEQ ID NO 13, 15, 17, 19, 21, 23, 25 or 27 (HD10, BR36 or BR33 sequences) in the region spanning positions 417 to 957 in the Core/E1 region as shown in FIG. 4;
- an HCV genomic sequence of HCV type 3a as having a homology of at least 74%, preferably more than 76%, most preferably 78% or more to any of the sequences as represented in SEQ ID NO 13, 15, 17, 19, 21, 23, 25 or 27 (HD10, BR36 or BR33 sequences) in the region spanning positions 574 to 957 in the E1 region as shown in FIG. 4;
- an HCV genomic sequence as having a homology of more than 73.5%, preferably more than 74%, most preferably 75% homology to the sequence as represented in SEQ ID NO 29 (HCC153 sequence) in the region spanning positions 4664 to 4730 of the NS3 region as shown in FIG. 6;
- an HCV genomic sequence having a homology of more than 70%, preferably more than 72%, most preferably more than 74% homology to any of the sequences as represented in SEQ ID NO 29, 31, 33, 35, 37 or 39 (HCC153, HD10, BR36 sequences) in the region spanning positions 4892 to 5292 in the NS3/NS4 region as shown in FIG. 6 or 10;
- an HCV genomic sequence of the BR36 subgroup of HCV type 3a as having a homology of more than 95%, preferably 95,5%, most preferably 96% homology to any of the sequences as represented in SEQ ID NO 5, 7, 1, 3, 9 or 11 (BR34, BR33, BR36 sequences) in the region spanning positions 8023 to 8235 of the NS5 region as shown in FIG. 1;
- an HCV genomic sequence of the BR36 subgroup of HCV type 3a as having a homology of more than 96%, preferably 96.5%, most preferably 97% homology to any of the sequences as represented in SEQ ID NO 5, 7, 1, 3, 9 or 11 (BR34, BR33, BR36 sequences) in the region spanning positions 8023 to 8192 of the NS5B region as shown in FIG. 1;
- an HCV genomic sequence of HCV type 3c being characterized as having a homology of more than 79%, more preferably more than 81%, and most preferably more than 83% to the sequence as represented in SEQ ID NO 149 (BE98 sequence) in the region spanning positions 7932 to 8271 in the NS5B region as shown in FIG. 1.

Preferentially the above-mentioned genomic HCV sequences depict sequences from the coding regions of all the above-mentioned sequences.

According to the nucleotide distance classification system (with said nucleotide distances being calculated as explained above), said sequences of said composition are selected from:

- an HCV genomic sequence being characterized as having a nucleotide distance of less than 0.44, preferably of less than 0.40, most preferably of less than 0.36 to any of the sequences as represented in SEQ ID NO 13, 15, 17, 19, 21, 23, 25 or 27 in the region spanning positions 417 to 957 of the Core/E1 region as shown in FIG. 4;
- an HCV genomic sequence being characterized having a nucleotide distance of less than 0.53, preferably less than 0.49, most preferably of less than 0.45 to any or the sequences as represented in SEQ ID NO 19, 21, 23, 25 or 27 in the region spanning positions 574 to 957 of the E1 region as shown in FIG. 4;
- an HCV genomic sequence characterized having a nucleotide distance of less than 0.15, preferably less than 0.13, and most preferably less than 0.11 to any of the sequences as represented in SEQ ID NO 147 in the region spanning positions 1 to 378 of the Core region as shown in FIG. 3;
- an HCV genomic sequence of HVC type 3a being characterized as having a nucleotide distance of less than 0.3, preferably less than 0.26, most preferably of less than 0.22 to any of the sequences as represented in SEQ ID NO 13, 15, 17, 19, 21, 23, 25 or 27 in the region spanning positions 417 to 957 in the Core/E1 region as shown in FIG. 4;
- an HCV genomic sequence of HCV type 3a being characterized as having a nucleotide distance of less than 0.35, preferably less than 0.31, most preferably of less than 0.27 to any of the sequences as represented in SEQ ID NO 13, 15, 17, 19, 21, 23, 25 or 27 in the region spanning positions 574 to 957 in the E1 region as shown in FIG. 4;
- an HCV genomic sequence of the BR36 subgroup of HCV type a being characterized as having a nucleotide sequence of less than 0.0423, preferably less than 0.042, preferably less than 0.0362 to any of the sequences as represented in SEQ ID NO 5, 7, 1, 3, 9 or 11 in the region spanning positions 8023 to 8235 of the NS5 region as shown in FIG. 1;
- an HCV genomic sequence of HCV type 3c being characterized as having a nucleotide distance of less than 0.255, preferably of less than 0.25, more preferably of less than 0.21, most preferably of less than 0.17 to the sequence as represented in SEQ ID NO 149 in the region spanning positions 7932 to 8271 in the NS5B region as shown in FIG. 1.

In the present application, the E1 sequences encoding the antigenic ectodomain of the E1 protein, which does not overlap the carboxyterminal signal-anchor sequences of E1 disclosed by Cha et al. (1992; WO 92/19743), in addition to the NS4 epitope region, and a part of the NS5 region are disclosed for 4 different isolates: BR33, BR34, BR36, HCC153 and HD10, all belonging to type 3a (SEQ ID NO 1, 3, 5, 7, 9, 11, 13, 15, 17, 19, 21, 23, 25, 27, 29, 31, 35, 37 or 39).

Also within the present invention are new subtype 3c sequences (SEQ ID NO 147, 149 of the isolate BE98 in the Core and NS5 regions (see FIGS. 3 and 1).

Finally the present invention also relates to a new subtype 3a sequence as represented in SEQ ID NO 217 (see FIG. 1).

Also included within the present invention are sequence variants of the polynucleic acids as selected from any of the nucleotide sequences as given in any of the above mentioned SEQ ID numbers, with said sequence variants containing either deletions and/or insertions of one or more nucleotides, mainly at the extremities of oligonucleotides (either 3' or 5'), or substitutions of some non-essential nucleotides by others (including modified nucleotides an/or inosine), for example, a type 1 or 2 sequence might be modified into a type 3 sequence by replacing some nucleotides of the type 1 or 2 sequence with type-specific nucleotides of type 3 as shown in FIG. 1 (NS5 region), FIG. 3 (Core region), FIG. 4 (Core/E1 region). FIGS. 6 and 10 (NS3/NS4 region).

According to another embodiment, the present invention relates to a polynucleic acid composition as defined above, wherein said polynucleic acids correspond to a nucleotide sequence selected from any of the following HCV type 5 genomic sequences:

- an HCV genomic sequence as having a homology of more than 85%, preferably more than 86%, most preferably more than 87% homology to any of the sequences as represented in SEQ ID NO 41, 43, 45, 47, 49, 51, 53 (PC sequences) or 151 (BE95 sequence) in the region spanning positions 1 to 573 of the Core region as shown in FIGS. 9 and 3;
- an HCV genomic sequence as having a homology of more than 61%, preferably more than 63%, more preferably more than 65% homology, even more preferably more than 66% homology and most preferably more than 67% homology (f.i. 69 and 71%) to any of the sequences as represented in SEQ ID NO 41, 43, 45, 47, 49, 51, 53 (PC sequences). 153 or 155 (BE95, BE100 sequences) in the region spanning positions 574 to 957 of the E1 region as shown in FIG. 4;
- an HCV genomic sequence having a homology of more than 76.5%, preferably of more than 77%, most preferably of more than 78% homology with any of the sequences as represented in SEQ ID NO 55, 57, 197 or 199 (PC sequences) in the region spanning positions 3856 to 4209 of the NS3 region as shown in FIG. 6 or 10;
- an HCV genomic sequence having a homology of more than 68%, preferably of more than 70%, most preferably of more than 72% homology with the sequence as represented in SEQ ID NO 157 (BE95 sequence) in the region spanning positions 980 to 1179 of the E1/E2 region as shown in FIG. 13;
- an HCV genomic sequence having a homology of more than 57%, preferably more than 59%, most preferably more than 61% homology to any of the sequences as represented in SEQ ID NO 59 or 61 (PC sequences) in the region spanning, positions 4936 to 5296 of the NS4 region as shown in FIG. 6 or 10;
- an HCV genomic sequence as having a homology of more than 93%, preferably more than 93.5%, most preferably more than 94% homology to any of the sequences as represented in SEQ ID NO 159 or 161 (BE95 or BE96 sequences) in the region spanning positions 7932 to 8271 of the NS5B region as shown in FIG. 1.

Preferentially the above-mentioned genomic HCV sequences depict sequences from the coding regions of all the above-mentioned sequences.

According to the nucleotide distance classification system (with said nucleotide distances being calculated as explained above), said sequences of said composition are selected from:

- a nucleotide distance of less than 0.53, preferably less than 0.51, more preferably less than 0.49 for the E1 region to the type 5 sequences depicted above;

a nucleotide distance of less than 0.3, preferably less than 0.28, more preferably of less than 0.26 for the Core region to the type 5 sequences depicted above;

a nucleotide distance of less than 0.072, preferably less than 0.071, more preferably less than 0.070 for the NS5B region to the type 5 sequences as depicted above.

Isolates with similar sequences in the 5'UR to a group of isolates including SA1, SA3, and SA7 described in the 5'UR by Bukh et al. (1992), have been reported and described in the 5'UR and NS5 region as group V by Cha et al. (1992; WO 92/19743). This group of isolates belongs to type 5a as described in the present invention (SEQ ID NO 41, 43, 45, 47, 49, 51, 53, 55, 57, 59, 61, 151, 153, 155, 157, 159, 161, 197 and 199).

Also included within the present invention are sequence variants of the polynucleic acids as selected from any of the nucleotide sequences as given in any of the above given SEQ ID numbers with said sequence variants containing either deletion and/or insertions of one or more nucleotides, mainly at the extremities of oligonucleotides (either 3' or 5'), or substitutions of some non-essential nucleotides (i.e. nucleotides not essential to discriminate between different genotypes of HCV) by others (including modified nucleotides an/or inosine), for example, a type 1 or 2 sequence might be modified into a type 5 sequence by replacing some nucleotides of the type 1 or 2 sequence with type-specific nucleotides of type 5 as shown in FIG. 3 (Core region), FIG. 4 (Core/E1 region), FIG. 10 (NS3/NS4 region), FIG. 14 (E1/E2 region).

Another group of isolates including BU74 and BU79 having similar sequences in the 5'UR to isolates including Z6 and Z7 as described in the 5'UR by Bukh et al. (1992), have been described in the 5'UR and classified as a new type 4 by the inventors of this application (Stuyver et al., 1993). Coding sequences, including core, E1 and NS5 sequences of several new Gabonese isolates belonging to this group, are disclosed in the present invention (SEQ ID NO 106, 108, 110, 112, 114, 116, 118, 120 and 122).

According to yet another embodiment, the present invention relates to a composition as defined above, wherein said polynucleic acids correspond to a nucleotide sequence selected from any of the following HCV type 4 genomic sequences:

an HCV genomic sequence having a homology of more than 66%, preferably more than 68%, most preferably more than 70% homology in the E1 region spanning positions 574 to 957 to any of the sequences as represented in SEQ ID NO 118, 120 or 122 (GB358. GB549, GB809 sequences) as shown in FIG. 4;

an HCV genomic sequence having a homology of more than 71%, preferably more than 72%, most preferably more than 74% homology to any of the sequences as represented in SEQ ID NO 118, 120 or 122 (GB358, GB549, GB809 sequences) in the region spanning positions 379 to 957 of the E1 region as shown in FIG. 4;

an HCV genomic sequence having a homology of more than 92%, preferably more than 93%, most preferably more than 94% homology to any of the sequences as represented in SEQ ID NO 163 or 165 (GB809, CAM600 sequences) in the region spanning positions 1 to 378 of the Core/E1 region as shown in FIG. 4;

an HCV genomic sequence (subtype 4c) having a homology of more than 85%, preferably more than 86%, more preferably more than 86.5% homology, most preferably more than 87, more than 88 or more than 89% homology to any of the sequences as represented in SEQ ID NO 183, 185 or 187 (GB116, GB215, GB809 sequences) in the region spanning positions 379 to 957 of the E1 region as shown in FIG. 4;

an HCV genomic sequence (subtype 4a) having a homology of more than 81%, preferably more than 83%, most preferably more than 85% homology to the sequence as represented in SEQ ID NO 189 (GB908 sequence) in the region spanning positions 379 to 957 of the E1 region as shown in FIG. 4;

an HCV genomic sequence (subtype 4e) having a homology of more than 85%, preferably more than 87%, most preferably more than 89% homology to any of the sequences as represented in SEQ ID NO 167 or 169 (CAM600, GB908 sequences) in the region spanning positions 379 to 957 of the E1 region as shown in FIG. 4;

an HCV genomic sequence (subtype 4f) having a homology of more the 79%, preferably more than 81%, most preferably more than 83% homology to any of the sequences as represented in SEQ ID NO 171 or 173 (CAMG22, CAMG27 sequences) in the region spanning positions 379 to 957 of the E1 region as shown in FIG. 4;

an HCV genomic sequence (subtype 4g) having a homology of more than 84%, preferably more than 86%, most preferably more than 88% homology to the sequence as represented in SEQ ID NO 175 (GB549 sequence) in the region spanning positions 379 to 957 of the E1 region as shown in FIG. 4;

an HCV genomic sequence (subtype 4h) having a homology of more than 83%, preferably more than 85%, most preferably more than 87% homology to the sequence as represented in SEQ ID NO 177 (GB438 sequence) in the region spanning positions 379 to 957 of the E1 region as shown in FIG. 4;

an HCV genomic sequence (subtype 4i) as having a homology of more than 76%, preferably more than 78%, most preferably more than 80% homology to the sequence as represented in SEQ ID NO 179 (CAR4/1205 sequence) in the region spanning positions 379 to 957 of the E1 region as shown in FIG. 4;

an HCV genomic sequence (subtype 4j?) having a homology of more than 84%, preferably more than 86%, most preferably more than 88% homology to the sequence as represented in SEQ ID NO 181 (CAR4/901 sequence) in the region spanning positions 379 to 957 of the E1 region as shown in FIG. 4;

an HCV genomic sequence as having a homology of more than 73%, preferably more than 75%, most preferably more than 77% homology to any of the sequences as represented in SEQ ID NO 106, 108, 110, 112, 114, or 116 (GB48, GB116, GB215, GB358, GB549, GB809 sequences) in the region spanning positions 7932 to 8271 of the NS5 region as shown in FIG. 1;

an HCV genomic sequence (subtype 4c) having a homology of more than 88%, preferably more than 89%, most preferably more than 90% homology to any of the sequences as represented in SEQ ID NO 106, 108, 110, or 112 (GB48, GB116, GB215, GB358 sequences) in the region spanning positions 7932 to 8271 of the NS5 region as shown in FIG. 1;

an HCV genomic sequence (subtype 4e) having a homology of more than 88%, preferably more than 89%, most preferably more than 90% homology to any of the sequences as represented in SEQ ID NO 116 or 201

(GB809 or CAM 600 sequences) in the region spanning positions 7932 to 8271 of the NS5 region as shown in FIG. 1;

an HCV genomic sequence (subtype 4f) having a homology of more than 87%, preferably more than 89%, most preferably more than 90% homology to the sequence as represented in SEQ ID NO 203 (CAMG22 sequence) in the region spanning positions 7932 to 8271 of the NS5 region as shown in FIG. 1;

an HCV genomic sequence (subtype 4g) as having a homology of more than 85%, preferably more than 87%, most preferably more than 89% homology to the sequence as represented in SEQ ID NO 114 (GB549 sequence) in the region spanning positions 7932 to 8271 of the NS5 region as shown in FIG. 1;

an HCV genomic sequence (subtype 4h) as having a homology of more than 86%, preferably more than 87%, more preferably more than 88% homology, more preferably more than 89% homology to the sequence as represented in SEQ ID NO 207 (GB437 sequence) in the region spanning positions 7932 to 8271 of the NS5 region as shown in FIG. 1;

an HCV genomic sequence (subtype 4i) having a homology of more than 84%, preferably more than 86%, most preferably more than 88% homology to the sequence as represented in SEQ ID NO 209 (CAR4/1205 sequence) in the region spanning positions 7932 to 8271 of the NS5 region as shown in FIG. 1;

an HCV genomic sequence (subtype 4j) having a homology of more than 81%, preferably more than 83%, most preferably more than 85% homology to the sequence as represented in SEQ ID NO 211 (CAR1/501 sequence) in the region spanning positions 7932 to 8271 of the NS5 region as shown in FIG. 1.

Preferentially the above-mentioned genomic HCV sequences depict sequences from the coding regions of all the above-mentioned sequences.

According to the nucleotide distance classification system (with said nucleotide distances being calculated as explained above), said sequences of said composition are selected from:

an HCV genomic sequence (type 4) being characterized as having a nucleotide distance of less than 0.52, 0.50, 0.4880, 0.46, 0.44, 0.43 or most preferably less than 0.42 in the region spanning positions 574 to 957 to any of the sequences as represented in SEQ ID NO 118, 120 or 122 in the region spanning positions 1 to 957 of the Core/E1 region as shown in FIG. 4;

an HCV genomic sequence (type 4) being characterized as having a nucleotide distance of less than 0.39, 0.36 0.34 0.32 or most preferably less than 0.31 to any of the sequences as represented in SEQ ID NO 118, 120 or 122 in the region spanning positions 379 to 957 of the E1 region as shown in FIG. 4;

an HCV genomic sequence (subtype 4c) being characterized as having a nucleotide distance of less than 0.27, 0.26, 0.24, 0.22, 0.20, 0.18, 0.17, 0.162, 0.16 or most preferably less than 0.15 to any of the sequences as represented in SEQ ID NO 183, 185 or 187 in the region spanning positions 379 to 957 of the E1 region as shown in FIG. 4;

an HCV genomic sequence (subtype 4a) being characterized as having a nucleotide distance of less than 0.30, 0.28, 0.26, 0.24, 0.22, 0.21 or most preferably of less than 0.205 to the sequence as represented in SEQ ID NO 189 in the region spanning positions 379 to 957 of the E1 region as shown in FIG. 4;

an HCV genomic sequence (subtype 4e) being characterized as having a nucleotide distance of less than 0.26, 0.25, 0.23, 0.21, 0.19, 0.17, 0.165, most preferably less than 0.16 to any of the sequences as represented in SEQ ID NO 167 or 169 in the region spanning positions 379 to 957 of the E1 region as shown in FIG. 4;

an HCV genomic sequence (subtype 4f) being characterized as having a nucleotide distance of less than 0.26, 0.24, 0.22, 0.20, 0.18, 0.16, 0.15 or most preferably less than 0.14 to any of the sequences as represented in SEQ ID NO 171 or 173 in the region spanning positions 379 to 957 of the E1 region as shown in FIG. 4;

an HCV genomic sequence (subtype 4g) being characterized as having a nucleotide distance of less than 0.20, 0.19, 0.18, 0.17 or most preferably of less than 0.16 to the sequence as represented in SEQ ID NO 175 in the region spanning positions 379 to 957 of the E1 region as shown in FIG. 4;

an HCV genomic sequence (subtype 4h) being characterized as having a nucleotide distance of less than 0.20.0.19, 0.18, 0.17 and most preferably of less than 0.16 to the sequence as represented in SEQ ID NO 177 in the region spanning positions 379 to 957 of the E1 region as shown in FIG. 4;

an HCV genomic sequence (subtype 4i) being characterized as having a nucleotide distance of less than 0.27, 0.25, 0.23, 0.21 and preferably less than 0.16 to the sequence as represented in SEQ ID NO 179 in the region spanning positions 379 to 957 of the E1 region as shown in FIG. 4;

an HCV genomic sequence (subtype 4j?) being characterized as having a nucleotide distance of less than 0.19, 0.18, 0.17, 0.165 and most preferably of less than 0.16 to the sequence as represented in SEQ ID NO 181 in the region spanning positions 379 to 957 of the E1 region as shown in FIG. 4;

an HCV genomic sequence (type 4) being characterized as having a nucleotide distance of less than 0.35, 0.34, 0.32 and most preferably of less than 0.30 to any of the sequences as represented in SEQ ID NO 106, 108, 110, 112, 114, or 116 in the region spanning positions 7932 to 8271 of the NS5 region as shown in FIG. 1;

an HCV genomic sequence (subtype 4c) being characterized as having a nucleotide distance of less than 0.18, 0.16, 0.14, 0.135, 0.13, 0.1275 or most preferably less than 0.125 to any of the sequences as represented in SEQ ID NO 106, 108, 110, or 112 in the region spanning positions 7932 to 8271 of the NS5 region as shown in FIG. 1;

an HCV genomic sequence (subtype 4e) being characterized as having a nucleotide distance of less than 0.15, 0.14, 0.135, 0.13 and most preferably of less than 0.125 to any of the sequences as represented in SEQ ID NO 116 or 201 in the region spanning positions 7932 to 8271 of the NS5 region as shown in FIG. 1;

an HCV genomic sequence (subtype 4f) being characterized as having a nucleotide distance of less than 0.15, 0.14, 0.135, 0.13 or most preferably less than 0.125 to the sequence as represented in SEQ ID NO 203 in the region spanning positions 7932 to 8271 of the NS5 region as shown in FIG. 1;

an HCV genomic sequence (subtype 4g) being characterized as having a nucleotide distance of less than 0.17, 0.16, 0.15, 0.14, 0.13 or most preferably less than 0.125 to the sequence as represented in SEQ ID NO 114 in the region spanning positions 7932 to 8271 of the NS5 region as shown in FIG. 1;

an HCV genomic sequence (subtype 4h) being characterized as having a nucleotide distance of less than 0.155, 0.15, 0.145, 0.14, 0.135, 0.13 or most preferably less than 0.125 to the sequence as represented in SEQ ID NO 207 in the region spanning positions 7932 to 8271 of the NS5 region as shown in FIG. 1;

an HCV genomic sequence (subtype 4i) being characterized as having a nucleotide distance of less than 0.17, 0.16, 0.15, 0.14, 0.13 or most preferably of less than 0.125 to the sequence as represented in SEQ ID NO 209 in the region spanning positions 7932 to 8271 of the NS5 region as shown in FIG. 1;

an HCV genomic sequence (subtype 4j) being characterized as having a nucleotide distance of less than 0.21, 0.20, 0.19, 0.18, 0.17, 0.16, 0.15, 0.14, 0.13 and most preferably of less than 0.125 to the sequence as represented in SEQ ID NO 211 in the region spanning positions 7932 to 8271 of the NS5 region as shown in FIG. 1.

Also included within the present invention are sequence variants of the polynucleic acids as selected from any of the nucleotide sequences as given in any of the above given SEQ ID numbers with said sequence variants containing either deletion and/or insertions of one or more nucleotides, mainly at the extremities of oligonucleotides (either 3' or 5'), or substitutions of some non-essential nucleotides (i.e. nucleotides not essential to discriminate between different genotypes of HCV) by others (including modified nucleotides an/or inosine), for example, a type 1 or 2 sequence might be modified into a type 4 sequence by replacing some nucleotides of the type 1 or 2 sequence with type-specific nucleotides of type 4 as shown in FIG. 3 (Core region), FIG. 4 (Core/E1 region), FIG. 10 (NS3/NS4 region), FIG. 14 (E1/E2 region).

The present invention also relates to a sequence as represented in SEQ ID NO 193 (GB724 sequence).

After aligning NS5 or E1 sequences of GB48, GB, 116, GB215, GB358, GB549 and GB809, these isolates clearly segregated into 3 subtypes within type 4: GB48, GB116, GB215 and GB358 belong to the subtype designated 4c, GB549 to subtype 4g and GB809 to subtype 4e. In NS5, GB809 (subtype 4e) showed a higher nucleic acids homology to subtype 4c isolates (85.6–86.8%) than to GB549 (subtype 4g, 79.7%), while GB549 showed similar homologies to both other subtypes (78.8 to 80% to subtype 4c and 79.7% to subtype 4e). In E1, subtype 4c showed equal nucleic acid homologies of 75.2% to subtypes 4g and 4e while 4g and 4e were 78.4% homologous. At the amino acid level however, subtype 4e showed a normal homology to subtype 4c (80.2%), while subtype 4g was more homologous to 4c (83.3%) and 4e (84.1%).

According to yet another embodiment, the present invention relates to a composition as defined above, wherein said polynucleic acids correspond to a nucleotide sequence selected from any of the following HCV type 2d genomic sequences:

an HCV genomic sequence as having a homology of more than 78%, preferably more than 80%, most preferably more than 82% homology to the sequence as represented in SEQ ID NO (NE92) 143 in the region spanning positions 379 to 957 of the Core/E1 region as shown in FIG. 4;

an HCV genomic sequence as having a homology of more than 74%, preferably more than 76%, most preferably more than 78% homology to the sequence as represented in SEQ ID NO 143 (NE92) in the region spanning positions 574 to 957 as shown in FIG. 4;

an HCV genomic sequence as having a homology of more than 87%, preferably more than 89%, most preferably more than 91% homology to the sequence as represented in SEQ ID NO 145 (NE92) in the region spanning positions 7932 to 8271 of the NS5B region as shown in FIG. 1.

Preferentially the above-mentioned genomic HCV sequences depict sequences from the coding regions of all the above-mentioned sequences.

According to the nucleotide distance classification system (with said nucleotide distances being calculated as explained above), said sequences of said composition are selected from:

a nucleotide distance of less than 0.32, preferably less than 0.31, more preferably less than 0.30 for the E1 region (574 to 957) to any of the above specified sequences;

a nucleotide distance of less than 0.08, preferably less than 0.07, more preferably less than 0.06 for the Core region (1 to 378) to any of the above given sequences a nucleotide distance of less than 0.15, preferentially less than 0.13, more preferentially less than 0.12 for the NS5B region to any of the above-specified sequences.

Polynucleic acid sequences according to the present invention which are homologous to the sequences as represented by a SEQ ID NO can be characterized and isolated according to any of the techniques known in the art, such as amplification by means of type or subtype specific primers, hybridization with type or subtype specific probes under more or less stringent conditions, serological screening methods (see examples 4 and 11) or via the LiPA typing system.

Polynucleic acid sequences of the genomes indicated above from regions not yet depicted in the present examples, figures and sequence listing can be obtained by any of the techniques known in the art, such as amplification techniques using suitable primers from the type or subtype specific sequences of the present invention.

The present invention relates also to a composition as defined above, wherein said polynucleic acid is liable to act as a primer for amplifying the nucleic acid of a certain isolate belonging to the genotype from which the primer is derived.

An example of a primer according to this embodiment of the invention is HCPr 152 as shown in table 7 (SEQ ID NO 79).

The term "primer" refers to a single stranded DNA oligonucleotide sequence capable of acting as a point of initiation for synthesis of a primer extension product which is complementary to the nucleic acid strand to be copied. The length and the sequence of the primer must be such that they allow to prime the synthesis of the extension products. Preferably the primer is about 5–50 nucleotides. Specific length and sequence will depend on the complexity of the required DNA or RNA targets, as well as on the conditions of primer use such as temperature and ionic strength.

The fact that amplification primers do not have to match exactly with corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton. 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules using primer extension. During amplification, the amplified products can be conveniently labelled either using labelled primers or by incorporating labelled nucleotides. Labels may be isotopic ($^{32}$P, $^{35}$S, etc.) or non-isotopic (biotin, digoxigenin, etc.). The amplification reaction is repeated between 20 and 80 times, advantageously between 30 and 50 times.

The present invention also relates to a composition as defined above, wherein said polynucleic acid is able to act as a hybridization probe for specific detection and/or classification into types of a nucleic acid containing said nucleotide sequence, with said oligonucleotide being possibly labelled or attached to a solid substrate.

The term "probe" refers to single stranded sequence-specific oligonucleotides which have a sequence which is complementary to the target sequence of the HCV genotype(s) to be detected.

Preferably, these probes are about 5 to 50 nucleotides long, more preferably from about 10 to 25 nucleotides.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin or haptens.

The present invention also relates to the use of a composition as defined above for detecting the presence of one or more HCV genotypes, more particularly for detecting the presence of a nucleic acid of any of the HCV genotypes having a nucleotide sequence as defined above, present in a biological sample liable to contain them, comprising at least the following steps:
(i) possibly extracting sample nucleic acid,
(ii) possibly amplifying the nucleic acid with at least one of the primers as defined above or any other HCV subtype 2d, HCV type 3, HCV type 4, HCV type 5 or universal HCV primer,
(iii) hybrizing the nucleic acids of the biological sample, possibly under denatured conditions, and with said nucleic acids being possibly labelled during or after amplification, at appropriate conditions with one or more probes as defined above, with said probes being preferably attached to a solid substrate,
(iv) washing at appropriate conditions.
(v) detecting the hybrids formed,
(vi) inferring the presence of one or more HCV genotypes present from the observed hybridization pattern.

Preferably, this technique could be performed in the Core or NS5B region.

The term "nucleic acid" can also be referred to as analyte strand and corresponds to a single- or double-stranded nucleic acid molecule. This analyte strand is preferentially positive- or negative stranded RNA, cDNA or amplified cDNA.

The term "biological sample" refers to any biological sample (tissue or fluid) containing HCV nucleic acid sequences and refers more particularly to blood serum or plasma samples.

The term "HCV subtype 2d primer" refers to a primer which specifically amplifies HCV subtype 2d sequences present in a sample (see Examples section and figures).

The term "HCV type 3 primer" refers to a primer which specifically amplifies HCV type 3 sequences present in a sample (see Examples section and figures).

The term "HCV type 4 primer" refers to a primer which specifically amplifies HCV type 4 genomes present in a sample.

The term "universal HCV primer" refers to oligonucleotide sequences complementary to any of the conserved regions of the HCV genome.

The term "HCV type 5 primer" refers to a primer which specifically amplifies HCV type 5 genomes present in a sample. The term "universal HCV primer" refers to oligonucleotide sequences complementary to any of the conserved regions of the HCV genome.

The expression "appropriate" hybridization and washing conditions are to be understood as stringent and are generally known in the art (e.g. Maniatis et al., Molecular Cloning: A Laboratory Manual, New York, Cold Spring Harbor Laboratory, 1982).

However, according to the hybridization solution (SSC, SSPE, etc.), these probes should be hybridized at their appropriate temperature in order to attain sufficient specificity.

The term "labelled" refers to the use of labelled nucleic acids. This may include the use of labelled nucleotides incorporated during the polymerase step of the amplification such as illustrated by Saiki et al. (1988) or Bej et al. (1990) or labelled primers, or by any other method known to the person skilled in the art.

The process of the invention comprises the steps of contacting any of the probes as defined above, with one of the following elements:
either a biological sample in which the nucleic acids are made available for hybridization,
or the purified nucleic acids contained in the biological sample
or a single copy derived from the purified nucleic acids,
or an amplified copy derived from the purified nucleic acids, with said elements or with said probes being attached to a solid substrate.

The expression "inferring the presence of one or more HCV genotypes present from the observed hybridization pattern" refers to the identification of the presence of HCV genomes in the sample by analyzing the pattern of binding of a panel of oligonucleotide probes. Single probes may provide useful information concerning the presence or absence of HCV genomes in a sample. On the other hand, the variation of the HCV genomes is dispersed in nature, so rarely is any one probe able to identify uniquely a specific HCV genome. Rather, the identity of an HCV genotype may be inferred from the pattern of binding of a panel of oligonucleotide probes, which are specific for (different) segments of the different HCV genomes. Depending on the choice of these oligonucleotide probes, each known HCV genotype will correspond to a specific hybridization pattern upon use of a specific combination of probes. Each HCV genotype will also be able to be discriminated from any other HCV genotype amplified with the same primers depending on the choice of the oligonucleotide probes. Comparison of the generated pattern of positively hybridizing probes for a sample containing one or more unknown HCV sequences to a scheme of expected hybridization patterns, allows one to clearly infer the HCV genotypes present in said sample.

The present invention thus relates to a method as defined above, wherein one or more hybridization probes are selected from any of SEQ ID NO 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, 106, 108, 110, 112, 114, 116, 118, 120, 122, 143, 145, 147, 149, 151, 153, 155, 157, 159, 161, 163, 165, 167, 169, 171, 173, 175, 177, 179, 181, 183, 185, 187, 198, 191, 193, 195, 197, 199, 201, 203, 205, 207, 209, 211, 213, 215, 217, 222, 269 or sequence variants thereof, with said sequence variants containing deletions and/or insertions of one or more nucleotides, mainly at their extremities (either 3' or 5'), or substitutions of some non-essential nucleotides (i.e. nucleotides not essential to discriminate between genotypes) by others (including modified nucleotides or inosine), or with said variants consisting of the complement of any of the above-mentioned oligonucleotide probes, or with said variants consisting of ribonucleotides instead of deoxyribonucleotides, all provided that said variant probes can be caused to hybridize with the same specificity as the oligonucleotide probes from which they are derived.

In order to distinguish the amplified HCV genomes from each other, the target polynucleic acids are hybridized to a set of sequence-specific DNA probes targetting HCV genotypic regions located in the HCV polynucleic acids.

Most of these probes target the most type-specific regions of HCV genotypes, but some can be caused to hybridize to more than one HCV genotype.

According to the hybridization solution (SSC, SSPE, etc.), these probes should be stringently hybridized at their appropriate temperature in order to attain sufficient specificity. However, by slightly modifying the DNA probes, either by adding or deleting one or a few nucleotides at their extremities (either 3' or 5'), or substituting some non-essential nucleotides (i.e. nucleotides not essential to discriminate between types) by others (including modified nucleotides or inosine) these probes or variants thereof can be caused to hybridize specifically at the same hybridization conditions (i.e. the same temperature and the same hybridization solution). Also changing the amount (concentration) of probe used may be beneficial to obtain more specific hybridization results. It should be noted in this context, that probes of the same length, regardless of their GC content, will hybridize specifically at approximately the same temperature in TMACl solutions (Jacobs et al., 1988).

Suitable assay methods for purposes of the present invention to detect hybrids formed between the oligonucleotide probes and the nucleic acid sequences in a sample may comprise any of the assay formats known in the art, such as the conventional dot-blot format, sandwich hybridization or reverse hybridization. For example, the detection can be accomplished using a dot blot format the unlabelled amplified sample being bound to a membrane, the membrane being incorporated with at least one labelled probe under suitable hybridization and wash conditions, and the presence of bound probe being monitored.

An alternative and preferred method is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the nucleic acids of the sample and the oligonucleotide probes according to the present invention may be used.

According to an advantageous embodiment, the process of detecting one or more HCV genotypes contained in a biological sample comprises the steps of contacting amplified HCV nucleic acid copies derived from the biological sample, with oligonucleotide probes which have been immobilized as parallel lines on a solid support.

According to this advantageous method, the probes are immobilized in a Line Probe Assay (LiPA) format. This is a reverse hybridization format (Saiki et al., 1989) using membrane strips onto which several oligonucleotide probes (including negative or positive control oligonucleotides) can be conveniently applied as parallel lines.

The invention thus also relates to a solid support, preferably a membrane strip, carrying on its surface, one or more probes as defined above, coupled to the support in the form of parallel lines.

The LiPA is a very rapid and user-friendly hybridization test. Results can be read 4 h. after the start of the amplification. After amplification during which usually a non-isotopic label is incorporated in the amplified product, and alkaline denaturation, the amplified product is contacted with the probes on the membrane and the hybridization is carried out for about 1 to 1,5 h hybridized polynucleic acid is detected. From the hybridization pattern generated, the HCV type can be deduced either visually, but preferably using dedicated software. The LiPA format is completely compatible with commercially available scanning devices, thus rendering automatic interpretation of the results very reliable. All those advantages make the LiPA format liable for the use of HCV detection in a routine setting. The LiPA format should be particularly advantageous for detecting the presence of different HCV genotypes.

The present invention also relates to a method for detecting and identifying novel HCV genotypes, different from the known HCV genomes, comprising the steps of:
  determining to which HCV genotype the nucleotides present in a biological sample belong, according to the process as defined above,
  in the case of observing a sample which does not generate a hybridization pattern compatible with those defined in Table 3, sequencing the portion of the HCV genome sequence corresponding to the aberrantly hybridizing probe of the new HCV genotype to be determined.

The present invention also relates to the use of a composition as defined above, for detecting one or more genotypes of HCV present in a biological sample liable to contain them, comprising the steps of:
  (i) possibly extracting sample nucleic acid,
  (ii) amplifying the nucleic acid with at least one of the primers as defined above,
  (iii) sequencing the amplified produces
  (iv) inferring the HCV genotypes present from the determined sequences by comparison to all known HCV sequences.

The present invention also relates to a composition consisting of or comprising at least one peptide or polypeptide comprising a contiguous sequence of at least 5 amino acids corresponding to a contiguous amino acid sequence encoded by at least one of the HCV genomic sequences as defined above, having at least one amino acid differing from the corresponding region of known HCV (type 1 and/or type 2 and/or type 3) polyprotein sequences as shown in Table 3, or muteins thereof.

It is to be noted that, at the level of the amino acid sequence, an amino acid difference (with respect to known HCV amino acid sequences) is necessary, which means that the polypeptides of the invention correspond to polynucleic acids having a nucleotide difference (with known HCV polynucleic acid sequences) involving an amino acid difference.

The new amino acid sequences, as deduced from the disclosed nucleotide sequences (see SEQ ID NO 1 to 62 and 106 to 123 and 143 to 218, 223 and 270), show homologies of only 59.9 to 78% with prototype sequences of type 1 and 2 for the NS4 region, and of only 53.9 to 68.8% with prototype sequences of type 1 and 2 for the E1 region. As the NS4 region is known to contain several epitopes, for example characterized in patent application EP-A-0 489 968, and as the E1 protein is expected to be subject to immune attack as part of the viral envelope and expected to contain epitopes, the NS4 and E1 epitopes of the new type 3, 4 and 5 isolates will consistently differ from the epitopes present in type 1 and 2 isolates. This is examplified by the type-specificity of NS4 synthetic peptides as presented in example 4, and the type-specificity of recombinant E1 proteins in example 11.

After aligning the new subtype 2d, type 3, 4 and 5 (see SEQ ID NO 1 to 62 and 106 to 123 and 143 to 218, 223 and 270) amino acid sequences with the prototype sequences of type 1a, 1b, 2a, and 2b, type- and subtype-specific variable regions can be delineated as presented in FIGS. 5 and 7.

As to the muteins derived from the polypeptides of the invention, Table 4 gives an overview of the amino acid substitutions which could be the basis of some of the muteins as defined above.

The peptides according to the present invention contain preferably at least 5 contiguous HCV amino acids, preferably however at least 8 contiguous amino acids, at least 10 or at least 15 (for instance at least 9, 11, 12, 13, 14, 20 or 25 amino acids) of the new HCV sequences of the invention.

TABLE 4

| Amino acids | Synonymous groups |
|---|---|
| Ser (S) | Ser, Thr, Gly, Asn |
| Arg (R) | Arg, His, Lys, Glu, Gln |
| Leu (L) | Leu; Ile, Met, Phe, Val, Tyr |
| Pro (P) | Pro, Ala, Thr, Gly |
| Thr (T) | Thr, Pro, Ser, Ala, Gly, His, Gln |
| Ala (A) | Ala, Pro, Gly, Thr |
| Val (V) | Val, Met, Ile, Tyr, Phe, Leu, Val |
| Gly (G) | Gly, Ala, Thr, Pro, Ser |
| Ile (I) | Ile, Met, Leu, Phe, Val, Ile, Tyr |
| Phe (F) | Phe, Met, Tyr, Ile, Leu, Trp, Val |
| Tyr (Y) | Tyr, Phe, Trp, Met, Ile, Val, Leu |
| Cys (C) | Cys, Ser, Thr, Met |
| His (H) | His, Gln, Arg, Lys, Glu, Thr |
| Gln (Q) | Gln, Glu, His, Lys, Asn, Thr, Arg |
| Asn (N) | Asn, Asp, Ser, Gln |
| Lys (K) | Lys, Arg, Glu, Gln, His |
| Asp (D) | Asp, Asn, Glu, Gln |
| Glu (E) | Glu, Gln, Asp, Lys, Asn, His, Arg |
| Met (M) | Met, Ile, Leu, Phe, Val |

The polypeptides of the invention, and particularly the fragments, can be prepared by classical chemical synthesis.

The synthesis can be carried out in homogeneous solution or in solid phase.

For instance, the synthesis technique in homogeneous solution which can be used is the one described by Houbenweyl in the book entitled "Methode der organischen chemie" (Method of organic chemistry) edited by E. Wunsh, vol. 15-I et II. THIEME, Stuttgart 1974.

The polypeptides of the invention can also be prepared in solid phase according to the methods described by Atherton and Shepard in their book entitled "Solid phase peptide synthesis" (IRL Press, Oxford, 1989).

The polypeptides according to this invention can be prepared by means of recombinant DNA techniques as described by Maniatis et al., Molecular Cloning: A Laboratory Manual, New York, Cold Spring Harbor Laboratory, 1982).

The present invention relates particularly to a polypeptide or peptide composition as defined above, wherein said contiguous sequence contains in its sequence at least one of the following amino acid residues:

L7, Q43, M44, S60, R67, Q70, T71, A79, A87, N 106, K115, A127, A190, S130, V134, G142, I144, E152, A157, V158, P165, S177 or Y177, I178, V180 or E180 or F182, R184, I186, H187, T189, A190, S191 or G191, Q192 or L192 or I192 or V192 or E192, N193 or H193 or P193, W194 or Y194, H195, A197 or I197 or V197 or T197, V202, I203 or L203, Q208, A210, V212, F214, T216, R217 or D217 or E217 or V217, H218 or N218, H219 or V219 or L219, L227 or I227, M231 or E231 or Q231, T232 or D232 or A232 or K232, Q235 or I235, A237 or T237, I242, I246, S247, S248, V249, S250 or Y250, I251 or V251 or M251 or F251, D252, T254 or V254, L255 or V255, E256 or A256, M258 or F258 or V258, A260 or Q260 or S260, A261, T264 or Y264, M265, I266 or A266, A267, G268 or T268, F271 or M271 or V271, I277, M280 or H280, I284 or A284 or L84, V274, V291, N292 or S292, R293 or I293 or Y293, Q294 or R294, L297 or I297 or Q297, A299 or K299 or Q299, N303 or T303, T308 or L308, T310 or F310 or A310 or D310 or V310, L313, G317 or Q317, L333, S351, A358, A359, A363, S364, A366, T369, L373, F376, Q386, I387, S392, I399, F402, I403, R405, D454, A461, A463, T464, K484, Q500, E501, S521, K522, H524, N528, S531, S532, V534, F536, F537, M539, I546, C1282, A1283, H1310, V1312, Q1321, P1368, V1372, V1373, K1405, Q1406, S1409, A1424, A1429, C1435, S1436, S1456, H1496, A1504, D1510, D1529, I1543, N1567, D1556, N1567, M1572, Q1579, L1581, S1583, F1585, V1595, E1606 or T1606, M1611, V1612 or L1612, P1630, C1636, P1651, T1656 or I1656, L1663, V1667, V1677, A1681, H1685, E1687, G1689, V1695, A1700, Q1704, Y1705, A1713, A1714 or S1714, M1718, D1719, A1721 or T1721, R1722, A1723 or V1723, H1726 or G1726, E1730, V1732, F1735, I1736, S1737, R1738, T1739, G1740, Q1741, K1742, Q1743, A1744, T1745, L1746, E1747 or K1747, I1749, A1750, T1751 or A1751, V1753, N1755, K1756, A1757, P1758, A1759, H1762, T1763, Y1764, P2645, A2647, K2650, K2653 or L2653, S2664, N2673, F2680, K2681, L2686, H2692, Q2695 or L2695 or I2695, V2712, F2715, V2719 or Q2719, T2722, T2724, S2725, R2726, G2729, Y2735, H2739, 12748, G2746 or I2746, I2748, P2752 or K2752, P2754 or T2754, T2757 or P2757, with said notation being composed of a letter representing the amino acid residue by its one-letter code, and a number representing the amino acid numbering according to Kato et al., 1990 as shown in Table 1 (comparison with other isolates). See also the numbering in FIGS. 2, 5, 7, and 11 (alignment amino acid sequences).

Within the group of unique and new amino acid residues of the present invention, the following residues were found to be specific for the following types of HCV according to the HCV classification system used in the present invention:

Q208, R217, E231, I235, I246, T264, I266, A267, F271, K299, L2686, Q2719 which are specific for the HCV subtype 2d sequences of the present invention as shown in FIGS. 5 and 2;

Q43, S60, R67, F182, I186, H187, A190, S191, L192, W194, V202, L203, V219, Q231, D232, A237, T254,

M280, Q299, T303, L308, and/or L313 which are specific for the Core/E1 region of HCV type 3 of the invention as shown in FIG. 5;

D1556, Q1579, L1581, S1584, F1585, E1606, V1612, P1630, C1636, T1656, L1663, H1685, E1687, G1689, V1695, Y1705, A1713, A1714, A1721, V1723, H1726, R1738, Q1743, A1744, E1747, I1749, A1751, A1759 and/or H1762 which are specific for the NS3/4 region of HCV type 3 sequences of the invention as shown in FIG. 7;

K2665, D2666, R2670 which are specific for the NS5B region of HCV type 3 of the invention as shown in FIG. 2;

L7, A79, A127, S130, E152, V158, S177 or Y177, V180 or E180, R184, T189, Q192 or E192 or I192, N193 or H193, I197 or V197, I203, A210, V212, E217, H218, H219, L227, A232, V249, I251 or M251, D252, L255 or V255, E256, M258 or V258 or F258, A260 or Q260, M265, T268, V271, V274, M280, I284, N292 or S292, Q294, L297 or I297, T308, A310 or D310 or V310 or T310, and G317 which are specific for the core/E1 region of HCV type 4 sequences of the present invention as shown in FIG. 5;

P2645, K-2650, K2653, G2656, V2658, T2668, N2673 or N2673, K2681, H2686, D2691, L2692, Q2695 or L2695 or I2695, Y2704, V2712, F2715, V2719, I2722, S2725, G2729, Y2735, G2746 or I2746, P2752 or K2752, Q2753, P2754 or T2754, T2757 or P2757 which are specific for the NS5B region of the HCV type 4 sequences of the present invention as shown in FIG. 2;

M44, Q70, A87, N106, K115, V137, G142, P165, I178, F251, A299, N303, Q317 which are specific for the Core/E1 region of the HCV type 5 sequence of the present invention as shown in FIG. 5;

L333, S351, A358, A359, A363, S364, A366, T369, L373, F376, Q386, I387, S392, I399, F102, I403, R405, D454, A461, A463, T464, K484, Q500, E501, S521, K522, H524, N528, S532, V534, F537, M539, I546 which are specific for the E1/E2 region of the HCV type 5 sequences of the present invention as shown in FIG. 12;

C1282, A1283, V1312, Q1321, P1368, V1372, K1405, Q1406, S1409, A1424, A1429, C1435, S1436, S1456, H1496, A1504, D1510, D1529, I1543, N1567, M1572, V1595, T1606, M1611, L1612, I1656, V1667, A1681, A1700, A1713, S1714, M1718, D1719, T1721, R1722, A1723, G1776, F1735, I1736, S1737, T1739, G1740, K1742, T1745, L1746, K1747, A1750, V1753, N1755, A1757, D1758, T1763, and Y1764 which are specific for the NS3/NS4 region of HCV type 5 sequences of the invention as shown in FIG. 7;

A2647, L2653, S2674, F2680, T2724, R2726, Y2730, H2739 which are specific for the NS5B region of the HCV type 5 sequences of the present invention as shown in FIG. 2;

A256, P1631, V1677, Q1704, E1730, V1732, Q1741 and T1751 which are specific for the HCV type 3 and 5 sequences of the present invention as shown in FIGS. 5 and 7;

T71, A157, I227, T237, T140, Y250, V251, S260, M271, T2673, T2722, I2748 which are specific for the HCV type 3 and 4 sequences of the present invention as shown in FIGS. 5 and 2;

V192, Y194, A197, P249, S250, R294 which are specific for the HCV type 4 and 5 sequences of the present invention as shown in FIG. 5;

I293 which is specific for the HCV type 4 and subtype 2d sequence of the present invention as shown in FIG. 5;

D217 and R294 which are specific for the HCV type 3, 4 and 5 sequences of the present invention as shown in FIG. 5;

L192 which is specific for the HCV type 3 and subtype 2d sequences of the present invention as shown in FIG. 5;

G191 and T197 which are specific for the HCV type 3, 4 and subtype 2d sequences of the present invention as shown in FIG. 5;

K232 which is specific for the HCV subtype 2d en type 5 sequences of the present invention as shown in FIG. 5.

and with said notation being composed of a letter, unambiguously representing the amino acid by its one-letter code, and a number representing the amino acid numbering according to Kato et al., 1990 (see also Table 1 for comparison with other isolates), as well as FIG. 2 (NS5 region), FIG. 5 (Core/E1 region), FIG. 7 (NS3/NS4 region), FIG. 12 (E1/E2 region). Some of the above-mentioned amino acids may be contained in type or subtype specific epitopes.

For example M231 (detected in type 5) refers to a methionine at position 231. A glutamine (Q) is present at the same position 231 in type 3 isolates, whereas this position is occupied by an arginine in type 1 isolates and by a lysine (K) or asparagine (N) in type 2 isolates (see FIG. 5).

The peptide or polypeptide according to this embodiment of the invention may be possibly labelled, or attached to a solid substrate, or coupled to a carrier molecule such as biotin, or mixed with a proper adjuvant.

The variable region in the core protein (V-CORE in FIG. 5) has been shown to be useful for serotyping (Machida et al., 1992). The sequence of the disclosed type 5 sequence in this region shows type-specific features. The peptide from amino acid 70 to 78 shows the following unique sequence for the sequences of the present inevntion (see FIG. 5):

QPTGRSWGQ (SEQ ID NO 93)
RSEGRTSWAQ (SEQ ID NO 220)
and RTEGRTSWAQ (SEQ ID NO 221)

Another preferred V-Core spanning region is the peptide spanning positions 60 to 78 of subtype 3c with sequence:

SRRQPIPRARRTEGRSWAQ (SEQ ID NO 268)

Five type-specific variable regions (V1 to V5) can be identified after aligning E1 amino acid sequences of the 4 genotypes, as shown in FIG. 5.

Region V1 encompasses amino acids 192 to 203, this is the amino-terminal 10 amino acids of the E1 protein. The following unique sequences as shown in FIG. 5 can be deduced:

| | |
|---|---|
| LEWRNTSGLYVL | (SEQ ID NO 83) |
| VNYRNASGIYHI | (SEQ ID NO 126) |
| QHYRNISGIYHV | (SEQ ID NO 127) |
| EHYRNASGIYHI | (SEQ ID NO 128) |
| IHYRNASGIYHI | (SEQ ID NO 224) |
| VPYRNASGIYHV | (SEQ ID NO 84) |
| VNYRNASGIYHI | (SEQ ID NO 225) |
| VNYRNASGVYHI | (SEQ ID NO 226) |
| VNYHNTSGIYHL | (SEQ ID NO 227) |

-continued

| | |
|---|---|
| QHYRNASGIYHV | (SEQ ID NO 228) |
| QHYRNVSGIYHV | (SEQ ID NO 229) |
| IHYRNASDGYYI | (SEQ ID NO 230) |
| LQVKNTSSSYMV | (SEQ ID NO 231) |

Region V2 encompasses amino acids 213 to 223. The following unique sequences can be found in the V2 region as shown in FIG. 5:

| | |
|---|---|
| VYEADDVILHT | (SEQ ID NO 85) |
| VYETEHHILHL | (SEQ ID NO 129) |
| VYEADHHIMHL | (SEQ ID NO 130) |
| VYETDHHILHL | (SEQ ID NO 131) |
| VYEADNLILHA | (SEQ ID NO 86) |
| VWQLRAIVLHV | (SEQ ID NO 232) |
| VYEADYHILHL | (SEQ ID NO 233) |
| VYETDNHILHL | (SEQ ID NO 234) |
| VYETENHILHL | (SEQ ID NO 235) |
| VFETVHHILHL | (SEQ ID NO 236) |
| VFETEHHILHL | (SEQ ID NO 237) |
| VFETDHHIMHL | (SEQ ID NO 238) |
| VYETENHILHL | (SEQ ID NO 239) |
| VYEADALILHA | (SEQ ID NO 240) |

Region V3 encompasses the amino acids 230 to 242. The following unique V3 region sequences can be deduced from FIG. 5:

| | |
|---|---|
| VQDGNTSTCWTPV | (SEQ ID NO 87) |
| VQDGNTSACWTPV | (SEQ ID NO 241) |
| VRVGNQSRCWVAL | (SEQ ID NO 132) |
| VRTGNTSRCWVPL | (SEQ ID NO 133) |
| VRAGNVSRCWTPV | (SEQ ID NO 134) |
| EEKGNISRCWIPV | (SEQ ID NO 242) |
| VKTGNQSRCWVAL | (SEQ ID NO 243) |
| VRTGNQSRCWVAL | (SEQ ID NO 244) |
| VKTGNQSRCWIAL | (SEQ ID NO 245) |
| VKTGNVSRCWIPL | (SEQ ID NO 247) |
| VKTGNVSRCWISL | (SEQ ID NO 248) |
| VRKDNVSRCWVQI | (SEQ ID NO 249) |

Region V4 encompasses the amino acids 248 to 257. The following unique V4 region sequences can be deduced from FIG. 5:

| | |
|---|---|
| VRYVGATTAS | (SEQ ID NO 89) |
| APYIGAPLES | (SEQ ID NO 135) |
| APYVGAPLES | (SEQ ID NO 136) |
| AVSMDAPLES | (SEQ ID NO 137) |
| APSLGAVTAP | (SEQ ID NO 90) |
| APSFGAVTAP | (SEQ ID NO 250) |
| VSQPGALTKG | (SEQ ID NO 251) |
| VKYVGATTAS | (SEQ ID NO 252) |
| APYIGAPVES | (SEQ ID NO 253) |
| AQHLNAPLES | (SEQ ID NO 254) |
| SPYVGAPLEP | (SEQ ID NO 255) |
| SPYAGAPLEP | (SEQ ID NO 256) |
| APYLGAPLEP | (SEQ ID NO 257) |
| APYLGAPLES | (SEQ ID NO 258) |
| APYVGAPLES | (SEQ ID NO 259) |
| VPYLGAPLTS | (SEQ ID NO 260) |
| APHLRAPLSS | (SEQ ID NO 261) |
| APYLGAPLTS | (SEQ ID NO 262) |

Region V5 encompasses the amino acids 294 to 303. The following unique V5 region peptides can be deduced from FIG. 5:

| | |
|---|---|
| RPRRHQTVQT | (SEQ ID NO 91) |
| QPRRHWTTQD | (SEQ ID NO 138) |
| RPRRHWTTQD | (SEQ ID NO 139) |
| RPRQHATVQN | (SEQ ID NO 92) |
| RPRQHATVQD | (SEQ ID NO 263) |
| SPQHHKFVQD | (SEQ ID NO 264) |
| RPRRLWTTQE | (SEQ ID NO 265) |
| PPRIHETTQD | (SEQ ID NO 266) |

The variable region in the E2 region (HVR-2) of type 5a as shown in FIG. 12 spanning amino acid positions 471 to 484 is also a preferred peptide according to the present invention with the following sequence:
TISYANGSGPSDDK (SEQ ID NO 267)

The above given list of peptides are particularly suitable for vaccine and diagnostic development.

Also comprised in the present invention is any synthetic peptide or polypeptide containing at least 5 contiguous amino acids derived from the above-defined peptides in their peptidic chain.

According to a specific embodiment, the present invention relates to a composition as defined above, wherein said contiguous sequence is selected from any of the following HCV amino acid type 3 sequences:
a sequence having a homology of more than 72%, preferably more than 74%, more preferably more than 77% and most preferably more than 80 or 84% homology to any of the amino acid sequences as represented in SEQ ID NO 14, 16, 18, 20, 22, 24, 26 or 28 (HD10, BR36, BR33 sequences) in the region spanning positions 140 to 319 in the Core/E1 region as shown in FIG. 5;

a sequence having a homology of more than 70%, preferably more than 72%, more preferably more than 75% homology, most preferably more than 81% homology to any of the amino acid sequences as represented in SEQ ID NO 14, 16, 18, 20, 22, 24, 26 or 28 (HD10, BR36, BR33 sequences) in the E1 region spanning positions 192 to 319 as shown in FIG. 5;

a sequence having a homology of more than 86%, preferably more than 88%, and most preferably more than 90% homology to the amino acid sequences as represented in SEQ ID NO 148 (type 3c); BE98 in the region spanning positions 1 to 110 in the Core region as shown in FIG. 5;

a sequence having a homology of more than 76%, preferably more than 78%, most preferably more than 80% to any of the amino acid sequences as represented in SEQ ID NO 30, 32, 34, 36, 38 or 40 (HCC153, HD10, BR6 sequences) in the region spanning positions 1646 to 1764 in the NS3/NS4 region as shown in FIGS. 7 and 11;

a sequence having a homology of more than 81%, preferably more than 83%, and most preferably more than 86% homology to any of the amino acid sequences as represented in SEQ ID NO 14, 16, 18, 20, 22, 24, 26 or 28 (HD10, BR36, BR33 sequences) in the region spanning positions 140 to 319 in the Core/E1 region as shown in FIG. 5;

a sequence having a homology of more than 81.5%, preferably more than 83%, and most preferably more than 86% homology to any of the amino acid sequences as represented in SEQ ID NO 14, 16, 18, 20, 22, 24, 26 or 28 (HD10, BR36, BR33 sequences) in the E1 region spanning positions 192 to 319 as shown in FIG. 5;

a sequence having a homology of more than 86%, preferably more than 88%, most preferably more than 90% to the amino acid sequence as represented in SEQ ID NO 150; (type 3c BE98) in the region spanning positions 2645 to 2757 in the NS5B region as shown in FIG. 2.

According to yet another embodiment, the present invention relates to a composition as defined above, wherein said contiguous sequence is selected from any of the following HCV amino acid type 4 sequences:

a sequence having a homology of more than 80%, preferably more than 82%, most preferably more than 84% homology to any of the amino acid sequences as represented in SEQ ID NO 119, 121, and 123 (GB358, GB549, GB809 sequences) in the region spanning positions 127 to 319 of the Core/E1 region as shown in FIG. 5;

a sequence having a homology of more than 73%, preferably more than 75%, most preferably more than 78% homology in the E1 region spanning positions 192 to 319 to any of the amino acid sequences as represented in SEQ ID NO 119, 121 and 123 (GB358, GB549, GB809 sequences) in the region spanning positions 140 to 319 of the Core/E1 region as shown in FIG. 5;

a sequence having more than 85%, preferably more than 86%, most preferably more than 87% homology to any of the amino acid sequences as represented in SEQ ID NO 118, 120 or 119, 121, or 123 (GB358, GB549, GB809 sequences) in the region spanning positions 192 to 319 of E1 as shown in FIG. 5;

a sequence showing more than 73%, preferably more than 74%, most preferably more than 75% homology to any of the amino acid sequences as represented in SEQ ID NO 107, 109, 111, 113, 115 or 117 (GB48, GB116, GB215, GB358, GB549, GB809 sequences) in the region spanning positions 2645 to 2757 of the NS5B region as shown in FIG. 2;

a sequence having any of the sequences as represented in SEQ ID NO 164 or 166 (GB809 and CAM600 sequences) in the Core region as shown in FIG. 5;

a sequence having any of the sequences as represented in SEQ ID NO 168, 170, 172, 174, 176, 178, 180, 182, 184, 186, 188 or 190 (CAM600, GB809, CAMG22, CAMG27, GB549, GB438, CAR4/1205, CAR4/901, GB116, GB215, GB958, GB809-4 sequences) in the Core/E1 region as shown in FIG. 5;

a sequence having any of the sequences as represented in SEQ ID NO 194, 196, 198, 200, 202, 204, 206, 208, 210, 212 (GB724, BE100, PC, CAM600, CAMG22, etc.) in the NS5B region or in SEQ ID NOs: 198, 200 in the NS3/4 region.

The above-mentioned type 4 peptides polypeptides comprise at least an amino acid sequence selected from any HCV type 4 polyprotein with the exception of core sequence as disclosed by Simmonds et al. (1993, EG-29, see FIG. 5).

According to yet another aspect, the present invention relates to a composition as defined above, wherein said contiguous sequence is selected from any of the following HCV amino acid type 5 sequences:

a sequence having more than 93%, preferably more than 94%, most preferably more than 95% homology in the region spanning Core positions 1 to 191 to any of the amino acid sequences as represented in SEQ ID NO 42, 44, 46, 48, 50, 52 or 54 (PC sequences) and SEQ ID NO 152 (BE95) as shown in FIG. 5;

a sequence having more than 73%, preferably more than 74%, most preferably more than 76% homology in the region spanning E1 positions 192 to 319 to any of the amino acid sequences as represented in SEQ ID NO 42, 44, 46, 48, 50, 52 or 54 (PC sequences) as shown in FIG. 5;

a sequence having a more than 78%, preferably more than 80%, most preferably more than 83% homology to any of the amino acid sequences as represented in SEQ ID NO 42, 44, 46, 48, 50, 52, 54, 154, 156 (BE95, BE100) (PC sequences) in the region spanning positions 1 to 319 of the Core/E1 region as shown in FIG. 5;

a sequence having more than 90%, preferably more than 91%, most preferably more than 92% homology to any of the amino acid sequences represented in SEQ ID NO 56 or 58 (PC sequences) in the region spanning positions 1286 to 1403 of the NS3 region as shown in FIG. 7 or 11;

a sequence having more than 66, more particularly 68%, most particularly 70% or more homology to any of the amino acid sequences as represented in SEQ ID NO 60 or 62 (PC sequences) in the region spanning positions 1646 to 1764 of the NS3/4 region as shown in FIG. 7 or 11.

According to yet another embodiment, the present invention relates to a composition as defined above, wherein said contiguous sequence is selected from any of the following HCV amino acid type 2d sequences:

a sequence having more than 83%, preferably more than 85%, most preferably more than 87% homology to the amino acid sequence as represented in SEQ ID NO 144

(NE92) in the region spanning positions 1 to 319 of the Core/E1 region as shown in FIG. 5;

a sequence having more than 79%, preferably more than 81%, most preferably more than 84% homology in the region spanning E1 positions 192 to 319 to the amino acid sequence as represented in SEQ ID NO 144 (NE92) as shown in FIG. 12;

a sequence having more than 95%, more particularly 96%, most particularly 97% or more homology to the amino acid sequence as represented in SEQ ID NO 146 (NE92) in the region spanning positions 2645 to 2757 of the NS5B region as shown in FIG. 2.

The present invention also relates to a recombinant vector, particularly for cloning and/or expression, with said recombinant vector comprising a vector sequence, an appropriate prokaryotic, eukaryotic or viral promoter sequence followed by the nucleotide sequences as defined above, with said recombinant vector allowing the expression of any one of the HCV type 2 and/or HCV type 3 and/or type 4 and/or type 5 derived polypeptides as defined above in a prokaryotic, or eukaryotic host or in living mammals when injected as naked DNA, and more particularly a recombinant vector allowing the expression of any of the following HCV type 2d, type 3, type 4 or type 5 polypeptides spanning the following amino acid positions:

a polypeptide starting at position 1 and ending at any position in the region between positions 70 and 326, more particularly a polypeptide spanning positions 1 to 70, 1 to 85, positions 1 to 120, positions 1 to 150, positions 1 to 191, positions 1 to 200, for expression of the Core protein, and a polypeptide spanning positions 1 to 263, positions 1 to 326, for expression of the Core and E1 protein;

a polypeptide starting at any position in the region between positions 117 and 192, and ending at any position in the region between positions 263 and 326, for expression of E1, or forms that have the putative membrane anchor deleted (positions 264 to 293 plus or minus 8 amino acids);

a polypeptide starting at any position in the region between positions 1556 and 1688, and ending at any position in the region between positions 1739 and 1764, for expression of the NS4 regions, more particularly a polypeptide starting at position 1658 and ending at position 1711 for expression of the NS4a antigen, and more particularly, a polypeptide starting at position 1712 and ending between positions 1743 and 1972, for example 1712–1743, 1712–1764, 1712–1782, 1712–1972, 1712 to 1782 and 1902 to 1972 for expression of the NS4b protein or parts thereof.

The term "vector" may comprise a plasmid, a cosmid, a phage, or a virus.

In order to carry out the expression of the polypeptides of the invention in bacteria such as *E. coli* or in eukaryotic cells such as in *S. cerevisiae*, or in cultured vertebrate or invertebrate hosts such as insect cells, Chinese Hamster Ovary (CHO), COS, BHK, and MDCK cells, the following steps are carried out:

transformation of an appropriate cellular host with a recombinant vector, in which a nucleotide sequence coding for one of the polypeptides of the invention has been inserted under the control of the appropriate regulatory elements, particularly a promoter recognized by the polymerases of the cellular host and, in the case of a prokaryotic host, an appropriate ribosome binding site (RBS), enabling the expression in said cellular host of said nucleotide sequence. In the case of an eukaryotic host any artificial signal sequence or pre/pro sequence might be provided, or the natural HCV signal sequence might be employed, e.g. for expression of E1 the signal sequence starting between amino acid positions 117 and 170 and ending at amino acid position 191 can be used, for expression of NS4, the signal sequence starting between amino acid positions 1646 and 1659 can be used, culture of said transformed cellular host under conditions enabling the expression of said insert.

The present invention also relates to a composition as defined above, wherein said polypeptide is a recombinant polypeptide expressed by means of an expression vector as defined above.

The present invention also relates to a composition as defined above, for use in a method for immunizing a mammal, preferably humans, against HCV comprising administering a sufficient amount of the composition possibly accompanied by pharmaceutically acceptable adjuvants, to produce an immune response, more particularly a vaccine composition including HCV type 3 polypeptides derived from the Core, E1 or the NS4 region and/or HCV type 4 and/or HCV type 5 polypeptides and/or HCV type 2d polypeptides.

The present invention also relates to an antibody raised upon immunization with a composition as defined above by means of a process as defied above, with said antibody being reactive with any of the polypeptides as defined above, and with said antibody being preferably a monoclonal antibody.

The monoclonal antibodies of the invention can be produced by any hybridoma liable to be formed according to classical methods from splenic cells of an animal, particularly from a mouse or rat, immunized against the HCV polypeptides according to the invention, or muteins thereof, or fragments thereof as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains, or from cDNA clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients infected with type 3, type 4 or type 5 HCV, or vaccinated against HCV. Such human monoclonal antibodies are prepared, for instance, by means of human peripheral blood lymphocytes (PBL) repopulation of severe combined immune deficiency (SCID) mice (for recent review, see Duchosal et al. 1992).

The invention also relates to the use of the proteins of the invention, muteins thereof, or peptides derived therefrom for the selection of recombinant antibodies by the process of repertoire cloning (Persson et al., 1991).

Antibodies directed to peptides derived from a certaing genotype may be used either for the detection of such HCV genotypes, or as therapeutic agents.

The present invention also relates to the use of a composition as defined above for incorporation into an immunoassay for detecting HCV, present in biological sample liable to contain it, comprising at least the following steps:
(i) contacting the biological sample to be analyzed for the presence of HCV antibodies with any of the compositions as defined above preferably in an immobilized form under appropriate conditions which allow the formation of an immune complex, wherein said polypeptide can be a biotinylated polypeptide which is covalently bound to a solid substrate by means of streptavidin or avidin complexes,
(ii) removing unbound components,
(iii) incubating the immune complexes formed with heterologous antibodies, which specifically bind to the antibodies present in the sample to be analyzed, with said heterologous antibodies having conjugated to a detectable label under appropriate conditions,
(iv) detecting the presence of said immunecomplexes visually or by means of densitometry and inferring the HCV serotype present from the observed hybridization pattern.

The present invention also relates to the use of a composition as defined above, for incorporation into a serotyping assay for detecting one or more serological types of HCV present in a biological sample liable to contain it, more particularly for detecting E1 and NS4 antigens or antibodies of the different types to be detected combined in one assay format, comprising at least the following steps:
(i) contacting the biological sample to be analyzed for the presence of HCV antibodies or antigens of one or more serological types, with at least one of the compositions as defined above, an immobilized form under appropriate conditions which allow the formation of an immunecomplex,
(ii) removing unbound components,
(iii) incubating the immunecomplexes formed with heterologous antibodies, which specifically bind to the antibodies present in the sample to be analyzed, with said heterologous antibodies having conjugated to a detectable label under appropriate conditions,
(iv) detecting the presence of said immunecomplexes visually or by means or densitometry and inferring the presence of one or more HCV serological types present from the observed binding pattern.

The present invention also relates to the use of a composition as defined above, for immobilization on a solid substrate and incorporation into a reversed phase hybridization assay, preferably for immobilization as parallel lines onto a solid support such as a membrane strip, for determining the presence or the genotype of HCV according to a method as defined above.

The present invention thus also relates to a kit for determining the presence of HCV genotypes as defied above present in a biological sample liable to contain them, comprising:
possibly at least one primer composition contacting any primer selected from those defined above or any other HCV type 3 and/or HCV type 4, and/or HCV type 5, or universal HCV primers,
at least one probe composition as defined above, with said probes being preferentially immobilized on a solid substrate, and more preferentially on one and the same membrane strip,
a buffer or components necessary for producing the buffer enabling hybridization reaction between these probes and the possibly amplified products to be carried out,
means for detecting the hybrids resulting from the preceding hybridization,
possibly also including an automated scanning and interpretation device for inferring the HCV genotypes present in the sample from the observed hybridization pattern.

The genotype may also be detected by means of a type-specific antibody as defined above, which is linked to any polynucleotide sequence that can afterwards be amplified by PCR to detect the immune complex formed (Immuno-PCR. Sano et al., 1992);

The present invention also relates to a kit for determining the presence of HCV antibodies as defined above present in a biological sample liable to contain them, comprising:
at least one polypeptide composition as defined above, preferentially in combination with other polypeptides or peptides from HCV type 1, HCV type 2 or other types of HCV, with said polypeptides being preferentially immobilized on a solid substrate, and more preferentially on one and the same membrane strip,
a buffer or components necessary for producing the buffer enabling binding reaction between these polypeptides and the antibodies against HCV present in the biological sample,
means for detecting the immunecomplexes formed in the preceding binding reaction,
possibly also including an automated scanning and interpretation device for inferring the HCV genotypes present in the sample from the observed binding pattern.

BRIEF DESCRIPTION OF THE DRAWINGS

FIG. 1
Alignment of consensus nucleotide sequences for each of the type 3a isolates BR34, BR36, and BR33, deduced from the clones with SEQ ID NO 1, 5, 9; type 4 isolates GB48, GB 116, GB215, GB358, GB549, GB809, CAM600, CAMG22, GB438, CAR4/1205, CAR1/501 (SEQ ID NO. 106, 108, 110, 112, 114, 116, 201, 203, 205, 207, 209 and 211); type 5a isolates BE95 and BE96 (SEQ ID NO 159 and 161) and type 2d isolate NE92 (SEQ ID NO 145) from the region between nucleotides 7932 and 8271, with known sequences from the corresponding region of isolates HCV-1, HCV-J, HC-J6, HC-J8, T1 and T9, and others as shown in Table 3.

FIG. 2
Alignment of amino acids sequences deduced from the nucleic acid sequences as represented in FIG. 1 from the subtype 3a clones BR34 (SEQ ID NO 2.4), BR36 (SEQ ID NO 6, 8) and BR33 (SEQ ID NO 10, 12), the subtype 3c clone BE98 (SEQ ID NO 150), and the type 4 clones GB48 (SEQ ID NO 107), GB116 (SEQ ID NO 109), GB215 (SEQ ID NO 111), GB358 (SEQ ID NO 113), GB549 (SEQ ID NO 115) GB809 (SEQ ID NO 117); CAM600, CAMG22, GB438, CAR4/1205, CAR1/501 (SEQ ID NO 202, 204, 206, 208, 210, 212); the type 5a clones BE95 and BE96 (SEQ ID NO 160 and 162); as well as the subtype 2d isolate NE92 (SEQ ID NO 146) from the region between amino acids 2645 to 2757 with known sequences from the corresponding region of isolates HCV-I, HCV-J, HC-J6, and HC-J8, T1 and T9, and other sequences as shown in Table 3.

FIG. 3
Aligment of type 2d, 3c, 4 and 5a nucleotide sequences from isolates NE92, BE98, GB358, GB809, CAM600, GB724, BE95 (SEQ ID NO 143, 147, 191, 163, 165, 193 and 151) in the Core region between nucleotide positions 1 and 500, with known sequences from the corresponding region of type 1, type 2, type 3 and type 4 sequences.

FIG. 4

Figure 8:
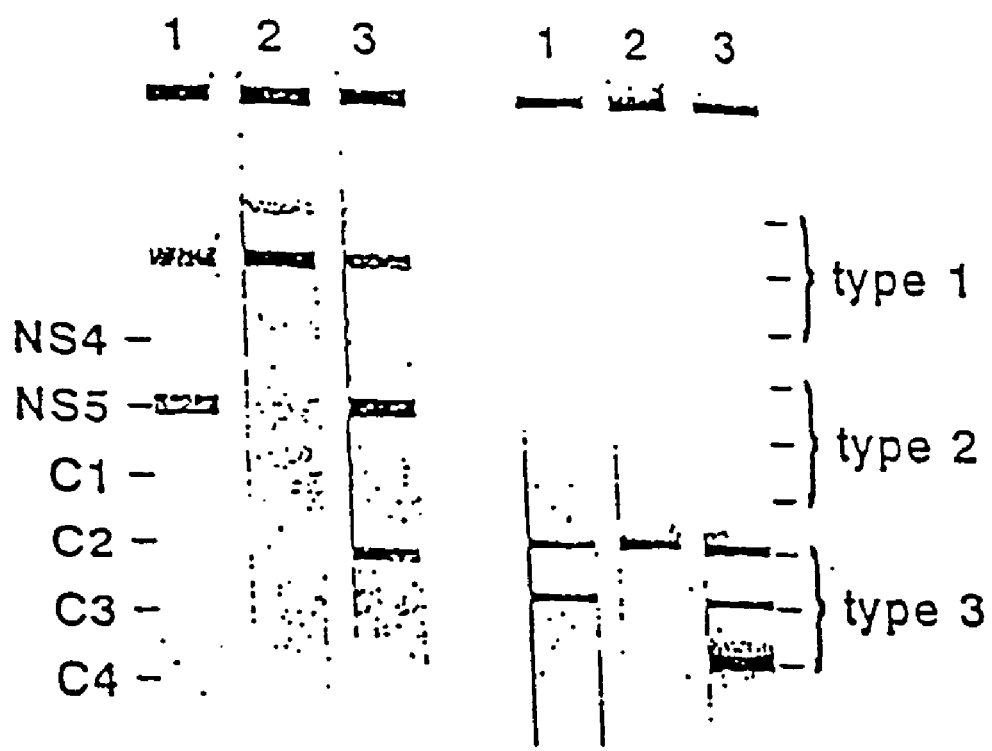

Alignment of nucleotide sequences for the subtype 2d isolate NE92 (SEQ ID NO 143), the type 4 isolates GB358 (SEQ ID NO 118 and 187), GB549 (SEQ ID NO 120 and 175), and GB809-2 (SEQ ID NO 122 and 169), GB 809-4, BG116, GB215, CAM600, CAMG22, CAMG27, GB438, CAR4/1205, CAR4/901 (SEQ ID NO 189, 183, 185, 167, 171, 173, 177, 179, 181), sequences for each of the subtype 3a isolates HD10, BR36, and BR33, (SEQ ID NO 13, 15, 17 (HD10), 19, 21 (BR36) and 23, 25 or 27 (BR-36) and the subtype 5a isolates BE 95 and BE100(SEQ ID NO 143 and 195) from the region between nucleotides 379 and 957, with known sequences from the corresponding region of type 1 and 2 and 3.

FIG. 5

Alignment of amino acid sequences deduced from the new HCV nucleotide sequences of the Core/E1 region of isolates BR33, BR36, HD10, GB358, GB549, and GB809, PC or BE95, CAM600, and GB724 (SEQ ID NO. 14, 20, 24, 119 or 192, 121, 123 or 164, 54 or 152, 166 and 194) from the region between positions 1 and 319, with known sequences from type 1a (HCV-1), type 1b (HCV-1), type 2a (HC-JG), type 2b (HC-J8). NZL1, HCV-TR, positions 7–89 of type 3a (E-b 1), and positions 8–88 of type 4a (EG-29). V-Core, variable region with type-specific features in the core protein, V1, variable region 1 of the E1 protein, V2, variable region 2 of the E1 protein, V3, variable region 3 of the E1 protein, V4, variable region 4 of the E1 protein, V5, variable region 5 of the E1 protein.

FIG. 6

Alignment of nucleotide sequences of isolates HCCL53, HD10 and BR36, deduced from clones with SEQ ID NO 29, 31, 33, 35, 37 and 39, from the NS3/4 region between nucleotides 4664 to 5292, with known sequences from the corresponding region of isolates HCV-1, HCV-J, HC-J6, and HC-J8, EB1, EB2, EB6 and EB7.

FIG. 7

Alignment of amino acid sequences deduced from the new HCV nucleotide sequences of the NS3/NS4 region of isolate BR36 (SEQ ID NO 36, 38 and 40) and BE95 (SEQ ID NO 270). NS4-1, indicates the region that was synthesized as synthetic peptide 1 of the NS4 region, NS4-5, indicates the region that was synthesized as synthetic peptide 5 of the NS4 region; NS4-7, indicates the region that was synthesized as synthetic peptide 7 of the NS4 region.

FIG. 8

Reactivity of the three LIPA-selected (Stuyver et al., 1993) type 3 sera on the Inno-LIA HCV Ab II assay (Innogenetics) (left), and on the NS4-LIA test. For the NS4-LIA rest, NS4-1, NS4-5, and NS4-7 peptides were synthesized based on the type 1 (HCV-1), type 2 (HC-J6) and type 3 (BR36) prototype isolate sequences as shown in Table 4, and applied as parallel lines onto a membrane strip as indicated. 1, serum BR33, 2, serum HD10, 3, serum DKH.

FIG. 9

Nucleotide sequences of Core/E1 clones obtained from the PCR fragments PC-2, PC-3, and PC4, obtained from serum BE95 (PC-2-1 (SEQ ID NO 41), PC-2-6 (SEQ ID NO 43), PC-4-1 (SEQ ID NO 45), PC-4-6 (SEQ ID NO 47), PC-3-4 (SEQ ID NO 49) and PC-3-8 (SEQ ID NO 51)) of subtype 5a isolate BE95.

A consensus sequence is shown for the Core and E1 region of isolate BE95, presented as PC C/E1 with SEQ ID NO 53. Y, C or T, R, A or G, S, C or G.

FIG. 10

Alignment of nucleotide sequences of clones with SEQ ID NO 197 and 199 (PC sequences, see also SEQ ID NO 55, 57, 59) and SEQ ID NO 35, 37 and 39 (BR36 sequences) from the NS3/4 region between nucleotides 3856 to 5292, with known sequences from the corresponding region of isolates HCV-1, HCV-J, HC-J6, and HC-J8.

FIG. 11

Alignment of amino acid sequences of subtype 5a BE95 isolate PC clones with SEQ ID NO 56 and 58, from the NS3/4 region between amino acids 1286 to 1764, with known sequences from the corresponding region of isolates HCV-1, HCV-J, HC-J6, and HC-J8.

FIG. 12

Alignment of amino acid sequences of subtype 5a isolate BE95 (SEQ ID NO 158) in the E1/E2 region spanning positions 328 to 546, with known sequences from the corresponding region of isolates HCV-1, HCV-J, HC-J6, HC-J8, NZL1 and HCV-TR (see Table 3).

FIG. 13

Alignment of the nucleotide sequences of subtype 5a isolate BE95 (SEQ ID NO 157) in the E1/E2 region with known HCV sequences as shown in Table 3.

EXAMPLES

Example 1

The NS5b Region of HCV Type 3

Type 3 sera, selected by means of the INNO-LiPA HCV research kit (Stuyver et al., 1993) from a number of Brazilian blood donors, were positive in the HCV antibody ELISA (Innotest HCV Ab II; Innogenetics) and/or in the INNO-LIA HCV Ab II confirmation test (Innogenetics). Only those sera that were positive after the first round of PCR reactions (Stuyver et al., 1993) were retained for further study.

Reverse transcription and nested PCR: RNA was extracted from 50 μl serum and subjected to cDNA synthesis as described (Stuyver et al., 1993). This cDNA was used as template for PCR, for which the total volume was increased to 50 μl containing 10 pmoles of each primer, 3 μl of 10× Pfu buffer 2 (Stratagene) and 2.5 U of Pfu DNA polymerase (Stratagene). The cDNA was amplified over 45 cycles consisting of 1 min 94° C., 1 min 50° C. and 2 min 72° C. The amplified products were separated by electrophoresis, isolated, cloned and sequenced as described (Stuyver et al., 1993).

Type 3a and 3b-specific primers in the NS5 region were selected from the published sequences (Mori et al., 1992) as follows:

for type 3a:

HCPr161(+): 5'-ACCGGAGGCCAGGAGAGATGATCTC-CTCC-3' (SEQ ID NO 63) and

HCPr162(−): 5'-GGGCTGCTCTATCCTCATCGACGC-CATC-3' (SEQ ID NO 64);

for type 3b:

HCPr163(+): 5'-GCCAGAGGCTCGGAAGGCGAT-CAGCGCT-3' (SEQ ID O 65) and

HCPr164(−): 5'-GAGCTGCTCTGTCCTCCTCGACGC-CGCA-3' (SEQ ID NO 66)

Using the Line Probe Assay (LiPA) (Stuyver et al., 1993), seven high-titer type 3 sera were selected and subsequently analyzed with the primer sets HCPr161/162 for type 3a, and HCPr163/164 for type 3b. None of these sera was positive with the type 3b primers. NS5 PCR fragments obtained using the type 3a primers from serum BR36 (BR36-23), serum BR33(BR33-2) and serum BR34 (BR34-4) were selected for cloning. The following sequences were obtained from the PCR fragments:

From fragment BR34-4:

BR34-4-20 (SEQ ID NO 1), BR34-4-19 (SEQ ID NO 3)
From fragment BR36-23:

BR36-23-18 (SEQ ID NO 5), BR36-23-20 (SEQ ID NO 7)
From fragment BR33-2:

BR33-2-17 (SEQ ID NO 9), BR33-2-21 (SEQ ID NO 11)

An alignment of sequences with SEQ ID NO 1, 5 and 9 with known sequences is given in FIG. 1. An alignment of the deduced amino acid sequences is shown in FIG. 2. The 3 isolates are very closely related to each other (mutual homologies of about 95%) and to the published sequences of type 3a (Mori et al., 1992), but are only distantly related to type 1 and type 2 sequences (Table 5). Therefore, it is clearly demonstrated that NS5 sequences from LiPA-selected type 3 sera are indeed derived from a type 3 genome. Moreover, by analyzing the NS5 region of serum BR34, for which no 5'UR sequences were determined as described in Stuyver et al. (1993), the excellent correlation between typing by means of the LiPA and genotyping as deduced from nucleotide sequencing was further proven.

Example 2

The Core/E1 Region of HCV Type 3

After aligning the sequences of HCV-1 (Choo et al., 1991), HCV-J (Kato et al., 1990), HC-J6 (Okamoto et al., 1991), and HC-J8 (Okamoto et al., 1992), PCR primers were chosen in those regions of little sequence variation. Primers HCPr23(-): 5'-CTCATGGGGTACATTCCGCT-3' (SEQ ID NO 67) and HCPr54(-): 5'-TATTACCAGTTCATCAT-CATATCCCA-3' (SEQ ID NO 68), were synthesized on a 392 DNA/RNA synthesizer (Applied Biosystems). This set of primers was selected to amplify; the sequence from nucleotide 397 to 957 encoding amino acids 140 to 319 (Kato et al., 1990): 52 amino acids from the carboxyterminus of core and 128 amino acids of E1 (Kato et al., 1990). The amplification products BR36-9, BRR33-1, and HD 10-2 were cloned as described (Stuyver et al., 1993). The following clones were obtained from the PCR fragments:

From fragment HD10-2:

HD10-2-5 (SEQ ID NO 13), HD10-2-14(SEQ ID NO 15), HD10-2-21 (SEQ ID NO 17)
From fragment BR36-9:

BR36-9-13 (SEQ ID NO 19), BR36-9-20 (SEQ ID NO 21),
From fragment BR33-1:

BR33-1-10 (SEQ ID NO 23), BR33-1-19 (SEQ ID NO 25), BR33-1-20 (SEQ ID NO 27),

An alignment of the type 3 E1 nucleotide sequences (HD10, BR36, BR33, with SEQ ID NO 13, 19 and 23 with known E1 sequences is presented in FIG. 4. Four variations were detected in the E1 clones from serum HD10 and BR36, while only 2 were found in BR33. All are silent third letter variations, with the exception of mutations at position 40 (L to P) and 125 (M to I). The homologies of the type 3 E1 region (without core) with type 1 and 2 prototype sequences are depicted in Table 5.

In total, 8 clones covering the core/E1 region of 3 different isolates were sequenced and the E1 portion was compared with the known genotypes (Table 3) as shown in FIG. 5. After computer analysis of the deduced amino acid sequence, a signal-anchor sequence at the core carboxy terminus was detected which might, through analogy with type 1b (Hijikata et al., 1991), promote cleavage before the LEWRN sequence (position 192, FIG. 5; SEQ ID NO:271). The L-to-P mutation in one of the HD10-2 clones resides in this signal-anchor region and potentially impairs recognition by signal peptidase (computer prediction). Since no examples of such substitutions were found at this position in previously described sequences, this mutation might have resulted from reverse transcriptase or Pfu polymerase misincorporation. The 4 amino-terminal potential N-linked glycosylation sites, which are also present in HCV types 1a and 2, remain conserved in type 3. The N-glycosylation site in type 1 b (aa 250, Kato et al., 1990) remains a unique feature of this subtype. All E1 cysteines, and the putative transmembrane region (aa 264 to 293, computer prediction) containing the aspartic acid at position 279, are conserved in all three HCV types. The following hypervariable regions can be delineated: V1 from aa 192 to 203 (numbering according to Kato et al., 1990), V2 (213–223), V3 (230–242), V4 (248–257), and V5 (294–303). Such hydrophilic regions are thought to be exposed to the host defense mechanisms. This variability might therefore have been induced by the host's immune response. Additional putative N-linked glycosylation sites in the V4 region in all type 1b isolates known today and in the V5 region of HC-J8 (type 2b) possibly further contribute to modulation of the immune response. Therefore, analysis of this region, in the present invention, for type 3 and 4 sequences has been instrumental in the delineation of epitopes that reside in the V-regions of E1, which will be critical for future vaccine and diagnostics development.

Example 3

The NS3/NS4 Region of HCV Type 3

For the NS3/NS4 border region, the following sets of primers were selected in the regions of little sequence variability after aligning the sequences of HCV-1 (Choo et al., 1991), HCV-J (Kato et al., 1990), HC-J6 (Okamoto et al., 1991), and HC-J8 (Okamoto et al., 1992) (smaller case lettering is used for nucleotides added for cloning purposes):

set A:

HCPr116(+): 5'-ttttAAATACATCATGRCITGYATG-3' (SEQ ID NO 69)

HCPr66(-): 5'-ctattaTTGTATCCCRCTGATGAARTTC-CACAT-3' (SEQ ID NO 70)

set B:

HCPr116(+): 5'-ttttAAATACATCATGRCITGYATG-3' (SEQ ID NO 69)

HCPr118(-): 5'-actagtcgactaYTGIATICCRCTIATR-WARTTCCACAT-3' (SEQ ID NO 71)

set C:

HCPr117(+): 5'-ttttAAATACATCGCIRCITGCATGACA-3' (SEQ ID NO 72)

HCPr66(−): 5'-ctattaTTGTATCCCRCTGATGAARTTC-CACAT-3' (SEQ ID NO 70)
 set D:

HCPr 117(+): 5'-ttttAAATACATCGCIRCITGCATGCA-3' (SEQ ID NO 72)

HCPr 118(−): 5'-actagtcgactaYTGIATICCRCTIATR-WARTTCCACAT-3' (SEQ ID NO 71)
 set E:

HCPr116(+): 5'-ttttAAATACATCATGRCITGYATG-3' (SEQ ID NO 69)

HCPr119(−): actagtcgactaRTTIGCIATIAGCCG/TRT-TCATCCAYTG-3' (SEQ ID NO 73)
 set F:

HCPr117(+): 5'-ttttAAATACATCGCIRCITGCATGCA-3' (SEQ ID NO 72)

HCPr119(−): actagtcgactaRTTIGCIATIAGGCCG/TRT-TCATCCAYTG-3' (SEQ ID NO 73)
 set G:

HCPr131(+): 5'-ggaattctagaCCITCITGGGAYGARAY-ITGGAARTG-3' (SEQ ID NO 74)

HCPr66(−): 5'-ctattaTTGTATCCCRCTGATGAARTTC-CACAT-3' (SEQ ID NO 70)
 set H:

HCPr130(+): 5'-ggaattctagACIGCITAYCARGCI-ACIGTITGYGC-3' (SEQ ID NO 75)

HCPr66(−): 5'-ctattaTTGTATCCCRCTGATGAARTTC-CACAT-3' (SEQ ID NO 70)
 set I:

HCPr134(+): 5'-CATATAGATGCCCACTTCCTATC-3' (SEQ ID NO 76)

HCPr66(−): 5'-ctattaTTGTATCCCRCTGATGAARTTC-CACAT-3' (SEQ ID NO 70)
 set J:

HCPr131(+): 5'-ggaattctagaCCITCITGGGAYGARAY-ITGGAARTG-3' (SEQ ID NO 74)

HCPr118(−): 5'-actagtcgactaYTGIATICCRCTIATR-WARTTCCACAT-3' (SEQ ID NO 71)
 set K:

HCPr130(+): 5'-ggaattctagACIGCITAYCARGCI-ACIGTITGYGC-3' (SEQ ID NO 75)

HCPr118(−): 5'-actagtcgactaYTGIATICCRCTIATR-WARTTCCACAT-3' (SEQ ID NO 71)
 set L:

HCPr134(−): 5'-CATATAGATGCCCACTCCTATC-3' (SEQ ID NO 76)

HCPr118(−): 5-actagtcgactaYTGIATICCRCTIATR-WARTTCCACAT-3' (SEQ ID NO 71)
 set M:

HCPr3(+): 5'-GTGTGCCAGGACCATC-3' (SEQ ID NO 77) and

HCPr4(−): 5-GACATGCATGTCATGATGTA-3 (SEQ ID NO 78)
 set N:

HCPr3(+): 5'-GTGTGCCAGGACCATC-3' (SEQ ID NO 77) and

HCPr 118(−): 5'-actagtcgactaYTGIATICCRCTIATR-WARTTCCACAT-3' (SEQ ID NO 71)
 set O:

HCPr3(+): 5'-GTGTGCCAGGACCATC-3' (SEQ ID NO 77) and

HCPr66(−): 5'-ctattaTTGTATCCCRCTGATGAARTTC-CACAT-3' (SEQ ID NO 70)

No PCR products could be obtained with the sets of primers A, B, C, D, E, F, G, H, I, J, K, L, M, and N, on random-primed cDNA obtained from type 3 sera. With the primer set O, no fragment could be amplified from type 3 sera. However, a smear containing a few weakly stainable bands was obtained from serum BR36. After sequence analysis of several DNA fragments, purified and cloned from the area around 300 bp on the agarose gel, only one clone, HCC153 (SEQ ID NO 29), was shown to contain HCV information. This sequence was used to design primer HCPr152.

A new primer set P was subsequently tested on several sera.
 set P:

HCPr152(+): 5'-TACGCCTCTTCTATATCGGTTGGGGC-CTG-3' (SEQ ID NO 79) and

HCPr66(−): 5'-CTATTATTGTATCCCRCTGATGAART-TCCACAT-3' (SEQ ID NO 70)

The 464-bp HCPr152/66 fragment was obtained from serum BR36 (BR36-20) and serum HD10(HD10-1). The following clones were obtained from these PCR products:
 From fragment HD10-1:

HD10-1-25 (SEQ ID NO 31), HD10-1-3 (SEQ ID NO 33),
 From fragment BR36-20:

BR36-20-164 (SEQ ID NO 35), BR36-20-165 (SEQ ID NO 37), BR36-20-166 (SEQ ID NO 39),

The nucleotide sequences obtained from clones with SEQ ID NO 29, 31, 33, 35, 37 or 39 are shown aligned with the sequences of prototype isolates of other types of HCV in FIG. 6. In addition to one silent 3rd letter variation, one 2nd letter mutation resulted in an E to G substitution at position 175 of the deduced amino acid sequence of BR36 (FIG. 7). Serum HD10 clones were completely identical. The two type 3 isolates were nearly 94% homologous in this NS4 region. The homologies with other types are presented in Table 5.

Example 4

Analysis of the Anti-NS4 Response to Type-Specific Peptides

As the NS4 sequence contains the information for an important epitope cluster, and since antibodies towards this region seem to exhibit little cross-reactivity (Chan et al., 1991), it was worthwhile to investigate the type-specific antibody response to this region. For each of the 3 genotypes, HCV-1 (Choo et al., 1991). HC-J6 (Okamoto et al., 1991) and BR36 (present invention), three 20-mer peptides were synthesized covering the epitope region between amino acids 1688 and 1743 (as depicted in table 6). The synthetic peptides were applied as parallel lines onto membrane strips. Detection of anti-NS4 antibodies and color development was performed according to the procedure described for the INNO-LIA HCV Ab II kit (Innogenetics, Antwerp). Peptide synthesis was carried out on a 9050 PepSynthesizer (Millipore). After incubation with 15 LiPA-selected type 3 sera, 9 samples showed reactivity towards NS4 peptides of at least 2 different types, but a clearly positive reaction was observed for 3 sera (serum BR. HD30 and DKH) on the type 3 peptides, while negative (serum BR33 and HD30) or indeterminate (serum DKH) on the type 1 and type 2 NS4 peptides; 3 sera tested negative for anti-NS4 antibodies (FIG. 8). Using the same membrane strips coated with the 9 peptides as indicated above and as shown in FIG. 8. 38 type 1 sera (10 type 1a and 28 type 1b), 11 type 2 sera (10 type 2a and 1 type 2b), 12 type 3a sera and 2 type 4 sera (as determined by the LiPA procedure) were also tested. As shown in Table 8, the sera reacted in a genotype-specific manner with the NS4 epitopes. These results demonstrate that type-specific anti-NS4 antibodies can be detected in the sera of some patients. Such genotype-specific synthetic peptides might be employed to develop serotyping assays, for example a mixture of the nine peptides as indicated above, or combined with the NS4 peptides from the HCV type 4 or 6 genotype or from new genotypes corresponding to the region between amino acids 1688 and 1743, or synthetic peptides of the NS4 region between amino acids 1688 and 1743 of at least one of the 6 genotypes, combined with the E1 protein or deletion mutants thereof, or synthetic E1 peptides of at least one of the genotypes. Such compositions could be further extended with type-specific peptides or proteins, including for example the region between amino acids 68 and 91 of the core protein, or more preferably the region between amino acids 68 and 78. Furthermore, such type-specific antigens may be advantageously used to improve current diagnostic screening and confirmation assays and/or HCV vaccines.

Example 5

The Core and E1 Regions of HCV Type 5

Sample BE95 was selected from a group of sera that reacted positive in a prototype Line Probe Assay as described earlier (Stuyver et al., 1993), because a high-titer of HCV RNA could be detected, enabling cloning of fragments by a single round of PCR. As no sequences from any coding region of type 5 has been disclosed yet, synthetic oligonucleotides for PCR amplification were chosen in the regions of little sequence variation after aligning the sequences of HCV-1 (Choo et al., 1991), HCV-J (Kato et al., 1990), HC-J6 (Okamoto et al., 1991), HC-J8 (Okamoto et al., 1992), and the new type 3 sequences of the present invention HD 10, BR33, and BR36 (see FIG. 5, Example 2). The following sets of primers were synthesized on a 392 DNA/RNA synthesizer (Applied Biosystems):

Set 1:

HCPr52(+): 5'-atgTTGGGTAAGGTCATCGATACCCT-3' (SEQ ID NO 80) and

HCPr54(−): 5'-ctattaCCAGTTCATCATCATATCCCA-3' (SEQ ID NO 78)

Set 2:

HCPr41(+): 5'-CCCGGGAGGTCTCGTAGACCGTGCA-3' (SEQ ID NO 81) and

HCPr40(−): 5'-ctattaAAGATAGAGAAAGAGCAAC-CGGG-3' (SEQ ID NO 82)

Set 3:

HCPr41(+): 5'-CCCGGGAGGTCTCGTAGACCGTGCA-3' (SEQ ID NO 81) and

HCPr54(−): 5'-ccattaCCAGTTCATCATCATATCCCA-3' (SEQ ID NO 78)

The three sets of primers were employed to amplify the regions of the type 5 isolate PC as described (Stuyver et al., 1993). Set 1 was used to amplify the E1 region and yielded fragment PC-4, set 2 was designed to yield the Core region and yielded fragment PC-2. Set 3 was used to amplify the Core and E1 region and yielded fragment PC-3. These fragments were cloned as described (Stuyver et al., 1993). The following clones were obtained from the PCR fragments:

From fragment PC-2:

PC-2-1 (SEQ ID NO 41), PC-2-6 (SEQ ID NO 43),

From fragment PC-4:

PC-4-1 (SEQ ID NO 45). PC-4-6 (SEQ ID NO 47),

From fragment PC-3:

PC-3-4 (SEQ ID NO 49), PC-3-8 (SEQ ID NO 51)

An alignment of sequences with SEQ ID NO 41, 43, 45, 47, 49 and 51, is given in FIG. 9. A consensus amino acid sequence (PC C/E1: SEQ ID NO 54) can be deduced from each of the 2 clones cloned from each of the three PCR fragments as depicted in FIG. 5, which overlaps the region between nucleotides 1 and 957 (Kato et al., 1990). The 6 clones are very closely related to each other (mutual homologies of about 99.7%).

An alignment of nucleotide sequence with SEQ ID NO 53 or 151 (PC C/E1 from isolate BE95) with known nucleotide sequences from the Core/E1 region is given in FIG. 3. The clone is only distantly related to type 1, type 2, type 3 and type 4 sequences (Table 5).

Example 6

NS3/NS4 Region of HCV Type 5

Attempts were undertaken to clone the NS3/NS4 region of the isolate BE95, described in example 5. The following sets of primers were selected in the regions of little sequence variability after aligning the sequences of HCV-1 (Choo et al., 1991), HCV-J (Kato et al., 1991), HC-J6 (Okamoto et al., 1991), and HC-J8 (Okamoto et al., 1992) and of the sequences obtained from type 3 sera of the present invention (SEQ ID NO 31, 33, 35, 37 and 39); smaller case lettering is used for nucleotides added for cloning purposes:

set A:

HCPr 116(+): 5'-ttttAATACATCATGRCITGYATG-3' (SEQ ID NO 66)

HCPr66(−): 5'-ctattaTTGTATCCCRCTGATGAARTTC-CACAT-3' (SEQ ID NO 70)

set B:

HCPr116(+): 5'-ttttAAATACATCATGRCITGYATG-3' (SEQ ID NO 69)

HCPr118(−): 5'-actagtcgactaYTGIATICCRCTIATR-WARTTCCACAT-3' (SEQ ID NO 71)

set C:

HCPr117(+): 5'-ttttAAATACATCGCIRCITGCATGCA-3' (SEQ ID NO 72)

HCPr66(−): 5'-ctattaTTGTATCCCRCTGATGAARTTC-CACAT-3' (SEQ ID NO 70)

set D:

HCPr117(+): 5'-ttttAAATACATCGCIRCITGCATGCA-3' (SEQ ID NO 72)

HCPr118(−): 5'-actagtcgactaYTGIATICCRCTIATR-WARTTCCACAT-3' (SEQ ID NO 71)
 set E:
HCPr116(+): 5'-tttAAATACATCATGRCITGYATG-3' (SEQ ID NO 69)
HCPr119(−): actagtcgactaRTTIGCIATIAGCCG/TRT-TCATCCAYTG-3' (SEQ ID NO 73)
 set F:
HCPr 17(+): 5'-ttttAAATACATCGCIRCITGCATGCA-3' (SEQ ID NO 72)
HCPr119(−): actagtcgactaRTTIGCIATIAGCCG/TRT-TCATCCAYTG-3' (SEQ ID NO 73)
 set G:
HCPr131(+): 5'-ggaattctagaCCITCITGGGAYGARAY-ITGGAARTG-3' (SEQ ID NO 74')
HCPr66(−): 5'-ctattaTTGTATCCCRCTGATGAARTTC-CACAT-3' (SEQ ID NO 70)
 set H:
HCPr130(+): 5'-ggaattctagACIGCITAYCARGCI-ACIGTITGYGC-3' (SEQ ID NO 75)
HCPr66(−): 5'-ctattaTTGTATCCCRCTGATGAARTTC-CACAT-3' (SEQ ID NO 70)
 set I:
HCPr134(+): 5'-CATATAGATGCCCACTTCCTATC-3' (SEQ ID NO 76)
HCPr66(−): 5'-ctattaTTGTATCCCRCTGATGAARTTC-CACAT-3' (SEQ ID NO 70)
 set J:
HCPr131(+): 5'-ggaattctagaCCITCITGGGAYGARAY-ITGGAARTG-3' (SEQ ID 74)
HCPr118(−): 5'-actagtcgactaYTGIATICCRCTIATR-WARTTCCACAT-3' (SEQ ID NO-71)
 set K:
HCPr130(+): 5'-ggaattctagACIGCITAYCARGCI-ACIGTITGYGC-3' (SEQ ID NO 75)
HCPr118(−): 5'-actagtcgactaYTGIATICCRCTIATR-WARTTCCACAT-3' (SEQ ID NO 71)
 set L:
HCPr134(+): 5'-CATATAGATGCCCACTTCCTATC-3' (SEQ ID NO 76)
HCPr118(−): 5'-actagtcgactaYTGIATICCRCTIATR-WARTTCCACAT-3' (SEQ ID NO 71)
 set M:
HCPr3(+): 5'-GTGTGCCAGGACCATC-3' (SEQ ID NO 77) and
HCPr4(−): 5'-GACATGCATGTCATGATGTA-3' (SEQ ID NO 78)
 set N:
HCPr3(−): 5'-GTGTGCCAGGACCATC-3' (SEQ ID NO 77) and
HCPr118(−): 5'-actagtcgactaYTGIATICCRCTIATR-WARTTCCACAT-3' (SEQ ID NO 71)
 set O:
HCPr3(+): 5'-GTGTGCCAGGACCATC-3' (SEQ ID NO 77) and HCPr66(−): 5'-ctattaTTGTATCCCRCTGATGAARTTC-CACAT-3' (SEQ ID NO 70)

No PCR products could be obtained with the sets of primers A, B, C, D, E, F, G, H, I, J, K, L, M, and N, on random-primed cDNA obtained from type 3 sera. However, set O yielded what appeared to be a PCR artifact fragment estimated about 1450 base pairs, instead of the expected 628 base pairs. Although it is not expected that PCR artifact fragments contain information of the gene or genome that was targetted in the experiment, efforts were put in cloning of this artifact fragment, which was designated fragment PC-1. The Following clones, were obtained from fragment PC-1:

PC-1-37 (SEQ ID NO 59 and SEQ ID NO 55), PC-1-48 (SEQ ID NO 61 and SEQ ID NO 57)

The sequences obtained from the 5' and 3' ends of the clones are given in SEQ ID NOS 55, 57, 59, and 61, and the complete sequences with SEQ ID NO 197 and 199 are shown aligned with the sequences of prototype isolates of other types of HCV in FIG. 10 and the alignment of the deduced amino acid sequences is shown in FIGS. 11 and 7. Surprisingly, the PCR artifact clone contained HCV information. The positions of the sequences within the HCV genome are compatible with a contiguous HCV sequence of 1437 nucleotides, which was the estimated size of the cloned PCR artifact fragment. Primer HCPr66 primed correctly at the expected position in the HCV genome. Therefore, primer HCPr3 must have incidentally misprimed at a position 809 nucleotides upstream of its legitimate position in the HCV genome. This could not be expected since no sequence information was available from a coding region of type 5.

Example 7

The E2 Region of HCV Type 5

Serum BE95 was chosen for experiments aimed at amplifying a part of the E2 region of HCV type 5.

After aligning the sequences of HCV-1 (2), H21CV-J(1), HC-J6 (3), and HC-J8-(4). PCR primers were chosen in those regions of little sequence variation.

Primers HCPr109(+): 5'-TGGGATATGATGAT-GAACTGGTC-3' (SEQ ID NO 141) and HCPr14(−): 5'-CCAGGTACAACCGAACCAATTGCC-3' (SEQ ID NO 142) were combined to amplify the aminoterminal region of the E2/NS1 region, and were synthesized on a 392 DNA/RNA synthesizer (Applied Biosystems). With primers HCPr109 and HCPr14, a PCR fragment of 661 bp was generated, containing 169 nucleodtides corresponding to the E1 carboxyterminus and 492 bases from the region encoding the E2 aminoterminus.

An alignment of the type 5 E1/E2 sequences with seq ID NO. 158 with known sequences is presented in FIG. 10. The deduced protein sequence was compared with the different genotypes (FIG. 12, amino acids 328–546). In the E1 region, there were no extra structural important motifs found. The aminoterminal part of E2 was hypervariable when compared with the other genotypes. All 6 N-glycosylation sites and all 7 cysteine residue's were conserved in this E2 region. To preserve alignment, it was necessary to introduce a gap between aa 474 and 475 as for type 3a, but not between aa 480 and 481, as for type 2.

Example 8

The NS5b Region of HCV Type 4

Type 4 sera GB48, GB116, GB215, and GB358, selected by means of the line probe assay (LiPA, Stuyver et al., 1993), as well as sera GB549 and GB809 that could not be typed by means of this LiPA (only hybridization was observed with the universal probes), were selected from Gabonese patients. All these sera were positive after the first round of PCR reactions for the 5' untranslated region (Stuyver et al., 1993) and were retained for further study.

RNA was isolated from the sera and cDNA synthesized as described in example 1. Universal primers in the NS5 region were selected after alignment of the published sequences as follows:

HCPr206(+): 5'-TGGGGATCCCGTATGATACCCGCT-GCTTTGA-3' (SEQ ID NO. 124) and

HCPr207(−): 5'-GGCGGAATTCCTGGTCATAGCCTC-CGTGAA-3' (SEQ ID NO. 125):

and were synthesized on a 392 DNA/RNA synthesizer (Applied Biosystems). Using the Line Probe Assay (LiPA), four high-titer type 4 sera and 2 sera that could not be classified were selected and subsequently analyzed with the primer set HCPr206/207. NS5 PCR fragments obtained using these primers from serum GB48 (GB48-3), serum GB116 (GB116-3), serum GB215 (GB215-3), serum GB358 (GB358-3), serum GB549 (GB549-3), and serum GB809 (GB809-3), were selected for cloning. The following sequences were obtained from the PCR fragments:

From fragment GB48-3: GB48-3-10 (SEQ ID NO. 106)

From fragment GB116-3: GB116-3-5 (SEQ ID NO. 108)

From fragment GB215-3: GB215-3-8 (SEQ ID NO. 110)

From fragment GB358-3: GB358-3-3 (SEQ ID NO. 112)

From fragment GB549-3: GB549-3-6 (SEQ ID NO. 114)

From fragment GB809-3: GB809-3-1 (SEQ ID NO. 116)

An alignment of nucleotide sequences with SEQ ID NO. 106, 108, 110, 112, 11', and 116 with known sequences is given in FIG. 1. An alignment of deduced amino acid sequences with SEQ ID NO. 107, 109, 111, 113, 115, and 117 with known sequences is given in FIG. 2. The 4 isolates that had been typed as type 4 by means of LiPA are very closely related to each other (mutual homologies of about 95%), but are only distantly related to type 1, type 2, and type 3 sequences (e.g. GB358 shows homologies of 65.6 to 67.7% with other genotypes, Table 4). The sequence obtained from sera GB549 and GB809 also show similar homologies with genotypes 1, 2, and 3 (65.9 to 68.8% for GB549 and 65.0 to 68.5% for GB809, Table 4), but an intermediate homology of 79.7 to 86.8% (often observed between subtypes of the same type) exists between GB549 or GB809 with the group of isolates consisting of GB48, GB 116, GB15, and GB358, or between GB549 and GB809. These data indicate the discovery of 3 new subtypes within the HCV genotype 4: in the present invention, these 3 subtypes are designated subtype 4c, represented by isolates GB18, GB 116, GB225, and GB358, subtype 4g, represented by isolate GB549, and subtype 4e, represented by isolate GB809. Although the homologies observed between subtypes in the N55 region seem to indicate a closer relationship between subtypes 4c and 4e, the homologies observed in the E1 region indicate that subtypes 4g and 4e show the closest relation (see example 8).

Example 9

The Core/E1 Region of HCV Type 4

From each of the 3 new type 4 subtypes, one representative serum was selected for cloning experiments in the Core/E1 region. GB549 (subtype 4g) and GB809 (subtype 4e) were analyzed together with isolate GB358 that was chosen from the subtype 4c group.

Synthetic oligonucleotides:

After aligning the sequences of HCV-1 (2), HCV-J(1), HC-J6 (3), and HC-J8 (4), PCR primers were chosen in those regions of little sequence variation.

Primers HCPr52(+): 5'-atgTTGGGTAAGGTCATC-GATACCCT-3' (SEQ ID NO:80), HCPr23(+): 5'-CT-CATGGGGTACATTCCGCT-3' (SEQ ID NO:67), and HCPr54(−): 5'-CTATTACCAGTTCATCATCATATCCCA-3' (SEQ ID NO:68), were synthesized on a 392 DNA/RNA synthesizer (Applied Biosystems). The sets of primers HCPr23/54 and HCPr52/54 were used, but only with the primer set HCPr52/54, PCR fragments could be obtained. This set of primers amplified the sequence from nucleotide 379 to 957 encoding amino acids 127 to 319: 65 amino acids from the carboxyterminus of core and 128 amino acids of E1. The amplification products GB358-4, GB549-4, and GB804-4 were cloned as described in example 1. The following were obtained from PCR fragments:

From fragment GB358-4: GB358-4-1 (SEQ ID NO 118)

From fragment GB549-4: GB549-4-3 (SEQ ID NO 120)

From fragment GB809-4: GB809-4-3 (SEQ ID NO 122)

An alignment of the type 4 Core/E1 nucleotide sequences with seq ID NO. 118, 120, and 122 with known sequences is presented in FIG. 4. The homologies of the type 4 E1 region (without core) with type 1, type 2, type 3, and type 5 prototype sequences are depicted in Table 4. Homologies of 53 to 66% are observed with representative isolates of non-type 4 genotypes. Observed homologies in the E1 region within type 4, between the different subtypes, ranges from 75.2 to 78.4%. The recently disclosed sequences of the core region of Egyptian type 4 isolates (for example EG-29 in FIG. 3) described by Simmonds et al. (1993) do not allow alignment with the Gabonese sequences (as described in the present invention) in the NSB region and may belong to different type 4 subtypes(s) as can be deduced from the core sequences. The deduced amino acid sequences with SEQ ID NO 119, 121, and 123 are aligned with other prototype sequences in FIG. 5. Again, type-specific variation mainly resides in the variable V regions, designated in the present invention, and therefore, type-4-specific amino acids or V regions will be instrumental in diagnosis and therapeutics for HCV type 4.

Example 10

The Core/E1 and NS5b Regions of New HCV Type 2, 3 and 4 Subtypes

Samples NE92 (subtype 2d), BE98 (subtype 3c), CAM1600 and GB809 (subtype 4e), CAMG22 and CAMG27 (subtype 4f), GB438 (subtype 4h), CAR4/1205 subtype (4i), CAR1/501 (subtype 4j). CAR1/901 (subtype 4?), and GB724(subtype 4?) were selected from a group of sera that reacted positive but aberrantly in a prototype Line Probe Assay as described earlier (Stuyver et al., 1993). Another type 5a isolate BE100 was also analyzed in the C/E1 region, and yet another type 5a isolate BE96 in the NS5b region. A high-titer of HCV RNA could be detected, enabling cloning of fragments by a single round of PCR. As no sequences from any coding region of these subtypes had been disclosed yet, synthetic oligonucleotides for PCR amplification were chosen in the regions of little sequence variation after aligning the sequences of HCV-1 (Choo et al., 1991), HCV-J (Kato et al., 1990). HC-J6 (Okamoto et al., 1991), HC-J8 (Okamoto et al., 1992), and the other new sequences of the present invention.

The above mentioned sets 1, 2 and 3 (see example 5) of primers were used, but only with set 1, PCR fragments could be obtained from all isolates (except for BE98, GB724, and CAR1/501). This set of primers amplified the sequence from nucleotide 379 to 957 encoding amino acids 127 to 319: 65 amino acids from the carboxyterminus of core and 128 amino acids of E1. With set 3, the core/E1 region from isolate NE92 and BE98 could be amplified, and with set 2, the core region of GB358. GB724, GB809, and CAM600 could be amplified. The amplification products were cloned as described in example 1. The following clones were obtained from the PCR fragments:

From isolate GB724, the clone with SEQ ID NO 193 from the core region.

From isolate NE92, the clone with SEQ ID NO 143

From isolate BE98, the clone from the core/E1 region of which part of the sequence has been analyzed and is given in SEQ ID NO 147, From isolate CAM600, the clone with SEQ ID NO 167 from the E1 region, or SEQ ID NO 165 from the Core/E1 region as shown in FIG. 3, From isolate CAMG22, the clone with SEQ ID NO 171 from the E1 region as shown in FIG. 4, from isolate GB358, the clone with SEQ ID NO 191 in the core region, from isolate CAMG27, the clone with SEQ ID NO 173 from the core/E1 region, from isolate GB438, the clone with SEQ ID NO 177 from the core/E1 region, from isolate CAR4/1205, the clone with SEQ ID NO 179 from the core/E1 region, from isolate CAR1/901, the clone with SEQ ID NO 181 from the core/E1 region, from isolate GB809, the clone GB8094 with SEQ ID NO 189 from the core/E1 region, clone GB809-2 with SEQ ID NO 169 from the core/E1 region and the clone with SEQ ID NO 163 from the core region, and from isolate BE100, the clone with SEQ ID NO 155 from the Core/E1 region as shown in FIG. 4.

An alignment of these Core/E1 sequences with known Core/E1 sequences is presented in FIG. 4. The deduced amino acid sequences with SEQ ID NO 144, 148, 164, 168, 170, 172, 174, 178, 180, 182, 190, 192, 194, 156, 166 are aligned with other prototype sequences in FIG. 5. Again, type-specific variation mainly resides in the variable V regions, designated in the present invention, and therefore, type 2d, 3c and type 4-specific amino acids or V regions will be instrumental in diagnosis and therapeutics for HCV type (subtype) 2d, 3c or the different type 4 subtypes.

The NS5b region of isolates NE92, BE98, CAM600, CAMG22, GB438, CAR4/1205, CAR1/501, and BE96 was amplified with primers HCPr206 and HCPr207 (Table 7). The corresponding clones were cloned and sequenced as in example 1 and the corresponding sequences (of which BE98 was partly sequenced) received the following identification numbers:

NE92: SEQ ID NO 145

BE98: SEQ ID NO 149

CAM600: SEQ ID NO 201

CAMG22: SEQ ID NO 203

GB438: SEQ ID NO 207

CAR4/1205: SEQ ID NO 209

CAR1/501: SEQ ID NO 211

BE95: SEQ ID NO 159

BE96: SEQ ID NO 161

An alignment of these NS5b sequences with known N55b sequences is presented in FIG. 1. The deduced amino acid sequences with SEQ ID NO 146, 150, 202, 202, 206, 208, 210, 212, 160, 162 are aligned with other prototype sequences in FIG. 2. Again, subtype-specific variations can be observed, and therefore, type 2d, 3c and type 4-specific amino acids or V regions will be instrumental in diagnosis and therapeutics for HCV type (subtype) 2d, 3c or the different type 4 subtypes.

Example 11

Genotype-Specific Reactivity of Anti-E1 Antibodies (Serotyping)

E1 proteins were expressed from vaccinia virus constructs containing a core/E1 region extending from nucleotide positions 355 to 978 (Core/E1 clones described in previous examples including the primers HCPr52 and HCPr54), and expressed proteins from L119 (after the initiator methionine) to W326 of the HCV polyprotein. The expressed protein was modified upon expression in the appropriate host cells (e.g. HeLa, RK13, HuTK-, HepG2) by cleavage between amino acids 191 and 192 of the HCV polyprotein and by the addition of high-mannose type carbohydrate motifs. Therefore, a 30 to 32 kDa glycoprotein could be observed on western blot by means of detection with serum from patients with hepatitis C.

As a reference, a genotype 1b clone obtained form the isolate HCV-B was also expressed in an identical way as described above, and was expressed from recombinant vaccinia virus vvHCV-11A.

A panel of 104 genotyped sera was first tested for reactivity with a cell lysate containing type 1b protein expressed from the recombinant vaccinia virus vvHCV-11A, and compared with cell lysate of RK13 cells infected with a wild type vaccinia virus ('E1/WT'). The lysates were coated as a 1/20 dilution on a normal ELISA microtiter plate (Nunc maxisorb) and left to react with a 1/20 diluation of the respective sera. The panel consisted of 14 type 1a, 38 type 1b, 21 type 2, 21 type 3a, and 9 type 4 sera. Human antibodies were subsequently detected by a goat anti-human IgG conjugated with peroxidase and the enzyme activity was detected. The optical density values of the E1 and wild type lysates were divided and a factor 2 was taken as the cut-off. The results are given in the table A. Eleven out of 14 type 1a sera (79%), 25 out of 38 type 1b sera (66%), 6 out of 21 (29%), 5 out of 21 (24%), and none of the 9 type 4 or the type 5 serum reacted (0%). These experiments clearly show the high prevalence of anti-E1 antibodies reactive with the type 1 E1 protein in patients infected with type 1 (36/52 (69%)) (either type 1a or type 1b), but the low prevalence or absence in non-type 1 sera (11/52 (21%)).

TABLE A

| serum | E1/WT |
|---|---|
| type 1a | |
| 3748 | 3.15 |
| 3807 | 3.51 |
| 5282 | 1.99 |
| 9321 | 3.12 |
| 9324 | 2.76 |
| 9325 | 6.12 |
| 9326 | 10.56 |
| 9356 | 1.79 |
| 9388 | 3.5 |
| 8366 | 10.72 |
| 8380 | 2.27 |
| 10925 | 4.02 |
| 10936 | 5.04 |
| 10938 | 1.36 |
| type 1b | |
| 5205 | 2.25 |
| 5222 | 1.33 |
| 5246 | 1.24 |
| 5250 | 13.58 |
| 5493 | 0.87 |
| 5573 | 1.75 |
| 8243 | 1.77 |
| 8244 | 2.05 |
| 8316 | 1.21 |
| 8358 | 5.04 |
| 9337 | 14.47 |
| 9410 | 5 |
| 9413 | 5.51 |
| 10905 | 1.26 |
| 10919 | 5.00 |
| 10928 | 8.72 |
| 10929 | 8.26 |
| 10931 | 2.3 |
| 10932 | 4.41 |
| 44 | 2.37 |
| 45 | 3.14 |
| 46 | 4.37 |
| 47 | 5.68 |
| 48 | 2.97 |
| 49 | 1.18 |
| 50 | 9.85 |
| 51 | 4.51 |
| 52 | 1.11 |
| 53 | 5.20 |
| 54 | 0.98 |
| 55 | 1.48 |
| 56 | 1.06 |
| 57 | 3.85 |
| 58 | 7.6 |
| 59 | 3.28 |
| 60 | 3.23 |
| 61 | 7.82 |
| 62 | 1.92 |
| type 2 | |
| 23 | 0.91 |
| 24 | 1.16 |
| 25 | 2.51 |
| 26 | 0.96 |
| 27 | 1.20 |

TABLE A-continued

| serum | E1/WT |
|---|---|
| 28 | 0.96 |
| 29 | 2.58 |
| 30 | 8.05 |
| 31 | 0.92 |
| 32 | 0.82 |
| 33 | 5.75 |
| 34 | 0.79 |
| 35 | 0.86 |
| 36 | 0.85 |
| 37 | 0.76 |
| 38 | 0.92 |
| 39 | 1.08 |
| 40 | 2.33 |
| 41 | 2.83 |
| 42 | 1.21 |
| 43 | 0.91 |
| type 3 | |
| 1 | 6.88 |
| 2 | 1.47 |
| 3 | 3.06 |
| 4 | 6.52 |
| 5 | 10.24 |
| 6 | 2.72 |
| 7 | 1.11 |
| 8 | 1.54 |
| 9 | 1.60 |
| 10 | 1.21 |
| 11 | 1.07 |
| 12 | 1.00 |
| 13 | 0.85 |
| 14 | 0.96 |
| 15 | 0.51 |
| 16 | 1.00 |
| 17 | 1.09 |
| 18 | 0.99 |
| 19 | 1.04 |
| 20 | 1.04 |
| 21 | 0.96 |
| type 4 | |
| 22 | 0.87 |
| GB48 | 0.49 |
| GB113 | 0.68 |
| GB116 | 0.73 |
| GB215 | 0.52 |
| GB358 | 0.56 |
| GB359 | 0.71 |
| GB438 | 1.08 |
| GB516 | 1.04 |
| type 5 | |
| BE95 | 0.86 |

Core/E1 clones of isolates BR36 (type 3a) and BE95 (type 5a) were subsequently recombined into the viruses vvHCV-62 and vvHCV-6', respectively. A genotyped panel of sera was subsequently tested onto cell lysates obtained from RK13 cells infected with the recombinant viruses vvHCV-62 and vvHCV-63. Tests were carried out as described above and the results are given in the table given below (TABLE B). From these results, it can clearly be seen that, although some cross-reactivity occurs (especially between type 1 and 3), the obtained values of a given serum are usually higher on its homologous E1 protein than on an E1 protein of another genotype. For type 5 sera, none of the 5 sera were reactive on type 1 or 3 E1 proteins, while 3 out of 5 were shown to contain anti-E1 antibodies when tested on their homologous type 5 protein. Therefore, in this simple test system, a considerable number of sera can already be serotyped. Combined with the reactivity to type-specific NS4 epitopes or epitopes derived from other type-specific parts of the HCV polyprotein, a serotyping assay may be developed for discriminating the major types of HCV. To overcome the problem of cross-reactivity, the position of cross-reactive epitopes may be determined by someone skilled in the art (e.g. by means of competition of the reactivity with synthetic peptides), and the epitopes evoking cross-reactivity may be left out of the composition to be included in the serotyping assay or may be included in sample diluent to outcompete cross-reactive antibodies.

TABLE B

| serum | E1$^{1b}$/WT | E1$^{3a}$/WT | E1$^{5a}$/WT |
|---|---|---|---|
| type 1b | | | |
| 8316 | 0.89 | 0.59 | 0.80 |
| 8358 | 2.22 | 2.65 | 1.96 |
| 9337 | 1.59 | 0.96 | 0.93 |
| 9410 | 16.32 | 9.60 | 3.62 |
| 9413 | 9.89 | 2.91 | 2.85 |
| 10905 | 1.04 | 0.96 | 1.05 |
| 10919 | 3.17 | 2.56 | 2.96 |
| 10928 | 4.39 | 2.28 | 2.07 |
| 10929 | 2.95 | 2.07 | 2.08 |
| 10931 | 3.11 | 1.49 | 2.11 |
| 5 | 0.86 | 0.86 | 0.96 |
| 6 | 3.48 | 1.32 | 1.32 |
| 7 | 6.76 | 4.00 | 3.77 |
| 8 | 10.88 | 3.44 | 4.04 |
| 9 | 1.76 | 1.88 | 1.58 |

TABLE B-continued

| serum | E1$^{1b}$/WT | E1$^{3a}$/WT | E1$^{5a}$/WT |
|---|---|---|---|
| 10 | 9.88 | 7.48 | 7.20 |
| 11 | 8.48 | 8.99 | 8.45 |
| 12 | 0.76 | 0.72 | 0.76 |
| 13 | 5.04 | 5.67 | 5.37 |
| 14 | 10.48 | 10.54 | 11.22 |
| 15 | 5.18 | 1.62 | 1.65 |
| type 3 | | | |
| 8332 | 3.39 | 4.22 | 0.66 |
| 10907 | 3.24 | 4.39 | 0.96 |
| 10908 | 0.99 | 0.94 | 0.98 |
| 10934 | 0.86 | 0.90 | 0.90 |
| 10927 | 2.58 | 2.71 | 2.44 |
| 8210 | 0.82 | 0.80 | 0.86 |
| 8344 | 1.09 | 6.66 | 1.17 |
| 8351 | 1.21 | 1.29 | 1.22 |
| 30 | 0.85 | 4.11 | 0.98 |
| 32 | 0.85 | 2.16 | 1.04 |
| type 5 | | | |
| | 0.78 | 0.95 | 1.54 |
| BE110 | 0.79 | 1.01 | 4.95 |
| BE95 | 0.47 | 0.52 | 0.65 |
| BE111 | 0.71 | 0.75 | 8.33 |
| BE112 | 1.01 | 1.27 | 2.37 |
| BE113 | 1.11 | 1.35 | 1.60 |

TABLE 5

Homologies of new HCV sequences with other known HCV types

| Region (nucleotides) | Isolate (type) | 1a HCV-I | 1b HCV-J | 2a HC-J6 | 2b HC-J8 | 3a T1 | 3a T7 | 3b T9 | 3b T10 |
|---|---|---|---|---|---|---|---|---|---|
| Core (1–573) | PC (5) | 83.8 (91.6) | 84.8 (92.1) | 82.6 (90.1) | 82.4 (89.0) | | | | |
| E1 (574–957) | HD10 (3) | 61.5 (68.0) | 64.6 (68.8) | 57.8 (55.5) | 56.3 (59.4) | | | | |
| | BR36 (3) | 62.0 (66.4) | 62.5 (67.2) | 56.5 (53.9) | 55.2 (58.6) | | | | |
| | BR33 (3) | 60.7 (67.2) | 63.3 (68.0) | 56.5 (54.7) | 56.0 (58.6) | | | | |
| | PC (5) | 61.4 (64.0) | 62.4 (64.8) | 54.1 (49.6) | 53.3 (47.2) | | | | |
| | GB358 (4a) | 62.5 (69.1) | 62.8 (65.9) | 59.4 (54.0) | 54.4 (54.0) | | | | |
| | GB549 (4b) | 66.0 (72.2) | 62.8 (69.8) | 59.1 (56.4) | 56.5 (54.0) | | | | |
| | GB809 (4c) | 63.3 (69.1) | 60.7 (64.3) | 56.7 (53.2) | 53.0 (51.6) | | | | |
| NS3 (3856–1209) | PC (5) | 74.7 (89) | 76.1 (86.4) | 76.1 (89.8) | 78.0 (89.0) | | | | |
| NS4 (4892–5292) | BR36 (3) | 67.8 (78.5) | 69.8 (75.1) | 62.0 (67.5) | 61.7 (66.0) | | | | |
| | HD 10 (3) | 69.8 (74.6) | 66.6 (69.7) | 57.8 (59.9) | 59.1 (59.9) | | | | |
| NS4 (4936–5292) | PC (5) | 61.3 (62.2) | 63.0 (65.5) | 52.9 (46.2) | 54.3 (43.7) | | | | |
| NS5b (8023–8235) | BR34 (3) | 65.7 | 66.7 | 63.9 | 64.3 | 94.8 | 93.9 | 75.6 | 77.0 |
| | BR36 (3) | 64.3 | 67.6 | 64.8 | 66.0 | 94.8 | 93.4 | 75.1 | 76.5 |
| | BR33 (3) | 65.7 | 67.1 | 64.3 | 64.8 | 94.8 | 93.9 | 76.0 | 77.5 |
| | GB358 (4a) | 67.7 (76.1) | 65.6 (77.0) | 66.5 (70.8) | 65.6 (71.7) | | | | |
| | GB549 (4b) | 68.8 (76.1) | 67.1 (77.0) | 65.9 (71.7) | 65.9 (74.4) | | | | |
| | GB809 (4c) | 68.5 (73.5) | 65.0 (73.5) | 67.7 (69.9) | 67.7 (73.5) | | | | |

Shown are the nucleotide homologies (the amino-acid homology is given between brackets) for the region indicated in the left column.

TABLE 6

NS4 sequences of the different genotypes

| prototype | TYPE | SYNTHETIC PEPTIDE NS4-1 (NS4a) | | SYNTHETIC PEPTIDE NS4-5 (NS4b) | | SYNTHETIC PEPTIDE NS4-7 (NS4b) | |
|---|---|---|---|---|---|---|---|
| position-> | | 1 6 9 0 | 1 7 0 0 | 1 7 2 0 | 1 7 3 0 | 1 7 3 0 | 1 7 4 0 |

TABLE 6-continued

NS4 sequences of the different genotypes

| prototype | TYPE | SYNTHETIC PEPTIDE NS4-1 (NS4a) | SYNTHETIC PEPTIDE NS4-5 (NS4b) | SYNTHETIC PEPTIDE NS4-7 (NS4b) |
|---|---|---|---|---|
| HCV-1 | 1a | ** * ** **<br>LSG KPAIIPDREV LYREFDE<br>(SEQ ID NO:272) | * * * * *<br>SQHLPYIEQ GMMLAEQFKQ K<br>(SEQ ID NO:273) | * * * *<br>LAEQFKQ KALGLLQTAS RQA<br>(SEQ ID NO:274) |
| HCV-J | 1b | LSG RPAVIPDREV LYQEFDE<br>(SEQ ID NO:275) | ASHLPYIEQ GMQLAEQFKQ K<br>(SEQ ID NO:276) | LAEQFKQ KALGLLQTAT KQA<br>(SEQ ID NO:277) |
| HC-J6 | 2a | VNQ RAVVAPDKEV LYEAFDE<br>(SEQ ID NO:278) | ASRAALIEE GQRIAEMLKS K<br>(SEQ ID NO:279) | IAEMLKS KIQGLLQQAS KQA<br>(SEQ ID NO:280) |
| HC-J8 | 2b | LND RVVVAPDKEI LYEAFDE<br>(SEQ ID NO:281) | ASKAALIEE GQRMAEMLKS K<br>(SEQ ID NO:282) | MAEMLKS KIQGLLQQAT RQA<br>(SEQ ID NO:283) |
| BR36 | 3a | LGG KPAIVPDKEV LYQ$\varrho$YDE<br>(SEQ ID NO:97) | SQAAPYIEQ AQVIAHQFKE K<br>(SEQ ID NO:99) | IAHQFKE KVLGLLQRAT QQQ<br>(SEQ ID NO:100) |
| PC | 5 | LSG KPAIIPDREA LYQ$\varrho$FDE<br>            V<br>(SEQ ID NO:102 and<br>SEQ ID NO:103, respectively) | AASLPYMDE TRAIAGQFKEK<br>(SEQ ID NO:284) | IAGQFKE KVLGFISTTG QKA<br>(SEQ ID NO:105) |

*, residues conserved in every genotype. Double underlined amino acids are type-specific, amino acids in italics are unique to type 3 and 5 sequences.

TABLE 7

| SEQ ID NO | Primer NO (polarity) | Sequence from 5' to 3' |
|---|---|---|
| 63 | HCPr161(−) | 5'-ACCGGAGGCCAGGAGAGTGATCTCCTCC-3' |
| 64 | HCPr162(−) | 5'-GGGCTGCTCTATCCTCATCGACGCCATC-3' |
| 65 | HCPr163(+) | 5'-GCCAGAGGCTCGGAAGGCGATCAGCGCT-3' |
| 66 | HCPr164(−) | 5'-GAGCTGCTCTGTCCTCCTCGACGCCGCA-3' |
| 67 | HCPr23(+) | 5'-CTCATGGGGTACATTCCGCT-3' |
| 68 | HCPr54(−) | 5'-CTATTACCAGTTCATCATCATATCCCA-3' |
| 69 | HCPr116(+) | 5'-ttttAAATACATCATGRCITGYATG-3' |
| 70 | HCPr66(−) | 5'-ctattaTTGTATCCCRCTGATGAARTTCCACAT-3' |
| 71 | HCPr118(−) | 5'actagtcgactaYTGIATICCRCTIATRWARTTCCACAT-3' |
| 72 | HCPr117(−) | 5'-ttttAAATACATCGCIRCITGCATGCA-3' |
| 73 | HCPr119(−) | 5'-actagtcgactaRTTIGCIATIAGCCKRTTCATCCAYTG-3' |
| 74 | HCPr131(+) | 5'-ggaattctagaCCITCITGGGAYGARAYITGGAARTG-3' |
| 75 | HCPr130(+) | 5'-ggaattctagACIGCITAYCARGCIACIGTITGYGC-3' |
| 76 | HCPr134(+) | 5'-CATATAGATGCCCACTTCCTATC-3' |
| 77 | HCPr3(+) | 5'-GTGTGCCAGGACCATC-3' |
| 78 | HCPr4(−) | 5'-GACATGCATGTCATGATGTA-3' |
| 79 | KCPr152(+) | 5'-TACGCCTCTTCTATATCGGTTGGGGCCTG-3' |
| 80 | HCPr52(+) | 5'-atgTTGGGTAAGGTCATCGATACCCT-3' |
| 81 | HCPr41(+) | 5'-CCCGGGAGGTCTCGTAGACCGTGCA-3' |
| 82 | HCPr40(−) | 5'-ctattaAAGATAGAGAAAGAGCAACCGGG-3' |
| 124 | HCPR206 | 5'-tggggatcccgtatgatacccgctgctttga-3' |
| 125 | HCPR207 | 5'-ggcggaattcctggtcatagcctccgtgaa-3' |
| 141 | HCPR109 | 5'-tgggatatgatgatgaactggtc-3' |
| 142 | HCPR14 | 5'-ccaggtacaaccgaaccaattgcc-3' |

TABLE 8

NS4 SEROTYPING

| serum | Type 1 NS4 | | | Type 2 NS4 | | | Type 3 NS4 | | |
|---|---|---|---|---|---|---|---|---|---|
| | 1 | 5 | 7 | 1 | 5 | 7 | 1 | 5 | 7 |
| type 1a | | | | | | | | | |
| 101 | 3 | 3 | 3 | − | 1 | 3 | +/− | +/− | 3 |
| 102 | 1 | +/− | 2 | − | − | 2 | − | − | 1 |
| 103 | 1 | 3 | 3 | − | +/− | 3 | − | +/− | 3 |
| 104 | 3 | 3 | 3 | 2 | 2 | 3 | 3 | +/− | 2 |
| 105 | 3 | 3 | 3 | − | 2 | 2 | +/− | +/− | 2 |
| 106 | 3 | 1 | 1 | − | 1 | 2 | +/− | +/− | +/− |
| 107 | 3 | 3 | 3 | − | 2 | 2 | 2 | − | 1 |
| 108 | 3 | 3 | 3 | − | +/− | 2 | +/− | 1 | 2 |
| 109 | 3 | 3 | 3 | +/− | 2 | 3 | 1 | − | 3 |
| 110 | 3 | 3 | 3 | − | +/− | 1 | − | − | 3 |

TABLE 8-continued

NS4 SEROTYPING

| | Type 1 NS4 | | | Type 2 NS4 | | | Type 3 NS4 | | |
|---|---|---|---|---|---|---|---|---|---|
| serum | 1 | 5 | 7 | 1 | 5 | 7 | 1 | 5 | 7 |
| type 1b | | | | | | | | | |
| 111 | +/- | +/- | - | - | - | - | - | - | - |
| 112 | - | 2 | 3 | - | - | 2 | - | - | 3 |
| 113 | 2 | 3 | 3 | - | - | 1 | - | - | 3 |
| 114 | 2 | 3 | 3 | 1 | + | 2 | + | 1 | 3 |
| 115 | 3 | 3 | 3 | - | + | 3 | - | - | 3 |
| 116 | 3 | 3 | 3 | - | +/- | 1 | - | - | 1 |
| 117 | 3 | - | - | 3 | +/- | +/- | +/- | - | - |
| 118 | 1 | 2 | 3 | - | +/- | 2 | - | +/- | 3 |
| 119 | +/- | 2 | 2 | +/- | +/- | 2 | + | 1 | 2 |
| 120 | - | 3 | 3 | -3 | +/- | +/- | - | - | - |
| 121 | 3 | 3 | 3 | +/- | 2 | 2 | 2 | 2 | 3 |
| 122 | 3 | 3 | 1 | - | 1 | 2 | 2 | 1 | 1 |
| 123 | 3 | 3 | 2 | - | 1 | 2 | - | 1 | 1 |
| 124 | 3 | 3 | 3 | - | +/- | 2 | - | - | 2 |
| 125 | 3 | 3 | 3 | 1 | 1 | 3 | 2 | 1 | 3 |
| 126 | 1 | 2 | 2 | 1 | 1 | 1 | 1 | 1 | 1 |
| 127 | 3 | 2 | +/- | - | +/- | 1 | +/- | +/- | +/- |
| 128 | 3 | 3 | 3 | - | +/- | 1 | 2 | +/- | +/- |
| 129 | 2 | 3 | 3 | - | - | 3 | - | - | 3 |
| 130 | - | 2 | 1 | +/- | - | - | - | - | - |
| 131 | - | 1 | 1 | - | - | - | - | - | +/- |
| 132 | - | - | - | +/- | - | +/- | +/- | - | - |
| 133 | 3 | 3 | 3 | - | 1 | 3 | - | 1 | 3 |
| 134 | - | 2 | 2 | - | - | - | - | - | - |
| 135 | 3 | 3 | 3 | 1 | + | 2 | 2 | 1 | 3 |
| 136 | - | 3 | 3 | +/- | +/- | +/- | +/- | - | 3 |
| 137 | +/- | +/- | +/- | +/- | +/- | +/- | +/- | - | - |
| 138 | 3 | 3 | 3 | +/- | 2 | 2 | 1 | + | 3 |
| type 2a | | | | | | | | | |
| 139 | 3 | - | - | 3 | 3 | +/- | 1 | - | - |
| 140 | +/- | - | - | 3 | 3 | 3 | 3 | - | - |
| 141 | 2 | - | - | 2 | 1 | +/- | 2 | - | - |
| 142 | - | - | - | - | +/- | - | - | - | - |
| 143 | - | +/- | +/- | 1 | 2 | 1 | 1 | +/- | +/- |
| 144 | 1 | 1 | + | 1 | 3 | 2 | 1 | 1 | 2 |
| 145 | - | +/- | +/- | 3 | 1 | 2 | 2 | +/- | +/- |
| 146 | - | - | - | +/- | +/- | - | - | - | - |
| 147 | - | +/- | - | 3 | 1 | 3 | - | - | - |
| 148 | - | - | - | +/- | - | - | +/- | - | - |
| type 2b | | | | | | | | | |
| 149 | - | +/- | +/- | 3 | 3 | 1 | 2 | +/- | +/- |
| type 3 | | | | | | | | | |
| 150 | +/- | +/- | +/- | +/- | +/- | +/- | 1 | 3 | 3 |
| 151 | - | - | - | - | - | - | 2 | - | 2 |
| 152 | +/- | - | - | - | - | - | 3 | - | - |
| 153 | - | - | - | - | - | - | - | 1 | - |
| 154 | +/- | 1 | 3 | - | +/- | 2 | 2 | 1 | 3 |
| 155 | - | 2 | 3 | - | 2 | 2 | 1 | 1 | 3 |
| 156 | - | - | - | - | - | - | - | - | - |
| 157 | - | - | - | +/- | +/- | - | +/- | 2 | 2 |
| 158 | 2 | - | - | - | 1 | 2 | 3 | 2 | 2 |
| 159 | - | - | - | - | +/- | +/- | - | 3 | 3 |
| 160 | - | - | - | - | +/- | - | - | 2 | 3 |
| 161 | - | - | - | - | 1 | 1 | +/- | 3 | 2 |
| type 4 | | | | | | | | | |
| 162 | 1 | - | - | - | - | - | - | - | - |
| 163 | 2 | - | - | - | +/- | +/- | +/- | - | - |

REFERENCES

Barany F (1991). Genetic disease detection and DNA amplification using cloned thermostable ligase. Proc Natl Acad Sci USA 88: 189–193.

Bej A, Mahbubani M, Miller R Di Cesare J, Haff L, Atlas R (1990) Multiplex PCR amplification and immobilized capture probes for detection of bacterial pathogens and indicators in water. Mol Cell Probes 4:353–365.

Bukh J, Purcell R, Miller R (1992). Sequence analysis of the 5' noncoding region or hepatitis C virus. Proc Natl Acad Sci USA 89:4942–4946.

Bukh J, Purcell R, Miller R (1993). At least 12 genotypes . . . PNAS 90,8234–8238.

Cha T, Beal E, Irvine B, Kolberg J, Chien D, Kuo G, Urdea M (1992) At least rive related, but distinct, hepatitis C viral genotypes exist. Proc Natl Acad Sci USA 39:7144–7148.

Chan S -W, Simmonds P, McOmish F, Yap P, Mitchell R, Dow B, Follet E (1991) Serological responses to infection with three different types of hepatitis C virus. Lancet 33:1991.

Chan S -W, McOmish F, Holmes E, Dow B, Peutherer J, Follett E, Yap, P Simmonds P (1992) Analysis of a new hepatitis C virus type and its phylogenetic relationship to existing variants. J Gen Virol 73:1131–1141.

Chomezynski P, Sacchi N (1987) Single step method of RNA isolation by acid guanidinium thiocyanate-phenol-chloroform extraction. Anal Biochem 162:156–159.

Choo Q, Richman K, Han J, Berger K, Lee C, Dong C, Gallegos C, Coit D, Medina-Selby A, Barr P, Weiner A, Bradley D, Kuo G, Houghton M (1991) Genetic or organization and diversity of the hepatitis C virus. Proc Natl Acad Sci USA 88:2451–2453.

Compton J (1991). Nucleic acid sequence-based amplification. Nature, 350: 91–92.

Duchosal A, Eming S, Fisher P (1992) Immunization of hu-PBL-SCID mice and the resue of human monoclonal Fab fragments through combinatorial libraries. Nature 355:258–262.

Duck P (1990). Probe amplifier system based on chimeric cycling oligonucleotides. Biotechniques 9, 142–147.

Guatelli J, Whitfield K, Kwoh D, Barringer K, Richman D, Gengeras T (1990) Isothermal, in vitro amplification of nucleic acids by a multienzyme reaction modeled after retroviral replication. Proc Natl Acad Sci USA 87: 1874–1878.

Hijikata M, Kato N, Ootsuyama Y, Nakagawa M, Shimotohmo K (1991) Gene mapping of the putative structural region of the hepatitis C virus genome by in vitro processing analysis. Proc Natl Acad Sci USA 88, 5547–5551.

Jacobs K. Rudersdorf R, Neill S, Dougherty J, Brown E, Fritsch E (1988) The thermal stability of oligonucleotide duplexes is sequence independent in tetraalkylammonium salt solutions: application to identifying recombinant DNA clones. Nucl Acids Res 16:4637–4650.

Kato N, Hijikata M, Ootsuyama Y, Nakagawa M, Ohkoshi S, Sugimura T, Shimotohno K (1990) Molecular cloning of the human hepatitis C virus genome from Japanese patients with non-A, non-B hepatitis. Proc Natl Acad Sci USA 87:9524–9528.

Kwoh D, Davis G, Whitfield K, Chappelle H, Dimichele L, Gingeras T (1989). Transcription-based amplification system and detection of amplified human immunodeficiency virus type 1 with a bead-based sandwich hybridization format. Proc Natl Acad Sci USA, 86: 1173–1177.

Kwok S, Kellogg D, McKinney N, Spasic D, Goda L, Levenson C, Sinisky J, (1990). Effects of primer-template mismatches on the polymerase chain reaction: Human immunodeficiency views type 1 model studies. Nucl. Acids Res., 18: 999.

Landgren U, Kaiser R, Sanders J, Hood L (1988). A ligase-mediated gene detection technique. Science 241:1077–1080.

Lizardi P, Guerra C, Lomeli H Tussie-Luna I, Kramer F (1988) Exponential amplification of recombinant RNA hybridization probes. Bio/Technology 6:1197–1202.

Lomeli H, Tyagi S. Printchard C, Lisardi P, Kramer F (1989) Quantitative assays based on the use of replicatable hybridization probes. Clin Chem 35: 1826–1831.

Machida A, Ohnuma H, Tsuda F, Munekata E, Tanaka T, Akahane Y, Okamoto H, Mishiro S (1992) Hepatology 16, 886–891.

Maniatis T, Fritsch E, Sambrook J (1982) Molecular cloning: a laboratory manual. Cold Spring Harbor Laboratory Press, Cold Spring Harbor, N.Y.

Mori S, Kato N, Yagyu A, Tanaka T, Ikeda Y, Petchclai B, Chiewsilp P, Kurimura T, Shimotohno K (1992) A new type of hepatitis C virus in patients in Thailand. Biochem Biophys Res Comm 183:334–342.

Okamoto H, Okada S, Sugiyama Y, Kurai K, Iizuka H, Machida A, Miyakawa Y, Mayumi M (1991) Nucleotide sequence of the genomic RNA of hepatitis C virus isolated from a human carrier: comparison with reported isolates for conserved and divergent regions. J Gen Virol 72:2697–2704.

Okamoto H, Kurai K, Okada S, Yamamoto K, Lizuka H, Tanaka T, Fukuda S. Tsuda F, Mishiro S (1992) Full-length sequences of a hepatitis C virus genome having poor homology to reported isolates: comparative study of four distinct genotypes. Virology 188:331–341.

Persson M, Caothien R, Burton D (1991). Generation of diverse high-affinity human monoclonal antibodies by repertoire cloning. Proc Natl Acad Sci USA 89:2432–2436.

Saiki R, Gelfand D, Stoffel S, Scharf S, Higuchi R, Horn G, Mullis K, Erlich H (1988). Primer-directed enzymatic amplification of DNA with a thermostable DNA polymerase. Science 239:487–491.

Saiki R, Walsh P, Levenson C, Erlich H (1989) Genetic analysis of amplified DNA with immobilized sequence-specific oligonucleotide probes (1989) Proc Natl Acad Sci USA 86:6230–6234.

Sano T, Smith C, Cantor C (1992) Immuno-PCR: very sensitive antigen detection by means of specific antibody-DNA conjugates. Science 258:120–122.

Simmonds P, McOmsh F, Yap P, Chan S, Lin C, Dusheiko G, Saeed A., Holmes E (1993), Sequence variability in the 5' non-coding region of hepatitis C virus: identification of a new virus type and restrictions on sequence diversity. J Gen Virology, 74:561–668.

Stuyver L., Rossau R, Wyseur A, Duhamel M, Vanderborght B, Van Heuverswyn H, Maertens G (1993) Typing of hepatitis C virus (HCV) isolates and characterization of new (sub)types using a Line Probe Assay. J Gen Virology, 74: 1093–1102.

Walker G, Little M, Nadeau J, Shank D (1992). Isothermal in vitro amplification of DNA by a restriction enzyme/DNA polymerase system. Proc Natl Acad Sci USA 89:392–396.

Wu D, Wallace B (1989). The ligation amplification reaction (LAR)—amplification of specific DNA sequences using sequential rounds of template-dependent ligation. Genomics 4:560–569.

SEQUENCE LISTING

```
<160> NUMBER OF SEQ ID NOS: 284

<210> SEQ ID NO 1
<211> LENGTH: 213
<212> TYPE: DNA
<213> ORGANISM: hepatitis C virus

<400> SEQUENCE: 1
ctcacggaac ggctttactg cggggcccct atgttcaaca gcaaggggc ccagtgtggt      60 tatcgccgct gccgtgccag tggagttctg cctaccagct tcggcaacac aatcacttgc    120
tacatcaagg ccacagcggc tgcaagggcc gcaggcctcc ggaacccgga ctttcttgtc    180
tgcggagatg atctggtcgt ggtggctgag agt                                  213

<210> SEQ ID NO 2
<211> LENGTH: 71
<212> TYPE: PRT
<213> ORGANISM: hepatitis C virus

<400> SEQUENCE: 2

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
        35                  40                  45

Arg Ala Ala Gly Leu Arg Asn Pro Asp Phe Leu Val Cys Gly Asp Asp
    50                  55                  60
```

Leu Val Val Val Ala Glu Ser
65               70

<210> SEQ ID NO 3
<211> LENGTH: 213
<212> TYPE: DNA
<213> ORGANISM: hepatitis C virus

<400> SEQUENCE: 3
ctcacggaac ggctttactg cgggggccct atgttcaaca gcaagggggc ccagtgtggt    60
tatcgccgct gccgtgccag tggagttctg cctaccagct tcggcaacac aatcacttgc   120
tacatcaagg ccacagcggc tgcaagggcc gcaggcctcc ggaacccgga ctttcttgtc   180
tgcggagatg atctggtcgt ggtggctgag agt                                213

<210> SEQ ID NO 4
<211> LENGTH: 71
<212> TYPE: PRT
<213> ORGANISM: hepatitis C virus

<400> SEQUENCE: 4

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
        35                  40                  45

Lys Ala Ala Gly Leu Arg Asn Pro Asp Phe Leu Val Cys Gly Asp Asp
    50                  55                  60

Leu Val Val Val Ala Glu Ser
65               70

<210> SEQ ID NO 5
<211> LENGTH: 213
<212> TYPE: DNA
<213> ORGANISM: hepatitis C virus

<400> SEQUENCE: 5
ctcacggagc ggctttactg cgggggccct atgtttaaca gcaagggggc ccagtgtggt    60
tatcgccgtt gccgtgccag tggagttctg cctaccagct tcggcaacac aatcacttgt   120
tacatcaaag ccacagcggc cgcaaaagcc gcaggcctcc ggagcccgga ctttcttgtc   180
tgcggagatg atctggtcgt ggtggctgag agt                                213

<210> SEQ ID NO 6
<211> LENGTH: 71
<212> TYPE: PRT
<213> ORGANISM: hepatitis C virus

<400> SEQUENCE: 6

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
        35                  40                  45

Lys Ala Ala Gly Leu Arg Ser Pro Asp Phe Leu Val Cys Gly Asp Asp
    50                  55                  60

```
Leu Val Val Val Ala Glu Ser
65                  70

<210> SEQ ID NO 7
<211> LENGTH: 213
<212> TYPE: DNA
<213> ORGANISM: hepatitis C virus

<400> SEQUENCE: 7
ctcacggagc ggctttactg cgggggccct atgtttaaca gcaaaggggc ccagtgtggt      60
tatcgccgtt gccgtgccag tggagttctg cctaccagct tcggcaacac aatcacttgt     120
tacatcaaag ccacagcggc cgcaaaagcc gcaggcctcc ggagcccgga ctttcttgtc     180
tgcggagatg atctggtcgt ggtggctgag agt                                  213

<210> SEQ ID NO 8
<211> LENGTH: 71
<212> TYPE: PRT
<213> ORGANISM: hepatitis C virus

<400> SEQUENCE: 8

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
        35                  40                  45

Lys Ala Ala Gly Leu Arg Ser Pro Asp Phe Leu Val Cys Gly Asp Asp
    50                  55                  60

Leu Val Val Val Ala Glu Ser
65                  70

<210> SEQ ID NO 9
<211> LENGTH: 213
<212> TYPE: DNA
<213> ORGANISM: hepatitis C virus

<400> SEQUENCE: 9
ctcacggagc ggctttactg cgggggccct atgttcaaca gcaaggggc ccagtgtggt       60 tatcgccgtt gtcgtgccag tggagttctg cctaccagtt tcggcaacac aatcacttgt     120
tacatcaagg ccacagcggc tgcaaaagcc gcaggcctcc ggaacccgga ctttcttgtt     180
tgcggagatg atttggtcgt ggtggctgag agt                                  213

<210> SEQ ID NO 10
<211> LENGTH: 71
<212> TYPE: PRT
<213> ORGANISM: hepatitis C virus

<400> SEQUENCE: 10

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
        35                  40                  45

Lys Ala Ala Gly Leu Arg Asn Pro Asp Phe Leu Val Cys Gly Asp Asp
    50                  55                  60

Leu Val Val Val Ala Glu Ser
```

<210> SEQ ID NO 11
<211> LENGTH: 213
<212> TYPE: DNA
<213> ORGANISM: hepatitis C virus

<400> SEQUENCE: 11

```
ctcacggagc ggctttactg cgggggccct atgttcaaca gcaaggggc ccagtgtggt      60
tatcgccgtt gtcgtgccag tggagttctg cctaccagtt tcggcaacac aatcacttgt    120
tacatcaagg ccacagcggc tgcaaaagcc gcaggcctcc ggaacccgga ctttcttgtt    180
tgcggagatg atttggtcgt ggtggctgag agt                                 213
```

<210> SEQ ID NO 12
<211> LENGTH: 71
<212> TYPE: PRT
<213> ORGANISM: hepatitis C virus

<400> SEQUENCE: 12

```
Leu Thr Glu Arg Leu Tyr Cys Gly Gly Pro Met Phe Asn Ser Lys Gly
1               5                  10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
        35                  40                  45

Lys Ala Ala Gly Leu Arg Asn Pro Asp Phe Leu Val Cys Gly Asp Asp
    50                  55                  60

Leu Val Val Val Ala Glu Ser
65                  70
```

<210> SEQ ID NO 13
<211> LENGTH: 541
<212> TYPE: DNA
<213> ORGANISM: hepatitis C virus

<400> SEQUENCE: 13

```
cgtcggcgct cctgtaggag gcgtcgcaag agcccttgcg catggcgtga gggcccttga      60
agacgggata aatttcgcaa cagggaattt gcccggttgc tccttttcta tcttccttct    120
tgctctgttc tcttgcttaa tccatccagc agctagtcta gagtggcgga cacgtctgg    180
cctctatgtc cttaccaacg actgttccaa tagcagtatt gtgtatgagg ccgatgacgt    240
tattctgcac acacccggct gtgtaccttg tgttcaggac ggtaatacat ctgcgtgctg    300
gaccccagtg acacctacag tggcagtcag gtacgtcgga gcaaccaccg cttcgatacg    360
caggcatgta gacatgttgg tgggcgcggc cacgatgtgc tctgctctct acgtgggtga    420
tatgtgtggg gccgtcttcc tcgtgggaca agccttcacg ttcagacctc gtcgccatca    480
aacggtccag acctgtaact gctcactgta cccaggccat ctttcaggac accgaatggc    540
t                                                                    541
```

<210> SEQ ID NO 14
<211> LENGTH: 180
<212> TYPE: PRT
<213> ORGANISM: hepatitis C virus

<400> SEQUENCE: 14

```
Val Gly Ala Pro Val Gly Gly Val Ala Arg Ala Leu Ala His Gly Val
1               5                  10                  15
```

```
Arg Ala Leu Glu Asp Gly Ile Asn Phe Ala Thr Gly Asn Leu Pro Gly
            20                  25                  30

Cys Ser Phe Ser Ile Phe Leu Leu Ala Leu Phe Ser Cys Leu Ile His
        35                  40                  45

Pro Ala Ala Ser Leu Glu Trp Arg Asn Thr Ser Gly Leu Tyr Val Leu
    50                  55                  60

Thr Asn Asp Cys Ser Asn Ser Ser Ile Val Tyr Glu Ala Asp Asp Val
65                  70                  75                  80

Ile Leu His Thr Pro Gly Cys Val Pro Cys Val Gln Asp Gly Asn Thr
                85                  90                  95

Ser Ala Cys Trp Thr Pro Val Thr Pro Thr Val Ala Val Arg Tyr Val
            100                 105                 110

Gly Ala Thr Thr Ala Ser Ile Arg Arg His Val Asp Met Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180

<210> SEQ ID NO 15
<211> LENGTH: 541
<212> TYPE: DNA
<213> ORGANISM: hepatitis C virus

<400> SEQUENCE: 15
cgtcggcgct cctgtaggag gcgtcgcaag agcccttgcg catggcgtga gggcccttga      60
agacgggata aatttcgcaa caggaatttt gcccggttgc tcctttcta tcttccttcc     120 tgctctgttc tcttgcttaa tccatccagc agctagtcta gagtggcgga acacgtctgg     180
cctctatgtc cttaccaacg actgttccaa tagcagtatt gtgtatgagg ccgatgacgt     240
tattctgcac acacccggct gtgtaccttg tgttcaggac ggtaatacat ctgcgtgctg     300
gaccccagtg acacctacag tggcagtcag gtacgtcgga gcaaccaccg cttcgatacg     360
caggcatgta gacatattgg tgggcgcggc cacaatgtgc tctgctctct acgtgggtga     420
tatgtgtggg gccgtcttcc tcgtgggaca agccttcacg ttcagacctc gtcgccatca     480
aacggtccag acctgtaact gctcactgta cccaggccat ctttcaggac accgaatggc     540
t                                                                    541

<210> SEQ ID NO 16
<211> LENGTH: 180
<212> TYPE: PRT
<213> ORGANISM: hepatitis C virus

<400> SEQUENCE: 16

Val Gly Ala Pro Val Gly Gly Val Ala Arg Ala Leu Ala His Gly Val
1               5                   10                  15

Arg Ala Leu Glu Asp Gly Ile Asn Phe Ala Thr Gly Asn Leu Pro Gly
            20                  25                  30

Cys Ser Phe Ser Ile Phe Leu Pro Ala Leu Phe Ser Cys Leu Ile His
        35                  40                  45
```

```
Pro Ala Ala Ser Leu Glu Trp Arg Asn Thr Ser Gly Leu Tyr Val Leu
    50                  55                  60

Thr Asn Asp Cys Ser Asn Ser Ser Ile Val Tyr Glu Ala Asp Asp Val
65                  70                  75                  80

Ile Leu His Thr Pro Gly Cys Val Pro Cys Val Gln Asp Gly Asn Thr
                85                  90                  95

Ser Ala Cys Trp Thr Pro Val Thr Pro Thr Val Ala Val Arg Tyr Val
                100                 105                 110

Gly Ala Thr Thr Ala Ser Ile Arg Arg His Val Asp Ile Leu Val Gly
            115                 120                 125

Ala Ala Thr Met Cys Ser Ala Leu Tyr Val Gly Asp Met Cys Gly Ala
        130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180

<210> SEQ ID NO 17
<211> LENGTH: 541
<212> TYPE: DNA
<213> ORGANISM: hepatitis C virus

<400> SEQUENCE: 17
cgtcggcgct cctgtaggag gcgtcgcaag agcccttgcg catggcgtga gggcccttga      60
agacgggata aatttcgcaa cagggaattt gcccggttgc tccttttcta tcttccttct     120
tgctctgttc tcttgcttaa tccatccagc agctagtcta gagtggcgga acacgtctgg     180
cctctacgtc cttaccaacg actgttccaa tagcagtatt gtgtatgagg ccgatgacgt     240
tattctgcac acacccggct gtgtaccttg tgttcaggac ggtaatacat ctgcgtgctg     300
gaccccagtg acacctacag tggcagtcag gtacgtcgga gcaaccaccg cttcgatacg     360
caggcatgta gacatattgg tgggcgcggc cacgatgtgc tctgctctct acgtgggtga     420
tatgtgtggg gccgtcttcc tcgtgggaca agccttcacg ttcagacctc gtcgccatca     480
aacggtccag acctgtaact gctcactgta cccaggccat ctttcaggac accgaatggc     540
t                                                                   541

<210> SEQ ID NO 18
<211> LENGTH: 180
<212> TYPE: PRT
<213> ORGANISM: hepatitis C virus

<400> SEQUENCE: 18

Val Gly Ala Pro Val Gly Gly Val Ala Arg Ala Leu Ala His Gly Val
1               5                   10                  15

Arg Ala Leu Glu Asp Gly Ile Asn Phe Ala Thr Gly Asn Leu Pro Gly
                20                  25                  30

Cys Ser Phe Ser Ile Phe Leu Leu Ala Leu Phe Ser Cys Leu Ile His
            35                  40                  45

Pro Ala Ala Ser Leu Glu Trp Arg Asn Thr Ser Gly Leu Tyr Val Leu
        50                  55                  60

Thr Asn Asp Cys Ser Asn Ser Ser Ile Val Tyr Glu Ala Asp Asp Val
65                  70                  75                  80

Ile Leu His Thr Pro Gly Cys Val Pro Cys Val Gln Asp Gly Asn Thr
```

-continued

```
                85                  90                  95
Ser Ala Cys Trp Thr Pro Val Thr Pro Thr Val Ala Val Arg Tyr Val
            100                 105                 110

Gly Ala Thr Thr Ala Ser Ile Arg Arg His Val Asp Ile Leu Val Gly
            115                 120                 125

Ala Ala Thr Met Cys Ser Ala Leu Tyr Val Gly Asp Met Cys Gly Ala
        130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180
```

<210> SEQ ID NO 19
<211> LENGTH: 541
<212> TYPE: DNA
<213> ORGANISM: hepatitis C virus

<400> SEQUENCE: 19

```
cgtcggcgct cccgtaggag gcgtcgcaag agcccttgcg catggcgtga gggcccttga    60
agacgggata aatttcgcaa cagggaattt gcccggttgc tccttttcta ttttccttct   120
tgctctgttc tcttgcttaa ttcatccagc agctagtcta gagtggcgga atacgtctgg   180
cctctatgtc cttaccaacg actgttccaa tagcagtatt gtgtacgagg ccgatgacgt   240
tattctgcac acacccggct gcatacctthg tgtccaggac ggcaatacat ccacgtgctg   300
gaccccagtg acacctacag tggcagtcaa gtacgtcgga gcaaccaccg cttcgatacg   360
cagtcatgtg gacctattag tgggcgcggc cacgatgtgc tcagcgctct acgtgggtga   420
tatgtgtggg gccgtcttcc ttgtgggaca agccttcacg ttcagacctc gtcgccatca   480
aacggtccag acctgtaact gctcgctgta cccaggccat ctttcaggac atcgaatggc   540
t                                                                    541
```

<210> SEQ ID NO 20
<211> LENGTH: 180
<212> TYPE: PRT
<213> ORGANISM: hepatitis C virus

<400> SEQUENCE: 20

```
Val Gly Ala Pro Val Gly Gly Val Ala Arg Ala Leu Ala His Gly Val
1               5                   10                  15

Arg Ala Leu Glu Asp Gly Ile Asn Phe Ala Thr Gly Asn Leu Pro Gly
            20                  25                  30

Cys Ser Phe Ser Ile Phe Leu Leu Ala Leu Phe Ser Cys Leu Ile His
        35                  40                  45

Pro Ala Ala Ser Leu Glu Trp Arg Asn Thr Ser Gly Leu Tyr Val Leu
    50                  55                  60

Thr Asn Asp Cys Ser Asn Ser Ser Ile Val Tyr Glu Ala Asp Asp Val
65                  70                  75                  80

Ile Leu His Thr Pro Gly Cys Ile Pro Cys Val Gln Asp Gly Asn Thr
                85                  90                  95

Ser Thr Cys Trp Thr Pro Val Thr Pro Thr Val Ala Val Lys Tyr Val
            100                 105                 110

Gly Ala Thr Thr Ala Ser Ile Arg Ser His Val Asp Leu Leu Val Gly
            115                 120                 125
```

```
Ala Ala Thr Met Cys Ser Ala Leu Tyr Val Gly Asp Met Cys Gly Ala
        130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180

<210> SEQ ID NO 21
<211> LENGTH: 541
<212> TYPE: DNA
<213> ORGANISM: hepatitis C virus

<400> SEQUENCE: 21
cgtcggcgct cccgtaggag gcgtcgcaag agcccttgcg catggcgtga gggcccttga    60
agacgggata aatttcgcaa cagggaattt gcccggttgc tccttttcta ttttccttct   120
tgctctgttc tcttgcttaa ttcatccagc agctagtcta gagtggcgga atacgtctgg   180
cctctatgtc cttaccaacg actgttccaa tagcagtatt gtgtacgagg ccgatgacgt   240
tattctgcac acacccggct gcataccttg tgtccaggac ggcaatacat ccacgtgctg   300
gacccccagtg acacctacag tggcagtcaa gtacgtcgga gcaaccaccg cttcgatacg   360
cagtcatgtg gacctattag tgggcgcggc cacgatgtgc tctgcgctct acgtgggtga   420
catgtgtggg gctgtcttcc tcgtgggaca agccttcacg ttcagacctc gtcgccatca   480
aacggtccag acctgtaact gctcgctgta cccaggccat ctttcaggac atcgaatggc   540
t                                                                    541

<210> SEQ ID NO 22
<211> LENGTH: 180
<212> TYPE: PRT
<213> ORGANISM: hepatitis C virus

<400> SEQUENCE: 22

Val Gly Ala Pro Val Gly Gly Val Ala Arg Ala Leu Ala His Gly Val
1               5                   10                  15

Arg Ala Leu Glu Asp Gly Ile Asn Phe Ala Thr Gly Asn Leu Pro Gly
            20                  25                  30

Cys Ser Phe Ser Ile Phe Leu Leu Ala Leu Phe Ser Cys Leu Ile His
        35                  40                  45

Pro Ala Ala Ser Leu Glu Trp Arg Asn Thr Ser Gly Leu Tyr Val Leu
    50                  55                  60

Thr Asn Asp Cys Ser Asn Ser Ser Ile Val Tyr Glu Ala Asp Asp Val
65                  70                  75                  80

Ile Leu His Thr Pro Gly Cys Ile Pro Cys Val Gln Asp Gly Asn Thr
                85                  90                  95

Ser Thr Cys Trp Thr Pro Val Thr Pro Thr Val Ala Val Lys Tyr Val
            100                 105                 110

Gly Ala Thr Thr Ala Ser Ile Arg Ser His Val Asp Leu Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160
```

```
Thr Val Gln Thr Cys Asn Cys Ser Leu Tyr Pro Gly His Leu Ser Gly
            165                 170                 175
His Arg Met Ala
        180

<210> SEQ ID NO 23
<211> LENGTH: 541
<212> TYPE: DNA
<213> ORGANISM: hepatitis C virus

<400> SEQUENCE: 23
cgtcggcgct cccgtaggag gcgtcgcaag agcccttgcg catggcgtga gggcccttga    60
ggacgggata aacttcgcaa cagggaattt gcccggttgc tccttttcta tcttccttct   120
tgctctgttc tcttgcttaa tccatccagc agctggtcta gagtggcgga atacgtctgg   180
cctctatgtc cttaccaacg actgttccaa tagtagtatt gtgtatgagg ccgatgacgt   240
tattctgcac gcgcccggct gtgtaccttg tgtccaggac ggcaatacgt ctacatgctg   300
gaccccagta acacctacag tggcagtcag gtacgtcggg gcaaccaccg cttcgatacg   360
cagtcatgtg gacctgttag taggcgcggc acgatgtgc tctgcgcttt acgtgggtga   420
tatgtgtggg gccgtcttcc tcgtgggaca agccttcacg ttcagacccc gccgccatca   480
aacggtccag acctgtaact gctcgctgta cccaggccat ctttcaggac atcgcatggc   540
t                                                                   541

<210> SEQ ID NO 24
<211> LENGTH: 180
<212> TYPE: PRT
<213> ORGANISM: hepatitis C virus

<400> SEQUENCE: 24

Val Gly Ala Pro Val Gly Gly Val Ala Arg Ala Leu Ala His Gly Val
1               5                   10                  15
Arg Ala Leu Glu Asp Gly Ile Asn Phe Ala Thr Gly Asn Leu Pro Gly
            20                  25                  30
Cys Ser Phe Ser Ile Phe Leu Leu Ala Leu Phe Ser Cys Leu Ile His
        35                  40                  45
Pro Ala Gly Leu Glu Trp Arg Asn Thr Ser Gly Leu Tyr Val Leu
    50                  55                  60
Thr Asn Asp Cys Ser Asn Ser Ser Ile Val Tyr Glu Ala Asp Asp Val
65                  70                  75                  80
Ile Leu His Ala Pro Gly Cys Val Pro Cys Val Gln Asp Gly Asn Thr
                85                  90                  95
Ser Thr Cys Trp Thr Pro Val Thr Pro Thr Val Ala Val Arg Tyr Val
            100                 105                 110
Gly Ala Thr Thr Ala Ser Ile Arg Ser His Val Asp Leu Leu Val Gly
        115                 120                 125
Ala Ala Thr Met Cys Ser Ala Leu Tyr Val Gly Asp Met Cys Gly Ala
    130                 135                 140
Val Phe Leu Val Gly Gln Ala Phe Thr Phe Arg Pro Arg Arg His Gln
145                 150                 155                 160
Thr Val Gln Thr Cys Asn Cys Ser Leu Tyr Pro Gly His Leu Ser Gly
                165                 170                 175
His Arg Met Ala
        180
```

```
<210> SEQ ID NO 25
<211> LENGTH: 541
<212> TYPE: DNA
<213> ORGANISM: hepatitis C virus

<400> SEQUENCE: 25
cgtcggcgct cccgtaggag gcgtcgcaag agcccttgcg catggcgtga gggcccttga      60
ggacgggata aacttcgcaa cagggaattt gcccggttgc tcttttcta tcttccttct     120
tgctctgttc tcttgcttaa tccatccagc agctggtcta gagtggcgga atacgtctgg     180
cctctatgtc cttaccaacg actgttccaa tagtagtatt tgtgtatgag ccgatgacgt     240
tattctgcac gcgcccggct gtgtaccttg tgtccaggac ggcaatacgt ctacatgctg     300
gaccccagta acacctacag tggcagtcag gtacgtcggg gcaaccaccg cttcgatacg     360
cagtcatgtg gacctgttag taggcgcggc cacgatgtgc tctgcgcttt acgtgggtga     420
tatgtgtggg gccgtcttcc tcgtgggaca agccttcacg ttcagacccc gccgccatca     480
aacggtccag acctgtaact gctcgctgta cccaggccat ctttcaggac atcgaatggc     540
t                                                                    541

<210> SEQ ID NO 26
<211> LENGTH: 180
<212> TYPE: PRT
<213> ORGANISM: hepatitis C virus

<400> SEQUENCE: 26

Val Gly Ala Pro Val Gly Gly Val Ala Arg Ala Leu Ala His Gly Val
  1               5                  10                  15

Arg Ala Leu Glu Asp Gly Ile Asn Phe Ala Thr Gly Asn Leu Pro Gly
             20                  25                  30

Cys Ser Phe Ser Ile Phe Leu Leu Ala Leu Phe Ser Cys Leu Ile His
         35                  40                  45

Pro Ala Ala Gly Leu Glu Trp Arg Asn Thr Ser Gly Leu Tyr Val Leu
     50                  55                  60

Thr Asn Asp Cys Ser Asn Ser Ser Ile Val Tyr Glu Ala Asp Asp Val
 65                  70                  75                  80

Ile Leu His Ala Pro Gly Cys Val Pro Cys Val Gln Asp Gly Asn Thr
                 85                  90                  95

Ser Thr Cys Trp Thr Pro Val Thr Pro Thr Val Ala Val Arg Tyr Val
            100                 105                 110

Gly Ala Thr Thr Ala Ser Ile Arg Ser His Val Asp Leu Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180

<210> SEQ ID NO 27
<211> LENGTH: 541
<212> TYPE: DNA
<213> ORGANISM: hepatitis C virus

<400> SEQUENCE: 27
```

```
cgtcggcgct cccgtaggag gcgtcgcaag agcccttgcg catggcgtga gggcccttga      60
ggacgggata aacttcgcaa cagggaattt gcccggttgc tcttttttcta tcttccttct    120 tgctctgttc tcttgcttaa tccatccagc agctggtcta gagtggcgga atacgtctgg    180
cctctatgtc cttaccaacg actgttccaa tagtagtatt gtgtatgagg ccgatgacgt    240
tattctgcac gcgcccggct gtgtaccttg tgtccaggac ggcaatacgt ctacatgctg    300
gaccccagta acacctacag tggcagtcag gtacgtcggg gcaaccaccg cttcgatacg    360
cagtcatgtg gacctgttag taggcgcggc cacgatgtgc tctgcgcttt acgtgggtga    420
tatgtgtggg gccgtcttcc tcgtgggaca agccttcacg ttcagacccc gccgccatca    480
aacggtccag acctgtaact gctcgctgta cccaggccat ctttcaggac atcgaatggc    540
t                                                                     541

<210> SEQ ID NO 28
<211> LENGTH: 180
<212> TYPE: PRT
<213> ORGANISM: hepatitis C virus

<400> SEQUENCE: 28

Val Gly Ala Pro Val Gly Gly Val Ala Arg Ala Leu Ala His Gly Val
1               5                   10                  15

Arg Ala Leu Glu Asp Gly Ile Asn Phe Ala Thr Gly Asn Leu Pro Gly
            20                  25                  30

Cys Ser Phe Ser Ile Phe Leu Leu Ala Leu Phe Ser Cys Leu Ile His
        35                  40                  45

Pro Ala Ala Gly Leu Glu Trp Arg Asn Thr Ser Gly Leu Tyr Val Leu
    50                  55                  60

Thr Asn Asp Cys Ser Asn Ser Ser Ile Val Tyr Glu Ala Asp Asp Val
65                  70                  75                  80

Ile Leu His Ala Pro Gly Cys Val Pro Cys Val Gln Asp Gly Asn Thr
                85                  90                  95

Ser Thr Cys Trp Thr Pro Val Thr Pro Thr Val Ala Val Arg Tyr Val
            100                 105                 110

Gly Ala Thr Thr Ala Ser Ile Arg Ser His Val Asp Leu Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180

<210> SEQ ID NO 29
<211> LENGTH: 287
<212> TYPE: DNA
<213> ORGANISM: hepatitis C virus

<400> SEQUENCE: 29
tagacttttg ggagagcgtc ttcactggac taactcacat agatgcccac tttctgtcac     60
agactaagca gcagggactc aacttctcgt tcctgactgc ctaccaagcc actgtgtgcg    120
ctcgcgcgca ggctcctccc ccaagttggg acgagatgtg gaagtgtctc gtacggctta    180
agccaacact acatggacct acgcctcttc tatatcggtt ggggcctgtc caaaatgaaa    240
```

```
tctgcttgac acccccatc acaaaataca tcatggcatg catgtca           287
```

<210> SEQ ID NO 30
<211> LENGTH: 95
<212> TYPE: PRT
<213> ORGANISM: hepatitis C virus

<400> SEQUENCE: 30

```
Asp Phe Trp Glu Ser Val Phe Thr Gly Leu Thr His Ile Asp Ala His
1               5                   10                  15

Phe Leu Ser Gln Thr Lys Gln Gln Gly Leu Asn Phe Ser Phe Leu Thr
            20                  25                  30

Ala Tyr Gln Ala Thr Val Cys Ala Arg Ala Gln Ala Pro Pro Pro Ser
        35                  40                  45

Trp Asp Glu Met Trp Lys Cys Leu Val Arg Leu Lys Pro Thr Leu His
    50                  55                  60

Gly Pro Thr Pro Leu Leu Tyr Arg Leu Gly Pro Val Gln Asn Glu Ile
65                  70                  75                  80

Cys Leu Thr His Pro Ile Thr Lys Tyr Ile Met Ala Cys Met Ser
                85                  90                  95
```

<210> SEQ ID NO 31
<211> LENGTH: 401
<212> TYPE: DNA
<213> ORGANISM: hepatitis C virus

<400> SEQUENCE: 31

```
tccaaaatga aatctgcttg acacaccccg tcacaaaata cattatggca tgcatgtcag     60
ctgatctgga agtaaccacc agcacctggg tgttgcttgg aggggtcctc gcggccctag    120
cggcctactg cttgtcagtc ggctgcgttg taatcgtggg tcatatcgag ctggggggca    180
agccggcact cgttccagac aaggaggtgt tgtatcaaca gtacgatgag atggaggagt    240
gctcgcaagc cgccccatac atcgaacaag ctcaggtaat agcccaccag ttcaaggaga    300
aaatccttgg actgctgcag cgagccaccc aacaacaagc tgtcattgag cccgtaatag    360
cttccaactg gcaaaagctt gaaaccttct ggcacaagca t                        401
```

<210> SEQ ID NO 32
<211> LENGTH: 133
<212> TYPE: PRT
<213> ORGANISM: hepatitis C virus

<400> SEQUENCE: 32

```
Gln Asn Glu Ile Cys Leu Thr His Pro Val Thr Lys Tyr Ile Met Ala
1               5                   10                  15

Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Leu Val
    50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Glu Lys Ile Leu Gly Leu Leu Gln Arg Ala Thr Gln Gln Gln
                100                 105                 110
```

Ala Val Ile Glu Pro Val Ile Ala Ser Asn Trp Gln Lys Leu Glu Thr
        115                 120                 125

Phe Trp His Lys His
        130

<210> SEQ ID NO 33
<211> LENGTH: 401
<212> TYPE: DNA
<213> ORGANISM: hepatitis C virus

<400> SEQUENCE: 33
tccaaaatga atctgcttg acacacccg tcacaaaata cattatggca tgcatgtcag        60
ctgatctgga agtaaccacc agcacctggg tgttgcttgg aggggtcctc gcggccctag    120
cggcctactg cttgtcagtc ggctgcgttg taatcgtggg tcatatcgag ctggggggca    180
agccggcact cgttccagac aaggaggtgt tgtatcaaca gtacgatgag atggaggagt    240
gctcgcaagc cgccccatac atcgaacaag ctcaggtaat agcccaccag ttcaaggaga    300
aaatccttgg actgctgcag cgagccacca acaacaagc tgtcattgag cccgtaatag    360
cttccaactg gcaaaagctt gaaaccttct ggcacaagca t                        401

<210> SEQ ID NO 34
<211> LENGTH: 133
<212> TYPE: PRT
<213> ORGANISM: hepatitis C virus

<400> SEQUENCE: 34

Gln Asn Glu Ile Cys Leu Thr His Pro Val Thr Lys Tyr Ile Met Ala
1               5                   10                  15

Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Leu Val
    50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Glu Lys Ile Leu Gly Leu Leu Gln Arg Ala Thr Gln Gln Gln
            100                 105                 110

Ala Val Ile Glu Pro Val Ile Ala Ser Asn Trp Gln Lys Leu Glu Thr
        115                 120                 125

Phe Trp His Lys His
        130

<210> SEQ ID NO 35
<211> LENGTH: 401
<212> TYPE: DNA
<213> ORGANISM: hepatitis C virus

<400> SEQUENCE: 35
tccaaaatga atctgcttg acacacccca tcacaaaata catcatggca tgcatgtcag        60
ctgatctgga agtaaccacc agcacctggg ttttgcttgg aggggtcctc gcggccctag    120
cggcctactg cttgtcagtc ggttgtgttg tgattgtggg tcatatcgag ctggggggca    180
agccggcaat cgttccagac aaagaggtgt tgtatcaaca atacgatgag atggaagagt    240

```
gctcacaagc tgccccatat atcgaacaag ctcaggtaat agctcaccag ttcaagggaa      300
aagtccttgg attgctgcag cgagccaccc aacaacaagc tgtcattgag cccatagtaa      360
ctaccaactg gcaaaagctt gaggcctttt ggcacaagca t                          401
```

```
<210> SEQ ID NO 36
<211> LENGTH: 133
<212> TYPE: PRT
<213> ORGANISM: hepatitis C virus

<400> SEQUENCE: 36
```

```
Gln Asn Glu Ile Cys Leu Thr His Pro Ile Thr Lys Tyr Ile Met Ala
1               5                   10                  15

Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Ile Val
    50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Gly Lys Val Leu Gly Leu Leu Gln Arg Ala Thr Gln Gln Gln
            100                 105                 110

Ala Val Ile Glu Pro Ile Val Thr Thr Asn Trp Gln Lys Leu Glu Ala
        115                 120                 125

Phe Trp His Lys His
        130
```

```
<210> SEQ ID NO 37
<211> LENGTH: 401
<212> TYPE: DNA
<213> ORGANISM: hepatitis C virus

<400> SEQUENCE: 37
tccaaaatga atctgcttg acacacccca tcacaaaata catcatggca tgcatgtcag       60
ctgatctgga agtaaccacc agcacctggg ttttgcttgg agggqtcctc gcggccctag      120 cggcctactg cttgtcagtc ggttgtgttg tgattgtggg tcatatcgag ctggggggca      180
agccggcaat cgttccagac aaagaggtgt tgtatcaaca atacgatgag atggaagagt      240
gctcacaagc tgccccatat atcgaacaag ctcaggtgat agctcaccag ttcaaggaaa      300
aagtccttgg attgctgcag cgagccaccc aacaacaagc tgtcattgag cccatagtaa      360
ctaccaactg gcaaaagctt gaggcctttt ggcacaagca t                          401
```

```
<210> SEQ ID NO 38
<211> LENGTH: 133
<212> TYPE: PRT
<213> ORGANISM: hepatitis C virus

<400> SEQUENCE: 38
```

```
Gln Asn Glu Ile Cys Leu Thr His Pro Ile Thr Lys Tyr Ile Met Ala
1               5                   10                  15

Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
```

-continued

```
                35                  40                  45
Val Val Ile Val Gly His Ile Glu Leu Gly Gly Lys Pro Ala Ile Val
     50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Glu Lys Val Leu Gly Leu Leu Gln Arg Ala Thr Gln Gln Gln
                100                 105                 110

Ala Val Ile Glu Pro Ile Val Thr Thr Asn Trp Gln Lys Leu Glu Ala
            115                 120                 125

Phe Trp His Lys His
            130

<210> SEQ ID NO 39
<211> LENGTH: 401
<212> TYPE: DNA
<213> ORGANISM: hepatitis C virus

<400> SEQUENCE: 39
tccaaaatga atctgcttg acacacccca tcacaaaata catcatggca tgcatgtcag      60
ctgatctgga agtaaccacc agcacctggg ttttgcttgg aggggtcctc gcggccctag   120
cggcctactg cttgtcagtc ggttgtgttg tgattgtggg tcatatcgag ctgggggggca  180 agccggcaat cgttccagac aaagaggtgt tgtatcaaca atacgatgag atggaagagt   240
gctcacaagc tgccccatat atcgaacaag ctcaggtaat agctcaccag ttcaaggaaa   300
aagtccttgg attgctgcag cgagccaccc aacaacaagc tgtcattgag cccatagtaa   360
ctaccaactg gcaaaagctt gaggcctttt ggcacaagca t                        401

<210> SEQ ID NO 40
<211> LENGTH: 133
<212> TYPE: PRT
<213> ORGANISM: hepatitis C virus

<400> SEQUENCE: 40

Gln Asn Glu Ile Cys Leu Thr His Pro Ile Thr Lys Tyr Ile Met Ala
1               5                   10                  15

Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Ile Val
     50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Glu Lys Val Leu Gly Leu Leu Gln Arg Ala Thr Gln Gln Gln
                100                 105                 110

Ala Val Ile Glu Pro Ile Val Thr Thr Asn Trp Gln Lys Leu Glu Ala
            115                 120                 125

Phe Trp His Lys His
            130

<210> SEQ ID NO 41
```

```
<211> LENGTH: 509
<212> TYPE: DNA
<213> ORGANISM: hepatitis C virus

<400> SEQUENCE: 41
ccatgagcac gaatcctaaa cctcaaagaa aaaccaaaag aaacaccaac cgtcgcccac        60
aggacgtcaa gttcccgggc ggtggtcaga tcgttggcgg agtttacttg ttgccgcgca       120
ggggccctag gatgggtgtg cgcgcgactc ggaagacttc ggaacggtcg caaccccgtg       180
gacggcgtca gcctattccc aaggcgcgcc agcccacggg ccggtcctgg ggtcaacccg       240 ggtaccttg gcccctttac gccaatgagg gcctcgggtg ggcagggtgg ctgctctccc       300
ctcgaggctc tcggcctaat tgggccccca atgaccccg gcgaaaatcg cgtaatttgg        360
gtaaggtcat cgatacccta acgtgcggat tcgccgatct catggggtat atcccgctcg       420
taggcggccc cattgggggc gtcgcaaggg ctctcgcaca cggtgtgagg gtccttgagg       480
acggggtaaa ctatgcaaca gggaattta                                         509
```

```
<210> SEQ ID NO 42
<211> LENGTH: 169
<212> TYPE: PRT
<213> ORGANISM: hepatitis C virus

<400> SEQUENCE: 42

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Met Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Ile
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu
                165
```

```
<210> SEQ ID NO 43
<211> LENGTH: 509
<212> TYPE: DNA
<213> ORGANISM: hepatitis C virus

<400> SEQUENCE: 43
ccatgagcac gaatcctaaa cctcaaagaa aaaccaaaag aaacaccaac cgtcgcccac        60
aggacgtcaa gttcccgggc ggtggtcaga tcgttggcgg agtttacttg ttgccgcgca       120
ggggccctag gatgggtgtg cgcgcgactc ggaagacttc ggaacggtcg caaccccgtg       180
```

```
gacggcgtca gcctattccc aaggcgcgcc agcccacggg ccggtcctgg ggtcaacccg      240 ggtaccttg gccccttac gccaatgagg gcctcgggtg ggcagggtgg ctgctctccc       300
ctcgaggctc tcggcctaat tgggccccca atgaccccg gcgaaaatcg cgtaatttgg      360
gtaaggtcat cgatacccta acgtgcggat tcgccgatct catgggtat atcccgctcg      420 taggcggccc cattgggggc gtcgcaaggg ctctcgcaca cggtgtgagg gtccttgagg     480
acggggtaaa ctatgcaaca gggaattta                                      509
```

<210> SEQ ID NO 44
<211> LENGTH: 169
<212> TYPE: PRT
<213> ORGANISM: hepatitis C virus

<400> SEQUENCE: 44

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Met Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Ile
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu
                165
```

<210> SEQ ID NO 45
<211> LENGTH: 580
<212> TYPE: DNA
<213> ORGANISM: hepatitis C virus

<400> SEQUENCE: 45

```
aacgtgcgga ttcgccgatc tcatgggta tatcccgctc gtaggcggcc ccattggggg      60
cgtcgcaagg gctctcgcac acggtgtgag ggtccttgag gacggggtaa actatgcaac    120
agggaattta cccggttgct ctttctctat ctttattctt gctcttctct cgtgtctgac    180
cgttccggcc tctgcagttc cctaccgaaa tgcctctggg atttatcatg ttaccaatga    240
ttgcccaaac tcttccatag tctatgaggc agataacctg atcctacacg cacctggttg    300
cgtgccttgt gtcatgacag gtaatgtgag tagatgctgg gtccaaatta ccctacact     360 gtcagccccg agcctcggag cagtcacggc tcctcttcgg agagccgttg actacctagc    420 gggagggct gccctctgct ccgcgttata cgtaggagac gcgtgtgggg cactattctt    480
ggtaggccaa atgttcacct ataggcctcg ccagcacgct acggtgcaga actgcaactg   540
```

```
ttccatttac agtggccatg ttaccggcca ccggatggca                         580
```

<210> SEQ ID NO 46
<211> LENGTH: 193
<212> TYPE: PRT
<213> ORGANISM: hepatitis C virus

<400> SEQUENCE: 46

```
Thr Cys Gly Phe Ala Asp Leu Met Gly Tyr Ile Pro Leu Val Gly Gly
  1               5                  10                  15

Pro Ile Gly Gly Val Ala Arg Ala Leu Ala His Gly Val Arg Val Leu
             20                  25                  30

Glu Asp Gly Val Asn Tyr Ala Thr Gly Asn Leu Pro Gly Cys Ser Phe
         35                  40                  45

Ser Ile Phe Ile Leu Ala Leu Leu Ser Cys Leu Thr Val Pro Ala Ser
     50                  55                  60

Ala Val Pro Tyr Arg Asn Ala Ser Gly Ile Tyr His Val Thr Asn Asp
 65                  70                  75                  80

Cys Pro Asn Ser Ser Ile Val Tyr Glu Ala Asp Asn Leu Ile Leu His
                 85                  90                  95

Ala Pro Gly Cys Val Pro Cys Val Met Thr Gly Asn Val Ser Arg Cys
            100                 105                 110

Trp Val Gln Ile Thr Pro Thr Leu Ser Ala Pro Ser Leu Gly Ala Val
        115                 120                 125

Thr Ala Pro Leu Arg Arg Ala Val Asp Tyr Leu Ala Gly Gly Ala Ala
    130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asn Cys Asn Cys Ser Ile Tyr Ser Gly His Val Thr Gly His Arg Met
            180                 185                 190

Ala
```

<210> SEQ ID NO 47
<211> LENGTH: 580
<212> TYPE: DNA
<213> ORGANISM: hepatitis C virus

<400> SEQUENCE: 47

```
aacgtgcgga ttcgccgatc tcatggggta tatcccgctc gtaggcggcc ccattggggg      60
cgtcgcaagg gctctcgcac acggtgtgag ggtccttgag gacggggtaa actatgcaac     120
agggaattta cccggttgct ctttctctat ctttattctt gctcttctct cgtgtctgac     180
cgttccggcc tctgcagttc cctaccgaaa tgcctctggg atttatcatg ttaccaatga     240
ttgcccaaac tcttccatag tctatgaggc agataacctg atcctacacg cacctggttg     300
cgtgccttgt gtcatgacag gtaatgtgag tagatgctgg gtccaaatta cccctacact     360 gtcagcccg agcctcggag cagtcacggc tcctcttcgg agagccgttg actacctagc      420 gggagggct gccctctgct ccgcgttata cgtaggagac gcgtgtgggg cactattctt      480
ggtaggccaa atgttcacct ataggcctcg ccagcacgct acggtgcaga actgcaactg     540
ttccatttac agtggccatg ttaccggcca ccggatggca                           580
```

<210> SEQ ID NO 48
<211> LENGTH: 193

```
<212> TYPE: PRT
<213> ORGANISM: hepatitis C virus

<400> SEQUENCE: 48

Thr Cys Gly Phe Ala Asp Leu Met Gly Tyr Ile Pro Leu Val Gly Gly
1               5                  10                  15

Pro Ile Gly Gly Val Ala Arg Ala Leu Ala His Gly Val Arg Val Leu
            20                  25                  30

Glu Asp Gly Val Asn Tyr Ala Thr Gly Asn Leu Pro Gly Cys Ser Phe
        35                  40                  45

Ser Ile Phe Ile Leu Ala Leu Leu Ser Cys Leu Thr Val Pro Ala Ser
    50                  55                  60

Ala Val Pro Tyr Arg Asn Ala Ser Gly Ile Tyr His Val Thr Asn Asp
65                  70                  75                  80

Cys Pro Asn Ser Ser Ile Val Tyr Glu Ala Asp Asn Leu Ile Leu His
                85                  90                  95

Ala Pro Gly Cys Val Pro Cys Val Met Thr Gly Asn Val Ser Arg Cys
            100                 105                 110

Trp Val Gln Ile Thr Pro Thr Leu Ser Ala Pro Ser Leu Gly Ala Val
        115                 120                 125

Thr Ala Pro Leu Arg Arg Ala Val Asp Tyr Leu Ala Gly Gly Ala Ala
    130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asn Cys Asn Cys Ser Ile Tyr Ser Gly His Val Thr Gly His Arg Met
            180                 185                 190

Ala

<210> SEQ ID NO 49
<211> LENGTH: 959
<212> TYPE: DNA
<213> ORGANISM: hepatitis C virus

<400> SEQUENCE: 49
ccatgagcac gaatcctaaa cctcaaagaa aaaccaaaag aaacaccaac cgtcgcccac      60
aggacgtcaa gttcccgggc ggtggtcaga tcgttggcgg agtttacttg ttgccgcgca    120
ggggccctag gatgggtgtg cgcgcgactc ggaagacttc ggaacggtcg caaccccgtg    180
gacggcgtca gcctattccc aaggcgcgcc agcccacggg ccggtcctgg ggtcaacccg    240
ggtacccttg gcccctttac gccaatgagg gcctcgggtg ggcagggtgg ctgctctccc    300
ctcgaggctc tcggcctaat tggggcccca atgaccccg gcgaaaatcg cgtaatttgg     360
gtaaggtcat cgataccta acgtgcggat tcgccgatct catggggtat atcccgctcg    420
taggcggccc cattgggggc gtcgcaaggg ctctcgcaca cggtgtgagg gtccttgagg    480
acggggtaaa ctatgcaaca gggaatttac ccggttgctc tttctctatc tttattcttg    540
ctcttctctc gtgtctgacc gttccggcct ctgcagttcc ctaccgaaat gcctctggga    600
tttatcatgt taccaatgat tgcccaaact cttccatagt ctatgaggca gataacctga    660
tcctacacgc acctggttgc gtgccttgtg tcatgacagg taatgtgagt agatgctggg    720
tccaaattac ccctacactg tcagccccga gctcggagc agtcacggct cctcttcgga    780
gagccgttga ctacctagcg ggaggggctg ccctctgctc cgcgttatac gtaggagacg    840
```

```
cgtgtggggc actattcttg gtaggccaaa tgttcaccta taggcctcgc cagcacgcta    900
cggtgcagaa ctgcaactgt tccatttaca gtggccatgt taccggccac cggatggca    959
```

<210> SEQ ID NO 50
<211> LENGTH: 319
<212> TYPE: PRT
<213> ORGANISM: hepatitis C virus

<400> SEQUENCE: 50

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Met Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Pro Thr Gly Asn Leu Pro Gly Cys Ser Phe Ser Ile
                165                 170                 175

Phe Ile Leu Ala Leu Leu Ser Cys Leu Thr Val Pro Ala Ser Ala Val
            180                 185                 190

Pro Tyr Arg Asn Ala Ser Gly Ile Tyr His Val Thr Asn Asp Cys Pro
        195                 200                 205

Asn Ser Ser Ile Val Tyr Glu Ala Asp Asn Leu Ile Leu His Ala Pro
    210                 215                 220

Gly Cys Val Pro Cys Val Met Thr Gly Asn Val Ser Arg Cys Trp Val
225                 230                 235                 240

Gln Ile Thr Pro Thr Leu Ser Ala Pro Ser Leu Gly Ala Val Thr Ala
                245                 250                 255

Pro Leu Arg Arg Ala Val Asp Tyr Leu Ala Gly Gly Ala Ala Leu Cys
            260                 265                 270

Ser Ala Leu Tyr Val Gly Asp Ala Cys Gly Ala Leu Phe Leu Val Gly
        275                 280                 285

Gln Met Phe Thr Tyr Arg Pro Arg Gln His Ala Thr Val Gln Asn Cys
    290                 295                 300

Asn Cys Ser Ile Tyr Ser Gly His Val Thr Gly His Arg Met Ala
305                 310                 315
```

<210> SEQ ID NO 51
<211> LENGTH: 959
<212> TYPE: DNA
<213> ORGANISM: hepatitis C virus

<400> SEQUENCE: 51

-continued

```
ccatgagcac gaatcctaaa cctcaaagaa aaaccaaaag aaacaccaac cgtcgcccac      60
aggacgtcaa gttcccgggc ggtggtcaga tcgttggcgg agtttacttg ttgccgcgca     120
ggggccctag gatgggtgtg cgcgcgactc ggaagacttc ggaacggtcg caaccccgtg     180
gacggcgtca gcctattccc aaggcgcgcc agcccacggg ccggtcctgg ggtcaacccg     240
ggtacccttg gcccctttac gccaatgagg gcctcgggtg ggcagggtgg ctgctctccc     300
ctcgaggctc tcggcctaat tggggcccca atgaccccg gcgaaaatcg cgtaatttgg      360
gtaaggtcat cgataccta acgtgcggat tcgccgatct catggggtac atcccgctcg      420
taggcggccc cgttgggggc gtcgcaaggg ctctcgcaca cggtgtgagg gtccttgagg     480
acggggtaaa ctatccaaca gggaatttac ccggttgctc tttctctatc tttattcttg     540
ctcttctctc gtgtctgacc gttccggcct ctgcagttcc ctaccgaaat gcctctggga     600
tttatcatgt taccaatgat tgcccaaact cttccatagt ctatgaggca gataacctga     660
tcctacacgc acctggttgc gtgccttgtg tcatgacagg taatgtgagt agatgctggg     720
tccaaattac ccctacactg tcagccccga gcctcggagc agtcacggct cctcttcgga     780
gagccgttga ctacctagcg ggaggggctg ccctctgctc cgcgttatac gtaggagacg     840 cgtgtgggc actattcttg gtaggccaaa tgttcaccta taggcctcgc cagcacgcta     900
cggtgcagaa ctgcaactgt tccatttaca gtggccatgt taccggccac cggatggca     959
```

<210> SEQ ID NO 52
<211> LENGTH: 319
<212> TYPE: PRT
<213> ORGANISM: hepatitis C virus

<400> SEQUENCE: 52

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Met Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Pro Thr Gly Asn Leu Pro Gly Cys Ser Phe Ser Ile
                165                 170                 175

Phe Ile Leu Ala Leu Leu Ser Cys Leu Thr Val Pro Ala Ser Ala Val
            180                 185                 190

Pro Tyr Arg Asn Ala Ser Gly Ile Tyr His Val Thr Asn Asp Cys Pro
        195                 200                 205
```

Asn Ser Ser Ile Val Tyr Glu Ala Asp Asn Leu Ile Leu His Ala Pro
        210                 215                 220

Gly Cys Val Pro Cys Val Met Thr Gly Asn Val Ser Arg Cys Trp Val
225                 230                 235                 240

Gln Ile Thr Pro Thr Leu Ser Ala Pro Ser Leu Gly Ala Val Thr Ala
                    245                 250                 255

Pro Leu Arg Arg Ala Val Asp Tyr Leu Ala Gly Gly Ala Ala Leu Cys
            260                 265                 270

Ser Ala Leu Tyr Val Gly Asp Ala Cys Gly Ala Leu Phe Leu Val Gly
        275                 280                 285

Gln Met Phe Thr Tyr Arg Pro Arg Gln His Ala Thr Val Gln Asn Cys
290                 295                 300

Asn Cys Ser Ile Tyr Ser Gly His Val Thr Gly His Arg Met Ala
305                 310                 315

<210> SEQ ID NO 53
<211> LENGTH: 959
<212> TYPE: DNA
<213> ORGANISM: hepatitis C virus

<400> SEQUENCE: 53

| ccatgagcac | gaatcctaaa | cctcaaagaa | aaaccaaaag | aaacaccaac | cgtcgcccac | 60 |
| aggacgtcaa | gttcccgggc | ggtggtcaga | tcgttggcgg | agtttacttg | ttgccgcgca | 120 |
| ggggccctag | gatgggtgtg | cgcgcgactc | ggaagacttc | ggaacggtcg | caaccccgtg | 180 |
| gacggcgtca | gcctattccc | aaggcgcgcc | agcccacggg | ccggtcctgg | ggtcaacccg | 240 |
| ggtaccttg | gcccctttac | gccaatgagg | gcctcgggtg | ggcagggtgg | ctgctctccc | 300 |
| ctcgaggctc | tcggcctaat | tggggcccca | atgaccccg | gcgaaaatcg | cgtaatttgg | 360 |
| gtaaggtcat | cgatacccta | acgtgcggat | tcgccgatct | catggggtay | atcccgctcg | 420 |
| taggcggccc | crttggggc | gtcgcaaggg | ctctcgcaca | cggtgtgagg | gtccttgagg | 480 |
| acggggtaaa | ctatscaaca | gggaatttac | ccggttgctc | tttctctatc | tttattcttg | 540 |
| ctcttctctc | gtgtctgacc | gttccggcct | ctgcagttcc | ctaccgaaat | gcctctggga | 600 |
| tttatcatgt | taccaatgat | tgcccaaact | cttccatagt | ctatgaggca | gataacctga | 660 |
| tcctacacgc | acctggttgc | gtgccttgtg | tcatgacagg | taatgtgagt | agatgctggg | 720 |
| tccaaattac | ccctacactg | tcagccccga | gcctcggagc | agtcacggct | cctcttcgga | 780 |
| gagccgttga | ctacctagcg | ggaggggctg | ccctctgctc | cgcgttatac | gtaggagacg | 840 |
| cgtgtgggc | actattcttg | gtaggccaaa | tgttcaccta | taggcctcgc | cagcacgcta | 900 |
| cggtgcagaa | ctgcaactgt | tccatttaca | gtggccatgt | taccggccac | cggatggca | 959 |

<210> SEQ ID NO 54
<211> LENGTH: 319
<212> TYPE: PRT
<213> ORGANISM: hepatitis C virus

<400> SEQUENCE: 54

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Met Gly Val Arg Ala
        35                  40                  45

```
Thr Arg Lys Thr Ser Glu Arg Ser Gln Pro Arg Gly Arg Arg Gln Pro
 50                  55                  60
Ile Pro Lys Ala Arg Gln Pro Thr Gly Arg Ser Trp Gly Gln Pro Gly
 65                  70                  75                  80
Tyr Pro Trp Pro Leu Tyr Ala Asn Glu Gly Leu Gly Trp Ala Gly Trp
                 85                  90                  95
Leu Leu Ser Pro Arg Gly Ser Arg Pro Asn Trp Gly Pro Asn Asp Pro
                100                 105                 110
Arg Arg Lys Ser Arg Asn Leu Gly Lys Val Ile Asp Thr Leu Thr Cys
                115                 120                 125
Gly Phe Ala Asp Leu Met Gly Tyr Ile Pro Leu Val Gly Gly Pro Val
                130                 135                 140
Gly Gly Val Ala Arg Ala Leu Ala His Gly Val Arg Val Leu Glu Asp
145                 150                 155                 160
Gly Val Asn Tyr Pro Thr Gly Asn Leu Pro Gly Cys Ser Phe Ser Ile
                165                 170                 175
Phe Ile Leu Ala Leu Leu Ser Cys Leu Thr Val Pro Ala Ser Ala Val
                180                 185                 190
Pro Tyr Arg Asn Ala Ser Gly Ile Tyr His Val Thr Asn Asp Cys Pro
                195                 200                 205
Asn Ser Ser Ile Val Tyr Glu Ala Asp Asn Leu Ile Leu His Ala Pro
210                 215                 220
Gly Cys Val Pro Cys Val Met Thr Gly Asn Val Ser Arg Cys Trp Val
225                 230                 235                 240
Gln Ile Thr Pro Thr Leu Ser Ala Pro Ser Leu Gly Ala Val Thr Ala
                245                 250                 255
Pro Leu Arg Arg Ala Val Asp Tyr Leu Ala Gly Gly Ala Ala Leu Cys
                260                 265                 270
Ser Ala Leu Tyr Val Gly Asp Ala Cys Gly Ala Leu Phe Leu Val Gly
                275                 280                 285
Gln Met Phe Thr Tyr Arg Pro Arg Gln His Ala Thr Val Gln Asn Cys
290                 295                 300
Asn Cys Ser Ile Tyr Ser Gly His Val Thr Gly His Arg Met Ala
305                 310                 315
```

<210> SEQ ID NO 55
<211> LENGTH: 354
<212> TYPE: DNA
<213> ORGANISM: hepatitis C virus
<220> FEATURE:
<221> NAME/KEY: misc_feature
<222> LOCATION: (191)..(191)
<223> OTHER INFORMATION: "n" is any nucleotide

<400> SEQUENCE: 55

```
accaccggag cttctatcac atactccact tacggcaagt tccttgctga tggagggtgt      60
tcaggcggcg cgcatgacgt gatcatatgc gacgagtgcc attcccagga cgccaccacc    120
attcttggga taggcactgt ccttgaccag gcagagacgg ctggagctag gctcgtcgtc    180
ttggccacgg ncaccctcc cggcagtgtg acaacgcccc accccaacat cgaggaagtg    240
gccctgcctc aggaggggga ggttcccttc tacggcagag ccattcccct tgcttttata    300
aagggtggta ggcatctcat cttctgccat tccaagaaaa attgtgatga actc           354
```

<210> SEQ ID NO 56
<211> LENGTH: 118
<212> TYPE: PRT

```
<213> ORGANISM: hepatitis C virus
<220> FEATURE:
<221> NAME/KEY: MISC_FEATURE
<222> LOCATION: (64)..(64)
<223> OTHER INFORMATION: "Xaa" is any amino acid

<400> SEQUENCE: 56

Thr Thr Gly Ala Ser Ile Thr Tyr Ser Thr Tyr Gly Lys Phe Leu Ala
1               5                   10                  15

Asp Gly Gly Cys Ser Gly Gly Ala His Asp Val Ile Ile Cys Asp Glu
            20                  25                  30

Cys His Ser Gln Asp Ala Thr Thr Ile Leu Gly Ile Gly Thr Val Leu
        35                  40                  45

Asp Gln Ala Glu Thr Ala Gly Ala Arg Leu Val Val Leu Ala Thr Xaa
    50                  55                  60

Thr Pro Pro Gly Ser Val Thr Thr Pro His Pro Asn Ile Glu Glu Val
65              70                  75                  80

Ala Leu Pro Gln Glu Gly Glu Val Pro Phe Tyr Gly Arg Ala Ile Pro
            85                  90                  95

Leu Ala Phe Ile Lys Gly Gly Arg His Leu Ile Phe Cys His Ser Lys
            100                 105                 110

Lys Asn Cys Asp Glu Leu
        115

<210> SEQ ID NO 57
<211> LENGTH: 354
<212> TYPE: DNA
<213> ORGANISM: hepatitis C virus
<220> FEATURE:
<221> NAME/KEY: misc_feature
<222> LOCATION: (185)..(185)
<223> OTHER INFORMATION: "n" is any nucleotide
<220> FEATURE:
<221> NAME/KEY: misc_feature
<222> LOCATION: (191)..(191)
<223> OTHER INFORMATION: "n" is any nucleotide
<220> FEATURE:
<221> NAME/KEY: misc_feature
<222> LOCATION: (276)..(276)
<223> OTHER INFORMATION: "n" is any nucleotide

<400> SEQUENCE: 57
accaccggag cttctatcac atactccact tacggcaagt tccttgctga tgagggtgt      60 tcaggcggcg cgtatgacgt gatcatatgc gacgagtgcc attcccagga cgccaccacc   120
attcttggga taggcactgt ccttgaccag gcagagacgc tggagctag gctcgtcgtc    180 ttggncacgg ncacccctcc cggcagtgtg acaacgcccc accccaacat cgaggaagtg   240
gccctgcctc aggaggggga ggttcccttc tacggnagag ccattcccct tgcttttata   300
aagggtggta ggcatctcat cttctgccat tccaagaaaa aatgtgatga actt          354

<210> SEQ ID NO 58
<211> LENGTH: 133
<212> TYPE: PRT
<213> ORGANISM: hepatitis C virus
<220> FEATURE:
<221> NAME/KEY: MISC_FEATURE
<222> LOCATION: (62)..(62)
<223> OTHER INFORMATION: "Xaa" is any amino acid
<220> FEATURE:
<221> NAME/KEY: MISC_FEATURE
<222> LOCATION: (64)..(64)
<223> OTHER INFORMATION: "Xaa" is any amino acid
<220> FEATURE:
<221> NAME/KEY: MISC_FEATURE
```

```
<222> LOCATION: (92)..(92)
<223> OTHER INFORMATION: "Xaa" is any amino acid

<400> SEQUENCE: 58
```

Thr Thr Gly Ala Ser Ile Thr Tyr Ser Thr Tyr Gly Lys Phe Leu Ala
1               5                   10                  15

Asp Gly Gly Cys Ser Gly Gly Ala Tyr Asp Val Ile Ile Cys Asp Glu
            20                  25                  30

Cys His Ser Gln Asp Ala Thr Thr Ile Leu Gly Ile Gly Thr Val Leu
        35                  40                  45

Asp Gln Ala Glu Thr Ala Gly Ala Arg Leu Val Val Leu Xaa Thr Xaa
    50                  55                  60

Thr Pro Pro Gly Ser Val Thr Thr Pro His Pro Asn Ile Glu Glu Val
65                  70                  75                  80

Ala Leu Pro Gln Glu Gly Glu Val Pro Phe Tyr Xaa Arg Ala Ile Pro
                85                  90                  95

Leu Ala Phe Ile Lys Gly Gly Arg His Leu Ile Phe Cys His Ser Lys
            100                 105                 110

Lys Lys Cys Asp Glu Leu Arg Gln Ala Thr Asp Gln Pro Gly Arg Glu
        115                 120                 125

Arg Pro Trp Glu Tyr
    130

```
<210> SEQ ID NO 59
<211> LENGTH: 357
<212> TYPE: DNA
<213> ORGANISM: hepatitis C virus
<220> FEATURE:
<221> NAME/KEY: misc_feature
<222> LOCATION: (38)..(38)
<223> OTHER INFORMATION: "n" is any nucleotide
<220> FEATURE:
<221> NAME/KEY: misc_feature
<222> LOCATION: (76)..(76)
<223> OTHER INFORMATION: "n" is any nucleotide
<220> FEATURE:
<221> NAME/KEY: misc_feature
<222> LOCATION: (79)..(79)
<223> OTHER INFORMATION: "n" is any nucleotide
<220> FEATURE:
<221> NAME/KEY: misc_feature
<222> LOCATION: (151)..(151)
<223> OTHER INFORMATION: "n" is any nucleotide
<220> FEATURE:
<221> NAME/KEY: misc_feature
<222> LOCATION: (232)..(232)
<223> OTHER INFORMATION: "n" is any nucleotide
<220> FEATURE:
<221> NAME/KEY: misc_feature
<222> LOCATION: (349)..(349)
<223> OTHER INFORMATION: "n" is any nucleotide

<400> SEQUENCE: 59
atggctttca tgtctccgga cttggaggtc attaccanca cttgggttct ggtgggggc    60 gttgtggcga ccctgncgnc ctactgcttg acggtgggtt cggtagccat agtcggtagg   120
atcatcctct ctgggaaacc tgccatcatt nccgataggg aggtattata ccagcaattt   180
gatgagatgg aggagtgctc ggcctcgttg ccctatatgg acgaaacacg tnccattgcc   240
ggacaattca agagaaagt gctcggcttc atcagcacga ccggccagaa ggctgaaact   300
ctgaagccgg cagccacgtc tgtgtggaac aaggctgatc agttctggnc cacatac      357

<210> SEQ ID NO 60
<211> LENGTH: 128
```

```
<212> TYPE: PRT
<213> ORGANISM: hepatitis C virus
<220> FEATURE:
<221> NAME/KEY: MISC_FEATURE
<222> LOCATION: (13)..(13)
<223> OTHER INFORMATION: "Xaa" is any amino acid
<220> FEATURE:
<221> NAME/KEY: MISC_FEATURE
<222> LOCATION: (26)..(27)
<223> OTHER INFORMATION: "Xaa" is any amino acid
<220> FEATURE:
<221> NAME/KEY: MISC_FEATURE
<222> LOCATION: (51)..(51)
<223> OTHER INFORMATION: "Xaa" is any amino acid
<220> FEATURE:
<221> NAME/KEY: MISC_FEATURE
<222> LOCATION: (78)..(78)
<223> OTHER INFORMATION: "Xaa" is any amino acid
<220> FEATURE:
<221> NAME/KEY: MISC_FEATURE
<222> LOCATION: (117)..(117)
<223> OTHER INFORMATION: "Xaa" is any amino acid

<400> SEQUENCE: 60

Met Ala Phe Met Ser Pro Asp Leu Glu Val Ile Thr Xaa Thr Trp Val
1               5                   10                  15

Leu Val Gly Gly Val Val Ala Thr Leu Xaa Xaa Tyr Cys Leu Thr Val
            20                  25                  30

Gly Ser Val Ala Ile Val Gly Arg Ile Ile Leu Ser Gly Lys Pro Ala
        35                  40                  45

Ile Ile Xaa Asp Arg Glu Val Leu Tyr Gln Gln Phe Asp Glu Met Glu
    50                  55                  60

Glu Cys Ser Ala Ser Leu Pro Tyr Met Asp Glu Thr Arg Xaa Ile Ala
65                  70                  75                  80

Gly Gln Phe Lys Glu Lys Val Leu Gly Phe Ile Ser Thr Thr Gly Gln
                85                  90                  95

Lys Ala Glu Thr Leu Lys Pro Ala Ala Thr Ser Val Trp Asn Lys Ala
            100                 105                 110

Asp Gln Phe Trp Xaa Thr Tyr Met Trp Asn Phe Ile Ser Gly Ile Gln
        115                 120                 125

<210> SEQ ID NO 61
<211> LENGTH: 357
<212> TYPE: DNA
<213> ORGANISM: hepatitis C virus
<220> FEATURE:
<221> NAME/KEY: misc_feature
<222> LOCATION: (38)..(38)
<223> OTHER INFORMATION: "n" is any nucleotide
<220> FEATURE:
<221> NAME/KEY: misc_feature
<222> LOCATION: (70)..(70)
<223> OTHER INFORMATION: "n" is any nucleotide
<220> FEATURE:
<221> NAME/KEY: misc_feature
<222> LOCATION: (174)..(174)
<223> OTHER INFORMATION: "n" is any nucleotide
<220> FEATURE:
<221> NAME/KEY: misc_feature
<222> LOCATION: (339)..(339)
<223> OTHER INFORMATION: "n" is any nucleotide

<400> SEQUENCE: 61
atggcttgca tgtctgcgga cctggaggtc attaccanca cttgggttct ggtgggggc      60 gttgtggcgn ccctggcggc ctactgcttg acggtgggtt cggtagccat agtcggtagg    120
atcatcctct ctgggaaacc tgccatcatt cccgataggg aggcattata ccancaattt    180
```

```
gatgagatgg aggagtgctc ggcctcgttg ccctatatgg acgagacacg tgccattgcc      240
ggacaattca aagagaaagt gctcggcttc atcagcacga ccggccagaa ggctgaaact      300
ctgaagccgg cagccacgtc tgtgtggaac aaggctganc agttctgggc cacatac        357
```

<210> SEQ ID NO 62
<211> LENGTH: 128
<212> TYPE: PRT
<213> ORGANISM: hepatitis C virus
<220> FEATURE:
<221> NAME/KEY: MISC_FEATURE
<222> LOCATION: (13)..(13)
<223> OTHER INFORMATION: "Xaa" is any amino acid
<220> FEATURE:
<221> NAME/KEY: MISC_FEATURE
<222> LOCATION: (24)..(24)
<223> OTHER INFORMATION: "Xaa" is any amino acid
<220> FEATURE:
<221> NAME/KEY: MISC_FEATURE
<222> LOCATION: (58)..(58)
<223> OTHER INFORMATION: "Xaa" is any amino acid
<220> FEATURE:
<221> NAME/KEY: MISC_FEATURE
<222> LOCATION: (113)..(113)
<223> OTHER INFORMATION: "Xaa" is any amino acid

<400> SEQUENCE: 62

```
Met Ala Cys Met Ser Ala Asp Leu Glu Val Ile Thr Xaa Thr Trp Val
1               5                   10                  15

Leu Val Gly Gly Val Val Ala Xaa Leu Ala Ala Tyr Cys Leu Thr Val
            20                  25                  30

Gly Ser Val Ala Ile Val Gly Arg Ile Ile Leu Ser Gly Lys Pro Ala
        35                  40                  45

Ile Ile Pro Asp Arg Glu Ala Leu Tyr Xaa Gln Phe Asp Glu Met Glu
    50                  55                  60

Glu Cys Ser Ala Ser Leu Pro Tyr Met Asp Glu Thr Arg Ala Ile Ala
65                  70                  75                  80

Gly Gln Phe Lys Glu Lys Val Leu Gly Phe Ile Ser Thr Thr Gly Gln
                85                  90                  95

Lys Ala Glu Thr Leu Lys Pro Ala Ala Thr Ser Val Trp Asn Lys Ala
            100                 105                 110

Xaa Gln Phe Trp Ala Thr Tyr Met Trp Asn Phe Ile Ser Gly Ile Gln
        115                 120                 125
```

<210> SEQ ID NO 63
<211> LENGTH: 28
<212> TYPE: DNA
<213> ORGANISM: artificial
<220> FEATURE:
<221> NAME/KEY: misc_feature
<223> OTHER INFORMATION: HCPr161

<400> SEQUENCE: 63

```
accggaggcc aggagagtga tctcctcc                                        28
```

<210> SEQ ID NO 64
<211> LENGTH: 28
<212> TYPE: DNA
<213> ORGANISM: artificial
<220> FEATURE:
<221> NAME/KEY: misc_feature
<223> OTHER INFORMATION: HCPr162

<400> SEQUENCE: 64

```
gggctgctct atcctcatcg acgccatc                                        28
```

<210> SEQ ID NO 65
<211> LENGTH: 28
<212> TYPE: DNA
<213> ORGANISM: artificial
<220> FEATURE:
<221> NAME/KEY: misc_feature
<223> OTHER INFORMATION: HCPr163

<400> SEQUENCE: 65
gccagaggct cggaaggcga tcagcgct                    28

<210> SEQ ID NO 66
<211> LENGTH: 28
<212> TYPE: DNA
<213> ORGANISM: artificial
<220> FEATURE:
<221> NAME/KEY: misc_feature
<223> OTHER INFORMATION: HCPr164

<400> SEQUENCE: 66
gagctgctct gtcctcctcg acgccgca                    28

<210> SEQ ID NO 67
<211> LENGTH: 20
<212> TYPE: DNA
<213> ORGANISM: artificial
<220> FEATURE:
<221> NAME/KEY: misc_feature
<223> OTHER INFORMATION: HCPr23

<400> SEQUENCE: 67
ctcatggggt acattccgct                             20

<210> SEQ ID NO 68
<211> LENGTH: 27
<212> TYPE: DNA
<213> ORGANISM: artificial
<220> FEATURE:
<221> NAME/KEY: misc_feature
<223> OTHER INFORMATION: HCPr54

<400> SEQUENCE: 68
ctattaccag ttcatcatca tatccca                     27

<210> SEQ ID NO 69
<211> LENGTH: 24
<212> TYPE: DNA
<213> ORGANISM: artificial
<220> FEATURE:
<221> NAME/KEY: misc_feature
<223> OTHER INFORMATION: HCPr116

<400> SEQUENCE: 69
ttttaaatac atcatgrctg yatg                        24

<210> SEQ ID NO 70
<211> LENGTH: 33
<212> TYPE: DNA
<213> ORGANISM: artificial
<220> FEATURE:
<221> NAME/KEY: misc_feature
<223> OTHER INFORMATION: HCPr66

<400> SEQUENCE: 70
ctattattgt atcccrctga tgaarttcca cat               33

```
<210> SEQ ID NO 71
<211> LENGTH: 36
<212> TYPE: DNA
<213> ORGANISM: artificial
<220> FEATURE:
<221> NAME/KEY: misc_feature
<223> OTHER INFORMATION: HCPr118

<400> SEQUENCE: 71
actagtcgac taytgatccr ctatrwartt ccacat                             36

<210> SEQ ID NO 72
<211> LENGTH: 25
<212> TYPE: DNA
<213> ORGANISM: artificial
<220> FEATURE:
<221> NAME/KEY: misc_feature
<223> OTHER INFORMATION: HCPr117

<400> SEQUENCE: 72
ttttaaatac atcgcrctgc atgca                                         25

<210> SEQ ID NO 73
<211> LENGTH: 36
<212> TYPE: DNA
<213> ORGANISM: artificial
<220> FEATURE:
<221> NAME/KEY: misc_feature
<223> OTHER INFORMATION: HCPr119

<400> SEQUENCE: 73
actagtcgac tarttgcata gcckrttcat ccaytg                             36

<210> SEQ ID NO 74
<211> LENGTH: 34
<212> TYPE: DNA
<213> ORGANISM: artificial
<220> FEATURE:
<221> NAME/KEY: misc_feature
<223> OTHER INFORMATION: HCPr131

<400> SEQUENCE: 74
ggaattctag acctctggga ygaraytgga artg                               34

<210> SEQ ID NO 75
<211> LENGTH: 31
<212> TYPE: DNA
<213> ORGANISM: artificial
<220> FEATURE:
<221> NAME/KEY: misc_feature
<223> OTHER INFORMATION: HCPr130

<400> SEQUENCE: 75
ggaattctag acgctaycar gcacgttgyg c                                  31

<210> SEQ ID NO 76
<211> LENGTH: 23
<212> TYPE: DNA
<213> ORGANISM: artificial
<220> FEATURE:
<221> NAME/KEY: misc_feature
<223> OTHER INFORMATION: HCPr134

<400> SEQUENCE: 76
catatagatg cccacttcct atc                                           23
```

```
<210> SEQ ID NO 77
<211> LENGTH: 16
<212> TYPE: DNA
<213> ORGANISM: artificial
<220> FEATURE:
<221> NAME/KEY: misc_feature
<223> OTHER INFORMATION: HCPr3

<400> SEQUENCE: 77
gtgtgccagg accatc                                                       16

<210> SEQ ID NO 78
<211> LENGTH: 20
<212> TYPE: DNA
<213> ORGANISM: artificial
<220> FEATURE:
<221> NAME/KEY: misc_feature
<223> OTHER INFORMATION: HCPr4

<400> SEQUENCE: 78
gacatgcatg tcatgatgta                                                   20

<210> SEQ ID NO 79
<211> LENGTH: 29
<212> TYPE: DNA
<213> ORGANISM: artificial
<220> FEATURE:
<221> NAME/KEY: misc_feature
<223> OTHER INFORMATION: HCPr152

<400> SEQUENCE: 79
tacgcctctt ctatatcggt tggggcctg                                         29

<210> SEQ ID NO 80
<211> LENGTH: 26
<212> TYPE: DNA
<213> ORGANISM: artificial
<220> FEATURE:
<221> NAME/KEY: misc_feature
<223> OTHER INFORMATION: HCPr52

<400> SEQUENCE: 80
atgttgggta aggtcatcga taccct                                            26

<210> SEQ ID NO 81
<211> LENGTH: 25
<212> TYPE: DNA
<213> ORGANISM: artificial
<220> FEATURE:
<221> NAME/KEY: misc_feature
<223> OTHER INFORMATION: HCPr41

<400> SEQUENCE: 81
cccgggaggt ctcgtagacc gtgca                                             25

<210> SEQ ID NO 82
<211> LENGTH: 29
<212> TYPE: DNA
<213> ORGANISM: artificial
<220> FEATURE:
<221> NAME/KEY: misc_feature
<223> OTHER INFORMATION: HCPr40

<400> SEQUENCE: 82
ctattaaaga tagagaaaga gcaaccggg                                         29

<210> SEQ ID NO 83
```

```
<211> LENGTH: 12
<212> TYPE: PRT
<213> ORGANISM: hepatitis C virus

<400> SEQUENCE: 83

Leu Glu Trp Arg Asn Thr Ser Gly Leu Tyr Val Leu
1               5                   10

<210> SEQ ID NO 84
<211> LENGTH: 12
<212> TYPE: PRT
<213> ORGANISM: hepatitis C virus

<400> SEQUENCE: 84

Val Pro Tyr Arg Asn Ala Ser Gly Ile Tyr His Val
1               5                   10

<210> SEQ ID NO 85
<211> LENGTH: 11
<212> TYPE: PRT
<213> ORGANISM: hepatitis C virus

<400> SEQUENCE: 85

Val Tyr Glu Ala Asp Asp Val Ile Leu His Thr
1               5                   10

<210> SEQ ID NO 86
<211> LENGTH: 11
<212> TYPE: PRT
<213> ORGANISM: hepatitis C virus

<400> SEQUENCE: 86

Val Tyr Glu Ala Asp Asn Leu Ile Leu His Ala
1               5                   10

<210> SEQ ID NO 87
<211> LENGTH: 13
<212> TYPE: PRT
<213> ORGANISM: hepatitis C virus

<400> SEQUENCE: 87

Val Gln Asp Gly Asn Thr Ser Thr Cys Trp Thr Pro Val
1               5                   10

<210> SEQ ID NO 88
<211> LENGTH: 13
<212> TYPE: PRT
<213> ORGANISM: hepatitis C virus

<400> SEQUENCE: 88

Val Met Thr Gly Asn Val Ser Arg Cys Trp Val Gln Ile
1               5                   10

<210> SEQ ID NO 89
<211> LENGTH: 10
<212> TYPE: PRT
<213> ORGANISM: hepatitis C virus

<400> SEQUENCE: 89

Val Arg Tyr Val Gly Ala Thr Thr Ala Ser
1               5                   10

<210> SEQ ID NO 90
<211> LENGTH: 10
<212> TYPE: PRT
```

```
<213> ORGANISM: hepatitis C virus

<400> SEQUENCE: 90

Ala Pro Ser Leu Gly Ala Val Thr Ala Pro
1               5                   10

<210> SEQ ID NO 91
<211> LENGTH: 10
<212> TYPE: PRT
<213> ORGANISM: hepatitis C virus

<400> SEQUENCE: 91

Arg Pro Arg Arg His Gln Thr Val Gln Thr
1               5                   10

<210> SEQ ID NO 92
<211> LENGTH: 10
<212> TYPE: PRT
<213> ORGANISM: hepatitis C virus

<400> SEQUENCE: 92

Arg Pro Arg Gln His Ala Thr Val Gln Asn
1               5                   10

<210> SEQ ID NO 93
<211> LENGTH: 9
<212> TYPE: PRT
<213> ORGANISM: hepatitis C virus

<400> SEQUENCE: 93

Gln Pro Thr Gly Arg Ser Trp Gly Gln
1               5

<210> SEQ ID NO 94
<211> LENGTH: 8
<212> TYPE: PRT
<213> ORGANISM: hepatitis C virus

<400> SEQUENCE: 94

Val Gln Asp Gly Asn Thr Ser Thr
1               5

<210> SEQ ID NO 95
<211> LENGTH: 8
<212> TYPE: PRT
<213> ORGANISM: hepatitis C virus

<400> SEQUENCE: 95

Val Gln Asp Gly Asn Thr Ser Ala
1               5

<210> SEQ ID NO 96
<211> LENGTH: 10
<212> TYPE: PRT
<213> ORGANISM: hepatitis C virus

<400> SEQUENCE: 96

Val Lys Tyr Val Gly Ala Thr Thr Ala Ser
1               5                   10

<210> SEQ ID NO 97
<211> LENGTH: 20
<212> TYPE: PRT
<213> ORGANISM: hepatitis C virus
```

-continued

```
<400> SEQUENCE: 97

Leu Gly Gly Lys Pro Ala Ile Val Pro Asp Lys Glu Val Leu Tyr Gln
1               5                   10                  15

Gln Tyr Asp Glu
            20

<210> SEQ ID NO 98
<211> LENGTH: 20
<212> TYPE: PRT
<213> ORGANISM: hepatitis C virus

<400> SEQUENCE: 98

Leu Gly Gly Lys Pro Ala Leu Val Pro Asp Lys Glu Val Leu Tyr Gln
1               5                   10                  15

Gln Tyr Asp Glu
            20

<210> SEQ ID NO 99
<211> LENGTH: 20
<212> TYPE: PRT
<213> ORGANISM: hepatitis C virus

<400> SEQUENCE: 99

Ser Gln Ala Ala Pro Tyr Ile Glu Gln Ala Gln Val Ile Ala His Gln
1               5                   10                  15

Phe Lys Glu Lys
            20

<210> SEQ ID NO 100
<211> LENGTH: 20
<212> TYPE: PRT
<213> ORGANISM: hepatitis C virus

<400> SEQUENCE: 100

Ile Ala His Gln Phe Lys Glu Lys Val Leu Gly Leu Leu Gln Arg Ala
1               5                   10                  15

Thr Gln Gln Gln
            20

<210> SEQ ID NO 101
<211> LENGTH: 20
<212> TYPE: PRT
<213> ORGANISM: hepatitis C virus

<400> SEQUENCE: 101

Ile Ala His Gln Phe Lys Glu Lys Ile Leu Gly Leu Leu Gln Arg Ala
1               5                   10                  15

Thr Gln Gln Gln
            20

<210> SEQ ID NO 102
<211> LENGTH: 20
<212> TYPE: PRT
<213> ORGANISM: hepatitis C virus

<400> SEQUENCE: 102

Leu Ser Gly Lys Pro Ala Ile Ile Pro Asp Arg Glu Ala Leu Tyr Gln
1               5                   10                  15

Gln Phe Asp Glu
            20
```

<210> SEQ ID NO 103
<211> LENGTH: 20
<212> TYPE: PRT
<213> ORGANISM: hepatitis C virus

<400> SEQUENCE: 103

Leu Ser Gly Lys Pro Ala Ile Ile Pro Asp Arg Glu Val Leu Tyr Gln
1               5                   10                  15

Gln Phe Asp Glu
            20

<210> SEQ ID NO 104
<211> LENGTH: 20
<212> TYPE: PRT
<213> ORGANISM: hepatitis C virus

<400> SEQUENCE: 104

Ser Ala Ser Leu Pro Tyr Met Asp Glu Thr Arg Ala Ile Ala Gly Gln
1               5                   10                  15

Phe Lys Glu Lys
            20

<210> SEQ ID NO 105
<211> LENGTH: 20
<212> TYPE: PRT
<213> ORGANISM: hepatitis C virus

<400> SEQUENCE: 105

Ile Ala Gly Gln Phe Lys Glu Lys Val Leu Gly Phe Ile Ser Thr Thr
1               5                   10                  15

Gly Gln Lys Ala
            20

<210> SEQ ID NO 106
<211> LENGTH: 340
<212> TYPE: DNA
<213> ORGANISM: hepatitis C virus

<400> SEQUENCE: 106
ctccactgta accgaaaagg acatcagggt cgaggaggag gtctatcagt gttgtgacct      60
ggagcccgaa gcccgcaagg caattaccgc cctaacagag agactctacg tgggcggtcc     120
catgcataac agcaagggag acctgtgcgg gtatcgcaga tgtcgcgcaa gcggcgtcta     180
caccaccagc ttcgggaaca cactgacgtg ctacctcaaa gcctcagccg ctatcaaagc     240
ggcgggctg agagactgca ccatgttggt ctgtggtgat gacctggttg tcatcgctga      300
gagcgatggc gtagaggagg acaaacgacc cctcggagcc                           340

<210> SEQ ID NO 107
<211> LENGTH: 113
<212> TYPE: PRT
<213> ORGANISM: hepatitis C virus

<400> SEQUENCE: 107

Ser Thr Val Thr Glu Lys Asp Ile Arg Val Glu Glu Val Tyr Gln
1               5                   10                  15

Cys Cys Asp Leu Glu Pro Glu Ala Arg Lys Ala Ile Thr Ala Leu Thr
                20                  25                  30

Glu Arg Leu Tyr Val Gly Gly Pro Met His Asn Ser Lys Gly Asp Leu
            35                  40                  45

Cys Gly Tyr Arg Arg Cys Arg Ala Ser Gly Val Tyr Thr Thr Ser Phe

```
                    50                  55                  60
Gly Asn Thr Leu Thr Cys Tyr Leu Lys Ala Ser Ala Ala Ile Lys Ala
65                  70                  75                  80

Ala Gly Leu Arg Asp Cys Thr Met Leu Val Cys Gly Asp Asp Leu Val
                85                  90                  95

Val Ile Ala Glu Ser Asp Gly Val Glu Glu Asp Lys Arg Pro Leu Gly
            100                 105                 110

Ala

<210> SEQ ID NO 108
<211> LENGTH: 340
<212> TYPE: DNA
<213> ORGANISM: hepatitis C virus

<400> SEQUENCE: 108
ctccactgta accgaaaagg acatcagggt cgaggaggag gtatatcagt gttgtgacct      60
ggagcccgag gcccgcagag caattaccgc cctaacagag agactctacg tgggcggtcc     120
catgcataac agcaggggag acctgtgcgg gtatcgcaga tgccgtgcga gcggcgtcta     180
caccaccagc ttcgggaaca cactgacgtg ctatctcaaa gcctcagccg ctatcagagc     240
ggcggggctg agagactgca ccatgttggt ctgtggtgat gacctggtcg tcattgctga     300
aagcgatggc gtagaggagg acaaacgagc cctcggagcc                           340

<210> SEQ ID NO 109
<211> LENGTH: 113
<212> TYPE: PRT
<213> ORGANISM: hepatitis C virus

<400> SEQUENCE: 109

Ser Thr Val Thr Glu Lys Asp Ile Arg Val Glu Glu Val Tyr Gln
1               5                   10                  15

Cys Cys Asp Leu Glu Pro Glu Ala Arg Arg Ala Ile Thr Ala Leu Thr
                20                  25                  30

Glu Arg Leu Tyr Val Gly Gly Pro Met His Asn Ser Arg Gly Asp Leu
            35                  40                  45

Cys Gly Tyr Arg Arg Cys Arg Ala Ser Gly Val Tyr Thr Thr Ser Phe
        50                  55                  60

Gly Asn Thr Leu Thr Cys Tyr Leu Lys Ala Ser Ala Ala Ile Arg Ala
65                  70                  75                  80

Ala Gly Leu Arg Asp Cys Thr Met Leu Val Cys Gly Asp Asp Leu Val
                85                  90                  95

Val Ile Ala Glu Ser Asp Gly Val Glu Glu Asp Lys Arg Ala Leu Gly
            100                 105                 110

Ala

<210> SEQ ID NO 110
<211> LENGTH: 340
<212> TYPE: DNA
<213> ORGANISM: hepatitis C virus

<400> SEQUENCE: 110
ctccactgta accgaaaaag acatcagggt cgaggaggag gtatatcagt gttgtgacct      60
ggagcccgaa gcccgcaagg taattaccgc cctaacagag agactctatg tgggcggtcc     120
catgcataat agcaaggag acctgtgcgg gtatcgcaga tgccgcgcaa gcggcgtcta      180
caccaccagc ttcgggaaca cactgacgtg ctatctcaaa gcctcagccg ccatcagggc     240
```

```
gtcagggctg agagactgca ctatgctggt ctatggtgac gacctggtcg tcattgccga      300
gagcgatggc gtagaggagg acaaacgagc cctcggagtc                            340
```

<210> SEQ ID NO 111
<211> LENGTH: 113
<212> TYPE: PRT
<213> ORGANISM: hepatitis C virus

<400> SEQUENCE: 111

```
Ser Thr Val Thr Glu Lys Asp Ile Arg Val Glu Glu Val Tyr Gln
1               5                   10                  15

Cys Cys Asp Leu Glu Pro Glu Ala Arg Lys Val Ile Thr Ala Leu Thr
                20                  25                  30

Glu Arg Leu Tyr Val Gly Gly Pro Met His Asn Ser Lys Gly Asp Leu
            35                  40                  45

Cys Gly Tyr Arg Arg Cys Arg Ala Ser Gly Val Tyr Thr Thr Ser Phe
    50                  55                  60

Gly Asn Thr Leu Thr Cys Tyr Leu Lys Ala Ser Ala Ala Ile Arg Ala
65                  70                  75                  80

Ser Gly Leu Arg Asp Cys Thr Met Leu Val Tyr Gly Asp Asp Leu Val
                85                  90                  95

Val Ile Ala Glu Ser Asp Gly Val Glu Glu Asp Lys Arg Ala Leu Gly
            100                 105                 110

Val
```

<210> SEQ ID NO 112
<211> LENGTH: 340
<212> TYPE: DNA
<213> ORGANISM: hepatitis C virus

<400> SEQUENCE: 112

```
ctccactgta accgaaaagg acatcagggt cgaggaggag gtgtatcagt gttgtgacct       60
ggagcccgag gcccgcaagg caattactgc cctaacagag agactctatg tgggcggtcc     120
catgcataac agcaagggag acctgtgtgg gtatcgcaga tgccgcgcaa gcggcgtcta     180
caccaccagc ttcgggaaca cactgacgtg ctacctcaaa gcctcagccg ctatcagagc     240
ggcggggctg agagactgca ccatgttggt ctgtggtgat gacctggtcg tcatcgctga     300
gagcgatggc gttgaggagg acaaacgagc cctcggagcc                           340
```

<210> SEQ ID NO 113
<211> LENGTH: 113
<212> TYPE: PRT
<213> ORGANISM: hepatitis C virus

<400> SEQUENCE: 113

```
Ser Thr Val Thr Glu Lys Asp Ile Arg Val Glu Glu Val Tyr Gln
1               5                   10                  15

Cys Cys Asp Leu Glu Pro Glu Ala Arg Lys Ala Ile Thr Ala Leu Thr
                20                  25                  30

Glu Arg Leu Tyr Val Gly Gly Pro Met His Asn Ser Lys Gly Asp Leu
            35                  40                  45

Cys Gly Tyr Arg Arg Cys Arg Ala Ser Gly Val Tyr Thr Thr Ser Phe
    50                  55                  60

Gly Asn Thr Leu Thr Cys Tyr Leu Lys Ala Ser Ala Ala Ile Arg Ala
65                  70                  75                  80
```

```
Ala Gly Leu Arg Asp Cys Thr Met Leu Val Cys Gly Asp Asp Leu Val
                85                  90                  95

Val Ile Ala Glu Ser Asp Gly Val Glu Glu Asp Lys Arg Ala Leu Gly
            100                 105                 110

Ala
```

<210> SEQ ID NO 114
<211> LENGTH: 340
<212> TYPE: DNA
<213> ORGANISM: hepatitis C virus

<400> SEQUENCE: 114

```
ctccacggtg accgaaaggg atatcaggac cgaggaagag atctaccagt gctgcgacct    60
ggagcccgaa gcccgcaagg tgatatccgc cctaacggaa agactctacg tgggcggtcc   120
catgtacaac tccaagggg acctatgcgg gcaacggagg tgccgcgcaa gcgggg tcta   180
caccaccagc ttcgggaaca ctgtaacgtg ttatctcaag gccgttgcgg ctactagggc   240
cgcaggtctg aaaggttgca gcatgctggt tgtggagac gacttagtcg tcatctgcga   300
gagcggcggc gtagaggagg atgcaagagc cctccgagcc                         340
```

<210> SEQ ID NO 115
<211> LENGTH: 113
<212> TYPE: PRT
<213> ORGANISM: hepatitis C virus

<400> SEQUENCE: 115

```
Ser Thr Val Thr Glu Arg Asp Ile Arg Thr Glu Glu Ile Tyr Gln
1               5                   10                  15

Cys Cys Asp Leu Glu Pro Glu Ala Arg Lys Val Ile Ser Ala Leu Thr
            20                  25                  30

Glu Arg Leu Tyr Val Gly Gly Pro Met Tyr Asn Ser Lys Gly Asp Leu
            35                  40                  45

Cys Gly Gln Arg Arg Cys Arg Ala Ser Gly Val Tyr Thr Thr Ser Phe
    50                  55                  60

Gly Asn Thr Val Thr Cys Tyr Leu Lys Ala Val Ala Ala Thr Arg Ala
65                  70                  75                  80

Ala Gly Leu Lys Gly Cys Ser Met Leu Val Cys Gly Asp Asp Leu Val
                85                  90                  95

Val Ile Cys Glu Ser Gly Gly Val Glu Glu Asp Ala Arg Ala Leu Arg
            100                 105                 110

Ala
```

<210> SEQ ID NO 116
<211> LENGTH: 340
<212> TYPE: DNA
<213> ORGANISM: hepatitis C virus

<400> SEQUENCE: 116

```
ctccactgtg actgagagag acatcaaggt cgaagaagaa gtctatcagt gttgtgatct    60
ggagcccgag gcccgcaagg taatagccgc cctcacggag agactctacg tgggcggccc   120
catgcataac agcaagggag acctttgcgg gtatcgtaga tgccgcgcga gcggcgtata   180
caccaccagc ttcgggaaca caatgacgtg ctaccttaag gcctcagcag ccatcagggc   240
tgcggggcta aaggattgca ccatgctggt ttgcggtgac gacctagtcg tgatcgccga   300
gagcggtggc gttgaggagg acaaacgagc cctcggagct                         340
```

<210> SEQ ID NO 117
<211> LENGTH: 113
<212> TYPE: PRT
<213> ORGANISM: hepatitis C virus

<400> SEQUENCE: 117

Ser Thr Val Thr Glu Arg Asp Ile Lys Val Glu Glu Val Tyr Gln
1               5                   10                  15

Cys Cys Asp Leu Glu Pro Glu Ala Arg Lys Val Ile Ala Ala Leu Thr
                20                  25                  30

Glu Arg Leu Tyr Val Gly Gly Pro Met His Asn Ser Lys Gly Asp Leu
            35                  40                  45

Cys Gly Tyr Arg Arg Cys Arg Ala Ser Gly Val Tyr Thr Thr Ser Phe
        50                  55                  60

Gly Asn Thr Met Thr Cys Tyr Leu Lys Ala Ser Ala Ala Ile Arg Ala
65                  70                  75                  80

Ala Gly Leu Lys Asp Cys Thr Met Leu Val Cys Gly Asp Asp Leu Val
                85                  90                  95

Val Ile Ala Glu Ser Gly Gly Val Glu Glu Asp Lys Arg Ala Leu Gly
            100                 105                 110

Ala

<210> SEQ ID NO 118
<211> LENGTH: 574
<212> TYPE: DNA
<213> ORGANISM: hepatitis C virus

<400> SEQUENCE: 118
acttgcggct tgccgacct catgggatac atcccgctcg taggcgcccc tgtgggtggc      60
gtcgccaggg ccctggcaca cggtgttagg gctgtggagg acgggatcaa ttatgcgaca     120
gggaatcttc ccggttgctc tttctctatc ttcctcttgg cacttctttc gtgcctgact    180
gttcccacct cggccgtcaa ctatcgcaat gcctcgggca tctatcacat caccaatgac    240
tgcccgaact cgagcatagt gtacgagacc gagcaccaca tcctacacct cccagggtgt    300
ttaccctgcg tgagggttgg gaatcagtca cgctgctggg tggccctcac tcccaccgtg    360
gcggcgcctt acatcggcgc tccgcttgaa tccctccgga gtcatgtgga tctgatggta    420
ggtgccgcta ctgcgtgctc cgctctttac atcggagacc tgtgcggtgg cgtattcttg    480
gttggtcaga tgttctcttt ccagccgcgg cgccactgga ctacgcagga ctgcaattgt    540
tccatctacg cggggcacgt tacgggccac agga                                  574

<210> SEQ ID NO 119
<211> LENGTH: 191
<212> TYPE: PRT
<213> ORGANISM: hepatitis C virus

<400> SEQUENCE: 119

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Thr Ser
        50                  55                  60

```
Ala Val Asn Tyr Arg Asn Ala Ser Gly Ile Tyr His Ile Thr Asn Asp
 65                  70                  75                  80

Cys Pro Asn Ser Ser Ile Val Tyr Glu Thr Glu His His Ile Leu His
                 85                  90                  95

Leu Pro Gly Cys Leu Pro Cys Val Arg Val Gly Asn Gln Ser Arg Cys
            100                 105                 110

Trp Val Ala Leu Thr Pro Thr Val Ala Ala Pro Tyr Ile Gly Ala Pro
        115                 120                 125

Leu Glu Ser Leu Arg Ser His Val Asp Leu Met Val Gly Ala Ala Thr
    130                 135                 140

Ala Cys Ser Ala Leu Tyr Ile Gly Asp Leu Cys Gly Gly Val Phe Leu
145                 150                 155                 160

Val Gly Gln Met Phe Ser Phe Gln Pro Arg Arg His Trp Thr Thr Gln
                165                 170                 175

Asp Cys Asn Cys Ser Ile Tyr Ala Gly His Val Thr Gly His Arg
            180                 185                 190

<210> SEQ ID NO 120
<211> LENGTH: 574
<212> TYPE: DNA
<213> ORGANISM: hepatitis C virus

<400> SEQUENCE: 120
acgtgcggct tgccgacct catgggatac atcccgctcg tgggcgcccc tgtgggtggc      60
gtcgccaggg ccttggcaca tggtgtcagg gccgtggagg acgggattaa ctatgcaaca     120
gggaatcttc ccggttgctc cttttctatc ttccttctag cacttctctc gtgcttgact     180
gtcccggcct cggcgcagca ctaccggaac atctcgggca tttatacgt caccaatgac      240 tgcccgaact ctagtatagt gtatgaagct gaccatcata tcatgcatct accagggtgt     300
gtgccttgcg tgagaaccgg aacaccctcg cgctgctggg ttccttaac acccactgtg      360 gctgccccct atgttggcgc gccgctcgaa tccatgcggc ggcacgtgga cttaatggtg     420
ggtgccgcca ccgtctgctc ggccctgtac atcggagacc tttgcggagg tgtcttcctg     480
gtcgggcaga tgttcacctt ccggccgcgc cgccattgga ctacccagga ctgcaactgc     540
tctatctatg atggccacat caccggccat agaa                                 574

<210> SEQ ID NO 121
<211> LENGTH: 191
<212> TYPE: PRT
<213> ORGANISM: hepatitis C virus

<400> SEQUENCE: 121

Thr Cys Gly Phe Ala Asp Leu Met Gly Tyr Ile Pro Leu Val Gly Ala
  1               5                  10                  15

Pro Val Gly Gly Val Ala Arg Ala Leu Ala His Gly Val Arg Ala Val
                 20                  25                  30

Glu Asp Gly Ile Asn Tyr Ala Thr Gly Asn Leu Pro Gly Cys Ser Phe
             35                  40                  45

Ser Ile Phe Leu Leu Ala Leu Leu Ser Cys Leu Thr Val Pro Ala Ser
     50                  55                  60

Ala Gln His Tyr Arg Asn Ile Ser Gly Ile Tyr His Val Thr Asn Asp
 65                  70                  75                  80

Cys Pro Asn Ser Ser Ile Val Tyr Glu Ala Asp His His Ile Met His
                 85                  90                  95

Leu Pro Gly Cys Val Pro Cys Val Arg Thr Gly Asn Thr Ser Arg Cys
```

```
                     100                 105                 110
Trp Val Pro Leu Thr Pro Thr Val Ala Ala Pro Tyr Val Gly Ala Pro
            115                 120                 125

Leu Glu Ser Met Arg Arg His Val Asp Leu Met Val Gly Ala Ala Thr
        130                 135                 140

Val Cys Ser Ala Leu Tyr Ile Gly Asp Leu Cys Gly Gly Val Phe Leu
145                 150                 155                 160

Val Gly Gln Met Phe Thr Phe Arg Pro Arg His Trp Thr Thr Gln
                165                 170                 175

Asp Cys Asn Cys Ser Ile Tyr Asp Gly His Ile Thr Gly His Arg
            180                 185                 190

<210> SEQ ID NO 122
<211> LENGTH: 574
<212> TYPE: DNA
<213> ORGANISM: hepatitis C virus

<400> SEQUENCE: 122
acgtgcggct cgccgacct catgggatac atcccgctcg tgggcgcccc cgttgggggc      60
gtcgccaggg ccctggcgca tggcgtcagg gctgtggagg acgggattaa ctatgcgaca     120
gggaatcttc ccggttgctc tttctctatc ttcctcctgg cacttctttc gtgcctcact     180
gtcccagcgt cagctgagca ctaccggaat gcttcgggca tctatcacat caccaatgac     240
tgtccgaatt ccagcgtagt ctatgaaact gaccaccata tattgcactt gccggggtgc     300
gtaccctgcg tgagggccgg gaacgtgtct cgttgctgga cgccggtaac acctacggtg     360
gctgccgtat ccatggacgc tccgctcgag tccttccggc ggcatgtgga cctaatggta     420
ggtgcggcca ccgtgtgttc tgtcctctat gttggagacc tctgtggagg tgctttccta     480
gtggggcaga tgttcacctt ccagccgcgt cgccactgga ccacgcagga ttgtaattgc     540
tccatctata ctggccatat caccggccac agga                                574

<210> SEQ ID NO 123
<211> LENGTH: 191
<212> TYPE: PRT
<213> ORGANISM: hepatitis C virus

<400> SEQUENCE: 123

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Phe Leu Leu Ala Leu Leu Ser Cys Leu Thr Val Pro Ala Ser
    50                  55                  60

Ala Glu His Tyr Arg Asn Ala Ser Gly Ile Tyr His Ile Thr Asn Asp
65                  70                  75                  80

Cys Pro Asn Ser Ser Val Val Tyr Glu Thr Asp His His Ile Leu His
                85                  90                  95

Leu Pro Gly Cys Val Pro Cys Val Arg Ala Gly Asn Val Ser Arg Cys
            100                 105                 110

Trp Thr Pro Val Thr Pro Thr Val Ala Ala Val Ser Met Asp Ala Pro
        115                 120                 125

Leu Glu Ser Phe Arg Arg His Val Asp Leu Met Val Gly Ala Ala Thr
    130                 135                 140
```

```
Val Cys Ser Val Leu Tyr Val Gly Asp Leu Cys Gly Ala Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Thr Gly His Ile Thr Gly His Arg
            180                 185                 190

<210> SEQ ID NO 124
<211> LENGTH: 31
<212> TYPE: DNA
<213> ORGANISM: artificial
<220> FEATURE:
<221> NAME/KEY: misc_feature
<223> OTHER INFORMATION: HCPr206

<400> SEQUENCE: 124
tggggatccc gtatgatacc cgctgctttg a                              31

<210> SEQ ID NO 125
<211> LENGTH: 30
<212> TYPE: DNA
<213> ORGANISM: artificial
<220> FEATURE:
<221> NAME/KEY: misc_feature
<223> OTHER INFORMATION: HCPr207

<400> SEQUENCE: 125
ggcggaattc ctggtcatag cctccgtgaa                                30

<210> SEQ ID NO 126
<211> LENGTH: 12
<212> TYPE: PRT
<213> ORGANISM: hepatitis C virus

<400> SEQUENCE: 126

Val Asn Tyr Arg Asn Ala Ser Gly Ile Tyr His Ile
1               5                   10

<210> SEQ ID NO 127
<211> LENGTH: 12
<212> TYPE: PRT
<213> ORGANISM: hepatitis C virus

<400> SEQUENCE: 127

Gln His Tyr Arg Asn Ile Ser Gly Ile Tyr His Val
1               5                   10

<210> SEQ ID NO 128
<211> LENGTH: 12
<212> TYPE: PRT
<213> ORGANISM: hepatitis C virus

<400> SEQUENCE: 128

Glu His Tyr Arg Asn Ala Ser Gly Ile Tyr His Ile
1               5                   10

<210> SEQ ID NO 129
<211> LENGTH: 11
<212> TYPE: PRT
<213> ORGANISM: hepatitis C virus

<400> SEQUENCE: 129

Val Tyr Glu Thr Glu His His Ile Leu His Leu
1               5                   10
```

```
<210> SEQ ID NO 130
<211> LENGTH: 11
<212> TYPE: PRT
<213> ORGANISM: hepatitis C virus

<400> SEQUENCE: 130

Val Tyr Glu Ala Asp His His Ile Met His Leu
1               5                   10

<210> SEQ ID NO 131
<211> LENGTH: 11
<212> TYPE: PRT
<213> ORGANISM: hepatitis C virus

<400> SEQUENCE: 131

Val Tyr Glu Thr Asp His His Ile Leu His Leu
1               5                   10

<210> SEQ ID NO 132
<211> LENGTH: 13
<212> TYPE: PRT
<213> ORGANISM: hepatitis C virus

<400> SEQUENCE: 132

Val Arg Val Gly Asn Gln Ser Arg Cys Trp Val Ala Leu
1               5                   10

<210> SEQ ID NO 133
<211> LENGTH: 13
<212> TYPE: PRT
<213> ORGANISM: hepatitis C virus

<400> SEQUENCE: 133

Val Arg Thr Gly Asn Thr Ser Arg Cys Trp Val Pro Leu
1               5                   10

<210> SEQ ID NO 134
<211> LENGTH: 13
<212> TYPE: PRT
<213> ORGANISM: hepatitis C virus

<400> SEQUENCE: 134

Val Arg Ala Gly Asn Val Ser Arg Cys Trp Thr Pro Val
1               5                   10

<210> SEQ ID NO 135
<211> LENGTH: 10
<212> TYPE: PRT
<213> ORGANISM: hepatitis C virus

<400> SEQUENCE: 135

Ala Pro Tyr Ile Gly Ala Pro Leu Glu Ser
1               5                   10

<210> SEQ ID NO 136
<211> LENGTH: 10
<212> TYPE: PRT
<213> ORGANISM: hepatitis C virus

<400> SEQUENCE: 136

Ala Pro Tyr Val Gly Ala Pro Leu Glu Ser
1               5                   10
```

```
<210> SEQ ID NO 137
<211> LENGTH: 10
<212> TYPE: PRT
<213> ORGANISM: hepatitis C virus

<400> SEQUENCE: 137

Ala Val Ser Met Asp Ala Pro Leu Glu Ser
1               5                   10

<210> SEQ ID NO 138
<211> LENGTH: 10
<212> TYPE: PRT
<213> ORGANISM: hepatitis C virus

<400> SEQUENCE: 138

Gln Pro Arg Arg His Trp Thr Thr Gln Asp
1               5                   10

<210> SEQ ID NO 139
<211> LENGTH: 10
<212> TYPE: PRT
<213> ORGANISM: hepatitis C virus

<400> SEQUENCE: 139

Arg Pro Arg Arg His Trp Thr Thr Gln Asp
1               5                   10

<210> SEQ ID NO 140
<211> LENGTH: 10
<212> TYPE: PRT
<213> ORGANISM: hepatitis C virus

<400> SEQUENCE: 140

Arg Pro Arg Arg His Trp Thr Thr Gln Asp
1               5                   10

<210> SEQ ID NO 141
<211> LENGTH: 23
<212> TYPE: DNA
<213> ORGANISM: artificial
<220> FEATURE:
<221> NAME/KEY: misc_feature
<223> OTHER INFORMATION: HCPr109

<400> SEQUENCE: 141
tgggatatga tgatgaactg gtc                                           23

<210> SEQ ID NO 142
<211> LENGTH: 24
<212> TYPE: DNA
<213> ORGANISM: artificial
<220> FEATURE:
<221> NAME/KEY: misc_feature
<223> OTHER INFORMATION: HCPr14

<400> SEQUENCE: 142
ccaggtacaa ccgaaccaat tgcc                                          24

<210> SEQ ID NO 143
<211> LENGTH: 957
<212> TYPE: DNA
<213> ORGANISM: hepatitis C virus

<400> SEQUENCE: 143
atgagcacaa atcctaaacc tcaaagaaaa accaaaagaa acactaaccg ccgcccacag   60
```

-continued

```
gacgtcaagt tcccgggcgg tggccagatc gttggtggag tatacttgtt gccgcgcagg      120
ggcccccggt tgggtgtgcg cgcgacgagg aaaacttccg agcggtccca gccacgtggg      180
aggcgccagc ccatccccaa agatcggcgc cccactggca agtcctgggg aaaaccagga      240
taccccttggc ccctgtacgg gaatgagggc ctcggctggg caggtggct cctgtccccc      300
cgagggtctc gcccgtcatg gggcccaact gaccccggc acaggtcacg caacttgggt      360
aaggtcatcg atacccttac gtgtggcttt gccgacctca tggggtacat ccctgtcgtc      420
ggcgccccag ttggtggtgt cgccagagct ctcgcgcatg gcgtgagagt tctggaagac      480
gggataaact atgcaacagg gaacttgccc ggttgctcct tttctatctt cttattggcc      540
ctgctatctt gtatcactgt gccggtctcc ggcttgcagg tcaagaacac cagcagctct      600
tacatggtaa ccaatgactg ccagaacagt agcatcgtct ggcagctcag ggatgctgtt      660
cttcacgtcc ccgggtgtgt cccttgtgag gagaagggca acatatcccg ctgttggata      720
ccggtttcgc ccaatatagc tgtgagccaa cctggtgcgc ttaccaaggg cctgcggacg      780
catattgata ccatcattgc atccgctacg ttttgctctg ccctgtacat aggagacctg      840
tgtggcgcgg tgatgttggc ttctcaagtc ttcatcatct cgccccagca tcataagttt      900
gtccaggact gcaactgttc catataccca ggccacatca ctggacatcg gatggcg        957
```

<210> SEQ ID NO 144
<211> LENGTH: 319
<212> TYPE: PRT
<213> ORGANISM: hepatitis C virus

<400> SEQUENCE: 144

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Asp Arg Arg Pro Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg His Arg Ser Arg Asn Leu Gly Lys Val Ile Asp Thr Leu Thr Cys
        115                 120                 125

Gly Phe Ala Asp Leu Met Gly Tyr Ile Pro Val Val Gly Ala Pro Val
    130                 135                 140

Gly Gly Val Ala Arg Ala Leu Ala His Gly Val Arg Val Leu Glu Asp
145                 150                 155                 160

Gly Ile Asn Tyr Ala Thr Gly Asn Leu Pro Gly Cys Ser Phe Ser Ile
                165                 170                 175

Phe Leu Leu Ala Leu Leu Ser Cys Ile Thr Val Pro Val Ser Gly Leu
            180                 185                 190

Gln Val Lys Asn Thr Ser Ser Tyr Met Val Thr Asn Asp Cys Gln
        195                 200                 205

Asn Ser Ser Ile Val Trp Gln Leu Arg Asp Ala Val Leu His Val Pro
    210                 215                 220
```

```
Gly Cys Val Pro Cys Glu Glu Lys Gly Asn Ile Ser Arg Cys Trp Ile
225                 230                 235                 240

Pro Val Ser Pro Asn Ile Ala Val Ser Gln Pro Gly Ala Leu Thr Lys
                245                 250                 255

Gly Leu Arg Thr His Ile Asp Thr Ile Ile Ala Ser Ala Thr Phe Cys
            260                 265                 270

Ser Ala Leu Tyr Ile Gly Asp Leu Cys Gly Ala Val Met Leu Ala Ser
        275                 280                 285

Gln Val Phe Ile Ile Ser Pro Gln His His Lys Phe Val Gln Asp Cys
    290                 295                 300

Asn Cys Ser Ile Tyr Pro Gly His Ile Thr Gly His Arg Met Ala
305                 310                 315

<210> SEQ ID NO 145
<211> LENGTH: 340
<212> TYPE: DNA
<213> ORGANISM: hepatitis C virus

<400> SEQUENCE: 145
ctcaacggtc acggagaggg acatcagaac tgaggagtcc atataccttg cttgctcttt       60
acccgagcag gcacggactg ccatacactc actgactgag aggctttacg tgggagggcc      120
catgctaaac agcaaagggc aaacctgcgg atacagacgc tgccgcgcca gcggagtgtt      180
caccactagc atgggaaata ccatcacgtg ctacgtgaag gcacaagcag cctgtaaggc      240
tgcgggcata attgccccca cgatgctggt gtgcggcgac gatctagttg tcatctcaga      300
gagtcagggg accgaggagg acgagcggaa cctacgagcc                            340

<210> SEQ ID NO 146
<211> LENGTH: 113
<212> TYPE: PRT
<213> ORGANISM: hepatitis C virus

<400> SEQUENCE: 146

Ser Thr Val Thr Glu Arg Asp Ile Arg Thr Glu Glu Ser Ile Tyr Leu
1               5                   10                  15

Ala Cys Ser Leu Pro Glu Gln Ala Arg Thr Ala Ile His Ser Leu Thr
            20                  25                  30

Glu Arg Leu Tyr Val Gly Gly Pro Met Leu Asn Ser Lys Gly Gln Thr
        35                  40                  45

Cys Gly Tyr Arg Arg Cys Arg Ala Ser Gly Val Phe Thr Thr Ser Met
    50                  55                  60

Gly Asn Thr Ile Thr Cys Tyr Val Lys Ala Gln Ala Ala Cys Lys Ala
65                  70                  75                  80

Ala Gly Ile Ile Ala Pro Thr Met Leu Val Cys Gly Asp Asp Leu Val
                85                  90                  95

Val Ile Ser Glu Ser Gln Gly Thr Glu Glu Asp Glu Arg Asn Leu Arg
            100                 105                 110

Ala

<210> SEQ ID NO 147
<211> LENGTH: 345
<212> TYPE: DNA
<213> ORGANISM: hepatitis C virus

<400> SEQUENCE: 147
atgagcacac ttcctaaacc acaaagaaaa accaaaagaa acaccaaccc cggccacagg       60
```

-continued

```
acgttaagtt cccaggcggc ggtcagatcg ttggtggagt ttacgtgcta ccacgcaggg      120
gcccccagtt gggtgtgcgt gcagtgcgca agacttccga gcggtcgcaa cctcgcagta      180
ggcgccaacc catccccagg gcgcgccgaa ccgagggcag gtcctgggct cagcccgggt      240
acccttggcc cctatatggg aatgagggct gcgggtgggc agggtggctc ctgtccccgc      300
gcggctctcg cccgtcgtgg ggcccaaatg accccggcg cagga                      345
```

```
<210> SEQ ID NO 148
<211> LENGTH: 115
<212> TYPE: PRT
<213> ORGANISM: hepatitis C virus

<400> SEQUENCE: 148
```

Met Ser Thr Leu Pro Lys Pro Gln Arg Lys Thr Lys Arg Asn Thr Asn
1               5                   10                  15

Pro Gly His Arg Thr Leu Ser Ser Gln Ala Ala Val Arg Ser Leu Val
            20                  25                  30

Glu Phe Thr Cys Tyr His Ala Gly Ala Pro Ser Trp Val Cys Val Gln
        35                  40                  45

Cys Ala Arg Leu Pro Ser Gly Arg Asn Leu Ala Val Gly Ala Asn Pro
    50                  55                  60

Ser Pro Gly Arg Ala Glu Pro Arg Ala Gly Pro Gly Leu Ser Pro Gly
65                  70                  75                  80

Thr Leu Gly Pro Tyr Met Gly Met Arg Ala Ala Gly Gly Gln Gly Gly
                85                  90                  95

Ser Cys Pro Arg Ala Ala Leu Ala Arg Arg Gly Ala Gln Met Thr Pro
            100                 105                 110

Gly Ala Gly
        115

```
<210> SEQ ID NO 149
<211> LENGTH: 280
<212> TYPE: DNA
<213> ORGANISM: hepatitis C virus

<400> SEQUENCE: 149
```

```
ggcctgtgac ctcaaggacg aggctaggag ggtgataact tcactcacgg agcggcttta      60
ctgtggtggt cctatgttca acagcaaggg acaacactgc ggttaccgcc gctgccgtgc     120
tagtggggtg ctaccacca gcttcgggaa cacaatcacc tgttacatca aagcaaaggc     180
agctaccaaa gctgccggaa ttaaaaatcc atcattcctt gtctgcggag atgacttggt     240
cgtgattgct gagagtgcag ggatcgatga ggacagagcg                          280
```

```
<210> SEQ ID NO 150
<211> LENGTH: 93
<212> TYPE: PRT
<213> ORGANISM: hepatitis C virus

<400> SEQUENCE: 150
```

Ala Cys Asp Leu Lys Asp Glu Ala Arg Arg Val Ile Thr Ser Leu Thr
1               5                   10                  15

Glu Arg Leu Tyr Cys Gly Gly Pro Met Phe Asn Ser Lys Gly Gln His
            20                  25                  30

Cys Gly Tyr Arg Arg Cys Arg Ala Ser Gly Val Leu Pro Thr Ser Phe
        35                  40                  45

Gly Asn Thr Ile Thr Cys Tyr Ile Lys Ala Lys Ala Ala Thr Lys Ala

```
                   50                55                 60
Ala Gly Ile Lys Asn Pro Ser Phe Leu Val Cys Gly Asp Asp Leu Val
 65                 70                 75                 80

Val Ile Ala Glu Ser Ala Gly Ile Asp Glu Asp Arg Ala
                 85                 90
```

<210> SEQ ID NO 151
<211> LENGTH: 499
<212> TYPE: DNA
<213> ORGANISM: hepatitis C virus

<400> SEQUENCE: 151

```
atgagcacga atcctaaacc tcaaagaaaa accaaaagaa acaccaaccg tcgcccacag     60
gacgtcaagt tcccgggcgg tggtcagatc gttggcggag tttacttgtt gccgcgcagg    120
ggccctagga tgggtgtgcg cgcgactcgg aagacttcgg aacggtcgca accccgtgga    180
cggcgtcagc ctattcccaa ggcgcgccag cccacgggcc ggtcctgggg tcaacccggg    240
taccctttggc cctttacgc caatgagggc ctcgggtggg cagggtggct gctctcccct    300
cgaggctctc ggcctaattg gggccccaat gaccccccggc gaaaatcgcg taatttgggt    360
aaggtcatcg atacccctaac gtgcggattc gccgatctca tggggtatat cccgctcgta    420
ggcggcccca ttgggggcgt cgcaagggct ctcgcacacg tgtgagggt ccttgaggac    480
ggggtaaact atgcaacag                                                499
```

<210> SEQ ID NO 152
<211> LENGTH: 166
<212> TYPE: PRT
<213> ORGANISM: hepatitis C virus

<400> SEQUENCE: 152

```
Met Ser Thr Asn Pro Lys Pro Gln Arg Lys Thr Lys Arg Asn Thr Asn
  1               5                  10                 15

Arg Arg Pro Gln Asp Val Lys Phe Pro Gly Gly Gly Gln Ile Val Gly
                 20                 25                 30

Gly Val Tyr Leu Leu Pro Arg Arg Gly Pro Arg Met Gly Val Arg Ala
             35                 40                 45

Thr Arg Lys Thr Ser Glu Arg Ser Gln Pro Arg Gly Arg Arg Gln Pro
         50                 55                 60

Ile Pro Lys Ala Arg Gln Pro Thr Gly Arg Ser Trp Gly Gln Pro Gly
 65                 70                 75                 80

Tyr Pro Trp Pro Leu Tyr Ala Asn Glu Gly Leu Gly Trp Ala Gly Trp
                 85                 90                 95

Leu Leu Ser Pro Arg Gly Ser Arg Pro Asn Trp Gly Pro Asn Asp Pro
            100                105                110

Arg Arg Lys Ser Arg Asn Leu Gly Lys Val Ile Asp Thr Leu Thr Cys
            115                120                125

Gly Phe Ala Asp Leu Met Gly Tyr Ile Pro Leu Val Gly Gly Pro Ile
            130                135                140

Gly Gly Val Ala Arg Ala Leu Ala His Gly Val Arg Val Leu Glu Asp
145                150                155                160

Gly Val Asn Tyr Ala Thr
                165
```

<210> SEQ ID NO 153
<211> LENGTH: 579
<212> TYPE: DNA

<213> ORGANISM: hepatitis C virus

<400> SEQUENCE: 153

| | | | | | |
|---|---|---|---|---|---|
| acgtg

```
gtcgcaaggg ctctcgcaca tggtgtgagg gttcttgagg acgggtgaa ttatgcaaca    120 gggaatctgc ctggttgctc tttctctatc ttcattcttg cacttctctc gtgcctcact    180
gtcccggcct ctgcagttcc ctaccgaaat gcctctggga tctatcatgt caccaatgat    240
tgcccaaact cttccatagt ctatgaggca gatgatctga tcctacacgc acctggctgc    300
gtgccttgtg tcaggaaaga taatgtgagt aggtgctggg tccaaattac ccccacgctg    360
tcagccccga gcttcggagc agtcacggct ccccttcgga gagccgttga ttacttggtg    420
ggaggggctg ccctctgctc cgcgttatac gttggagacg cgtgtgggc actattttg    480 gtaggccaaa tgttcaccta taggcctcgc cagcatgcta cggtgcagga ctgcaactgt    540
tccatctaca gtggccacgt caccggccat cagatggca                         579
```

<210> SEQ ID NO 156  
<211> LENGTH: 193  
<212> TYPE: PRT  
<213> ORGANISM: hepatitis C virus
<400> SEQUENCE: 156

```
Thr Cys Gly Phe Ala Asp Leu Val Gly Tyr Ile Pro Leu Val Gly Gly
1               5                   10                  15

Pro Val Gly Gly Val Ala Arg Ala Leu Ala His Gly Val Arg Val Leu
            20                  25                  30

Glu Asp Gly Val Asn Tyr Ala Thr Gly Asn Leu Pro Gly Cys Ser Phe
        35                  40                  45

Ser Ile Phe Ile Leu Ala Leu Leu Ser Cys Leu Thr Val Pro Ala Ser
    50                  55                  60

Ala Val Pro Tyr Arg Asn Ala Ser Gly Ile Tyr His Val Thr Asn Asp
65                  70                  75                  80

Cys Pro Asn Ser Ser Ile Val Tyr Glu Ala Asp Asp Leu Ile Leu His
                85                  90                  95

Ala Pro Gly Cys Val Pro Cys Val Arg Lys Asp Asn Val Ser Arg Cys
            100                 105                 110

Trp Val Gln Ile Thr Pro Thr Leu Ser Ala Pro Ser Phe Gly Ala Val
        115                 120                 125

Thr Ala Pro Leu Arg Arg Ala Val Asp Tyr Leu Val Gly Gly Ala Ala
    130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asp Cys Asn Cys Ser Ile Tyr Ser Gly His Val Thr Gly His Gln Met
            180                 185                 190

Ala
```

<210> SEQ ID NO 157  
<211> LENGTH: 530  
<212> TYPE: DNA  
<213> ORGANISM: hepatitis C virus
<400> SEQUENCE: 157

```
cacctacgac agctctgctg gtggcccagt tactgcggat tccccaagtg gtcattgaca    60
tcatcgcagg gagccactgg ggggtcttgt ttgccgccgc atactatgca tcggtggcta   120
actggaccaa ggtcgtgctg gtcttgtttc tgtttgcagg ggttgatgct actacccaga   180
```

```
tttcgggcgg ctccagcgcc caaacgacgt atggcatcgc ctcatttatc acccgcggcg        240
cgcagcagaa actgcagctc ataaatacca acggaagctg gcacatcaac aggaccgccc        300
ttaattgtaa tgacagcctc cagactgggt tcatagccgg cctcttctac taccataagt        360
tcaactcttc tggatgcccg gatcggatgg ctagctgtag ggcccttgcc acttttgacc        420
agggctgggg aactatcagc tatgccaaca tatcgggtcc cagtgatgac aaaccatatt        480
gctggcacta tccccacgg ccgtgcggag tggtgccagc ccaagaggtc                    530
```

<210> SEQ ID NO 158
<211> LENGTH: 176
<212> TYPE: PRT
<213> ORGANISM: hepatitis C virus

<400> SEQUENCE: 158

```
Pro Thr Thr Ala Leu Leu Val Ala Gln Leu Leu Arg Ile Pro Gln Val
1               5                   10                  15

Val Ile Asp Ile Ile Ala Gly Ser His Trp Gly Val Leu Phe Ala Ala
                20                  25                  30

Ala Tyr Tyr Ala Ser Val Ala Asn Trp Thr Lys Val Val Leu Val Leu
            35                  40                  45

Phe Leu Phe Ala Gly Val Asp Ala Thr Thr Gln Ile Ser Gly Gly Ser
        50                  55                  60

Ser Ala Gln Thr Thr Tyr Gly Ile Ala Ser Phe Ile Thr Arg Gly Ala
65                  70                  75                  80

Gln Gln Lys Leu Gln Leu Ile Asn Thr Asn Gly Ser Trp His Ile Asn
                85                  90                  95

Arg Thr Ala Leu Asn Cys Asn Asp Ser Leu Gln Thr Gly Phe Ile Ala
            100                 105                 110

Gly Leu Phe Tyr Tyr His Lys Phe Asn Ser Ser Gly Cys Pro Asp Arg
        115                 120                 125

Met Ala Ser Cys Arg Ala Leu Ala Thr Phe Asp Gln Gly Trp Gly Thr
    130                 135                 140

Ile Ser Tyr Ala Asn Ile Ser Gly Pro Ser Asp Asp Lys Pro Tyr Cys
145                 150                 155                 160

Trp His Tyr Pro Pro Arg Pro Cys Gly Val Val Pro Ala Gln Glu Val
                165                 170                 175
```

<210> SEQ ID NO 159
<211> LENGTH: 340
<212> TYPE: DNA
<213> ORGANISM: hepatitis C virus

<400> SEQUENCE: 159

```
ctcgaccgtt accgaacatg acataatgac cgaagagtcc atttaccaat catgtgactt         60
gcagcccgag gcacgcgcag caatacggtc actcacccaa cgcctctact gtggaggccc        120
catgtacaac agcaagggc aacagtgtgg ttatcgcaga tgccgcgcca gcggcgtttt        180
caccaccagt atgggcaaca ccatgacgtg ctacatcaag gctttagcct cctgtagagc        240
cgcaaggctc cgggactgca cgctcctggt gtgtggtgac gatcttgtgg ccatctgcga        300
gagccagggg acacacgagg atgaagcaag cctgagagcc                             340
```

<210> SEQ ID NO 160
<211> LENGTH: 113
<212> TYPE: PRT
<213> ORGANISM: hepatitis C virus -continued

```
<400> SEQUENCE: 160

Ser Thr Val Thr Glu His Asp Ile Met Thr Glu Ser Ile Tyr Gln
1               5                   10                  15

Ser Cys Asp Leu Gln Pro Glu Ala Arg Ala Ala Ile Arg Ser Leu Thr
            20                  25                  30

Gln Arg Leu Tyr Cys Gly Gly Pro Met Tyr Asn Ser Lys Gly Gln Gln
                35                  40                  45

Cys Gly Tyr Arg Arg Cys Arg Ala Ser Gly Val Phe Thr Thr Ser Met
50                  55                  60

Gly Asn Thr Met Thr Cys Tyr Ile Lys Ala Leu Ala Ser Cys Arg Ala
65                  70                  75                  80

Ala Arg Leu Arg Asp Cys Thr Leu Leu Val Cys Gly Asp Asp Leu Val
                85                  90                  95

Ala Ile Cys Glu Ser Gln Gly Thr His Glu Asp Glu Ala Ser Leu Arg
            100                 105                 110

Ala

<210> SEQ ID NO 161
<211> LENGTH: 340
<212> TYPE: DNA
<213> ORGANISM: hepatitis C virus

<400> SEQUENCE: 161
ctcaaccgcc accgaacatg acatattgac tgaagagtcc atataccaat catgtgactc      60
gcagcccgac gcacgcgcag caatacggtc actcacccaa cgcttgttct gtggaggccc     120
catgtataac agcaaggggc aacaatgtgg ttatcgcaga tgccgcgcca gcggcgtctt     180
caccaccagt atgggcaaca ccatgacgtg ctacattaag gctttagcct cctgtagaac     240
cgctgggctc cgggactaca cgctcctggt gtgtggtgac gatcatgtgg ccatctgcga     300
gagccagggg acacacgagg atgaagcgaa cctgagagcc                           340

<210> SEQ ID NO 162
<211> LENGTH: 113
<212> TYPE: PRT
<213> ORGANISM: hepatitis C virus

<400> SEQUENCE: 162

Ser Thr Ala Thr Glu His Asp Ile Leu Thr Glu Ser Ile Tyr Gln
1               5                   10                  15

Ser Cys Asp Ser Gln Pro Asp Ala Arg Ala Ala Ile Arg Ser Leu Thr
            20                  25                  30

Gln Arg Leu Phe Cys Gly Gly Pro Met Tyr Asn Ser Lys Gly Gln Gln
                35                  40                  45

Cys Gly Tyr Arg Arg Cys Arg Ala Ser Gly Val Phe Thr Thr Ser Met
50                  55                  60

Gly Asn Thr Met Thr Cys Tyr Ile Lys Ala Leu Ala Ser Cys Arg Thr
65                  70                  75                  80

Ala Gly Leu Arg Asp Tyr Thr Leu Leu Val Cys Gly Asp Asp His Val
                85                  90                  95

Ala Ile Cys Glu Ser Gln Gly Thr His Glu Asp Glu Ala Asn Leu Arg
            100                 105                 110

Ala

<210> SEQ ID NO 163
<211> LENGTH: 499
```

```
<212> TYPE: DNA
<213> ORGANISM: hepatitis C virus

<400> SEQUENCE: 163
atgagcacga atcctaaact tcaaagaaaa accaaacgta acaccaaccg ccgccccatg      60
gacgttaagt tcccgggtgg tggccagatc gttggcggag tttacttgtt gccgcgcagg     120
ggccctaggt tgggtgtgcg cgcgactcgg aagacttcgg agcggtcgca acctcgtggg     180
aggcgccaac ctatccccaa ggcgcgccga tccgagggca gatcctgggc gcagcccggg     240
tatccttggc cctttacgg caatgagggc tgtgggtggg cagggtggct cctgtcccct     300
cgcgggtctc ggccgtcttg gggccctaat gatccccggc ggaggtcccg caacctgggt     360
aaggtcatcg ataccctaac atgcggcttc gccgacctca tgggatacat cccgcttgta     420
ggcgcccccg tgggtggcgt cgccagagcc ctggcacacg tgttagggc tgtggaagac     480 gggatcaact acgcaacag                                                   499

<210> SEQ ID NO 164
<211> LENGTH: 166
<212> TYPE: PRT
<213> ORGANISM: hepatitis C virus

<400> SEQUENCE: 164

Met Ser Thr Asn Pro Lys Leu Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Val Glu Asp
145                 150                 155                 160

Gly Ile Asn Tyr Ala Thr
                165

<210> SEQ ID NO 165
<211> LENGTH: 499
<212> TYPE: DNA
<213> ORGANISM: hepatitis C virus
<220> FEATURE:
<221> NAME/KEY: misc_feature
<222> LOCATION: (306)..(306)
<223> OTHER INFORMATION: "n" is any nucleotide
<220> FEATURE:
<221> NAME/KEY: misc_feature
<222> LOCATION: (313)..(313)
<223> OTHER INFORMATION: "n" is any nucleotide
<220> FEATURE:
<221> NAME/KEY: misc_feature
```

```
<222> LOCATION: (340)..(340)
<223> OTHER INFORMATION: "n" is any nucleotide

<400> SEQUENCE: 165
atgagcacga atcctaaacc tcaaagaaaa accaaacgta acaccaaccg ccgccctatg      60
gacgttaagt tcccaggcgg tggtcagatc gttggcggag tttacttgtt gccgcgcagg    120
ggccccaggt tgggtgtgcg cgcgactcgg aagacttcgg agcggtcgca acctcgtggg    180
aggcgccaac ctatccccaa ggcgcgccga accgagggca gatcctgggc gcagcccggg    240
tatccttggc ccctttacgg caatgagggc tgtgggtggg cagggtggct cctgtcccct    300
cgcggntctc ggncgtcttg gggccccaat gatccccggn ggagatcccg caacttgggt    360
aaggtcatcg ataccctaac atgcggcttc gccgacctca tgggatacat cccgcttgta    420
ggcgcccccg tgggtggcgt cgccagggcc ctggcacatg gtgttagggc tgtggaagac    480
gggatcaatt atgcaacag                                                  499

<210> SEQ ID NO 166
<211> LENGTH: 126
<212> TYPE: PRT
<213> ORGANISM: hepatitis C virus
<220> FEATURE:
<221> NAME/KEY: MISC_FEATURE
<222> LOCATION: (102)..(102)
<223> OTHER INFORMATION: "Xaa" is any amino acid
<220> FEATURE:
<221> NAME/KEY: MISC_FEATURE
<222> LOCATION: (105)..(105)
<223> OTHER INFORMATION: "Xaa" is any amino acid
<220> FEATURE:
<221> NAME/KEY: MISC_FEATURE
<222> LOCATION: (114)..(114)
<223> OTHER INFORMATION: "Xaa" is any amino acid

<400> SEQUENCE: 166

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Thr Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Xaa Ser Arg Xaa Ser Trp Gly Pro Asn Asp Pro
            100                 105                 110

Arg Xaa Arg Ser Arg Asn Leu Gly Lys Val Ile Asp Thr Leu
        115                 120                 125

<210> SEQ ID NO 167
<211> LENGTH: 579
<212> TYPE: DNA
<213> ORGANISM: hepatitis C virus

<400> SEQUENCE: 167
acatgcggct cgccgacct catgggatac atcccgcttg taggcgcccc cgtgggtggc      60
gtcgccaggg ccctggcaca tggtgttagg gctgtggaag acgggatcaa ttatgcaaca   120
```

```
gggaaccttc ccggttgctc cttttctatc ttcctcttgg cgctcctctc gtgcctgact      180
gttcccacat cggccgttaa ctatcgcaat gcttcgggca tttatcacat caccaatgac      240
tgcccgaatg caagcatagt gtacgagacc gaaaatcaca tcttacacct cccagggtgc      300
gtaccctgtg tgaggactgg gaaccagtcg cggtgttggg tggccctcac tcccacagta      360
gcgtcgccat acgccggtgc tccgcttgag cccttgcggc gtcatgtgga cctgatggta      420
ggtgctgcca ccatgtgttc cgccctctac atcggcgact gtgcggtgg cttattcttg       480 gtgggccaaa tgttcacctt ccaaccgcga cgtcactgga ccactcagga ctgcaattgt      540
tccatctaca cgggccacat tacgggtcat cggatggca                              579
```

```
<210> SEQ ID NO 168
<211> LENGTH: 193
<212> TYPE: PRT
<213> ORGANISM: hepatitis C virus

<400> SEQUENCE: 168

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Phe Leu Leu Ala Leu Leu Ser Cys Leu Thr Val Pro Thr Ser
    50                  55                  60

Ala Val Asn Tyr Arg Asn Ala Ser Gly Ile Tyr His Ile Thr Asn Asp
65                  70                  75                  80

Cys Pro Asn Ala Ser Ile Val Tyr Glu Thr Glu Asn His Ile Leu His
                85                  90                  95

Leu Pro Gly Cys Val Pro Cys Val Arg Thr Gly Asn Gln Ser Arg Cys
            100                 105                 110

Trp Val Ala Leu Thr Pro Thr Val Ala Ser Pro Tyr Ala Gly Ala Pro
        115                 120                 125

Leu Glu Pro Leu Arg Arg His Val Asp Leu Met Val Gly Ala Ala Thr
    130                 135                 140

Met Cys Ser Ala Leu Tyr Ile Gly Asp Leu Cys Gly Gly Leu Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Thr Gly His Ile Thr Gly His Arg Met
            180                 185                 190

Ala
```

```
<210> SEQ ID NO 169
<211> LENGTH: 579
<212> TYPE: DNA
<213> ORGANISM: hepatitis C virus

<400> SEQUENCE: 169
acatgcggct tcgccgacct catgggatac atcccgcttg taggcgcccc cgtgggtggc      60
gtcgccagag ccctggcaca cggtgttagg gctgtggaag acgggatcaa ctacgcaaca      120
gggaatctcc ccggttgctc cttttctatc ttcctcttgg cacttctctc gtgcctcact      180
gttcccgcgt cggggcgttaa ctatcgcaat gcttcgggcg tttatcacat caccaacgac     240
tgcccgaatg cgagcatagt gtacgagacc gacaatcaca tcttacacct cccagggtgc      300
```

```
gtaccctgtg tgaagaccgg gaaccagtcg cggtgttggg tggccctcac tcccacagtg    360
gcgtcgcctt acgtcggtgc tccgctcgag cccttgcggc gccatgtgga cctgatggta    420
ggtgctgcca ccgtgtgctc cgccctctac gtcggcgacc tgtgcggtgg cttattcttg    480
gtaggccaaa tgttcacctt ccaaccgcga cgccactgga cgacccagga ctgtaattgt    540
tccatctacg caggcatat tacgggccat cggatggct                            579
```

<210> SEQ ID NO 170
<211> LENGTH: 193
<212> TYPE: PRT
<213> ORGANISM: hepatitis C virus

<400> SEQUENCE: 170

```
Thr Cys Gly Phe Ala Asp Leu Met Gly Tyr Ile Pro Leu Val Gly Ala
  1               5                  10                  15

Pro Val Gly Gly Val Ala Arg Ala Leu Ala His Gly Val Arg Ala Val
             20                  25                  30

Glu Asp Gly Ile Asn Tyr Ala Thr Gly Asn Leu Pro Gly Cys Ser Phe
         35                  40                  45

Ser Ile Phe Leu Leu Ala Leu Leu Ser Cys Leu Thr Val Pro Ala Ser
     50                  55                  60

Gly Val Asn Tyr Arg Asn Ala Ser Gly Val Tyr His Ile Thr Asn Asp
 65                  70                  75                  80

Cys Pro Asn Ala Ser Ile Val Tyr Glu Thr Asp Asn His Ile Leu His
                 85                  90                  95

Leu Pro Gly Cys Val Pro Cys Val Lys Thr Gly Asn Gln Ser Arg Cys
            100                 105                 110

Trp Val Ala Leu Thr Pro Thr Val Ala Ser Pro Tyr Val Gly Ala Pro
        115                 120                 125

Leu Glu Pro Leu Arg Arg His Val Asp Leu Met Val Gly Ala Ala Thr
    130                 135                 140

Val Cys Ser Ala Leu Tyr Val Gly Asp Leu Cys Gly Gly Leu Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Ala Gly His Ile Thr Gly His Arg Met
            180                 185                 190

Ala
```

<210> SEQ ID NO 171
<211> LENGTH: 579
<212> TYPE: DNA
<213> ORGANISM: hepatitis C virus

<400> SEQUENCE: 171

```
acatgcggct tcgccgacct catgggatac atcccgcttg tgggcgcccc tgttggtggc     60
gtcgccagag cccttgcgca cggcgtcagg gctgtggaag acgggattaa ctatgcaaca    120
gggaaccttc ctggttgctc ctttctatc ttccttctgg cacttctctc gtgcctgact    180
gtccccgcct cggctgtgca ttatcacaac acctcgggca tctaccacct caccaatgac    240
tgccctaact ctagcatagt ctttgaggca gtccatcaca tcttgcacct tccaggatgc    300
gtcccttgtg taagaactgg gaaccagtct cggtgctggg tagccttgac ccccacgctg    360
gccgcgccat accttggcgc tccactcgag tccatgcggc gtcacgtgga tttgatggtg    420
```

```
ggcactgcta cattgtgctc agcactctac gttggggacc tgtgcggggg catattccta      480
gcgggccaga tgttcacctt ccggccccgc ctccattgga ccacccagga gtgcaattgt      540
tccacctatc cgggccacat cacgggtcat agaatggcg                             579
```

<210> SEQ ID NO 172
<211> LENGTH: 193
<212> TYPE: PRT
<213> ORGANISM: hepatitis C virus

<400> SEQUENCE: 172

```
Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Phe Leu Leu Ala Leu Leu Ser Cys Leu Thr Val Pro Ala Ser
    50                  55                  60

Ala Val His Tyr His Asn Thr Ser Gly Ile Tyr His Leu Thr Asn Asp
65                  70                  75                  80

Cys Pro Asn Ser Ser Ile Val Phe Glu Ala Val His His Ile Leu His
                85                  90                  95

Leu Pro Gly Cys Val Pro Cys Val Arg Thr Gly Asn Gln Ser Arg Cys
            100                 105                 110

Trp Val Ala Leu Thr Pro Thr Leu Ala Ala Pro Tyr Leu Gly Ala Pro
        115                 120                 125

Leu Glu Ser Met Arg Arg His Val Asp Leu Met Val Gly Thr Ala Thr
    130                 135                 140

Leu Cys Ser Ala Leu Tyr Val Gly Asp Leu Cys Gly Gly Ile Phe Leu
145                 150                 155                 160

Ala Gly Gln Met Phe Thr Phe Arg Pro Arg Leu His Trp Thr Thr Gln
                165                 170                 175

Glu Cys Asn Cys Ser Thr Tyr Pro Gly His Ile Thr Gly His Arg Met
            180                 185                 190

Ala
```

<210> SEQ ID NO 173
<211> LENGTH: 579
<212> TYPE: DNA
<213> ORGANISM: hepatitis C virus

<400> SEQUENCE: 173

```
acgtgcggtt ccgccgacct catgggatac atcccgctcg taggcgcccc tgtgggtggc       60
gtcgccaggg ccttggcgca tggcgtcagg gctgtggagg acgggataaa ctatgcaaca      120
gggaaccttc ctggttgctc ttttttctatc ttccttctgg cacttctctc gtgcctgact     180
gtccccgcct cagctgtgca ttatcacaac acctcgggca tctatcacat cactaatgac      240
tgccctaact ctagcatagt ctttgaggca gagcatcaca tcttgcatct tccaggatgc      300
gtcccctgtg tgagaactgg gaaccagtca cgatgctgga tagccttgac ccctacgttg      360
gccgcgccac acattggcgc tccacttgag tccatgcgac gtcatgtgga tttgatggta      420
ggcactgcca cattgtgctc cgcactctac attggagatc tgtgcggagg catatttcta      480
gtgggccaga tgttcaactt caggccccgc ctgcactgga ccacccagga gtgcaattgt      540
tccatctatc caggccacat cacgggtcac agaatggcg                             579
```

<210> SEQ ID NO 174
<211> LENGTH: 193
<212> TYPE: PRT
<213> ORGANISM: hepatitis C virus

<400> SEQUENCE: 174

Thr Cys Gly Ser Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Phe Leu Leu Ala Leu Leu Ser Cys Leu Thr Val Pro Ala Ser
    50                  55                  60

Ala Val His Tyr His Asn Thr Ser Gly Ile Tyr His Ile Thr Asn Asp
65                  70                  75                  80

Cys Pro Asn Ser Ser Ile Val Phe Glu Ala Glu His Ile Leu His
                85                  90                  95

Leu Pro Gly Cys Val Pro Cys Val Arg Thr Gly Asn Gln Ser Arg Cys
            100                 105                 110

Trp Ile Ala Leu Thr Pro Thr Leu Ala Ala Pro His Ile Gly Ala Pro
        115                 120                 125

Leu Glu Ser Met Arg Arg His Val Asp Leu Met Val Gly Thr Ala Thr
    130                 135                 140

Leu Cys Ser Ala Leu Tyr Ile Gly Asp Leu Cys Gly Gly Ile Phe Leu
145                 150                 155                 160

Val Gly Gln Met Phe Asn Phe Arg Pro Arg Leu His Trp Thr Thr Gln
                165                 170                 175

Glu Cys Asn Cys Ser Ile Tyr Pro Gly His Ile Thr Gly His Arg Met
            180                 185                 190

Ala

<210> SEQ ID NO 175
<211> LENGTH: 579
<212> TYPE: DNA
<213> ORGANISM: hepatitis C virus

<400> SEQUENCE: 175
acgtgcggct tgccgacct catgggatac atcccgctcg tgggcgcccc tgtgggtggc      60
gtcgccaggg ccttggcaca tggtgtcagg gccgtggagg acgggattaa ctatgcaaca     120
gggaatcttc ccggttgctc ctttctatc ttccttctag cacttctctc gtgcttgact      180
gtcccggcct cggcgcagca ctaccggaac atctcgggca tttatcacgt caccaatgac    240
tgcccgaact ctagtatagt gtatgaagct gaccatcata tcatgcatct accagggtgt    300
gtgccttgcg tgagaaccgg gaacacctcg cgctgctggg ttcctttaac acccactgtg    360
gctgcccct atgttggcgc gccgctcgaa tccatgcggc ggcacgtgga cttaatggtg     420
ggtgccgcca ccgtctgctc ggccctgtac atcggagacc tttgcggagg tgtcttcctg    480
gtcgggcaga tgttcacctt ccggccgcgc cgccattgga ctacccagga ctgcaactgc    540
tctatctatg atggccacat caccggccat agaatggct                            579

<210> SEQ ID NO 176
<211> LENGTH: 193
<212> TYPE: PRT

<213> ORGANISM: hepatitis C virus

<400> SEQUENCE: 176

```
Thr Cys Gly Phe Ala Asp Leu Met Gly Tyr Ile Pro Leu Val Gly Ala
1               5                   10                  15
Pro Val Gly Gly Val Ala Arg Ala Leu Ala His Gly Val Arg Ala Val
            20                  25                  30
Glu Asp Gly Ile Asn Tyr Ala Thr Gly Asn Leu Pro Gly Cys Ser Phe
        35                  40                  45
Ser Ile Phe Leu Leu Ala Leu Leu Ser Cys Leu Thr Val Pro Ala Ser
    50                  55                  60
Ala Gln His Tyr Arg Asn Ile Ser Gly Ile Tyr His Val Thr Asn Asp
65                  70                  75                  80
Cys Pro Asn Ser Ser Ile Val Tyr Glu Ala Asp His His Ile Met His
                85                  90                  95
Leu Pro Gly Cys Val Pro Cys Val Arg Thr Gly Asn Thr Ser Arg Cys
            100                 105                 110
Trp Val Pro Leu Thr Pro Thr Val Ala Ala Pro Tyr Val Gly Ala Pro
        115                 120                 125
Leu Glu Ser Met Arg Arg His Val Asp Leu Met Val Gly Ala Ala Thr
    130                 135                 140
Val Cys Ser Ala Leu Tyr Ile Gly Asp Leu Cys Gly Gly Val Phe Leu
145                 150                 155                 160
Val Gly Gln Met Phe Thr Phe Arg Pro Arg Arg His Trp Thr Thr Gln
                165                 170                 175
Asp Cys Asn Cys Ser Ile Tyr Asp Gly His Ile Thr Gly His Arg Met
            180                 185                 190
Ala
```

<210> SEQ ID NO 177
<211> LENGTH: 579
<212> TYPE: DNA
<213> ORGANISM: hepatitis C virus

<400> SEQUENCE: 177

```
acgtgcgggt tcgccgacct catgggatac atcccgctcg tgggcgctcc agtaggaggc      60
gtcgccagag ccttggcgca tggcgtcagg gctgtggagg acgggatcaa ttacgcaaca     120
gggaaccttc ccggctgctc ctttctatc ttcctcttgg tacttctctc gcgcctaact      180
gtcccagcgt ctgctcagca ctaccggaat gcatcgggca tctaccatgt caccaacgac     240
tgcccgaact ccagtattgt gtatgaagcc gaccatcaca tcatgcacct acccgggtgt     300
gtgccctgtg taagaactgg gaatgtctcg cgttgctgga ttcctttaac accactgta      360
gccgtcccct acctcggggc tccacttacg tctgtacggc agcatgtgga cctgatggtg     420
ggggcggcca cctatgctc tgccctctac atcggagacc attgcggagg tgtcttcttg     480
gcagggcaga tggtcagttt ccaaccccgg cgtcattgga ctacccagga ttgcaactgt     540
tccatctatg tgggccacat caccggccac aggatggcc                            579
```

<210> SEQ ID NO 178
<211> LENGTH: 193
<212> TYPE: PRT
<213> ORGANISM: hepatitis C virus

<400> SEQUENCE: 178

Thr Cys Gly Phe Ala Asp Leu Met Gly Tyr Ile Pro Leu Val Gly Ala

```
              1               5                  10                 15
     Pro Val Gly Gly Val Ala Arg Ala Leu Ala His Gly Val Arg Ala Val
                      20                  25                  30

Glu Asp Gly Ile Asn Tyr Ala Thr Gly Asn Leu Pro Gly Cys Ser Phe
                      35                  40                  45

Ser Ile Phe Leu Leu Val Leu Leu Ser Arg Leu Thr Val Pro Ala Ser
                 50                  55                  60

Ala Gln His Tyr Arg Asn Ala Ser Gly Ile Tyr His Val Thr Asn Asp
     65                  70                  75                  80

Cys Pro Asn Ser Ser Ile Val Tyr Glu Ala Asp His His Ile Met His
                     85                  90                  95

Leu Pro Gly Cys Val Pro Cys Val Arg Thr Gly Asn Val Ser Arg Cys
                     100                 105                 110

Trp Ile Pro Leu Thr Pro Thr Val Ala Val Pro Tyr Leu Gly Ala Pro
                     115                 120                 125

Leu Thr Ser Val Arg Gln His Val Asp Leu Met Val Gly Ala Ala Thr
                     130                 135                 140

Leu Cys Ser Ala Leu Tyr Ile Gly Asp His Cys Gly Gly Val Phe Leu
     145                 150                 155                 160

Ala Gly Gln Met Val Ser Phe Gln Pro Arg Arg His Trp Thr Thr Gln
                     165                 170                 175

Asp Cys Asn Cys Ser Ile Tyr Val Gly His Ile Thr Gly His Arg Met
                     180                 185                 190

Ala

<210> SEQ ID NO 179
<211> LENGTH: 579
<212> TYPE: DNA
<213> ORGANISM: hepatitis C virus
<220> FEATURE:
<221> NAME/KEY: misc_feature
<222> LOCATION: (568)..(579)
<223> OTHER INFORMATION: "n" is any nucleotide

<400> SEQUENCE: 179
acctgcggct cgccgacct  catgggatac atcccgctcg taggcgcccc cgtgggaggc      60
gtcgccagar ctctggcgca tggcgtcagg gctctggaag acgggatcaa ttatgcaaca     120
gggaatcttc ctggttgctc tttctctatc tcccttcttg aacttctctc gtgcctgact     180
gttcccgcct cagccatcca ctatcgcaat gcttcggacg ttattatat  caccaatgat     240 tgcccgaact ctagcatagt gtatgaagcc gagaaccaca tcttgcacct tccggggtgt     300 atacctgtg  tgaagaccgg gaatcagtcg cggtgctggg tggctctcac ccccacgctg     360
gcggccccac acctacgtgc tccgctttcg tccttacggg cgcatgtgga cctaatggtg     420
ggggccgcca cggcatgctc cgcttttttac attggagatc tgtgcggggg tgtgtttttg     480
gcgggccaac tgttcactat ccggccacgc attcatgaaa ccactcagga ctgcaattgc     540
tccatctact cagggcacat cacgggtnnn nnnnnnnn                              579

<210> SEQ ID NO 180
<211> LENGTH: 193
<212> TYPE: PRT
<213> ORGANISM: hepatitis C virus
<220> FEATURE:
<221> NAME/KEY: MISC_FEATURE
<222> LOCATION: (24)..(24)
<223> OTHER INFORMATION: "Xaa" is any amino acid
<220> FEATURE:
```

-continued

```
<221> NAME/KEY: MISC_FEATURE
<222> LOCATION: (190)..(193)
<223> OTHER INFORMATION: "Xaa" is any amino acid

<400> SEQUENCE: 180
```

| Thr | Cys | Gly | Phe | Ala | Asp | Leu | Met | Gly | Tyr | Ile | Pro | Leu | Val | Gly | Ala |
|---|---|---|---|---|---|---|---|---|---|---|---|---|---|---|---|
| 1 | | | | 5 | | | | | 10 | | | | | 15 | |

| Pro | Val | Gly | Gly | Val | Ala | Arg | Xaa | Leu | Ala | His | Gly | Val | Arg | Ala | Leu |
|---|---|---|---|---|---|---|---|---|---|---|---|---|---|---|---|
| | | | 20 | | | | | 25 | | | | | 30 | | |

| Glu | Asp | Gly | Ile | Asn | Tyr | Ala | Thr | Gly | Asn | Leu | Pro | Gly | Cys | Ser | Phe |
|---|---|---|---|---|---|---|---|---|---|---|---|---|---|---|---|
| | | | 35 | | | | | 40 | | | | | 45 | | |

| Ser | Ile | Ser | Leu | Leu | Glu | Leu | Leu | Ser | Cys | Leu | Thr | Val | Pro | Ala | Ser |
|---|---|---|---|---|---|---|---|---|---|---|---|---|---|---|---|
| | 50 | | | | | 55 | | | | | 60 | | | | |

| Ala | Ile | His | Tyr | Arg | Asn | Ala | Ser | Asp | Gly | Tyr | Tyr | Ile | Thr | Asn | Asp |
|---|---|---|---|---|---|---|---|---|---|---|---|---|---|---|---|
| 65 | | | | | 70 | | | | | 75 | | | | | 80 |

| Cys | Pro | Asn | Ser | Ser | Ile | Val | Tyr | Glu | Ala | Glu | Asn | His | Ile | Leu | His |
|---|---|---|---|---|---|---|---|---|---|---|---|---|---|---|---|
| | | | | 85 | | | | | 90 | | | | | 95 | |

| Leu | Pro | Gly | Cys | Ile | Pro | Cys | Val | Lys | Thr | Gly | Asn | Gln | Ser | Arg | Cys |
|---|---|---|---|---|---|---|---|---|---|---|---|---|---|---|---|
| | | | 100 | | | | | 105 | | | | | 110 | | |

| Trp | Val | Ala | Leu | Thr | Pro | Thr | Leu | Ala | Ala | Pro | His | Leu | Arg | Ala | Pro |
|---|---|---|---|---|---|---|---|---|---|---|---|---|---|---|---|
| | | | 115 | | | | | 120 | | | | | 125 | | |

| Leu | Ser | Ser | Leu | Arg | Ala | His | Val | Asp | Leu | Met | Val | Gly | Ala | Ala | Thr |
|---|---|---|---|---|---|---|---|---|---|---|---|---|---|---|---|
| | 130 | | | | | 135 | | | | | 140 | | | | |

| Ala | Cys | Ser | Ala | Phe | Tyr | Ile | Gly | Asp | Leu | Cys | Gly | Gly | Val | Phe | Leu |
|---|---|---|---|---|---|---|---|---|---|---|---|---|---|---|---|
| 145 | | | | | 150 | | | | | 155 | | | | | 160 |

| Ala | Gly | Gln | Leu | Phe | Thr | Ile | Arg | Pro | Arg | Ile | His | Glu | Thr | Thr | Gln |
|---|---|---|---|---|---|---|---|---|---|---|---|---|---|---|---|
| | | | | 165 | | | | | 170 | | | | | 175 | |

| Asp | Cys | Asn | Cys | Ser | Ile | Tyr | Ser | Gly | His | Ile | Thr | Gly | Xaa | Xaa | Xaa |
|---|---|---|---|---|---|---|---|---|---|---|---|---|---|---|---|
| | | | 180 | | | | | 185 | | | | | 190 | | |

Xaa

```
<210> SEQ ID NO 181
<211> LENGTH: 579
<212> TYPE: DNA
<213> ORGANISM: hepatitis C virus
<220> FEATURE:
<221> NAME/KEY: misc_feature
<222> LOCATION: (152)..(152)
<223> OTHER INFORMATION: "n" is any nucleotide

<400> SEQUENCE: 181
gcgtgcggct tcgccgatct catgggatac atcccgctcg taggcgcccc cgtgggtggc      60
gtcgccagag ccctggcgca cggtgttagg gctgtggagg acgggattaa ctacgcaaca     120
gggaatcttc ctggttgctc tttctctatc tnccttctgg cacttctctc gtgcctgact     180
gtcccggcct cggctcagca ctaccggaat gtctcgggca tctaccacgt caccaatgat     240
tgcccgaatt ccagcatagt gtatgaagcc gatcaccaca tcatgcactt accagggtgc     300
ataccctgcg tgaggaccgg gaacgtttcg cgctgctggg tatctctgac acctactgtg     360
gctgctccct acctcggggc tccgcttacg tcgctacggc ggcatgtgga tttgatggtg     420
ggtgcagcca cccttttgctc tgccctctac gtcggagacc tctgtggagg tgtcttccta     480
gtgggacaga tgttcaccct tccagccgcg cgccactgga ccactcagga ctgcaactgc     540
tccatttacg tcggccacat cacaggccac agaatggct                            579

<210> SEQ ID NO 182
<211> LENGTH: 193
```

-continued

```
<212> TYPE: PRT
<213> ORGANISM: hepatitis C virus
<220> FEATURE:
<221> NAME/KEY: MISC_FEATURE
<222> LOCATION: (51)..(51)
<223> OTHER INFORMATION: "Xaa" is any amino acid

<400> SEQUENCE: 182

Ala Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Xaa Leu Leu Ala Leu Leu Ser Cys Leu Thr Val Pro Ala Ser
    50                  55                  60

Ala Gln His Tyr Arg Asn Val Ser Gly Ile Tyr His Val Thr Asn Asp
65                  70                  75                  80

Cys Pro Asn Ser Ser Ile Val Tyr Glu Ala Asp His Ile Met His
                85                  90                  95

Leu Pro Gly Cys Ile Pro Cys Val Arg Thr Gly Asn Val Ser Arg Cys
            100                 105                 110

Trp Val Ser Leu Thr Pro Thr Val Ala Ala Pro Tyr Leu Gly Ala Pro
        115                 120                 125

Leu Thr Ser Leu Arg Arg His Val Asp Leu Met Val Gly Ala Ala Thr
    130                 135                 140

Leu Cys Ser Ala Leu Tyr Val Gly Asp Leu Cys Gly Gly Val Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Val Gly His Ile Thr Gly His Arg Met
            180                 185                 190

Ala

<210> SEQ ID NO 183
<211> LENGTH: 579
<212> TYPE: DNA
<213> ORGANISM: hepatitis C virus

<400> SEQUENCE: 183
acctgcggct tgccgacct  catgggatac atcccgctcg taggcgcccc tgtgggtggc     60
gtcgccaggg ccctagaaca cggtgttagg gctgtggagg acggtattaa ttatgcaaca    120
gggaatctcc ccggttgctc tttttctatc tccctcttgg cacttctttc gtgcctgact    180
gttcccacct cagccgtcaa ctatcgcaac gcctcgggcg tctatcatat caccaatgac    240
tgcccgaatt cgagcatagt gtacgaggct gactaccaca tcctacacct ccctgggtgc    300
ttaccctgcg tgagggttgg gaatcagtca cgctgctggg tggcccttac tcccaccgtg    360
gcggcgcctt acgttggtgc tccgctagaa tccctccgga gtcatgtgga tctgatggta    420
ggtgctgcta ctgtgtgctc cgctctttac atcggggacc tgtgcggtgg cgtatttttg    480
gttggtcaga tgttttcttt ccagccgcga cgccactgga ccacgcagga ctgcaattgt    540
tctatctacg cggggcacgt tacgggccac aggatggca                           579

<210> SEQ ID NO 184
<211> LENGTH: 193
<212> TYPE: PRT
```

<213> ORGANISM: hepatitis C virus

<400> SEQUENCE: 184

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Phe Leu Leu Ala Leu Leu Ser Cys Leu Thr Val Pro Thr Ser
    50                  55                  60

Ala Val Asn Tyr Arg Asn Ala Ser Gly Ile Tyr His Ile Thr Asn Asp
65                  70                  75                  80

Cys Pro Asn Ala Ser Ile Val Tyr Glu Thr Glu Asn His Ile Leu His
                85                  90                  95

Leu Pro Gly Cys Val Pro Cys Val Arg Thr Gly Asn Gln Ser Arg Cys
            100                 105                 110

Trp Val Ala Leu Thr Pro Thr Val Ala Ser Pro Tyr Ala Gly Ala Pro
        115                 120                 125

Leu Glu Pro Leu Arg Arg His Val Asp Leu Met Val Gly Ala Ala Thr
    130                 135                 140

Met Cys Ser Ala Leu Tyr Ile Gly Asp Leu Cys Gly Gly Leu Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Thr Gly His Ile Thr Gly His Arg Met
            180                 185                 190

Ala

<210> SEQ ID NO 185
<211> LENGTH: 579
<212> TYPE: DNA
<213> ORGANISM: hepatitis C virus

<400> SEQUENCE: 185
acttgcggct tgccgacct catgggatac atcccgctcg taggcgcccc cgtgggtggc      60
gtcgccagag ccctggaaca tggtgttagg gctgtggagg acggcatcaa ttatgcaaca    120
gggaatctcc ccggttgctc tttctctatc tacctcttgg cacttctctc gtgcctgact    180
gttcccacct cggccatcca ctatcgcaat gcctcgggcg tctaccacgt caccaatgac    240
tgcccgaact cgagcatagt gtacgaggcc gaccaccaca tcctacacct tccagggtgc    300
ttaccctgtg tgagggttgg gaatcagtca cgttgttggg tggccctctc tccaccgtg     360 gcggcgcctt acatcggtgc tccagttgaa tccttccgga gacacgtgga catgatggtg    420
ggcgctgcta ctgtgtgctc cgctctctat attgggact tgtgtggtgg cgtattcttg     480
gttggtcaga tgttttcttt ccggccacga cgccactgga ctacgcagga ctgcaattgt    540
tccatctacg cggggcacat cactggccac ggaatggca                            579

<210> SEQ ID NO 186
<211> LENGTH: 193
<212> TYPE: PRT
<213> ORGANISM: hepatitis C virus

<400> SEQUENCE: 186

Thr Cys Gly Phe Ala Asp Leu Met Gly Tyr Ile Pro Leu Val Gly Ala

```
                 1               5                  10                 15
Pro Val Gly Gly Val Ala Arg Ala Leu Glu His Gly Val Arg Ala Val
                20                  25                 30

Glu Asp Gly Ile Asn Tyr Ala Thr Gly Asn Leu Pro Gly Cys Ser Phe
                35                  40                 45

Ser Ile Tyr Leu Leu Ala Leu Leu Ser Cys Leu Thr Val Pro Thr Ser
                50                  55                 60

Ala Ile His Tyr Arg Asn Ala Ser Gly Val Tyr His Val Thr Asn Asp
65                  70                  75                     80

Cys Pro Asn Ser Ser Ile Val Tyr Glu Ala Asp His His Ile Leu His
                85                  90                 95

Leu Pro Gly Cys Leu Pro Cys Val Arg Val Gly Asn Gln Ser Arg Cys
                100                 105                110

Trp Val Ala Leu Ser Pro Thr Val Ala Ala Pro Tyr Ile Gly Ala Pro
                115                 120                125

Val Glu Ser Phe Arg Arg His Val Asp Met Met Val Gly Ala Ala Thr
                130                 135                140

Val Cys Ser Ala Leu Tyr Ile Gly Asp Leu Cys Gly Gly Val Phe Leu
145                 150                 155                    160

Val Gly Gln Met Phe Ser Phe Arg Pro Arg Arg His Trp Thr Thr Gln
                165                 170                175

Asp Cys Asn Cys Ser Ile Tyr Ala Gly His Ile Thr Gly His Gly Met
                180                 185                190

Ala
```

<210> SEQ ID NO 187
<211> LENGTH: 579
<212> TYPE: DNA
<213> ORGANISM: hepatitis C virus

<400> SEQUENCE: 187

```
acttgcggct tgccgacct catgggatac atcccgctcg taggcgcccc tgtgggtggc      60
gtcgccaggg ccctggcaca cggtgttagg gctgtgagg acgggatcaa ttatgcgaca     120
gggaatcttc ccggttgctc tttctctatc ttcctcttgg cacttctttc gtgcctgact    180
gttcccacct cggccgtcaa ctatcgcaat gcctcgggca tctatcacat caccaatgac    240
tgcccgaact cgagcatagt gtacgagacc gagcaccaca tcctacacct cccagggtgt    300
ttaccctgcg tgagggttgg gaatcagtca cgctgctggg tggccctcac tcccaccgtg    360
gcggcgcctt acatcggcgc tccgcttgaa tccctccgga gtcatgtgga tctgatggta    420
ggtgccgcta ctgcgtgctc cgctctttac atcggagacc tgtgcggtgg cgtatttttg    480
gttggtcaga tgttctcttt ccagccgcgg cgccactgga ctacgcagga ctgcaattgt    540
tccatctacg cggggcacgt tacgggccac aggatggca                           579
```

<210> SEQ ID NO 188
<211> LENGTH: 193
<212> TYPE: PRT
<213> ORGANISM: hepatitis C virus

<400> SEQUENCE: 188

```
Thr Cys Gly Phe Ala Asp Leu Met Gly Tyr Ile Pro Leu Val Gly Ala
1               5                  10                 15

Pro Val Gly Gly Val Ala Arg Ala Leu Ala His Gly Val Arg Ala Val
                20                  25                 30
```

```
Glu Asp Gly Ile Asn Tyr Ala Thr Gly Asn Leu Pro Gly Cys Ser Phe
        35                  40                  45

Ser Ile Phe Leu Leu Ala Leu Leu Ser Cys Leu Thr Val Pro Thr Ser
 50                  55                  60

Ala Val Asn Tyr Arg Asn Ala Ser Gly Ile Tyr His Ile Thr Asn Asp
 65                  70                  75                  80

Cys Pro Asn Ser Ser Ile Val Tyr Glu Thr Glu His His Ile Leu His
                 85                  90                  95

Leu Pro Gly Cys Leu Pro Cys Val Arg Val Gly Asn Gln Ser Arg Cys
                100                 105                 110

Trp Val Ala Leu Thr Pro Thr Val Ala Ala Pro Tyr Ile Gly Ala Pro
            115                 120                 125

Leu Glu Ser Leu Arg Ser His Val Asp Leu Met Val Gly Ala Ala Thr
130                 135                 140

Ala Cys Ser Ala Leu Tyr Ile Gly Asp Leu Cys Gly Gly Val Phe Leu
145                 150                 155                 160

Val Gly Gln Met Phe Ser Phe Gln Pro Arg Arg His Trp Thr Thr Gln
                165                 170                 175

Asp Cys Asn Cys Ser Ile Tyr Ala Gly His Val Thr Gly His Arg Met
            180                 185                 190

Ala
```

<210> SEQ ID NO 189
<211> LENGTH: 579
<212> TYPE: DNA
<213> ORGANISM: hepatitis C virus

<400> SEQUENCE: 189

```
acgtgcggct tcgccgacct catgggatac atcccgctcg tgggcgcccc cgttgggggc      60
gtcgccaggg ccctggcgca tggcgtcagg gctgtggagg acgggattaa ctatgcgaca     120
gggaatcttc ccggttgctc tttctctatc ttcctcctgg cacttctttc gtgcctcact     180
gtcccagcgt cagctgagca ctaccggaat gcttcgggca tctatcacat caccaatgac     240
tgtccgaatt ccagcgtagt ctatgaaact gaccaccata tattgcactt gccggggtgc     300
gtaccctgcg tgagggccgg gaacgtgtct cgttgctgga cgccggtaac acctacggtg     360
gctgccgtat ccatggacgc tccgctcgag tccttccggc ggcatgtgga cctaatggta     420
ggtgcggcca ccgtgtgttc tgtcctctat gttggagacc tctgtggagg tgctttccta     480
gtggggcaga tgttcacctt ccagccgcgt cgccactgga ccacgcagga ttgtaattgc     540
tccatctata ctggccatat caccggccac aggatggcg                            579
```

<210> SEQ ID NO 190
<211> LENGTH: 193
<212> TYPE: PRT
<213> ORGANISM: hepatitis C virus

<400> SEQUENCE: 190

```
Thr Cys Gly Phe Ala Asp Leu Met Gly Tyr Ile Pro Leu Val Gly Ala
 1               5                  10                  15

Pro Val Gly Gly Val Ala Arg Ala Leu Ala His Gly Val Arg Ala Val
                 20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Ala Ser
 50                  55                  60
```

```
Ala Glu His Tyr Arg Asn Ala Ser Gly Ile Tyr His Ile Thr Asn Asp
 65                  70                  75                  80

Cys Pro Asn Ser Ser Val Val Tyr Glu Thr Asp His His Ile Leu His
                 85                  90                  95

Leu Pro Gly Cys Val Pro Cys Val Arg Ala Gly Asn Val Ser Arg Cys
            100                 105                 110

Trp Thr Pro Val Thr Pro Thr Val Ala Ala Val Ser Met Asp Ala Pro
        115                 120                 125

Leu Glu Ser Phe Arg Arg His Val Asp Leu Met Val Gly Ala Ala Thr
    130                 135                 140

Val Cys Ser Val Leu Tyr Val Gly Asp Leu Cys Gly Gly Ala Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Thr Gly His Ile Thr Gly His Arg Met
            180                 185                 190

Ala
```

<210> SEQ ID NO 191
<211> LENGTH: 289
<212> TYPE: DNA
<213> ORGANISM: hepatitis C virus

<400> SEQUENCE: 191

```
atgagcacga atcctaaacc tcaaagaaaa accaaacgta acaccaaccg ccgcccatg     60 gacgttaagt tcccgggcgg tggccagatc gttggtggag tttacttgtt gccgcgcagg   120
ggccccaggt tgggtgtgcg cgcgactagg aagacttcgg agcggtcgca acctcgtggg   180
agacgtcagc ctatccccaa ggcacgtcga tctgagggaa ggtcctgggc tcagcccggg   240
tacccatggc ctctttacgg taatgagggt tgtgggtggg caggatggg              289
```

<210> SEQ ID NO 192
<211> LENGTH: 96
<212> TYPE: PRT
<213> ORGANISM: hepatitis C virus

<400> SEQUENCE: 192

```
Met Ser Thr Asn Pro Lys Pro Gln Arg Lys Thr Lys Arg Asn Thr Asn
  1               5                  10                  15

Arg Arg Pro Met Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Arg Ser Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95
```

<210> SEQ ID NO 193
<211> LENGTH: 498
<212> TYPE: DNA
<213> ORGANISM: hepatitis C virus

<400> SEQUENCE: 193

-continued

```
atgagcacga atcctaaacc tcaaagaaaa accaaacgta acaccaaccg ccgccctatg      60
gacgtaaagt tcccgggcgg tggacagatc gttggcggag tttacttgtt gccgcgcagg     120
ggcccccggt tgggtgtgcg cgcgactcgg aagacttcgg agcggtcgca acctcgtggc     180
aggcgtcaac ctatccccaa ggcgcgccgg tccgagggca ggtcctgggc gcaagccggg     240 taccccctggc ccctctatgg caatgagggc tgtgggtggg cagggtggct cctgtctcct    300
cgcggctctc ggccatcttg gggcccaaat gatccccggc ggagatcgcg caatctgggt    360
aaggtcatcg ataccctgac gtgcggcttc gccgacctca tgggatacat cccgctcgtg    420
ggcgcccccg tcggggggcgt cgccagggcc ctggcgcatg gcgtcagggc tgtggaggac    480
gggattaact atcgacag                                                   498
```

<210> SEQ ID NO 194
<211> LENGTH: 166
<212> TYPE: PRT
<213> ORGANISM: hepatitis C virus

<400> SEQUENCE: 194

```
Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Ser Glu Gly Arg Ser Trp Ala Gln Ala Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Val Glu Asp
145                 150                 155                 160

Gly Ile Asn Tyr Arg Gln
                165
```

<210> SEQ ID NO 195
<211> LENGTH: 579
<212> TYPE: DNA
<213> ORGANISM: hepatitis C virus

<400> SEQUENCE: 195

```
acgtgcggat cgccgacct cgtggggtac atcccgctcg taggcggccc cgttgggggc      60
gtcgcaaggg ctctcgcaca tggtgtgagg gttcttgagg acggggtgaa ttatgcaaca    120
gggaatctgc ctggttgctc tttctctatc ttcattcttg cacttctctc gtgcctcact    180
gtcccggcct ctgcagttcc ctaccgaaat gcctctggga tctatcatgt caccaatgat    240
tgcccaaact cttccatagt ctatgaggca gatgatctga tcctacacgc acctggctgc    300
gtgccttgtg tcaggaaaga taatgtgagt agggtgctggg tccaaattac ccccacgctg    360
```

```
tcagccccga gcttcggagc agtcacggct ccccttcgga gagccgttga ttacttggtg    420 ggagggctg ccctctgctc cgcgttatac gttggagacg cgtgtggggc actattttg     480 gtaggccaaa tgttcaccta taggcctcgc cagcatgcta cggtgcagga ctgcaactgt    540
tccatctaca gtgccacgt caccggccat cagatggca                           579
```

<210> SEQ ID NO 196
<211> LENGTH: 193
<212> TYPE: PRT
<213> ORGANISM: hepatitis C virus

<400> SEQUENCE: 196

```
Thr Cys Gly Phe Ala Asp Leu Val Gly Tyr Ile Pro Leu Val Gly Gly
1               5                   10                  15

Pro Val Gly Gly Val Ala Arg Ala Leu Ala His Gly Val Arg Val Leu
            20                  25                  30

Glu Asp Gly Val Asn Tyr Ala Thr Gly Asn Leu Pro Gly Cys Ser Phe
        35                  40                  45

Ser Ile Phe Ile Leu Ala Leu Leu Ser Cys Leu Thr Val Pro Ala Ser
    50                  55                  60

Ala Val Pro Tyr Arg Asn Ala Ser Gly Ile Tyr His Val Thr Asn Asp
65                  70                  75                  80

Cys Pro Asn Ser Ser Ile Val Tyr Glu Ala Asp Asp Leu Ile Leu His
                85                  90                  95

Ala Pro Gly Cys Val Pro Cys Val Arg Lys Asp Asn Val Ser Arg Cys
            100                 105                 110

Trp Val Gln Ile Thr Pro Thr Leu Ser Ala Pro Ser Phe Gly Ala Val
        115                 120                 125

Thr Ala Pro Leu Arg Arg Ala Val Asp Tyr Leu Val Gly Gly Ala Ala
    130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asp Cys Asn Cys Ser Ile Tyr Ser Gly His Val Thr Gly His Gln Met
            180                 185                 190

Ala
```

<210> SEQ ID NO 197
<211> LENGTH: 1485
<212> TYPE: DNA
<213> ORGANISM: hepatitis C virus
<220> FEATURE:
<221> NAME/KEY: misc_feature
<222> LOCATION: (787)..(787)
<223> OTHER INFORMATION: "n" is any nucleotide
<220> FEATURE:
<221> NAME/KEY: misc_feature
<222> LOCATION: (1011)..(1011)
<223> OTHER INFORMATION: "n" is any nucleotide
<220> FEATURE:
<221> NAME/KEY: misc_feature
<222> LOCATION: (1444)..(1444)
<223> OTHER INFORMATION: "n" is any nucleotide

<400> SEQUENCE: 197

```
tgtgccagga ccatcaccac cggagcttct atcacatact ccacttacgg caagttcctt    60
gctgatggag ggtgttcagg cggcgcgcat gacgtgatca tatgcgacga gtgccattcc   120
caggacgcca ccaccattct tgggataggc actgtccttg accaggcaga gacggctgga   180
```

-continued

```
gctaggctcg tcgtcttggc cacggccacc cctcccggca gtgtgacaac gccccacccc    240
aacatcgagg aagtggccct gcctcaggag ggggaggttc ccttctacgg cagagccatt    300 cccttgctt ttataaaggg tggtaggcat ctcatcttct gccattccaa gaaaaaatgt    360
gatgaactcg ccaagcaact gaccagcctg ggcgtgaacg ccgtggcata ttatagaggt    420
ctagacgtcg ccgtcatacc cacaacagga gacgtggtcg tgtgcagcac cgacgcgctc    480
atgacgggat tcaccggcga cttgattct gtcatagact gcaactccgc cgtcactcag    540
acggtggact tcagtctgga tcccactttt accattgaga ctaccacagt gccccaggac    600
gcagtgtcca gaagccagcg ttggggccgc acggggagag gtaggcacgg catataccgg    660
tatgtctcgg ctggagagag accgtctggc atgttcgact ccgtggtgct ctgtgagtgc    720
tacgatgccg gatgtgcatg gtacgatctg actcctgccg agactaccgt gaggttgcgc    780
gcttacntaa acaccccgg gctccctgtc tgtcaggacc atttggaatt ctgggagggg    840
gtgttcacgg ggctcactaa catcgacgct cacatgctgt cacagaccaa acagggtggg    900
gagaatttcc catacctttgt agcgtaccaa gcaacagtct gtgttcgcgc gaaagcgccc    960 cccccagct gggacacaat gtggaaatgc atgctccgtc tcaaaccgac nttaactggc   1020
cctactcccc tcttgtacag gctggggccc gtccagaatg agatcacact gacgcacccc   1080
atcaccaagt acattatggc ttgcatgtct gcggacttgg aggtcattac cagcacttgg   1140
gttctggtgg ggggcgttgt ggcggccctg gcggcctact gcttgacggt gggttcggta   1200
gccatagtcg gtaggatcat cctctctggg aaacctgcca tcattcccga tagggaggta   1260
ttataccagc aatttgatga gatggaggag tgctcggcct cgttgcccta tatggacgaa   1320
acacgtgcca ttgccggaca attcaaagag aaagtgctcg gcttcatcag cacgaccggc   1380
cagaaggctg aaactctgaa gccggcagcc acgtctgtgt ggaacaaggc tgagcagttc   1440
tggnccacat acatgtggaa cttcatcagt gggatacaat aatag                   1485
```

<210> SEQ ID NO 198
<211> LENGTH: 484
<212> TYPE: PRT
<213> ORGANISM: hepatitis C virus
<220> FEATURE:
<221> NAME/KEY: MISC_FEATURE
<222> LOCATION: (263)..(263)
<223> OTHER INFORMATION: "Xaa" is any amino acid
<220> FEATURE:
<221> NAME/KEY: MISC_FEATURE
<222> LOCATION: (337)..(337)
<223> OTHER INFORMATION: "Xaa" is any amino acid
<220> FEATURE:
<221> NAME/KEY: MISC_FEATURE
<222> LOCATION: (482)..(482)
<223> OTHER INFORMATION: "Xaa" is any amino acid

<400> SEQUENCE: 198

```
Cys Ala Arg Thr Ile Thr Thr Gly Ala Ser Ile Thr Tyr Ser Thr Tyr
1               5                   10                  15

Gly Lys Phe Leu Ala Asp Gly Gly Cys Ser Gly Gly Ala His Asp Val
            20                  25                  30

Ile Ile Cys Asp Glu Cys His Ser Gln Asp Ala Thr Thr Ile Leu Gly
        35                  40                  45

Ile Gly Thr Val Leu Asp Gln Ala Glu Thr Ala Gly Ala Arg Leu Val
    50                  55                  60

Val Leu Ala Thr Ala Thr Pro Pro Gly Ser Val Thr Thr Pro His Pro
65                  70                  75                  80
```

-continued

```
Asn Ile Glu Glu Val Ala Leu Pro Gln Glu Gly Val Pro Phe Tyr
                85                  90                  95
Gly Arg Ala Ile Pro Leu Ala Phe Ile Lys Gly Gly Arg His Leu Ile
            100                 105                 110
Phe Cys His Ser Lys Lys Cys Asp Glu Leu Ala Lys Gln Leu Thr
        115                 120                 125
Ser Leu Gly Val Asn Ala Val Ala Tyr Tyr Arg Gly Leu Asp Val Ala
    130                 135                 140
Val Ile Pro Thr Thr Gly Asp Val Val Cys Ser Thr Asp Ala Leu
145                 150                 155                 160
Met Thr Gly Phe Thr Gly Asp Phe Asp Ser Val Ile Asp Cys Asn Ser
                165                 170                 175
Ala Val Thr Gln Thr Val Asp Phe Ser Leu Asp Pro Thr Phe Thr Ile
            180                 185                 190
Glu Thr Thr Thr Val Pro Gln Asp Ala Val Ser Arg Ser Gln Arg Trp
        195                 200                 205
Gly Arg Thr Gly Arg Gly Arg His Gly Ile Tyr Arg Tyr Val Ser Ala
    210                 215                 220
Gly Glu Arg Pro Ser Gly Met Phe Asp Ser Val Val Leu Cys Glu Cys
225                 230                 235                 240
Tyr Asp Ala Gly Cys Ala Trp Tyr Asp Leu Thr Pro Ala Glu Thr Thr
                245                 250                 255
Val Arg Leu Arg Ala Tyr Xaa Asn Thr Pro Gly Leu Pro Val Cys Gln
            260                 265                 270
Asp His Leu Glu Phe Trp Glu Gly Val Phe Thr Gly Leu Thr Asn Ile
        275                 280                 285
Asp Ala His Met Leu Ser Gln Thr Lys Gln Gly Gly Glu Asn Phe Pro
    290                 295                 300
Tyr Leu Val Ala Tyr Gln Ala Thr Val Cys Val Arg Ala Lys Ala Pro
305                 310                 315                 320
Pro Pro Ser Trp Asp Thr Met Trp Lys Cys Met Leu Arg Leu Lys Pro
                325                 330                 335
Xaa Leu Thr Gly Pro Thr Pro Leu Leu Tyr Arg Leu Gly Pro Val Gln
            340                 345                 350
Asn Glu Ile Thr Leu Thr His Pro Ile Thr Lys Tyr Ile Met Ala Cys
        355                 360                 365
Met Ser Ala Asp Leu Glu Val Ile Thr Ser Thr Trp Val Leu Val Gly
    370                 375                 380
Gly Val Val Ala Ala Leu Ala Ala Tyr Cys Leu Thr Val Gly Ser Val
385                 390                 395                 400
Ala Ile Val Gly Arg Ile Ile Leu Ser Gly Lys Pro Ala Ile Ile Pro
                405                 410                 415
Asp Arg Glu Val Leu Tyr Gln Gln Phe Asp Glu Met Glu Glu Cys Ser
            420                 425                 430
Ala Ser Leu Pro Tyr Met Asp Glu Thr Arg Ala Ile Ala Gly Gln Phe
        435                 440                 445
Lys Glu Lys Val Leu Gly Phe Ile Ser Thr Thr Gly Gln Lys Ala Glu
    450                 455                 460
Thr Leu Lys Pro Ala Ala Thr Ser Val Trp Asn Lys Ala Glu Gln Phe
465                 470                 475                 480
Trp Xaa Thr Tyr
```

```
<210> SEQ ID NO 199
<211> LENGTH: 1485
<212> TYPE: DNA
<213> ORGANISM: hepatitis C virus
<220> FEATURE:
<221> NAME/KEY: misc_feature
<222> LOCATION: (684)..(684)
<223> OTHER INFORMATION: "n" is any nucleotide
<220> FEATURE:
<221> NAME/KEY: misc_feature
<222> LOCATION: (909)..(909)
<223> OTHER INFORMATION: "n" is any nucleotide
<220> FEATURE:
<221> NAME/KEY: misc_feature
<222> LOCATION: (1058)..(1058)
<223> OTHER INFORMATION: "n" is any nucleotide
<220> FEATURE:
<221> NAME/KEY: misc_feature
<222> LOCATION: (1133)..(1133)
<223> OTHER INFORMATION: "n" is any nucleotide

<400> SEQUENCE: 199
tgtgccagga ccatcaccac cggagcttct atcacatact ccacttacgg caagttcctt      60
gctgatggag ggtgttcagg cggcgcgtat gacgtgatca tatgcgacga gtgccattcc     120
caggacgcca ccaccattct tgggataggc actgtccttg accaggcaga gacggctgga     180
gctaggctcg tcgtcttggc cacggccacc cctcccggca gtgtgacaac gccccacccc     240
aacatcgagg aagtggccct gcctcaggag ggggaggttc ccttctacgg cagagccatt     300
ccccttgctt ttataaaggg tggtaggcat ctcatcttct gccattccaa gaaaaaatgt     360
gatgaactcg ccaagcaact gaccagcctg gcgtgaacg ccgtggcata ttatagaggt      420
ctagacgtcg ccgtcatccc cacagcagga gacgtggtcg tgtgcagcac cgacgcgctc     480
atgacgggat tcaccggcga ctttgattct gtcatagact gcaactccgc cgtcactcag     540
acggtggact tcagtctgga tcccactttt accattgaga ctaccacagt gccccaggac     600
gcagtgtcca gaagccagcg taggggccgc acggggagag gtaggcacgg catataccgg     660
tatgtctcgg ctggagagag accntctgac atgttcgact ccgtggtgct ctgtgagtgc     720
tacgatgccg gatgtgcgtg gtatgatctg actcctgccg agactaccgt gaggttgcgc     780
gcttacataa acacccccgg gctccctgtc tgtcaggacc atttggaatt ctgggagggg     840
gtgttcacgg ggctcactaa catcgacgct cacatgctgt cacagaccaa acagggtggg     900
gagaatttnc ataccttgt agcgtaccaa gcaacagtct gtgttcgcgc gaaagcgccc      960
ccccccagct gggacacaat gtggaaatgc atgctccgtc tcaaaccgac tttaactggc    1020
cctactcccc tcttgtacag gctggggccc gtccagantg agatcacact gacgcaccc     1080 atcaccaagt acattatggc ttgcatgtct gcggacttgg aggtcattac cancacttgg    1140
gttctggtgg gggcgttgt ggcggccctg gcggcctact gcttgacggt gggttcggta    1200
gccatagtcg gtaggatcat cctctctggg aaacctgcca tcattcccga taggaggca    1260 ttataccagc aatttgatga gatggaggag tgctcggcct cgttgcccta tatggacgag    1320
acacgtgcca ttgccggaca attcaaagag aaagtgctcg gcttcatcag cacgaccggc    1380
cagaaggctg aaactctgaa gccggcagcc acgtctgtgt ggaacaaggc tgagcagttc    1440
tgggccacat acatgtggaa cttcatcagc gggatacaat aatag                    1485

<210> SEQ ID NO 200
<211> LENGTH: 484
<212> TYPE: PRT
<213> ORGANISM: hepatitis C virus
<220> FEATURE:
```

```
<221> NAME/KEY: MISC_FEATURE
<222> LOCATION: (228)..(228)
<223> OTHER INFORMATION: "Xaa" is any amino acid
<220> FEATURE:
<221> NAME/KEY: MISC_FEATURE
<222> LOCATION: (303)..(303)
<223> OTHER INFORMATION: "Xaa" is any amino acid
<220> FEATURE:
<221> NAME/KEY: MISC_FEATURE
<222> LOCATION: (353)..(353)
<223> OTHER INFORMATION: "Xaa" is any amino acid
<220> FEATURE:
<221> NAME/KEY: MISC_FEATURE
<222> LOCATION: (378)..(378)
<223> OTHER INFORMATION: "Xaa" is any amino acid

<400> SEQUENCE: 200

Cys Ala Arg Thr Ile Thr Thr Gly Ala Ser Ile Thr Tyr Ser Thr Tyr
  1               5                  10                  15

Gly Lys Phe Leu Ala Asp Gly Gly Cys Ser Gly Gly Ala Tyr Asp Val
             20                  25                  30

Ile Ile Cys Asp Glu Cys His Ser Gln Asp Ala Thr Thr Ile Leu Gly
         35                  40                  45

Ile Gly Thr Val Leu Asp Gln Ala Glu Thr Ala Gly Ala Arg Leu Val
 50                  55                  60

Val Leu Ala Thr Ala Thr Pro Pro Gly Ser Val Thr Thr Pro His Pro
 65                  70                  75                  80

Asn Ile Glu Glu Val Ala Leu Pro Gln Glu Gly Glu Val Pro Phe Tyr
                 85                  90                  95

Gly Arg Ala Ile Pro Leu Ala Phe Ile Lys Gly Gly Arg His Leu Ile
            100                 105                 110

Phe Cys His Ser Lys Lys Lys Cys Asp Glu Leu Ala Lys Gln Leu Thr
        115                 120                 125

Ser Leu Gly Val Asn Ala Val Ala Tyr Tyr Arg Gly Leu Asp Val Ala
130                 135                 140

Val Ile Pro Thr Ala Gly Asp Val Val Cys Ser Thr Asp Ala Leu
145                 150                 155                 160

Met Thr Gly Phe Thr Gly Asp Phe Asp Ser Val Ile Asp Cys Asn Ser
                165                 170                 175

Ala Val Thr Gln Thr Val Asp Phe Ser Leu Asp Pro Thr Phe Thr Ile
            180                 185                 190

Glu Thr Thr Thr Val Pro Gln Asp Ala Val Ser Arg Ser Gln Arg Arg
        195                 200                 205

Gly Arg Thr Gly Arg Gly His Gly Ile Tyr Arg Tyr Val Ser Ala
210                 215                 220

Gly Glu Arg Xaa Ser Asp Met Phe Asp Ser Val Val Leu Cys Glu Cys
225                 230                 235                 240

Tyr Asp Ala Gly Cys Ala Trp Tyr Asp Leu Thr Pro Ala Glu Thr Thr
                245                 250                 255

Val Arg Leu Arg Ala Tyr Ile Asn Thr Pro Gly Leu Pro Val Cys Gln
            260                 265                 270

Asp His Leu Glu Phe Trp Glu Gly Val Phe Thr Gly Leu Thr Asn Ile
        275                 280                 285

Asp Ala His Met Leu Ser Gln Thr Lys Gln Gly Glu Asn Xaa Pro
    290                 295                 300

Tyr Leu Val Ala Tyr Gln Ala Thr Val Cys Val Arg Ala Lys Ala Pro
305                 310                 315                 320

Pro Pro Ser Trp Asp Thr Met Trp Lys Cys Met Leu Arg Leu Lys Pro
```

-continued

```
                         325                 330                 335
Thr Leu Thr Gly Pro Thr Pro Leu Leu Tyr Arg Leu Gly Pro Val Gln
            340                 345                 350

Xaa Glu Ile Thr Leu Thr His Pro Ile Thr Lys Tyr Ile Met Ala Cys
        355                 360                 365

Met Ser Ala Asp Leu Glu Val Ile Thr Xaa Thr Trp Val Leu Val Gly
    370                 375                 380

Gly Val Val Ala Ala Leu Ala Ala Tyr Cys Leu Thr Val Gly Ser Val
385                 390                 395                 400

Ala Ile Val Gly Arg Ile Ile Leu Ser Gly Lys Pro Ala Ile Ile Pro
                405                 410                 415

Asp Arg Glu Ala Leu Tyr Gln Gln Phe Asp Glu Met Glu Glu Cys Ser
            420                 425                 430

Ala Ser Leu Pro Tyr Met Asp Glu Thr Arg Ala Ile Ala Gly Gln Phe
        435                 440                 445

Lys Glu Lys Val Leu Gly Phe Ile Ser Thr Thr Gly Gln Lys Ala Glu
    450                 455                 460

Thr Leu Lys Pro Ala Ala Thr Ser Val Trp Asn Lys Ala Glu Gln Phe
465                 470                 475                 480

Trp Ala Thr Tyr
```

```
<210> SEQ ID NO 201
<211> LENGTH: 340
<212> TYPE: DNA
<213> ORGANISM: hepatitis C virus

<400> SEQUENCE: 201
ctccactgtg actgagagag acatcagggt cgaagaagaa gtctatcagt gttgtgatct    60
ggagcccgag gcccgcaagg taataaccgc cctcacggag agactctacg tgggcggccc   120
tatgtacaat agcaagggag acctttgcgg gtatcgcagg tgccgcgcaa gcggcgtata   180
taccaccagc ttcgggaaca cactgacgtg ctaccttaaa gcctcagcag ccatcagggc   240
tgcggggctg aaggactgca ccatgctggt ttgcggtgac gacttagtcg tgatcgctga   300
aagcggtggc gtcgaggagg acaagcgagc cctcggagct                         340
```

```
<210> SEQ ID NO 202
<211> LENGTH: 113
<212> TYPE: PRT
<213> ORGANISM: hepatitis C virus

<400> SEQUENCE: 202

Ser Thr Val Thr Glu Arg Asp Ile Arg Val Glu Glu Val Tyr Gln
1               5                   10                  15

Cys Cys Asp Leu Glu Pro Glu Ala Arg Lys Val Ile Thr Ala Leu Thr
            20                  25                  30

Glu Arg Leu Tyr Val Gly Gly Pro Met Tyr Asn Ser Lys Gly Asp Leu
        35                  40                  45

Cys Gly Tyr Arg Arg Cys Arg Ala Ser Gly Val Tyr Thr Thr Ser Phe
    50                  55                  60

Gly Asn Thr Leu Thr Cys Tyr Leu Lys Ala Ser Ala Ala Ile Arg Ala
65                  70                  75                  80

Ala Gly Leu Lys Asp Cys Thr Met Leu Val Cys Gly Asp Asp Leu Val
            85                  90                  95

Val Ile Ala Glu Ser Gly Gly Val Glu Glu Asp Lys Arg Ala Leu Gly
        100                 105                 110
```

<210> SEQ ID NO 203
<211> LENGTH: 340
<212> TYPE: DNA
<213> ORGANISM: hepatitis C virus

<400> SEQUENCE: 203

```
ctccacagtg actgaaagag acatcagggt cgaggaagag gtctaccagt gttgtgacct    60
ggagcctgaa acccgcaagg taatatctgc cctcactgaa agactctatg tgggcggtcc   120
catgcacaac agcaggggag acctatgcgg gtaccgtaga tgccgcgcga gcggcgtata   180
caccacaagc ttcgggaaca ctctgacgtg cttcctcaag gccacagcgg ccaccaaagc   240
cgctggccta aaggactgca ccatgttggt gtgtggtgac gacttagtcg ttatcgccga   300
aagcgatggt gtcgaagagg accgccgagc cctcggagct                         340
```

<210> SEQ ID NO 204
<211> LENGTH: 113
<212> TYPE: PRT
<213> ORGANISM: hepatitis C virus

<400> SEQUENCE: 204

```
Ser Thr Val Thr Glu Arg Asp Ile Arg Val Glu Glu Val Tyr Gln
  1               5                  10                  15

Cys Cys Asp Leu Glu Pro Glu Thr Arg Lys Val Ile Ser Ala Leu Thr
             20                  25                  30

Glu Arg Leu Tyr Val Gly Gly Pro Met His Asn Ser Arg Gly Asp Leu
         35                  40                  45

Cys Gly Tyr Arg Arg Cys Arg Ala Ser Gly Val Tyr Thr Thr Ser Phe
     50                  55                  60

Gly Asn Thr Leu Thr Cys Phe Leu Lys Ala Thr Ala Ala Thr Lys Ala
 65                  70                  75                  80

Ala Gly Leu Lys Asp Cys Thr Met Leu Val Cys Gly Asp Asp Leu Val
                 85                  90                  95

Val Ile Ala Glu Ser Asp Gly Val Glu Glu Asp Arg Arg Ala Leu Gly
            100                 105                 110

Ala
```

<210> SEQ ID NO 205
<211> LENGTH: 340
<212> TYPE: DNA
<213> ORGANISM: hepatitis C virus

<400> SEQUENCE: 205

```
ctccacggtg accgaaaggg atatcaggac cgaggaagag atctaccagt gctgcgacct    60
ggagcccgaa gcccgcaagg tgatatccgc cctaacggaa agactctacg tgggcggtcc   120
catgtacaac tccaaggggg acctatgcgg gcaacggagg tgccgcgcaa gcggggtcta   180
caccaccagc ttcgggaaca ctgtaacgtg ttatctcaag gccgttgcgg ctactagggc   240
cgcaggtctg aaaggttgca gcatgctggt ttgtggagac gacttagtcg tcatctgcga   300
gagcggcggc gtagaggagg atgcaagagc cctccgagcc                         340
```

<210> SEQ ID NO 206
<211> LENGTH: 113
<212> TYPE: PRT
<213> ORGANISM: hepatitis C virus

```
<400> SEQUENCE: 206

Ser Thr Val Thr Glu Arg Asp Ile Arg Thr Glu Glu Ile Tyr Gln
1               5                   10                  15

Cys Cys Asp Leu Glu Pro Glu Ala Arg Lys Val Ile Ser Ala Leu Thr
                20                  25                  30

Glu Arg Leu Tyr Val Gly Gly Pro Met Tyr Asn Ser Lys Gly Asp Leu
            35                  40                  45

Cys Gly Gln Arg Arg Cys Arg Ala Ser Gly Val Tyr Thr Thr Ser Phe
        50                  55                  60

Gly Asn Thr Val Thr Cys Tyr Leu Lys Ala Val Ala Ala Thr Arg Ala
65                  70                  75                  80

Ala Gly Leu Lys Gly Cys Ser Met Leu Val Cys Gly Asp Asp Leu Val
                85                  90                  95

Val Ile Cys Glu Ser Gly Gly Val Glu Glu Asp Ala Arg Ala Leu Arg
            100                 105                 110

Ala

<210> SEQ ID NO 207
<211> LENGTH: 340
<212> TYPE: DNA
<213> ORGANISM: hepatitis C virus

<400> SEQUENCE: 207
ctccacggtg actgaaaggg acattagggt cgaggaagag atctaccagt gctgtgacct      60
ggagcccgag gcacgcaagg tgatatccgc tctcacagaa agactctaca agggcggccc    120
catgtataac agcaagggggg acctatgcgg gcttcgagg tgccgcgcaa gcggggtata   180
caccacaagc ttcgggaaca cggtgacatg ctaccttaaa gccacagcag ccaccagggc   240
tgcagggctg aaagattgca ctatgctggt atgcggtgac gacttagtcg ttattgccga   300
aagcggtggc gtggaggagg acgcccgagc cctccgagcc                         340

<210> SEQ ID NO 208
<211> LENGTH: 113
<212> TYPE: PRT
<213> ORGANISM: hepatitis C virus

<400> SEQUENCE: 208

Ser Thr Val Thr Glu Arg Asp Ile Arg Val Glu Glu Ile Tyr Gln
1               5                   10                  15

Cys Cys Asp Leu Glu Pro Glu Ala Arg Lys Val Ile Ser Ala Leu Thr
                20                  25                  30

Glu Arg Leu Tyr Lys Gly Gly Pro Met Tyr Asn Ser Lys Gly Asp Leu
            35                  40                  45

Cys Gly Leu Arg Arg Cys Arg Ala Ser Gly Val Tyr Thr Thr Ser Phe
        50                  55                  60

Gly Asn Thr Val Thr Cys Tyr Leu Lys Ala Thr Ala Ala Thr Arg Ala
65                  70                  75                  80

Ala Gly Leu Lys Asp Cys Thr Met Leu Val Cys Gly Asp Asp Leu Val
                85                  90                  95

Val Ile Ala Glu Ser Gly Gly Val Glu Glu Asp Ala Arg Ala Leu Arg
            100                 105                 110

Ala

<210> SEQ ID NO 209
```

-continued

```
<211> LENGTH: 340
<212> TYPE: DNA
<213> ORGANISM: hepatitis C virus
<220> FEATURE:
<221> NAME/KEY: misc_feature
<222> LOCATION: (13)..(13)
<223> OTHER INFORMATION: "n" is any nucleotide
<220> FEATURE:
<221> NAME/KEY: misc_feature
<222> LOCATION: (23)..(23)
<223> OTHER INFORMATION: "n" is any nucleotide
<220> FEATURE:
<221> NAME/KEY: misc_feature
<222> LOCATION: (65)..(65)
<223> OTHER INFORMATION: "n" is any nucleotide
<220> FEATURE:
<221> NAME/KEY: misc_feature
<222> LOCATION: (72)..(72)
<223> OTHER INFORMATION: "n" is any nucleotide
<220> FEATURE:
<221> NAME/KEY: misc_feature
<222> LOCATION: (277)..(277)
<223> OTHER INFORMATION: "n" is any nucleotide
<220> FEATURE:
<221> NAME/KEY: misc_feature
<222> LOCATION: (337)..(337)
<223> OTHER INFORMATION: "n" is any nucleotide

<400> SEQUENCE: 209
ccccaccgtg acngagaggg acntcagggt cgaggaagag gtctatcagt gctgtaatct      60
ggagnccgat gnccgcaagg tcatcaacgc cctcacagag agactctacg tgggcggccc    120
tatgcacaac agcaagggag acctgtgtgg catccgtaga tgccgcgcga gcggcgttta    180
caccacgagc ttcggaaaca cgctgacttg ctacctcaaa gccacagcgg ccaccagggc    240
cgcgggcttg aaggattgca ccatgctggt ctgcggngac gacctggttg tcattgctga    300
gagcattggc atagacgagg acaagcaagc cctccgnact                           340

<210> SEQ ID NO 210
<211> LENGTH: 113
<212> TYPE: PRT
<213> ORGANISM: hepatitis C virus
<220> FEATURE:
<221> NAME/KEY: MISC_FEATURE
<222> LOCATION: (8)..(8)
<223> OTHER INFORMATION: "Xaa" is any amino acid
<220> FEATURE:
<221> NAME/KEY: MISC_FEATURE
<222> LOCATION: (22)..(22)
<223> OTHER INFORMATION: "Xaa" is any amino acid
<220> FEATURE:
<221> NAME/KEY: MISC_FEATURE
<222> LOCATION: (24)..(24)
<223> OTHER INFORMATION: "Xaa" is any amino acid

<400> SEQUENCE: 210

Pro Thr Val Thr Glu Arg Asp Xaa Arg Val Glu Glu Val Tyr Gln
1               5                   10                  15

Cys Cys Asn Leu Glu Xaa Asp Xaa Arg Lys Val Ile Asn Ala Leu Thr
            20                  25                  30

Glu Arg Leu Tyr Val Gly Gly Pro Met His Asn Ser Lys Gly Asp Leu
        35                  40                  45

Cys Gly Ile Arg Arg Cys Arg Ala Ser Gly Val Tyr Thr Thr Ser Phe
    50                  55                  60

Gly Asn Thr Leu Thr Cys Tyr Leu Lys Ala Thr Ala Thr Arg Ala
65                  70                  75                  80

Ala Gly Leu Lys Asp Cys Thr Met Leu Val Cys Gly Asp Asp Leu Val
                85                  90                  95
```

```
Val Ile Ala Glu Ser Ile Gly Ile Asp Glu Asp Lys Gln Ala Leu Arg
            100                 105                 110

Thr

<210> SEQ ID NO 211
<211> LENGTH: 340
<212> TYPE: DNA
<213> ORGANISM: hepatitis C virus
<220> FEATURE:
<221> NAME/KEY: misc_feature
<222> LOCATION: (11)..(11)
<223> OTHER INFORMATION: "n" is any nucleotide
<220> FEATURE:
<221> NAME/KEY: misc_feature
<222> LOCATION: (327)..(327)
<223> OTHER INFORMATION: "n" is any nucleotide
<220> FEATURE:
<221> NAME/KEY: misc_feature
<222> LOCATION: (333)..(334)
<223> OTHER INFORMATION: "n" is any nucleotide
<220> FEATURE:
<221> NAME/KEY: misc_feature
<222> LOCATION: (340)..(340)
<223> OTHER INFORMATION: "n" is any nucleotide

<400> SEQUENCE: 211
ctcgactgtg nccgagaggg acatcaggac agagggagag gtctatcagt gttgcgacct      60
ggaaccggaa gcccgcaagg taatcaccgc cctcactgag agactctatg tgggcggacc     120
catgttcaac agcaagggag acctgtgcgg acaacgccgg tgccgcgcaa gcggcgtgtt     180
caccaccagc ttcgggaaca cactgacgtg ctaccttaaa gccacagctg ctactagagc     240
agccggctta aaagattgca ccatgctggt ctgcggtgac gacttagtcg ttatttccga     300
gagcgccggt gtggaggagg atcccanaac ccnncgaccn                           340

<210> SEQ ID NO 212
<211> LENGTH: 113
<212> TYPE: PRT
<213> ORGANISM: hepatitis C virus
<220> FEATURE:
<221> NAME/KEY: MISC_FEATURE
<222> LOCATION: (4)..(4)
<223> OTHER INFORMATION: "Xaa" is any amino acid
<220> FEATURE:
<221> NAME/KEY: MISC_FEATURE
<222> LOCATION: (109)..(109)
<223> OTHER INFORMATION: "Xaa" is any amino acid
<220> FEATURE:
<221> NAME/KEY: MISC_FEATURE
<222> LOCATION: (111)..(111)
<223> OTHER INFORMATION: "Xaa" is any amino acid

<400> SEQUENCE: 212

Ser Thr Val Xaa Glu Arg Asp Ile Arg Thr Glu Gly Glu Val Tyr Gln
1               5                   10                  15

Cys Cys Asp Leu Glu Pro Glu Ala Arg Lys Val Ile Thr Ala Leu Thr
                20                  25                  30

Glu Arg Leu Tyr Val Gly Gly Pro Met Phe Asn Ser Lys Gly Asp Leu
            35                  40                  45

Cys Gly Gln Arg Arg Cys Arg Ala Ser Gly Val Phe Thr Thr Ser Phe
        50                  55                  60

Gly Asn Thr Leu Thr Cys Tyr Leu Lys Ala Thr Ala Ala Thr Arg Ala
65                  70                  75                  80

Ala Gly Leu Lys Asp Cys Thr Met Leu Val Cys Gly Asp Asp Leu Val
                85                  90                  95
```

Val Ile Ser Glu Ser Ala Gly Val Glu Glu Asp Pro Xaa Thr Xaa Arg
            100                 105                 110
Pro

<210> SEQ ID NO 213
<211> LENGTH: 340
<212> TYPE: DNA
<213> ORGANISM: hepatitis C virus

<400> SEQUENCE: 213
ctcaacagtc accgagaacg acatccgtgt tgaggagtca atttaccaat gttgtgactt      60
ggcccccgag gccagacagg ccataaagtc gctcacagag cggctttata tcggggtcc     120 cctgactaat tcaaaggggc agaactgtgg ctatcgccga tgccgcgcaa gcggcgtgct    180
gacgaccagc tgcggtaata cccttacatg ttacctaaag gcctctgcag cctgtcgagc    240
tgcgaagctc caggactgca cgatgctcgt gtgcggggac gaccttgtcg ttatctgtga    300
aagcgcggga acccaagagg acgcggcgag cctacgagtc                          340

<210> SEQ ID NO 214
<211> LENGTH: 113
<212> TYPE: PRT
<213> ORGANISM: hepatitis C virus

<400> SEQUENCE: 214

Ser Thr Val Thr Glu Asn Asp Ile Arg Val Glu Glu Ser Ile Tyr Gln
1               5                   10                  15

Cys Cys Asp Leu Ala Pro Glu Ala Arg Gln Ala Ile Lys Ser Leu Thr
            20                  25                  30

Glu Arg Leu Tyr Ile Gly Gly Pro Leu Thr Asn Ser Lys Gly Gln Asn
        35                  40                  45

Cys Gly Tyr Arg Arg Cys Arg Ala Ser Gly Val Leu Thr Thr Ser Cys
    50                  55                  60

Gly Asn Thr Leu Thr Cys Tyr Leu Lys Ala Ser Ala Ala Cys Arg Ala
65                  70                  75                  80

Ala Lys Leu Gln Asp Cys Thr Met Leu Val Cys Gly Asp Asp Leu Val
                85                  90                  95

Val Ile Cys Glu Ser Ala Gly Thr Gln Glu Asp Ala Ala Ser Leu Arg
            100                 105                 110

Val

<210> SEQ ID NO 215
<211> LENGTH: 340
<212> TYPE: DNA
<213> ORGANISM: hepatitis C virus

<400> SEQUENCE: 215
ctcaaccgtc acggagaggg atataagaac agaagaatcc atatatcaag cttgttccct      60
gccccaagag gccagaactg tcatacactc gctcaccgag agactctacg tgggagggcc     120
catgataaac agcaaagggc aatcctgcgg ttacaggcgt tgccgcgcaa gcggtgtttt     180
caccaccagc atggggaata ccatgacgtg ttacatcaaa gcccttgcag cgtgtaaagc     240
cgcagggatc gtggaccccg tcatgctggt gtgtggagac gacctggtcg tcatctcgga     300
gagccagggt aacgaggagg acgagcgaaa cctgagagct                          340

<210> SEQ ID NO 216

```
<211> LENGTH: 113
<212> TYPE: PRT
<213> ORGANISM: hepatitis C virus

<400> SEQUENCE: 216

Ser Thr Val Thr Glu Arg Asp Ile Arg Thr Glu Glu Ser Ile Tyr Gln
1               5                   10                  15

Ala Cys Ser Leu Pro Gln Glu Ala Arg Thr Val Ile His Ser Leu Thr
            20                  25                  30

Glu Arg Leu Tyr Val Gly Gly Pro Met Ile Asn Ser Lys Gly Gln Ser
        35                  40                  45

Cys Gly Tyr Arg Arg Cys Arg Ala Ser Gly Val Phe Thr Thr Ser Met
    50                  55                  60

Gly Asn Thr Met Thr Cys Tyr Ile Lys Ala Leu Ala Ala Cys Lys Ala
65                  70                  75                  80

Ala Gly Ile Val Asp Pro Val Met Leu Val Cys Gly Asp Asp Leu Val
                85                  90                  95

Val Ile Ser Glu Ser Gln Gly Asn Glu Glu Asp Glu Arg Asn Leu Arg
            100                 105                 110

Ala

<210> SEQ ID NO 217
<211> LENGTH: 340
<212> TYPE: DNA
<213> ORGANISM: hepatitis C virus

<400> SEQUENCE: 217
ctcgactgtc actgaacagg acatcagggt ggaagaggag atatatcaat gctgcaacct      60
tgaaccggag gccaggaaag tgatctcctc cctcacggag cggctttact gcggaggccc     120
tatgtttaac agcaagggg cccagtgtgg ttatcgccgt tgccgtgcca gtggagttct     180
gcctaccagc tttggcaaca caatcacttg ttacatcaag gccacaacgg ccgcgaaggc     240
cgcaggcctc cggaacccgg actttcttgt ctgcggagat gatctggtcg tggtggctga     300
gagtgatggc gtcgacgagg atagagcagc cctgagagcc                           340

<210> SEQ ID NO 218
<211> LENGTH: 113
<212> TYPE: PRT
<213> ORGANISM: hepatitis C virus

<400> SEQUENCE: 218

Ser Thr Val Thr Glu Gln Asp Ile Arg Val Glu Glu Ile Tyr Gln
1               5                   10                  15

Cys Cys Asn Leu Glu Pro Glu Ala Arg Lys Val Ile Ser Ser Leu Thr
            20                  25                  30

Glu Arg Leu Tyr Cys Gly Gly Pro Met Phe Asn Ser Lys Gly Ala Gln
        35                  40                  45

Cys Gly Tyr Arg Arg Cys Arg Ala Ser Gly Val Leu Pro Thr Ser Phe
    50                  55                  60

Gly Asn Thr Ile Thr Cys Tyr Ile Lys Ala Thr Ala Ala Lys Ala
65                  70                  75                  80

Ala Gly Leu Arg Asn Pro Asp Phe Leu Val Cys Gly Asp Asp Leu Val
                85                  90                  95

Val Val Ala Glu Ser Asp Gly Val Asp Glu Asp Arg Ala Ala Leu Arg
            100                 105                 110

Ala
```

```
<210> SEQ ID NO 219
<211> LENGTH: 10
<212> TYPE: PRT
<213> ORGANISM: hepatitis C virus

<400> SEQUENCE: 219

Arg Ser Glu Gly Arg Thr Ser Trp Ala Gln
1               5                   10

<210> SEQ ID NO 220
<211> LENGTH: 10
<212> TYPE: PRT
<213> ORGANISM: hepatitis C virus

<400> SEQUENCE: 220

Arg Ser Glu Gly Arg Thr Ser Trp Ala Gln
1               5                   10

<210> SEQ ID NO 221
<211> LENGTH: 10
<212> TYPE: PRT
<213> ORGANISM: hepatitis C virus

<400> SEQUENCE: 221

Arg Thr Glu Gly Arg Thr Ser Trp Ala Gln
1               5                   10

<210> SEQ ID NO 222
<211> LENGTH: 629
<212> TYPE: DNA
<213> ORGANISM: hepatitis C virus

<400> SEQUENCE: 222 tagactttg  ggagagcgtc  ttcactggac  taactcacat  agatgcccac  tttctgtcac      60
agactaagca  gcagggactc  aacttctcgt  tcctgactgc  ctaccaagcc  actgtgtgcg    120
ctcgcgcgca  ggctcctccc  ccaagttggg  acgagatgtg  gaagtgtctc  gtacggctta   180
agccaacact  acatggacct  acgcctcttc  tatatcggtt  ggggcctgtc  caaaatgaaa    240
tctgcttgac  acaccccatc  acaaaataca  tcatggcatg  catgtcagct  gatctggaag    300
taaccaccag  cacctgggtt  tgcttggag   gggtcctcgc  ggccctagcg  gcctactgct    360
tgtcagtcgg  ttgtgttgtg  attgtgggtc  atatcgagct  gggggcaag   ccggcaatcg    420
ttccagacaa  agaggtgttg  tatcaacaat  acgatgagat  ggaagagtgc  tcacaagctg    480
ccccatatat  cgaacaagct  caggtaatag  ctcaccagtt  caaggaaaaa  gtccttggat    540
tgctgcagcg  agccacccaa  caacaagctg  tcattgagcc  catagtaact  accaactggc    600
aaaagcttga  ggcctttgg   cacaagcat                                         629

<210> SEQ ID NO 223
<211> LENGTH: 209
<212> TYPE: PRT
<213> ORGANISM: hepatitis C virus

<400> SEQUENCE: 223

Asp Phe Trp Glu Ser Val Phe Thr Gly Leu Thr His Ile Asp Ala His
1               5                   10                  15

Phe Leu Ser Gln Thr Lys Gln Gln Gly Leu Asn Phe Ser Phe Leu Thr
            20                  25                  30

Ala Tyr Gln Ala Thr Val Cys Ala Arg Ala Gln Ala Pro Pro Pro Ser
```

```
                35                  40                  45
Trp Asp Glu Met Trp Lys Cys Leu Val Arg Leu Lys Pro Thr Leu His
         50                  55                  60
Gly Pro Thr Pro Leu Leu Tyr Arg Leu Gly Pro Val Gln Asn Glu Ile
 65                  70                  75                  80
Cys Leu Thr His Pro Ile Thr Lys Tyr Ile Met Ala Cys Met Ser Ala
                 85                  90                  95
Asp Leu Glu Val Thr Thr Ser Thr Trp Val Leu Leu Gly Gly Val Leu
            100                 105                 110
Ala Ala Leu Ala Ala Tyr Cys Leu Ser Val Gly Cys Val Val Ile Val
        115                 120                 125
Gly His Ile Glu Leu Gly Gly Lys Pro Ala Ile Val Pro Asp Lys Glu
    130                 135                 140
Val Leu Tyr Gln Gln Tyr Asp Glu Met Glu Glu Cys Ser Gln Ala Ala
145                 150                 155                 160
Pro Tyr Ile Glu Gln Ala Gln Val Ile Ala His Gln Phe Lys Glu Lys
                165                 170                 175
Val Leu Gly Leu Leu Gln Arg Ala Thr Gln Gln Gln Ala Val Ile Glu
            180                 185                 190
Pro Ile Val Thr Thr Asn Trp Gln Lys Leu Glu Ala Phe Trp His Lys
        195                 200                 205
His

<210> SEQ ID NO 224
<211> LENGTH: 12
<212> TYPE: PRT
<213> ORGANISM: hepatitis C virus

<400> SEQUENCE: 224

Ile His Tyr Arg Asn Ala Ser Gly Ile Tyr His Ile
1               5                   10

<210> SEQ ID NO 225
<211> LENGTH: 12
<212> TYPE: PRT
<213> ORGANISM: hepatitis C virus

<400> SEQUENCE: 225

Val Asn Tyr Arg Asn Ala Ser Gly Ile Tyr His Ile
1               5                   10

<210> SEQ ID NO 226
<211> LENGTH: 12
<212> TYPE: PRT
<213> ORGANISM: hepatitis C virus

<400> SEQUENCE: 226

Val Asn Tyr Arg Asn Ala Ser Gly Val Tyr His Ile
1               5                   10

<210> SEQ ID NO 227
<211> LENGTH: 12
<212> TYPE: PRT
<213> ORGANISM: hepatitis C virus

<400> SEQUENCE: 227

Val Asn Tyr His Asn Thr Ser Gly Ile Tyr His Leu
1               5                   10
```

```
<210> SEQ ID NO 228
<211> LENGTH: 12
<212> TYPE: PRT
<213> ORGANISM: hepatitis C virus

<400> SEQUENCE: 228

Gln His Tyr Arg Asn Ala Ser Gly Ile Tyr His Val
1               5                   10

<210> SEQ ID NO 229
<211> LENGTH: 12
<212> TYPE: PRT
<213> ORGANISM: hepatitis C virus

<400> SEQUENCE: 229

Gln His Tyr Arg Asn Val Ser Gly Ile Tyr His Val
1               5                   10

<210> SEQ ID NO 230
<211> LENGTH: 12
<212> TYPE: PRT
<213> ORGANISM: hepatitis C virus

<400> SEQUENCE: 230

Ile His Tyr Arg Asn Ala Ser Asp Gly Tyr Tyr Ile
1               5                   10

<210> SEQ ID NO 231
<211> LENGTH: 12
<212> TYPE: PRT
<213> ORGANISM: hepatitis C virus

<400> SEQUENCE: 231

Leu Gln Val Lys Asn Thr Ser Ser Ser Tyr Met Val
1               5                   10

<210> SEQ ID NO 232
<211> LENGTH: 11
<212> TYPE: PRT
<213> ORGANISM: hepatitis C virus

<400> SEQUENCE: 232

Val Trp Gln Leu Arg Ala Ile Val Leu His Val
1               5                   10

<210> SEQ ID NO 233
<211> LENGTH: 11
<212> TYPE: PRT
<213> ORGANISM: hepatitis C virus

<400> SEQUENCE: 233

Val Tyr Glu Ala Asp Tyr His Ile Leu His Leu
1               5                   10

<210> SEQ ID NO 234
<211> LENGTH: 11
<212> TYPE: PRT
<213> ORGANISM: hepatitis C virus

<400> SEQUENCE: 234

Val Tyr Glu Thr Asp Asn His Ile Leu His Leu
1               5                   10

<210> SEQ ID NO 235
<211> LENGTH: 11
```

```
<212> TYPE: PRT
<213> ORGANISM: hepatitis C virus

<400> SEQUENCE: 235

Val Tyr Glu Thr Glu Asn His Ile Leu His Leu
1               5                   10

<210> SEQ ID NO 236
<211> LENGTH: 11
<212> TYPE: PRT
<213> ORGANISM: hepatitis C virus

<400> SEQUENCE: 236

Val Phe Glu Thr Val His His Ile Leu His Leu
1               5                   10

<210> SEQ ID NO 237
<211> LENGTH: 11
<212> TYPE: PRT
<213> ORGANISM: hepatitis C virus

<400> SEQUENCE: 237

Val Phe Glu Thr Glu His His Ile Leu His Leu
1               5                   10

<210> SEQ ID NO 238
<211> LENGTH: 11
<212> TYPE: PRT
<213> ORGANISM: hepatitis C virus

<400> SEQUENCE: 238

Val Phe Glu Thr Asp His His Ile Met His Leu
1               5                   10

<210> SEQ ID NO 239
<211> LENGTH: 11
<212> TYPE: PRT
<213> ORGANISM: hepatitis C virus

<400> SEQUENCE: 239

Val Tyr Glu Thr Glu Asn His Ile Leu His Leu
1               5                   10

<210> SEQ ID NO 240
<211> LENGTH: 11
<212> TYPE: PRT
<213> ORGANISM: hepatitis C virus

<400> SEQUENCE: 240

Val Tyr Glu Ala Asp Ala Leu Ile Leu His Ala
1               5                   10

<210> SEQ ID NO 241
<211> LENGTH: 13
<212> TYPE: PRT
<213> ORGANISM: hepatitis C virus

<400> SEQUENCE: 241

Val Gln Asp Gly Asn Thr Ser Ala Cys Trp Thr Pro Val
1               5                   10

<210> SEQ ID NO 242
<211> LENGTH: 13
<212> TYPE: PRT
<213> ORGANISM: hepatitis C virus
```

```
<400> SEQUENCE: 242

Val Lys Thr Gly Asn Gln Ser Arg Cys Trp Val Ala Leu
1               5                   10

<210> SEQ ID NO 243
<211> LENGTH: 13
<212> TYPE: PRT
<213> ORGANISM: hepatitis C virus

<400> SEQUENCE: 243

Val Lys Thr Gly Asn Gln Ser Arg Cys Trp Val Ala Leu
1               5                   10

<210> SEQ ID NO 244
<211> LENGTH: 13
<212> TYPE: PRT
<213> ORGANISM: hepatitis C virus

<400> SEQUENCE: 244

Val Arg Thr Gly Asn Gln Ser Arg Cys Trp Val Ala Leu
1               5                   10

<210> SEQ ID NO 245
<211> LENGTH: 13
<212> TYPE: PRT
<213> ORGANISM: hepatitis C virus

<400> SEQUENCE: 245

Val Lys Thr Gly Asn Gln Ser Arg Cys Trp Ile Ala Leu
1               5                   10

<210> SEQ ID NO 246
<211> LENGTH: 13
<212> TYPE: PRT
<213> ORGANISM: hepatitis C virus

<400> SEQUENCE: 246

Val Lys Thr Gly Asn Gln Ser Arg Cys Trp Ile Ala Leu
1               5                   10

<210> SEQ ID NO 247
<211> LENGTH: 13
<212> TYPE: PRT
<213> ORGANISM: hepatitis C virus

<400> SEQUENCE: 247

Val Lys Thr Gly Asn Ser Val Arg Cys Trp Ile Pro Leu
1               5                   10

<210> SEQ ID NO 248
<211> LENGTH: 13
<212> TYPE: PRT
<213> ORGANISM: hepatitis C virus

<400> SEQUENCE: 248

Val Lys Thr Gly Asn Val Ser Arg Cys Trp Ile Ser Leu
1               5                   10

<210> SEQ ID NO 249
<211> LENGTH: 13
<212> TYPE: PRT
<213> ORGANISM: hepatitis C virus

<400> SEQUENCE: 249
```

-continued

```
Val Arg Lys Asp Asn Val Ser Arg Cys Trp Val Gln Ile
1               5                   10

<210> SEQ ID NO 250
<211> LENGTH: 10
<212> TYPE: PRT
<213> ORGANISM: hepatitis C virus

<400> SEQUENCE: 250

Ala Pro Ser Phe Gly Ala Val Thr Ala Pro
1               5                   10

<210> SEQ ID NO 251
<211> LENGTH: 10
<212> TYPE: PRT
<213> ORGANISM: hepatitis C virus

<400> SEQUENCE: 251

Val Ser Gln Pro Gly Ala Leu Thr Lys Gly
1               5                   10

<210> SEQ ID NO 252
<211> LENGTH: 10
<212> TYPE: PRT
<213> ORGANISM: hepatitis C virus

<400> SEQUENCE: 252

Val Lys Tyr Val Gly Ala Thr Thr Ala Ser
1               5                   10

<210> SEQ ID NO 253
<211> LENGTH: 10
<212> TYPE: PRT
<213> ORGANISM: hepatitis C virus

<400> SEQUENCE: 253

Ala Pro Tyr Ile Gly Ala Pro Val Glu Ser
1               5                   10

<210> SEQ ID NO 254
<211> LENGTH: 10
<212> TYPE: PRT
<213> ORGANISM: hepatitis C virus

<400> SEQUENCE: 254

Ala Gln His Leu Asn Ala Pro Leu Glu Ser
1               5                   10

<210> SEQ ID NO 255
<211> LENGTH: 10
<212> TYPE: PRT
<213> ORGANISM: hepatitis C virus

<400> SEQUENCE: 255

Ser Pro Tyr Val Gly Ala Pro Leu Glu Pro
1               5                   10

<210> SEQ ID NO 256
<211> LENGTH: 10
<212> TYPE: PRT
<213> ORGANISM: hepatitis C virus

<400> SEQUENCE: 256

Ser Pro Tyr Ala Gly Ala Pro Leu Glu Pro
```

```
1               5                   10
```

<210> SEQ ID NO 257
<211> LENGTH: 10
<212> TYPE: PRT
<213> ORGANISM: hepatitis C virus

<400> SEQUENCE: 257

```
Ala Pro Tyr Leu Gly Ala Pro Leu Glu Ser
1               5                   10
```

<210> SEQ ID NO 258
<211> LENGTH: 10
<212> TYPE: PRT
<213> ORGANISM: hepatitis C virus

<400> SEQUENCE: 258

```
Ala Pro Tyr Leu Gly Ala Pro Leu Glu Ser
1               5                   10
```

<210> SEQ ID NO 259
<211> LENGTH: 10
<212> TYPE: PRT
<213> ORGANISM: hepatitis C virus

<400> SEQUENCE: 259

```
Ala Pro Tyr Val Gly Ala Pro Leu Glu Ser
1               5                   10
```

<210> SEQ ID NO 260
<211> LENGTH: 11
<212> TYPE: PRT
<213> ORGANISM: hepatitis C virus

<400> SEQUENCE: 260

```
Asn Val Pro Tyr Leu Gly Ala Pro Leu Thr Ser
1               5                   10
```

<210> SEQ ID NO 261
<211> LENGTH: 10
<212> TYPE: PRT
<213> ORGANISM: hepatitis C virus

<400> SEQUENCE: 261

```
Ala Pro His Leu Arg Ala Pro Leu Ser Ser
1               5                   10
```

<210> SEQ ID NO 262
<211> LENGTH: 10
<212> TYPE: PRT
<213> ORGANISM: hepatitis C virus

<400> SEQUENCE: 262

```
Ala Pro Tyr Leu Gly Ala Pro Leu Thr Ser
1               5                   10
```

<210> SEQ ID NO 263
<211> LENGTH: 10
<212> TYPE: PRT
<213> ORGANISM: hepatitis C virus

<400> SEQUENCE: 263

```
Arg Pro Arg Gln His Ala Thr Val Gln Asp
1               5                   10
```

<210> SEQ ID NO 264
<211> LENGTH: 10
<212> TYPE: PRT
<213> ORGANISM: hepatitis C virus

<400> SEQUENCE: 264

Ser Pro Gln His His Lys Phe Val Gln Asp
1               5                   10

<210> SEQ ID NO 265
<211> LENGTH: 10
<212> TYPE: PRT
<213> ORGANISM: hepatitis C virus

<400> SEQUENCE: 265

Arg Pro Arg Arg Leu Trp Thr Thr Gln Glu
1               5                   10

<210> SEQ ID NO 266
<211> LENGTH: 10
<212> TYPE: PRT
<213> ORGANISM: hepatitis C virus

<400> SEQUENCE: 266

Pro Pro Arg Ile His Glu Thr Thr Gln Asp
1               5                   10

<210> SEQ ID NO 267
<211> LENGTH: 14
<212> TYPE: PRT
<213> ORGANISM: hepatitis C virus

<400> SEQUENCE: 267

Thr Ile Ser Tyr Ala Asn Gly Ser Gly Pro Ser Asp Asp Lys
1               5                   10

<210> SEQ ID NO 268
<211> LENGTH: 19
<212> TYPE: PRT
<213> ORGANISM: hepatitis C virus

<400> SEQUENCE: 268

Ser Arg Arg Gln Pro Ile Pro Arg Ala Arg Arg Thr Glu Gly Arg Ser
1               5                   10                  15

Trp Ala Gln

<210> SEQ ID NO 269
<211> LENGTH: 1443
<212> TYPE: DNA
<213> ORGANISM: hepatitis C virus

<400> SEQUENCE: 269
accatcacca ccggagcttc tatcacatac tccacttacg gcaagttcct tgctgatgga      60
gggtgttcag gcggcgcgta tgacgtgatc atatgcgacg agtgccattc ccaggacgcc     120
accaccattc ttgggatagg cactgtcctt gaccaggcag agacggctgg agctaggctc     180
gtcgtcttgg ccacgccac ccctcccggc agtgtgacaa cgccccaccc caacatcgag     240
gaagtggccc tgcctcagga ggggaggtt cccttctacg gcagagccat tcccctttgct    300 tttataaagg gtggtaggca tctcatcttc tgccattcca agaaaaaatg tgatgaactc     360
gccaagcaac tgaccagcct gggcgtgaac gccgtggcat attatagagg tctagacgtc     420

-continued

```
gccgtcatcc ccacagcagg agacgtggtc gtgtgcagca ccgacgcgct catgacggga    480
ttcaccggcg actttgattc tgtcatagac tgcaactccg ccgtcactca gacggtggac    540
ttcagtctgg atcccacttt taccattgag actaccacag tgccccagga cgcagtgtcc    600
agaagccagc gtaggggccg cacggggaga ggtaggcacg gcatataccg gtatgtctcg    660
gctggagaga gaccgtctga catgttcgac tccgtggtgc tctgtgagtg ctacgatgcc    720
ggatgtgcgt ggtatgatct gactcctgcc gagactaccg tgaggttgcg cgcttacata    780
aacacccccg ggctccctgt ctgtcaggac catttggaat tctgggaggg ggtgttcacg    840
gggctcacta acatcgacgc tcacatgctg tcacagacca aacagggtgg ggagaatttc    900
ccataccttg tagcgtacca agcaacagtc tgtgttcgcg cgaaagcgcc cccccccagc    960
tgggacacaa tgtggaaatg catgctccgt ctcaaaccga ctttaactgg ccctactccc   1020
ctcttgtaca ggctggggcc cgtccagaat gagatcacac tgacgcaccc catcaccaag   1080
tacattatgg cttgcatgtc tgcggacttg gaggtcatta ccagcacttg ggttctggtg   1140
gggggcgttg tggcggccct ggcggcctac tgcttgacgg tgggttcggt agccatagtc   1200
ggtaggatca tcctctctgg gaaacctgcc atcattcccg atagggaggc attataccag   1260
caatttgatg agatggagga gtgctcggcc tcgttgccct atatggacga gacacgtgcc   1320
attgccggac aattcaaaga gaaagtgctc ggcttcatca gcacgaccgg ccagaaggct   1380
gaaactctga agccggcagc cacgtctgtg tggaacaagg ctgagcagtt ctgggccaca   1440
tac                                                                 1443
```

```

<210> SEQ ID NO 270
<211> LENGTH: 481
<212> TYPE: PRT
<213> ORGANISM: hepatitis C virus

<400> SEQUENCE: 270

Thr Ile Thr Thr Gly Ala Ser Ile Thr Tyr Ser Thr Tyr Gly Lys Phe
1               5                   10                  15

Leu Ala Asp Gly Gly Cys Ser Gly Gly Ala Tyr Asp Val Ile Ile Cys
            20                  25                  30

Asp Glu Cys His Ser Gln Asp Ala Thr Thr Ile Leu Gly Ile Gly Thr
        35                  40                  45

Val Leu Asp Gln Ala Glu Thr Ala Gly Ala Arg Leu Val Val Leu Ala
    50                  55                  60

Thr Ala Thr Pro Pro Gly Ser Val Thr Thr Pro His Pro Asn Ile Glu
65                  70                  75                  80

Glu Val Ala Leu Pro Gln Glu Gly Glu Val Pro Phe Tyr Gly Arg Ala
                85                  90                  95

Ile Pro Leu Ala Phe Ile Lys Gly Gly Arg His Leu Ile Phe Cys His
            100                 105                 110

Ser Lys Lys Lys Cys Asp Glu Leu Ala Lys Gln Leu Thr Ser Leu Gly
        115                 120                 125

Val Asn Ala Val Ala Tyr Tyr Arg Gly Leu Asp Val Ala Val Ile Pro
    130                 135                 140

Thr Ala Gly Asp Val Val Val Cys Ser Thr Asp Ala Leu Met Thr Gly
145                 150                 155                 160

Phe Thr Gly Asp Phe Asp Ser Val Ile Asp Cys Asn Ser Ala Val Thr
                165                 170                 175

Gln Thr Val Asp Phe Ser Leu Asp Pro Thr Phe Thr Ile Glu Thr Thr
            180                 185                 190
```

Thr Val Pro Gln Asp Ala Val Ser Arg Ser Gln Arg Arg Gly Arg Thr
            195                 200                 205
Gly Arg Gly Arg His Gly Ile Tyr Arg Tyr Val Ser Ala Gly Glu Arg
    210                 215                 220
Pro Ser Asp Met Phe Asp Ser Val Val Leu Cys Glu Cys Tyr Asp Ala
225                 230                 235                 240
Gly Cys Ala Trp Tyr Asp Leu Thr Pro Ala Glu Thr Thr Val Arg Leu
                245                 250                 255
Arg Ala Tyr Ile Asn Thr Pro Gly Leu Pro Val Cys Gln Asp His Leu
            260                 265                 270
Glu Phe Trp Glu Gly Val Phe Thr Gly Leu Thr Asn Ile Asp Ala His
        275                 280                 285
Met Leu Ser Gln Thr Lys Gln Gly Gly Glu Asn Phe Pro Tyr Leu Val
        290                 295                 300
Ala Tyr Gln Ala Thr Val Cys Val Arg Ala Lys Ala Pro Pro Pro Ser
305                 310                 315                 320
Trp Asp Thr Met Trp Lys Cys Met Leu Arg Leu Lys Pro Thr Leu Thr
                325                 330                 335
Gly Pro Thr Pro Leu Leu Tyr Arg Leu Gly Pro Val Gln Asn Glu Ile
            340                 345                 350
Thr Leu Thr His Pro Ile Thr Lys Tyr Ile Met Ala Cys Met Ser Ala
            355                 360                 365
Asp Leu Glu Val Ile Thr Ser Thr Trp Val Leu Val Gly Gly Val Val
370                 375                 380
Ala Ala Leu Ala Ala Tyr Cys Leu Thr Val Gly Ser Val Ala Ile Val
385                 390                 395                 400
Gly Arg Ile Ile Leu Ser Gly Lys Pro Ala Ile Ile Pro Asp Arg Glu
                405                 410                 415
Ala Leu Tyr Gln Gln Phe Asp Glu Met Glu Glu Cys Ser Ala Ser Leu
            420                 425                 430
Pro Tyr Met Asp Glu Thr Arg Ala Ile Ala Gly Gln Phe Lys Glu Lys
        435                 440                 445
Val Leu Gly Phe Ile Ser Thr Thr Gly Gln Lys Ala Glu Thr Leu Lys
    450                 455                 460
Pro Ala Ala Thr Ser Val Trp Asn Lys Ala Glu Gln Phe Trp Ala Thr
465                 470                 475                 480
Tyr

<210> SEQ ID NO 271
<211> LENGTH: 5
<212> TYPE: PRT
<213> ORGANISM: hepatitis C virus

<400> SEQUENCE: 271

Leu Glu Trp Arg Asn
1               5

<210> SEQ ID NO 272
<211> LENGTH: 20
<212> TYPE: PRT
<213> ORGANISM: hepatitis C virus

<400> SEQUENCE: 272

Leu Ser Gly Lys Pro Ala Ile Ile Pro Asp Arg Glu Val Leu Tyr Arg
1               5                   10                  15

-continued

Glu Phe Asp Glu
        20

<210> SEQ ID NO 273
<211> LENGTH: 20
<212> TYPE: PRT
<213> ORGANISM: hepatitis C virus

<400> SEQUENCE: 273

Ser Gln His Leu Pro Tyr Ile Glu Gln Gly Met Met Leu Ala Glu Gln
1               5                   10                  15

Phe Lys Gln Lys
        20

<210> SEQ ID NO 274
<211> LENGTH: 20
<212> TYPE: PRT
<213> ORGANISM: hepatitis C virus

<400> SEQUENCE: 274

Leu Ala Glu Gln Phe Lys Gln Lys Ala Leu Gly Leu Leu Gln Thr Ala
1               5                   10                  15

Ser Arg Gln Ala
        20

<210> SEQ ID NO 275
<211> LENGTH: 20
<212> TYPE: PRT
<213> ORGANISM: hepatitis C virus

<400> SEQUENCE: 275

Leu Ser Gly Arg Pro Ala Val Ile Pro Asp Arg Glu Val Leu Tyr Gln
1               5                   10                  15

Glu Phe Asp Glu
        20

<210> SEQ ID NO 276
<211> LENGTH: 20
<212> TYPE: PRT
<213> ORGANISM: hepatitis C virus

<400> SEQUENCE: 276

Ala Ser His Leu Pro Tyr Ile Glu Gln Gly Met Gln Leu Ala Glu Gln
1               5                   10                  15

Phe Lys Gln Lys
        20

<210> SEQ ID NO 277
<211> LENGTH: 20
<212> TYPE: PRT
<213> ORGANISM: hepatitis C virus

<400> SEQUENCE: 277

Leu Ala Glu Gln Phe Lys Gln Lys Ala Leu Gly Leu Leu Gln Thr Ala
1               5                   10                  15

Thr Lys Gln Ala
        20

<210> SEQ ID NO 278
<211> LENGTH: 20
<212> TYPE: PRT
<213> ORGANISM: hepatitis C virus -continued

<400> SEQUENCE: 278

Val Asn Gln Arg Ala Val Val Ala Pro Asp Lys Glu Val Leu Tyr Glu
1               5                   10                  15

Ala Phe Asp Glu
            20

<210> SEQ ID NO 279
<211> LENGTH: 20
<212> TYPE: PRT
<213> ORGANISM: hepatitis C virus

<400> SEQUENCE: 279

Ala Ser Arg Ala Ala Leu Ile Glu Glu Gly Gln Arg Ile Ala Glu Met
1               5                   10                  15

Leu Lys Ser Lys
            20

<210> SEQ ID NO 280
<211> LENGTH: 20
<212> TYPE: PRT
<213> ORGANISM: hepatitis C virus

<400> SEQUENCE: 280

Ile Ala Glu Met Leu Lys Ser Lys Ile Gln Gly Leu Leu Gln Gln Ala
1               5                   10                  15

Ser Lys Gln Ala
            20

<210> SEQ ID NO 281
<211> LENGTH: 20
<212> TYPE: PRT
<213> ORGANISM: hepatitis C virus

<400> SEQUENCE: 281

Leu Asn Asp Arg Val Val Val Ala Pro Asp Lys Glu Ile Leu Tyr Glu
1               5                   10                  15

Ala Phe Asp Glu
            20

<210> SEQ ID NO 282
<211> LENGTH: 20
<212> TYPE: PRT
<213> ORGANISM: hepatitis C virus

<400> SEQUENCE: 282

Ala Ser Lys Ala Ala Leu Ile Glu Glu Gly Gln Arg Met Ala Glu Met
1               5                   10                  15

Leu Lys Ser Lys
            20

<210> SEQ ID NO 283
<211> LENGTH: 20
<212> TYPE: PRT
<213> ORGANISM: hepatitis C virus

<400> SEQUENCE: 283

Met Ala Glu Met Leu Lys Ser Lys Ile Gln Gly Leu Leu Gln Gln Ala
1               5                   10                  15

Thr Arg Gln Ala
            20

```
<210> SEQ ID NO 284
<211> LENGTH: 20
<212> TYPE: PRT
<213> ORGANISM: hepatitis C virus

<400> SEQUENCE: 284

Ala Ala Ser Leu Pro Tyr Met Asp Glu Thr Arg Ala Ile Ala Gly Gln
 1               5                  10                  15

Phe Lys Glu Lys
            20
```

The invention claimed is:

1. An isolated polypeptide or peptide comprising 8 or more contiguous amino acids of an HCV type 3a polypeptide or peptide
selected from the region spanning positions 1646 to 1764 of the NS3/NS4 region of HCV type 3a;
wherein said peptide or polypeptide contains at least one amino acid selected from the group consisting of T1656, L1663, H1685, E1687, G1689, Y1705, A1714, A1721, V1723, H1726, Q1743, A1744, E1747, I1749, A1759 and H1762, wherein said amino acid numbering is relative to the HCV polyprotein.

2. An isolated HCV type 3a polypeptide comprising an amino acid sequence or peptide selected from the group consisting of
(i) SEQ ID NO: 36, and
(ii) at least 8 contiguous amino acids from the polypeptide or peptide of (i) having at least one amino acid selected from the group consisting of T1656, L1663, H1685, E1687, G1689, Y1705, A1714, A1721, V1723, H1726, Q1743, A1744, E1747, I1749, A1759 and H1762, wherein said amino acid numbering is relative to the HCV polyprotein.

3. A polypeptide or peptide according to claim 1, wherein said polypeptide or peptide is selected from the following peptides:

| | |
|---|---|
| LGGKPAIVPDKEVLYQQYDE | (SEQ ID NO:97) |
| SQAAPYIEQAQVIAHQFKEK | (SEQ ID NO:99) |
| IAHQFKEKVLGLLQRATQQQ | (SEQ ID NO:100). |

4. A composition comprising an isolated polypeptide or peptide according to any of claims 1 or 2 or 3.

5. A method of detecting, screening or confirmation of the presence of HCV antibodies present in a biological sample, comprising the following steps:
(i) providing a sample suspected of containing HCV antibody,
(ii) contacting the sample with a polypeptide or peptide according to any of claims 1 or 2 or 3, under appropriate conditions allowing the formation of an immune complex,
(iii) inferring from the presence of the immune complex of step (ii) the presence of HCV antibodies in said sample.

6. A method of detecting, screening or confirmation of one or more HCV serotypes present in a biological sample, comprising the following steps:
(i) providing a sample suspected of containing HCV antibody,
(ii) contacting the sample with a polypeptide or peptide according to any of claims 1 or 2 or 3, under appropriate conditions allowing the formation of an immune complex,
(iii) inferring from the presence of one or more of these immune complexes of step (ii) the serotype(s) present in said sample.

7. A method for detecting HCV serotype(s) present in a biological sample liable to contain it, comprising at least the following steps:
(i) contacting the biological sample to be analyzed for the presence of HCV antibodies with at least one peptide or polypeptide according to any of claims 1 or 2 or 3, preferentially in an immobilized form under appropriate conditions which allow the formation of an immune complex, wherein said polypeptide or peptide is preferentially in the form of a biotinylated polypeptide or peptide and is covalently bound to a solid substrate by means of streptavidin or avidin complexes,
(ii) removing unbound components,
(iii) incubating the immune complexes formed with heterologous antibodies, which specifically bind to the antibodies present in the sample to be analyzed, with said heterologous antibodies having conjugated to a detectable label under appropriate conditions,
(iv) detecting the presence of said immune complexes visually or by means of densitometry and inferring the HCV serotype(s) present from the observed binding pattern.

8. A method for confirmation of HCV serotype(s) present in a biological sample liable to contain it, comprising at least the following steps:
(i) contacting the biological sample to be analyzed for the presence of HCV antibodies with at least one peptide or polypeptide according to any of claims 1 or 2 or 3, preferentially in an immobilized form under appropriate conditions which allow the formation of an immune complex, wherein said polypeptide or peptide is preferentially in the form of a biotinylated polypeptide or peptide and is covalently bound to a solid substrate by means of streptavidin or avidin complexes,
(ii) removing unbound components,
(iii) incubating the immune complexes formed with heterologous antibodies, which specifically bind to the antibodies present in the sample to be analyzed, with said heterologous antibodies having conjugated to a detectable label under appropriate conditions,
(iv) detecting the presence of said immune complexes visually or by means of densitometry and confirm the HCV serotype(s) present from the observed binding pattern.

9. A kit for detecting, screening or confirmation for one or more HCV serotype(s) present in a biological sample, comprising:
- (i) a polypeptide or peptide according to any of claims 1 or 2 or 3,
- (ii) optionally a buffer and components necessary for producing the formation of an immune complex,
- (iii) optionally a means for detecting, screening or confirming the immune complex(es) formed.

10. A kit for detecting, screening or confirmation for the presence of HCV antibodies present in a biological sample, comprising:
- (i) a polypeptide or peptide according to any of claims 1 or 2 or 3,
- (ii) optionally a buffer and components necessary for producing the formation of an immune complex,
- (iii) optionally a means for detecting, screening or confirming the immune complex formed.

11. A kit for detecting HCV serotype(s) present in a biological sample liable to contain it, comprising at least the following components:
- (i) at least a polypeptide or peptide according to any of claims 1 or 2 or 3, with said polypeptide or peptide being preferentially immobilized on a solid substrate, and more preferentially on one and the same membrane strip,
- (ii) a buffer and components necessary for producing the buffer enabling binding reaction between these polypeptides or peptides and the antibodies against HCV present in the biological sample,
- (iii) optionally, a detector for determining the presence of immune complexes formed in the preceding binding reaction, and
- (iv) optionally an automated scanning and interpretation device to confirm the HCV serotype(s) present in the sample from the observed binding pattern.

12. A kit for confirmation of HCV serotype(s) present in a biological sample liable to contain it, comprising at least the following components:
- (i) at least a polypeptide or peptide according to any of claims 1 or 2 or 3, with said polypeptide or peptide being preferentially immobilized on a solid substrate, and more preferentially on one and the same membrane strip,
- (ii) a buffer and components necessary for producing the buffer enabling binding reaction between these polypeptides or peptides and the antibodies against HCV present in the biological sample,
- (iii) optionally, a detector for determining the presence of immune complexes formed in the preceding binding reaction, and
- (iv) optionally, an automated scanning and interpretation device to confirm the HCV serotype(s) present in the sample from the observed binding pattern.

13. A method for raising antibodies comprising administering to a mammal a polypeptide or peptide selected from the group consisting of
- (i) an isolated polypeptide or peptide comprising at least 14 contiguous amino acids selected from the region spanning positions 1646 to 1764 of the NS3/4 protein of HCV type 3a;
- (ii) an isolated polypeptide or peptide with SEQ ID NO:36; and
- (iii) an isolated polypeptide or peptide comprising at least 14 contiguous amino acids of SEQ ID NO:36;
- wherein said polypeptide or peptide of (i), (ii) or (iii) contains at least one amino acid selected from the group consisting of T1656, L1663, H1685, E1687, G1689, Y1705, A1714, A1721, V1723, H1726, Q1743, A1744, E1747, I1749, A1759, and H1762, wherein said amino acid numbering is relative to the HCV polyprotein.

\* \* \* \* \*